United States Patent
Ramasubramanyan et al.

(10) Patent No.: US 9,315,574 B2
(45) Date of Patent: *Apr. 19, 2016

(54) LOW ACIDIC SPECIES COMPOSITIONS AND METHODS FOR PRODUCING AND USING THE SAME

(71) Applicant: AbbVie, Inc., North Chicago, IL (US)

(72) Inventors: Natarajan Ramasubramanyan, Westborough, MA (US); Lihua Yang, Westborough, MA (US); Matthew Omon Herigstad, Charlestown, MA (US); Hong Yang, Worcester, MA (US); Kartik Subramanian, Northborough, MA (US); Xiaobei Zeng, Carolina, PR (US); Diane D. Dong, Shrewsbury, MA (US); Wen Chung Lim, Worcester, MA (US); Kathreen A. Gifford, Marlborough, MA (US); Zehra Kaymakcalan, Westborough, MA (US); Christopher Chumsae, North Andover, MA (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/584,619

(22) Filed: Dec. 29, 2014

(65) Prior Publication Data

US 2015/0166650 A1 Jun. 18, 2015

Related U.S. Application Data

(62) Division of application No. 14/077,871, filed on Nov. 12, 2013, now Pat. No. 9,085,618.

(60) Provisional application No. 61/893,068, filed on Oct. 18, 2013.

(51) Int. Cl.
  *C07K 14/525* (2006.01)
  *A61K 39/395* (2006.01)
  (Continued)

(52) U.S. Cl.
  CPC ............... *C07K 16/241* (2013.01); *C07K 16/00* (2013.01); *A61K 2039/505* (2013.01); *C07K 2317/10* (2013.01); *C07K 2317/14* (2013.01); *C07K 2317/21* (2013.01); *C07K 2317/76* (2013.01)

(58) Field of Classification Search
  CPC ............ A61K 39/395; A61K 2039/505; C07K 16/241; C07K 1/165; C07K 2317/14; C07K 2317/21; C07K 2317/76
  See application file for complete search history.

(56) References Cited

U.S. PATENT DOCUMENTS

RE30,985 E 6/1982 Cartaya
4,399,216 A 8/1983 Axel et al.
(Continued)

FOREIGN PATENT DOCUMENTS

CN 1563090 A 1/2005
DE 3631229 A1 3/1988
(Continued)

OTHER PUBLICATIONS

Du et al., (MAbs Sep.-Oct. 2012;4(5):578-85. doi: 10.4161/mabs. 21328. Epub Jul. 23, 2012).*
(Continued)

*Primary Examiner* — Cherie M Stanfield
(74) *Attorney, Agent, or Firm* — McCarter & English, LLP; Maria Laccotripe Zacharakis; Lisa Tyner

(57) ABSTRACT

The instant invention relates to low acidic species (AR) compositions comprising a protein, e.g., an antibody, or antigen-binding portion thereof, and methods, e.g., cell culture and/or protein purification methods, for producing such low AR compositions. Methods for using such compositions to treat a disorder, e.g., a disorder in which TNFα is detrimental, are also provided.

42 Claims, 95 Drawing Sheets

(51) Int. Cl.
*C07K 16/24* (2006.01)
*C07K 16/00* (2006.01)
*A61K 39/00* (2006.01)

(56) References Cited

U.S. PATENT DOCUMENTS

| | | |
|---|---|---|
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 * | 2/2015 | Herigstad ............... C07K 1/20 530/412 |
| 9,017,687 B1 * | 4/2015 | Wang ................... C07K 16/241 424/142.1 |
| 9,067,990 B2 * | 6/2015 | Wang ................... C07K 16/241 |
| 2002/0045207 A1 | 4/2002 | Krummen et al. |
| 2002/0132299 A1 | 9/2002 | Field |
| 2002/0187526 A1 | 12/2002 | Ruben et al. |

(56) References Cited

U.S. PATENT DOCUMENTS

| | | |
|---|---|---|
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |

(56) References Cited

U.S. PATENT DOCUMENTS

| | | |
|---|---|---|
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1 | 9/2014 | Nti-gyabaah et al. |
| 2014/0314745 A1 | 10/2014 | Rives at al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |

FOREIGN PATENT DOCUMENTS

| | | |
|---|---|---|
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 A1 | 1/2015 |
| JP | 7289288 A | 11/1995 |
| WO | WO-87/00195 A1 | 1/1987 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/24883 A2 | 6/1998 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A1 | 1/2004 |
| WO | WO-2004/058944 A2 | 7/2004 |
| WO | WO-2004058800 A2 | 7/2004 |
| WO | WO-2004/097006 A1 | 11/2004 |
| WO | WO-2005042569 A1 | 5/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007/087384 A2 | 8/2007 |
| WO | WO-2007/117490 A2 | 10/2007 |
| WO | WO 2007117490 A2 * | 10/2007 |

(56) References Cited

FOREIGN PATENT DOCUMENTS

| WO | WO-2008/033517 A2 | 3/2008 |
|---|---|---|
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009135656 A1 | 11/2009 |
| WO | WO-2010036443 A1 | 4/2010 |
| WO | WO-2010043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2014/207763 A1 | 12/2014 |
| WO | WO-2015/004679 A1 | 1/2015 |

OTHER PUBLICATIONS

Santora et al., (Anal Biochem. Nov. 1, 1999;275(1):98-108).*
Adams. et al., "Aggressive cutaneous T-cell lymphomas after TNFα blockade," J. Am. Acad. Dermatol 2004;51 :660-2.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Andersen DC, The effect of cell-culture conditions on the oligosaccharide structures of secreted glycoproteins. Curr Opin Biotechnol. Oct. 1994;5(5):546-9.
Awdeh, Z.L., A.R. Williamson, and B.A. Askonas, One cell-one immunoglobulin. Origin of limited heterogeneity of myeloma proteins. Biochem J, 1970. 116(2): p. 241-8.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pdf>), (last accessed Jan. 8, 2015), 4 pages.
Biastoff, S.; et al.; Colorimetric Activity Measurement of a Recombinant Putrescine N-Methyltransferase from Datura stramonium; Planta Med. 2006, 72, 1136.
Burteau et al. (In Vitro Cell Dev Biol—Animal, Jul. / Aug. 2003. 39-291-296).
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary cells grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Cordoba, A.J., et al., Non-enzymatic hinge region fragmentation of antibodies in solution. Journal of Chromatography B, 2005. 818(2): p. 115-121.
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
DIONEX Application Note 125 (Monitoring Protein Deamidation by Cation-Exchange Chromatography. 2009; pp. 1-7).
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Ellison, Jay W. et al., "The Nucleotide Sequence of a Human Immunoglobulin Cγ1 Gene," Nucleic Acids Research, vol. 10, No. 13 (1982), 9 pages.
Fahrner et al., "Industrial purification of pharmaceutical antibodies: development, operation, and validation of chromatography processes" Biotechnology and Genetic Engineering Reviews, 18, 2001, pp. 301-327.
FDA Package insert for Adalimumab, Sep. 26, 2003, pp. 1-16.

(56) References Cited

OTHER PUBLICATIONS

Fleisher B., Mechanism of glycosylation in the Golgi apparatus. J Histochem Cytochem, Aug. 1983; 31(8):1033-1040.

Gauthier, M. A.& Klok, H.-A. Arginine-Specific Modification of Proteins with Polyethylene Glycol Biomacromolecules; 2011, 12, 482-493.

Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.

Goochee CF The Oligosaccharides of Glycoproteins: Bioprocess Factors Affecting Oligosaccharide Structure and their Effect on Glycoprotein Properties. Nature Biotechnology Dec. 1991 1346-1355.

Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.

Harlow et al., Eds ("Antibodies: A Laboratory Manual" 1988. Cold Spring Harbor Laboratory Press, Chapter 7, pp. 245, 247,and 253).

Harris, R.J., et al., Identification of multiple sources of charge heterogeneity in a recombinant antibody. Journal of Chromatography B: Biomedical Sciences and Applications, 2001. 752(2): p. 233-245.

Harris, Reed J. et al., "Structural Characterization of a Recombinant CD4-IgG Hybrid Molecule," Eur. J. Biochem. 194:611-620 (1990).

Hills, A.E. et al., Metabolic control of recombinant monoclonal antibody N-glycosylation in GS-NS0 cells, Biotechnology and Bioengineering, Oct. 20, 2001; 75(2):239-251.

Hipkiss, A.; Can the beneficial effects of methionine restriction in rats be explained in part by decreased methylglyoxal generation resulting from suppressed carbohydrate metabolism?; Biogerontology 2012, 13, 633-636.

Hossler et al., "Optimal and consistent protein glycosylation in mammalian cell culture", Glycobiology; (2009), 19(9):936-949.

Huang, L., et al., In Vivo Deamidation Characterization of Monoclonal Antibody by LC/MS/MS. Analytical Chemistry, 2005. 77(5): p. 1432-1439.

HyClone™ CDM4CHO Catalog listing (last accessed Nov. 17, 2014).

International Preliminary Report on Patentability for Application No. PCT/US2013/031352 dated Nov. 25, 2014, pp. 1-10.

International Preliminary Report on Patentability for Application No. PCT/US2013/031365, dated Mar. 3, 2015, 9 pages.

International Preliminary Report on Patentability for Application No. PCT/US2013/041954, dated Nov. 25, 2014, pp. 1-14.

International Preliminary Report on Patentability for Application No. PCT/US2013/041958, dated Dec. 4, 2014, pp. 1-2.

International Search Report and Written Opinion for PCT/US2012/035266, dated Feb. 7, 2013 (corresponds to U.S. Appl. No. 13/547,020), 4 pages.

International Search Report for Application No. PCT/US2014/026606, Dated Dec. 8, 2014, 8 pages.

International Search Report for Application No. PCT/US2014/026636, Dated Jul. 29, 2014, 5 pages.

Jack, M.; Wright, D.; The Role of Advanced Glycation Endproducts and Glyoxalase I in Diabetic Peripheral Sensory Neuropathy; Transl. Res. 2012, 159, 355-365.

Jakubowski, H., Protein N-homocysteinylation: implications for atherosclerosis. Biomedicine; Pharmacotherapy, 2001. 55(8): p. 443-447.

Jayapal, Karthik P., et al., "Recombinant Protein Therapeutics from CHO Cells—20 Years and Counting," CHO Consortium, SBE Special Section, 40-47 (2007).

Jefferis, R., Glycosylation of Recombinant Antibody Therapeutics. Biotechnology Progress, 2005.21(1): p. 11-16.

Johnson, K.A., et al., Cation exchange HPLC and mass spectrometry reveal C-terminal amidation of an IqG1 heavy chain. Analytical Biochemistry, 2007. 360(1): p. 75-83.

Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.

Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

Kingkeohoi, S., Analysis of methylglyoxal metabolism in CHO celis grown in culture, Cytotechnology (2005) 48:1-13.

Kwon et al., "Production of lactic acid by *Lactobacillus rhamnosus* with vitamin-supplemented soybean hydrolysate", Enzyme Microb Technol. (2000), 26:209-215.

Li, Feng, et al., "Cell Culture Processes for Monoclonal Antibody Production," mAbs 2:5, 466-479 (Sep.-Oct. 2010).

Liu et al. "Recovery and purificaiton process development for monoclonal antibody production" MABS, 2(5), pp. 480-499 (2010).

Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.

Liu, H., et al., Heterogeneity of monoclonal antibodies. Journal of Pharmaceutical Sciences, 2008. 97(7): p. 2426-2447.

Liu, M, et al.; Discovery of Undefined Protein Cross-Linking Chemistry: A Comprehensive Methodology Utilizing 18O-Labeling and Mass Spectrometry; Anal. Chem. 2013, 5900-5908.

Liu, M.et al.; Protein Isoaspartate Methyltransferase-Mediated 18O-Labeling of Isoaspartic Acid for Mass Spectrometry Analysis; Anal. Chem. 2011, 84, 1056-1062.

Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistry, 269, 32299-32305.

Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.

Manning, M., et al., *Stability of Protein Pharmaceuticals: An Update*. Pharmaceutical Research, 2010.27(4): p. 544-575.

Matthews, R. G.; et al.; Cobalamin-Dependent and Cobalamin-Independent Methionine Synthases: Are There Two Solutions to the Same Chemical Problem?; Hely. Chim. Acta 2003, 86, 3939-3954.

Mizuochi, T., et al., Structural and numerical variations of the carbohydrate moiety of immunoglobulin G. J Immunol, 1982. 129(5): p. 2016-20.

Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.

Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.

Ni, W.; Analysis of Isoaspartic Acid by Selective Proteolysis with Asp-N and Electron Transfer Dissociation Mass Spectrometry; Anal. Chem. 2010, 82,7485-7491.

Oh, et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.

Ouellette, D.; Studies in serum support rapid formation of disulfide bond between unpaired cysteine residues in the VH domain of an immunoglobulin G1 molecule; Anal. Biochem. 2010, 397, 37.

Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.

Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.

(56) References Cited

OTHER PUBLICATIONS

Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. Al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methylglyoxal in hybridoma cell culture, Cytotechnology (2004) 46:97-107.
Saxena, R. K. et al.; Microbial production and applications of 1, 2-propanediol; Indian J. Microbiol. 2010,50,2-11.
Shen, Amy Y. et al., "Recombinant DNA Technology and Cell Line Development," from "Cell Culture Technology for Pharmaceutical and Cell-Based Therapies," CRC Press, 1995, 15-40.
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
Sigma Catalog "RPMI1640" (last accessed Jan. 22, 2015), 3 pages.
Sigma MSDS for RMPI1640 (last accessed Jan. 22, 2015), 6 pages.
Tess database "Hyclone" Trademark #76244963. Filing date Apr. 23, 2001. Live mark. Last accessed Jan. 21, 2015.
Tess database "Hyclone" Trademark #85769283. Filing date Sep. 30, 2012. Live mark. Last accessed Jan. 21, 2015.
United States Food and Drug Administration (FDA) Biological Licensing Application File No. 125057 (Adalimumab) (Dec. 31, 2002) (Last Accessed Mar. 4, 2015 at www.fda.gov/Drugs/DevelopmentApprovalProcess/HowDrugsareDevelopedandApproved/ApprovalApplications/TherapeuticBiologicApplications/ucm080610.htm>), 1 page.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P. et al., The Pathophysiology of Tumor Necrosis Factors, Annu. Rev. Immunol. 10:411-452 (1992).
Vlasak, J. & Ionescu, R., *Heterogeneity of Monoclonal Antibodies Revealed by Charge-Sensitive Methods.* Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011, Biotechnology and Bioengineering, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS.
"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS.
"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.
"Plaintiffs' Memorandum in Support of Their Motion for Partial Summary Judgment", dated Aug. 1, 2013 and submitted by plaintiff in Civil Action No. 09-40089-FDS.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.
Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Abraham, E., et al., "Efficacy and Safety of Monoclonal Antibody to Human Tumor Necrosis Factor α in Patients with Sepsis Syndrome," *JAMA,* vol. 273(12):934-941 (1995).
Adams. et al. J. Am. Acad. Dermatol 2004;51 :660-2.
Altamirano, C., et al., "Strategies for fed batch cultivation of t-PA producing CHO cells: substitution of glucose and glutamine and rational design of culture medium", *J. Biotechn.* 110:171-179, 2004.
Anonymous, "SACHEM Displacement Chromatography," Aug. 29, 2012, Retrieved from the Internet: www.displacementchromatography.com>, retrieved on Jul. 30, 2014.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

(56) References Cited

OTHER PUBLICATIONS

Averginos, Gab '04 Abstracts—GE Healthcare Life Sciences, "Humira manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).
Barnes et al., "Stability of Protein Production from Recombinant Mammalian Cells," Biotechnology and Bioengineering, 81:6, Mar. 20, 2003, pp. 631-639.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biblia, T.A. et al., "In Pursuit of the Optimal Fed-Batch Process for Monoclonal Antibody Production", Biotechnol. Prog 11(1):1-13, Jan.-Feb. 1995.
Birch, JR. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. ;455-458 (1997).
Bruggemann, M., Neuberger, M.S., "Strategies for expressing human antibody repertoires in transgenic mice," *Immunol. Today* 17:391-397 (1996).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.

Cambridge Antibody Technology, advertisement of phage display services, Science vol. 253, No. 5018 (1991).
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Carter et al., "Humanization of an anti-p185$^{HER2}$ antibody for human cancer therapy," *Proc. Nat. Acad. Sci* 89:4285-4289 (1992).
Chang KH, et al. "N-Acetylcysteine Increases the Biosynthesis of Recombinant EPO in Apoptotic Chinese Hamster Ovary Cells", Free Radic Res. 30(2):85-91, 1999.
Charter, Edward A., "A New Process for the Separation and Purification of Egg Yolk; Antibodies," BASc., The University of British Columbia; A Thesis; Apr. 1993.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Chung et al., "Utilization of Lysozyme Charge Ladders to Examine the Effects of Protein Surface; Charge Distribution on Binding Affinity in Ion Exchange Systems," Langmuir 26(2): 759-768 (2010).
Chung et al., "Cetuximab-Induced Anaphylaxis and IgE Specific for Galactose-α-1, 3-Galactose", *N. Engl. J. Med.*, 358:11, pp. 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).
Cox, J. et al. "A directory of human germ-line $V_\kappa$ segments reveals a strong bias in their usage" *Eur. J. Immunol.*, 24(2):827-36 (1994).
Cromwell (GAB '04 Abstracts—GE Healthcare Life Sciences, Franc Oct. 3-5, 2004, pp. 17-18 published 2005).
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).
Doring, E., "Identification and Characterization of a TNFa Antagonist Derived from a Monoclonal Antibody" (1994) *Mol. Immunol* .31 (14): 1059-1067.

(56) References Cited

OTHER PUBLICATIONS

Du et al., "Chromatographic analysis of the acidic and basic species of recombinant monoclonal antibodies" *MAbs*, Sep.-Oct. 2012; 4(5):578-85.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Emery, P. "Adalimumab therapy: Clinical findings and implications for integration into clinical guidelines for rheumatoid arthritis." *Drugs of Today*, 41(3): p. 155-153. (2005).
ERBITUX (cetuximab) label, Revised Aug. 2013.
Ewert et al., "Biophysical Properties of Human Antibody Variable Domains," J. Mol. Biol. 324: 531-; 553 (2003).
Exhibit dated Aug. 1, 2013 and cited by defendant in Civil Action No. 09-40089-FDS providing the Jun. 23, 2009 trial transcript of the PM session in the matter of *Centocor, et al. v. Abbott Laboratories*.
Exhibit dated Aug. 1, 2013 and cited by defendant in Civil Action No. 09-40089-FDS providing the trial transcript in the matter of *Abbott Laboratories, et al. v. The Mathilda and Terrance Kennedy Institute*, S.D.N.Y.
Exhibit dated Aug. 1, 2013 and cited by plaintiff in Civil Action No. 09-40089-FDS providing excerpts from the File History of U.S. Appl. No. 12/578,487.
Exhibit dated Aug. 1, 2013 and cited by defendant in Civil Action No. 09-40089-FDS providing the Jun. 24, 2009 trial transcript of the AM session in the matter of *Centocor, et al. v. Abbott Laboratories*, E.D. TX.
Exhibit dated Aug. 1, 2013 and cited by defendant in Civil Action No. 09-40089-FDS providing the Sep. 20, 2012 Day 8 trial transcript in the matter of *Abbott v. Centocor Ortho Biotech Inc.*, D. MA.
Exhibit dated Aug. 1, 2013 and cited by plaintiff in Civil Action No. 09-40089-FDS providing Declaration by Jochen Salfeld, dated Jan. 17, 2013.
FDA Package insert for Adalimumab, Sep. 26, 2003, pp. 1-18.
Feldmann, "Anti-TNF-alpha Therapy of Rheumatoid Arthritis: What Have We Learned?" (2001) *Annu. Rev. Immunol.*, 19:163-196.
Feng et al., "Cell Culture Processes for Monoclonal Antibody Production," mAbs, 2:5, 466-477, Sep./Oct. 2010.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).

Gonzalez et al. "Purification of Lactic Acid from Fermentation Broths by Ion-Exchange Resins" Ind. Eng. Chem. Res. 45:3243 (2006).
Graf et al., "Ion exchange resins for the purification of monoclonal antibodies from animal cell culture" Bioseparation 4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Gramer M J et al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Harding et al., "Class switching in human immunoglobulin transgenic mice" (1995) *Ann. NY Acad. Sci.*, 764:536-547.
Harlow and Lane, Antibodies A Laboratory Manual, Purification of Antibodies by using a; Deae-matrix (Batch), Storing and Purifying Antibodies; Chapter 8: 302-303 (1988).
Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).

(56) References Cited

OTHER PUBLICATIONS

Hoogenboom et al., "By-passing immunisation : Human antibodies from synthetic repertoires of germline $V_H$ gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al.; "Improvement of mammalian cell culture performance through surfactant enabled concentrated feed media"; Biotechnology Progress; 29(4):1023-1033 (2013).
Hossler P. et al., "Improvement of mammalian cell culture performance through surfactant enabled concentrated feed media," Biotechnol. Prog. 29(4): 1023-1033, 2013.
www.cygnustechnologies.com/product_detail/host-cell-protein-antibodies/anti-cho-h . . . CYGNUS Technologies, Anti-CHO HCP (Apr. 18, 2012).
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
HUMIRA (adalimumab) label, Revised Sep. 2013.
HUMIRA (adalimumab) prescribing information, Dec. 20, 2002, pp. 1-16.
Huse, "Generation of a large combinatorial library of the immunoglobulin repertoire in phage lambda" (1989) *Science*, 246:1275-81.
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011.
International Preliminary Report on Patentability for Application No. PCT/US2011/060388, dated May 30, 2012.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Search Report and Written Opinion for Application No. PCT/US2008/085066, dated May 12, 2009.
International Search Report and Written Opinion for Application No. PCT/US2010/033387, dated Aug. 7, 2012.
International Search Report and Written Opinion for Application No. PCT/US2013/031380, dated Feb. 5, 2014.
International Search Report and Written Opinion for Application No. PCT/US2013/041954, dated Dec. 17, 2013.
International Search Report and Written Opinion for Application No. PCT/US2013/041958, dated Dec. 17, 2013.
International Search Report and Written Opinion for Application No. PCT/US2013/065720, dated Dec. 16, 2013.
International Search Report and Written Opinion for Application No. PCT/US2013/065797, dated Nov. 26, 2013.
International Search Report and Written Opinion from PCT/US2013/065749 dated Mar. 18, 2014.
International Search Report and Written Opinion from PCT/US2014/024151 dated Aug. 7, 2014, pp. 1-16.
International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
International Search Report from PCT/US2014/024256 dated Jul. 30, 2014, pp. 1-15.
Invitation to Pay Additional Fees for International Application No. PCT/US2013/031380, Dated Nov. 28, 2013.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jakobovits, A., "Production of fully human antibodies by transgenic mice" (1995) *Curr. Op. Biotechnol.*, 6:561-566.
Jayme et al.; "Media formulation options and manufacturing process controls to safeguard against introduction of animal origin contaminants in animal cell culture"; Cytotechnology; 33:27-36 (2000).
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGI: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Lerner, "Antibodies without immunization" (1992) *Science*, 258:1313-1314.
Leusch, "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.

(56) References Cited

OTHER PUBLICATIONS

Low, "Mimicking Somatic Hypermutation: Affinity Maturation of Antibodies Displayed on Bacteriophage Using a Bacterial Mutator Strain" (1996) *J. Mol. Biol.,* 260:359-368.
Low, Nigel: thesis extract (1996) *Cambridge University.*
Luo et al., "Understanding of C-terminal lysine variants in antibody production using mammalian cells" Abstract of papers, ACS, Anaheim, CA, US, Mar. 2011.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Ma, et al., "Generation and Assembly of Secretory Antibodies in Plants", *Science,* 268:716-719 (1995).
Maeda, et al., "Analysis of Nonhuman N-Glycans as the Minor Constituents in Recombinant Monoclonal Antibody Pharmaceuticals", *Anal. Chem.,* 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Marks et al., "Human antibody fragments specific for human blood group antigens from a phage display library" (1993) *Bio/Technology,* 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.,* 222:581-597.
Marks, "Human Monoclonal Antibodies from V-gene Repertoires Expressed on Bacteriophage." In *Antibody Engineering,* Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology,* 10:779-783.
Martin, A.C.R. "Accessing the Kabat antibody sequence database by computer" (1996)*Proteins: Structure, Function and Genetics,* 25:130-133.
Martinelle, K. et al., Cells and Culture, Proceedings of the 20th ESACT Meeting v4 819-822, Jun. 17-20, 2007.
Medynski, "Phage Display: All Dressed Up and Ready to Role" (1994) *Bio/Technology,* 12:1134-1136.
Mendez et al., "Functional transplant of megabase human immunoglobulin loci recapitulates human antibody response in mice" (1997) *Nature Genetics,* 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and in vivo application (1990) *Cytokine,* 2(3):162-69.
Neuberger M. et al., "Mice perform a human repertoire" (1997) *Nature,* 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology,* 5:450-456.

Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron,* 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.,* 117:59-62 (1995).
Oh, D-K. et al., "Increased erythritol production in fed-batch cultures of *Torula* sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods,* 36(1):61-68.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Perchiacca et al., "Aggregation-resistance domain antibodies engineered with charged mutations; near the edges of the complementarity-determining regions," Protein Engineering Design & Selection, 25: 10 (591-601) 2012.
Pietersz et al. "In vitro and in vivo Antitumor Activity of a Chimeric anti-CD19 Antibody", *Cancer Immunol. Immunother.,* 41:53-60 (1995).
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Potter at al., "Antibody Production in the Baculovirus Expression System", *Intern. Rev. Immunol.,* 10:103-112 (1993).
Poul at al., "Design of Cassette Baculovirus Vectors for the Production of Therapeutic Antibodies in Insect Cells", *Immunotechnology,* 1:189-196 (1995).
Queen, C., "A humanized antibody that binds to the interleukin 2 receptor" (1989) *Proc. Natl. Acad. Sci. USA,* 86(24):10029-10033.
Rader et al. "A phage display approach to rapid antibody humanization: Designed combinatorial V gene libraries" (1998) *Proc Natl Acad Sci USA,* 95:8910-8915.
Raju, TS. "Glycosylation Variations with Expression Systems and Their Impact on Biological Activity of Therapeutic Immunoglobulins", *BioProcess International.,* 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.,* 24(5):733-742.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", Biotechnology, 13:255-260 (1995).
Riechmann, "Phage display and selection of a site-directed randomized single-chain antibody Fv fragment for its affinity improvement" (1993) *Biochemistry,* 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Rube et al. (Int. J. Radiation Oncology Biol. Phys., vol. 56, No. 5, pp. 1414-1425,2003).

(56) References Cited

OTHER PUBLICATIONS

Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.
Sato et al, "Stimulation of monoclonal antibody production by human-human hybridoma cells with an elevated concentration of potassium or sodium phosphate in serum-free medium," Cytotechnology 2:63-67, 1989.
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Schiestl et al. "Acceptable changes in quality attributes of glycosylated biopharmaceuticals" Nature Biotechnology, 29(4), 310-312 (2011).
Schwieterman, "Immunosuppression in Combination with Monoclonal Antibodies" in Biologic Agents in Autoimmune Disease (Mar. 2-4, 1995).
Senczuk et al. "Hydrophobic interaction chromatography in dual salt system increases protein binding capacity" Biotechnology and Bioengineering, 103(5), 930-935 (2009).
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shih, "Effects of Anions on the Deamidation of Soy Protein". Journal of Food Science. 1991, 56: 452-454.
Shukla et al., "Host cell protein clearance during protein A chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sundaram et al., "An innovative approach for the characterization of the isoforms of a monoclonal antibody product," Mabs, 3(6):505-512, 2011.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.
Tan et al. (Biotechnol. Appl. Biochem. (1999) 30, 59-64).
Taylor et al.,"Human immunoglobulin transgenes undergo rearrangement, somatic mutation and class switching in mice that lack endogenous IgM" (1994) *Int. Immunol.*, 6:579-591.
Teichmann, S. Declaration dated Dec. 7, 2010 from opposition proceedings in EP 0929578.
Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action".
The MW Calculator available at the Sequence Manipulation Suite (see http://bioinformatics.org/sms2/index.html), downloaded Feb. 25, 2014.
The pI Calculator available at the Sequence Manipulation Suite (see bioinformatics.org/sms2/index.html>), downloaded Feb. 25, 2014, p. 1).
The Statement on a Nonproprietary Name Adopted by the USAN Council for Adalimumab, p. 1, downloaded on May 19, 2011 from www.ama-assn.org/resources/doc/usan/adalimumab.doc.
Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.
Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.
Tomiya et al., "Comparing N-glycan processing in mammalian cell lines to native and engineered; lepidopteran insect cell lines," Glycoconjuqate Journal 21 :343-360 (2004).
Tomlinson, "The repertoire of human germline VH sequences reveals about fifty groups of VH segments with different hypervariable loops" (1992) *J. Mol. Biol.*, 227:776-98.
Tomlinson, "The structural repertoire of the human Vk domain" (1995) *The EMBO J.*, 14(18):4628-38.
Tracey, "Tumor necrosis factor: A pleiotropic cytokine and therapeutic target" (1994) *Annu. Rev. Med.*, 45:491-503.
Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.
Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vaughan, "Human antibodies by design" (1998) *Nature Biotechnology*, 16:535-539.
Wagner et al., "Antibodies generated from human immunoglobulin miniloci in transgenic mice" (1994) *Nucl. Acids Res.* 22:1389-1393.

(56) References Cited

OTHER PUBLICATIONS

Wagner et al., "The diversity of antigen-specific monoclonal antibodies from transgenic mice bearing human immunoglobulin gene miniloci" (1994) *Eur. J. Immunol.*, 24:2672-2681.
Ward, "Binding activities of a repertoire of single immunoglobulin variable domains secreted from *Escherichia coli*" (1989) *Nature*, 341:544-546.
Wedemayer et al., "Structural insights into the evolution of an antibody combining site" (1997) *Science*, 276:1665-1669.
Wiendl et al. (BioDrugs. 2002;16(3):183-200).
Williams et al., "Kinetic analysis by stopped-flow radiationless energy transfer studies: effect of anions on the activity of carboxypeptidase A". Biochemistry. 1986, 25, 94-100.
Winter, "Humanized antibodies" (1993) *Immunol. Today*, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Yigzaw et al., "Exploitation of the adsorptive properties of depth filters for host cell protein removal during monoclonal antibody purification," Biotechnology Progress, (2006) 22(1):288-296.
Yumioka et al., "Screening of effective column rinse solvent for Protein-A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) *FASEB J.*, 10:1227-1232.
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Goswami et al., "Developments and Challenges for mAb-Based Therapeutics," *Antibodies*, 2:452-500, 2013.

\* cited by examiner

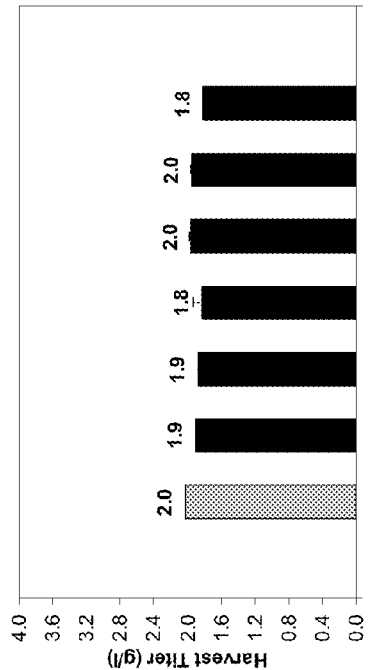

Figure 1) Effect of total arginine concentration in adalimumab producing cell line 2, media 1 on viable cell density (n=2)

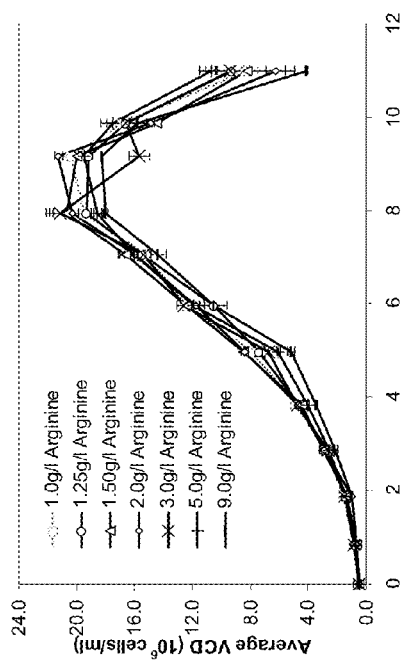

Figure 3) Effect of total arginine concentration in adalimumab producing cell line 2, media 1 on harvest titer (n=2)

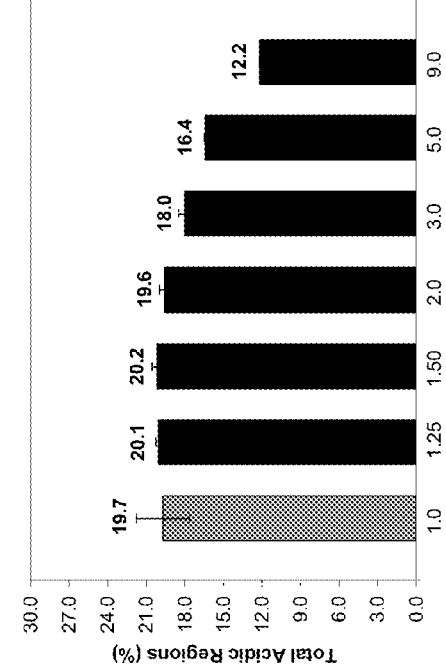

Figure 2) Effect of total arginine concentration in adalimumab producing cell line 2, media 1 on viability (n=2)

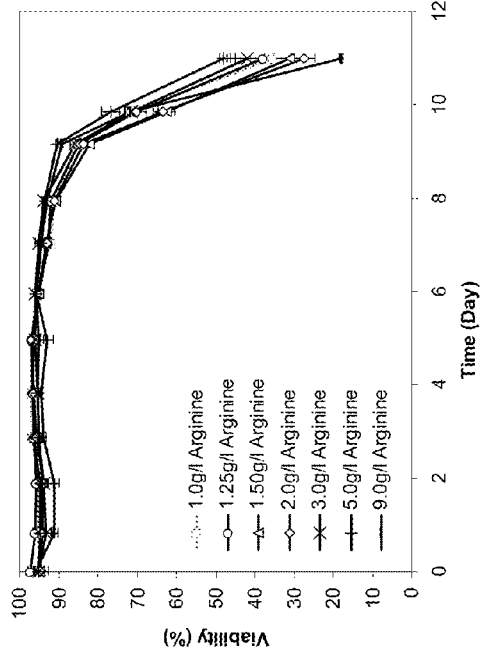

Figure 4) Effect of total arginine concentration in adalimumab producing cell line 2, media 1 on day 10 WCX 10 profile total acidic regions (n=2)

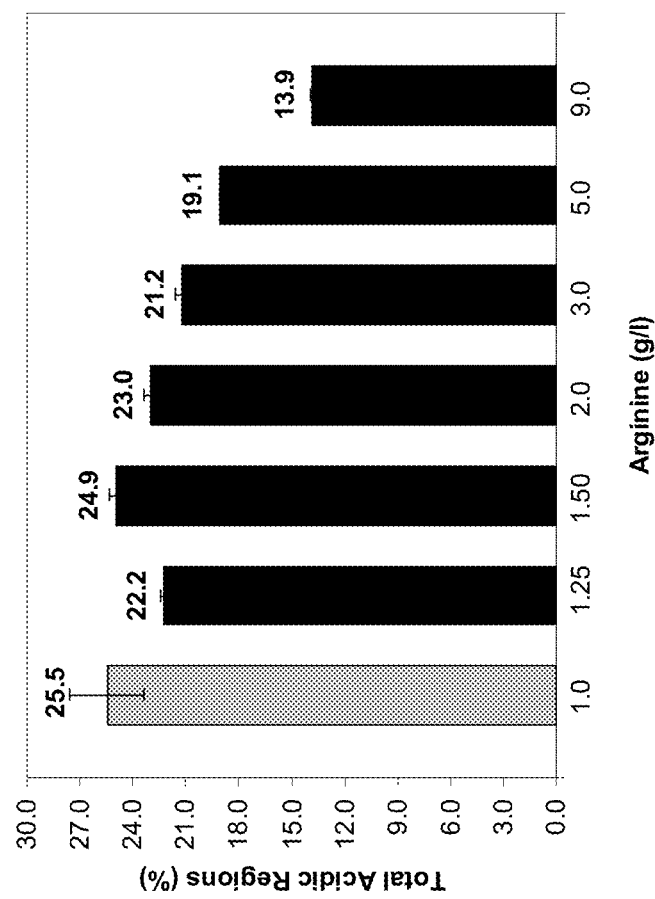
Figure 5) Effect of total arginine concentration in adalimumab producing cell line 2, media 1 on day 12 WCX 10 profile total acidic regions (n=2)

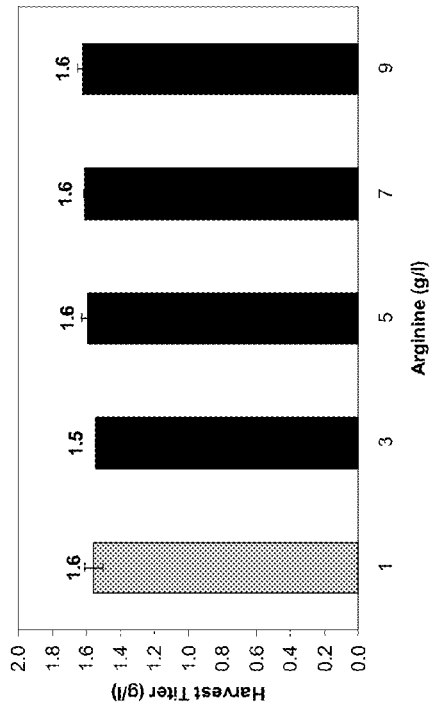

Figure 6) Effect of total arginine concentration in adalimumab producing cell line 3, media 1 on viable cell density (n=2)

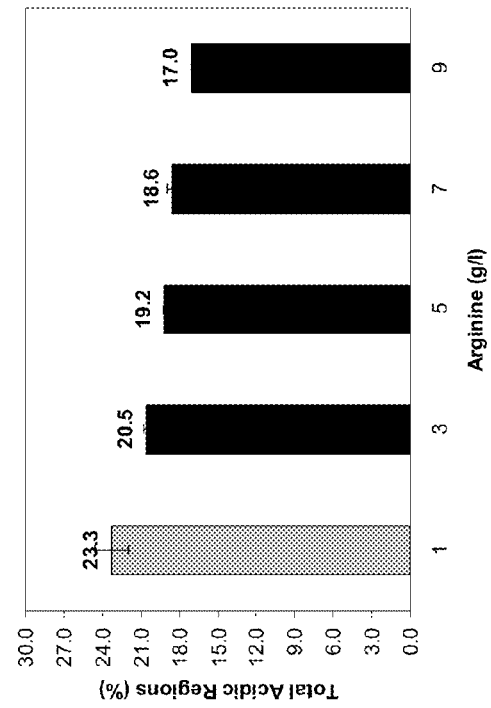

Figure 8) Effect of total arginine concentration in adalimumab producing cell line 3, media 1 on harvest titer (n=2)

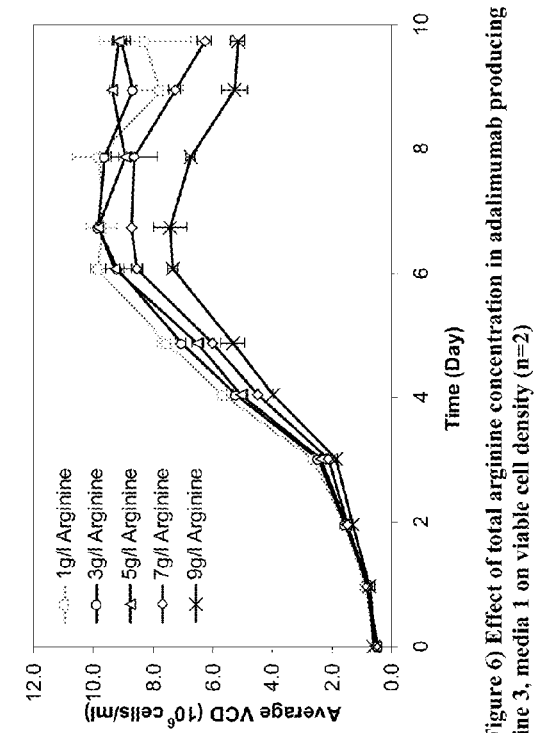

Figure 7) Effect of total arginine concentration in adalimumab producing cell line 3, media 1 on viability (n=2)

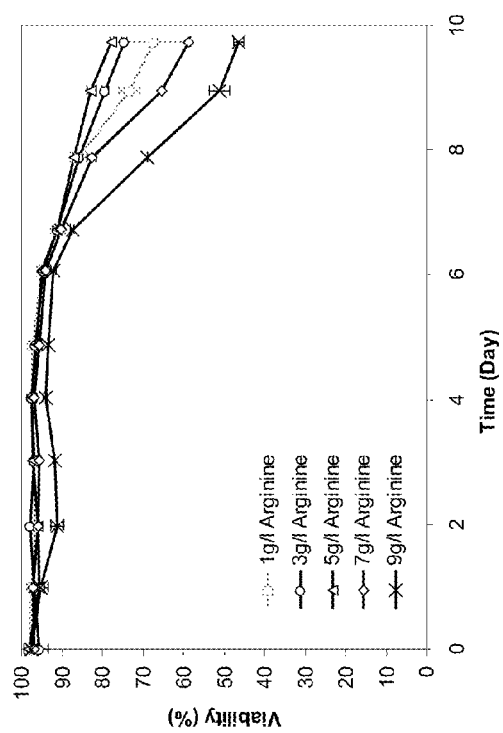

Figure 9) Effect of total arginine concentration in adalimumab producing cell line 3, media 1 on WCX 10 profile total acidic regions (n=2)

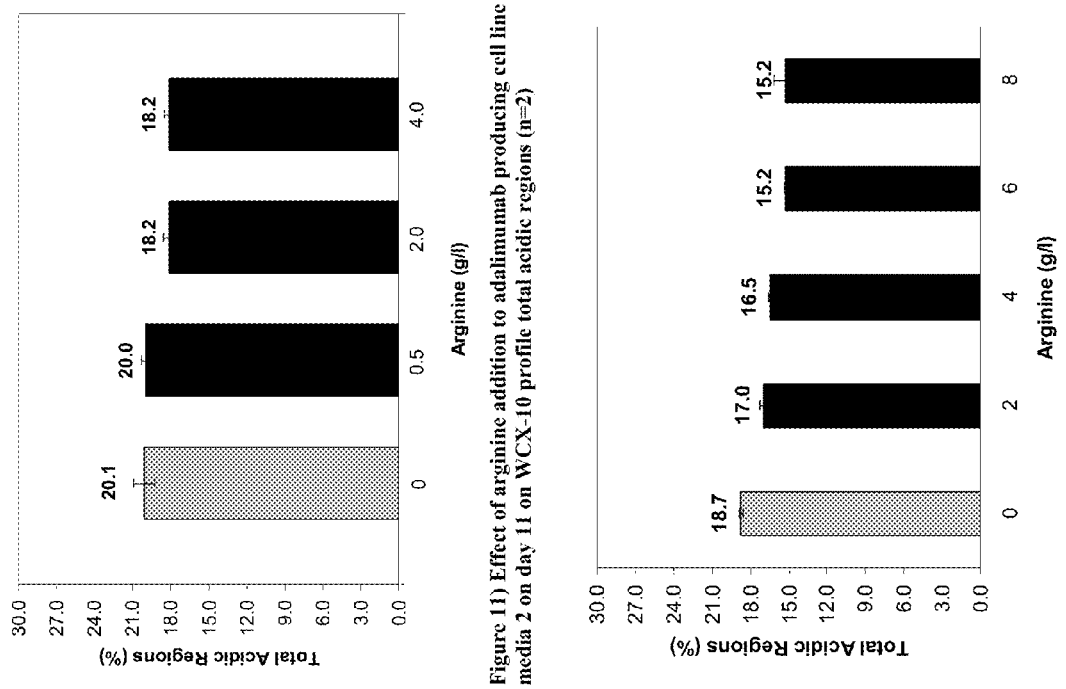

Figure 11) Effect of arginine addition to adalimumab producing cell line 1, media 2 on day 11 on WCX-10 profile total acidic regions (n=2)

Figure 12) Effect of arginine addition to adalimumab producing cell line 2, media 3 on WCX-10 profile total acidic regions (n=2)

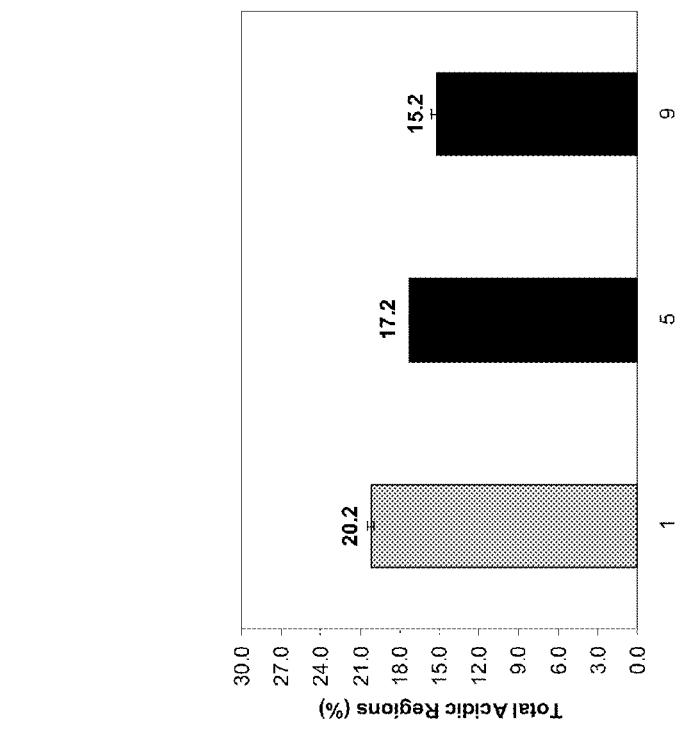

Figure 10) Effect of total arginine concentration in adalimumab producing cell line 1, media 1 on WCX 10 profile total acidic regions (n=2)

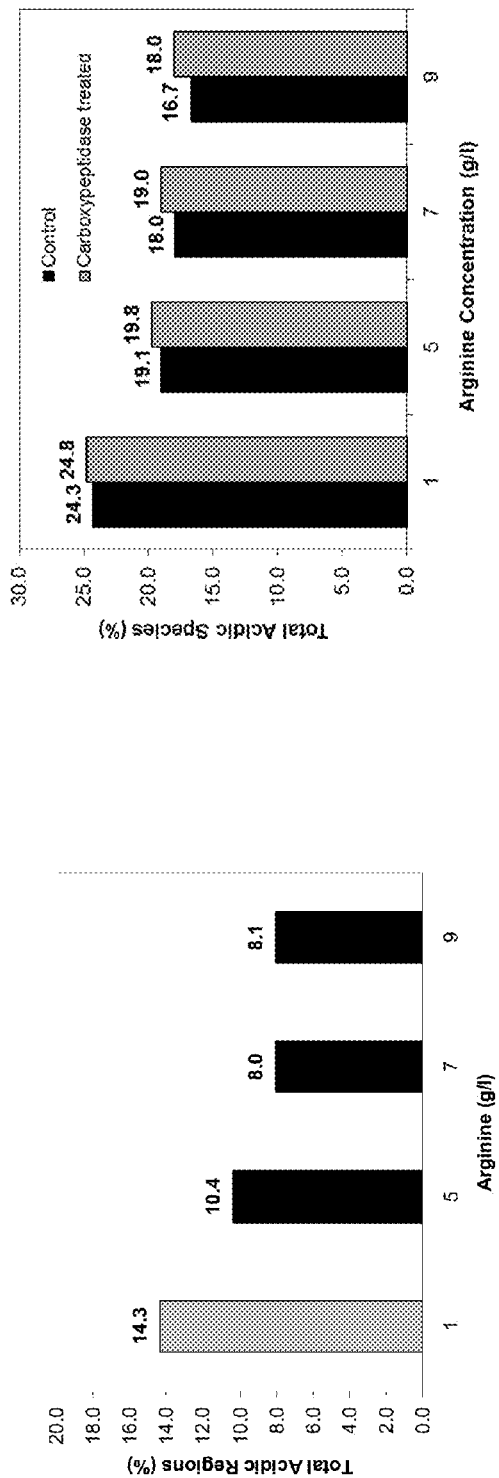

Figure 13) Effect of total arginine concentration in mAB1 producing cell line on WCX-10 profile total acidic regions (n=1)

Figure 14) Effect of total arginine concentration in mAB2 producing cell line on WCX-10 profile total acidic regions (n=2)

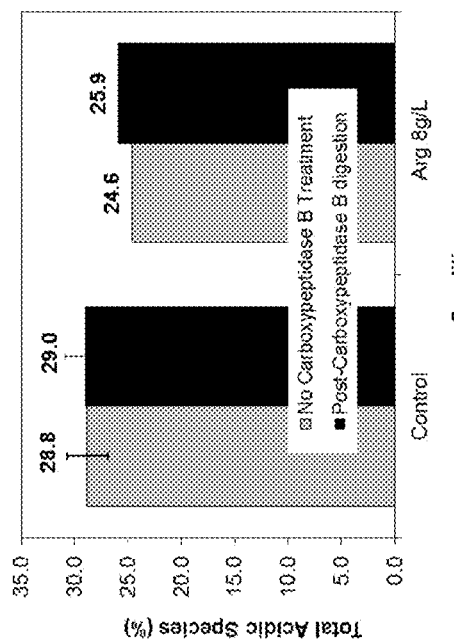

Figure 15) Effect of carboxypeptidase digestion of product from adalimumab producing cell line 3, media 1 experiment on WCX-10 profile total acidic regions (n=1)

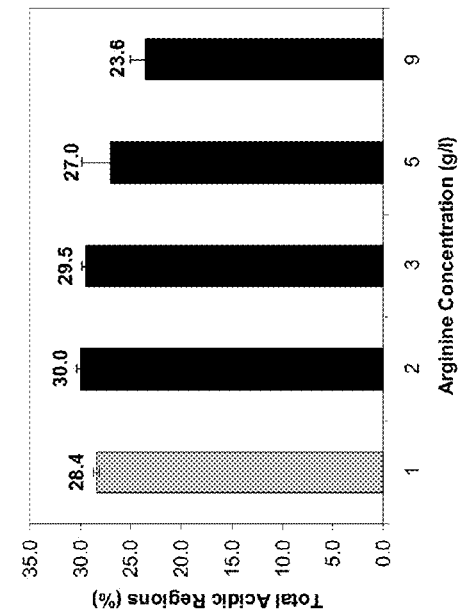

Figure 16) Effect of carboxypeptidase digestions of product from mAB2 producing cell line on WCX-10 profile total acidic regions (n=2)

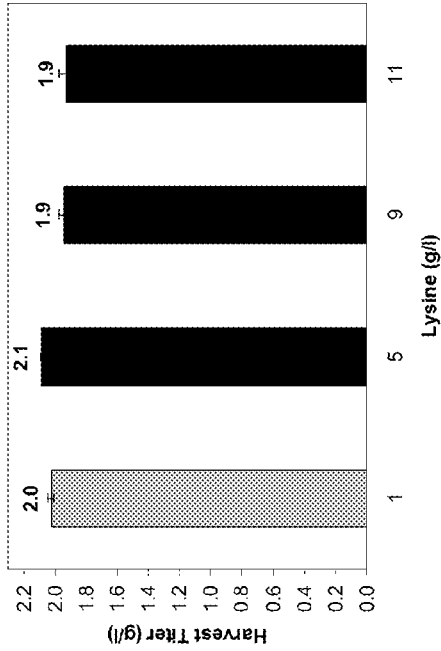

Figure 17) Effect of total lysine concentration in adalimumab producing cell line 2, media 1 on viable cell density (n=2)

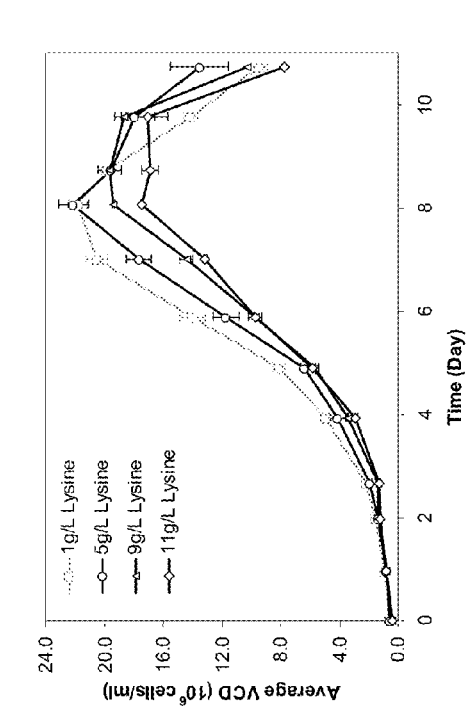

Figure 18) Effect of total lysine concentration in adalimumab producing cell line 2, media 1 on viability (n=2)

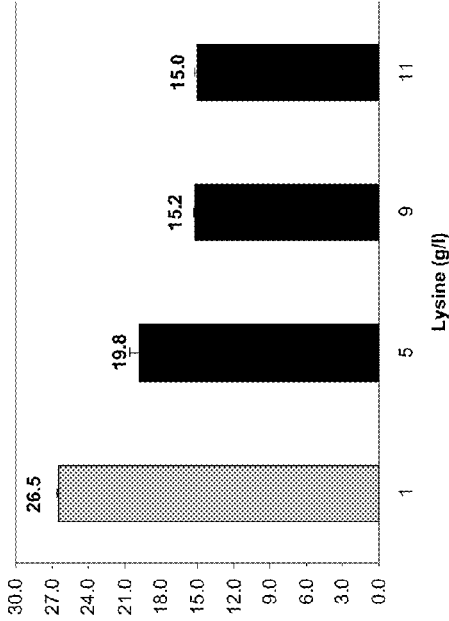

Figure 19) Effect of total lysine concentration in adalimumab producing cell line 2, media 1 on harvest titer (n=2)

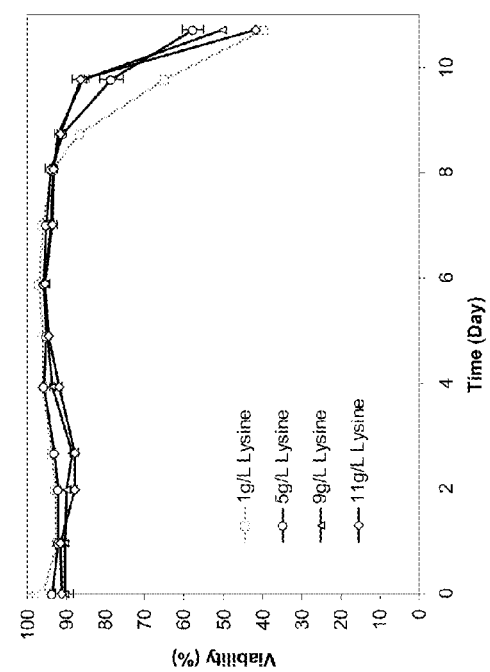

Figure 20) Effect of total lysine concentration in adalimumab producing cell line 2, media 1 on WCX 10 profile total acidic regions (n=2)

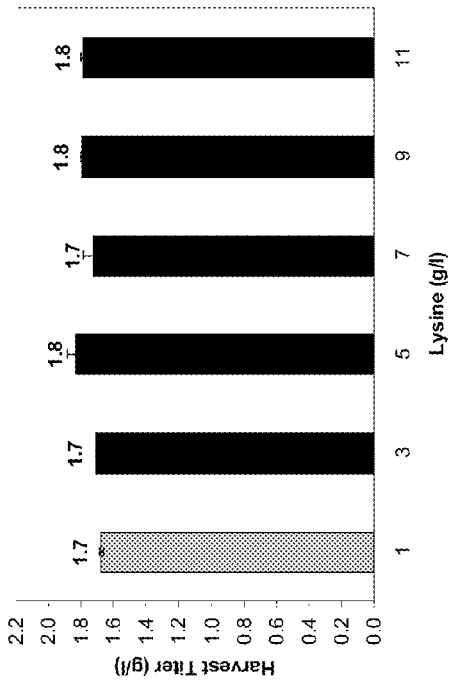

Figure 23) Effect of total lysine concentration in adalimumab producing cell line 3, media 1 on harvest titer (n=2)

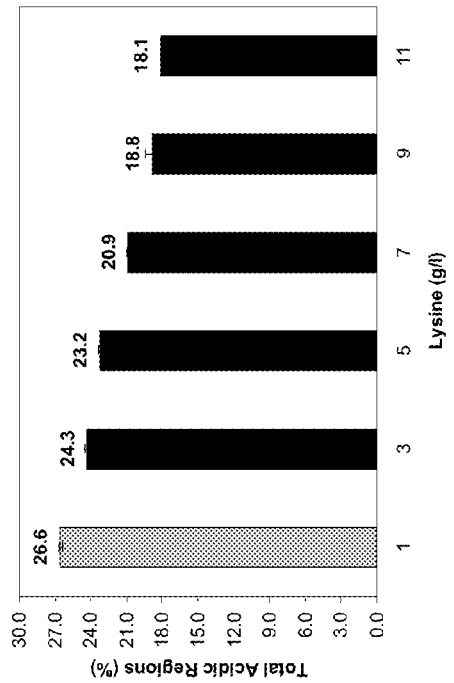

Figure 24) Effect of total lysine concentration in adalimumab producing cell line 3, media 1 on WCX 10 profile total acidic regions (n=2)

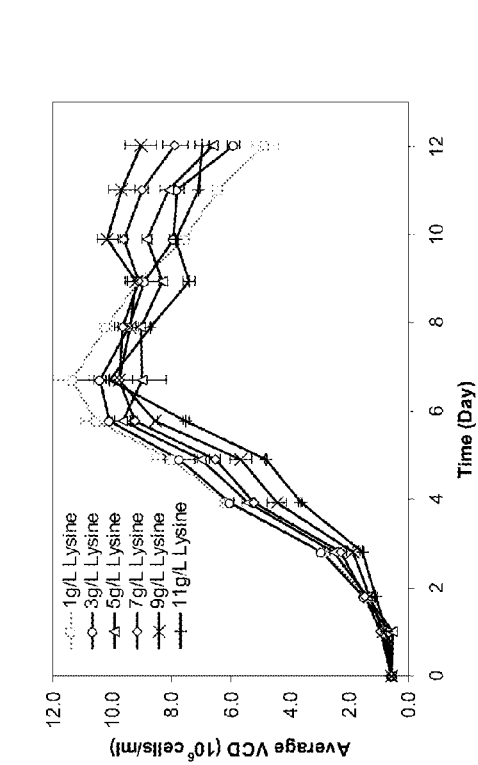

Figure 21) Effect of total lysine concentration in adalimumab producing cell line 3, media 1 on viable cell density (n=2)

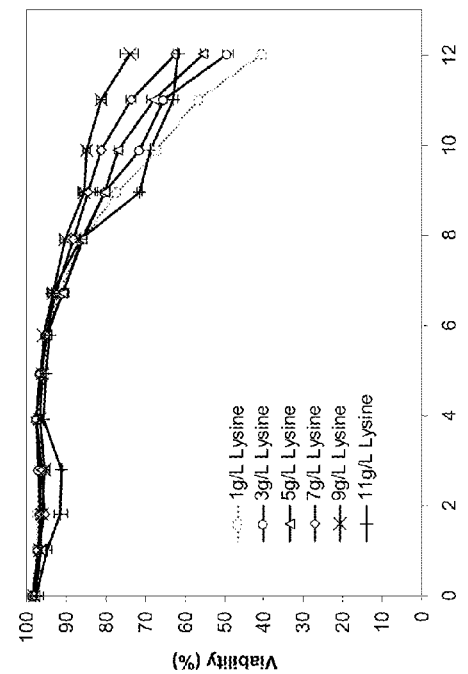

Figure 22) Effect of total lysine concentration in adalimumab producing cell line 3, media 1 on viability (n=2)

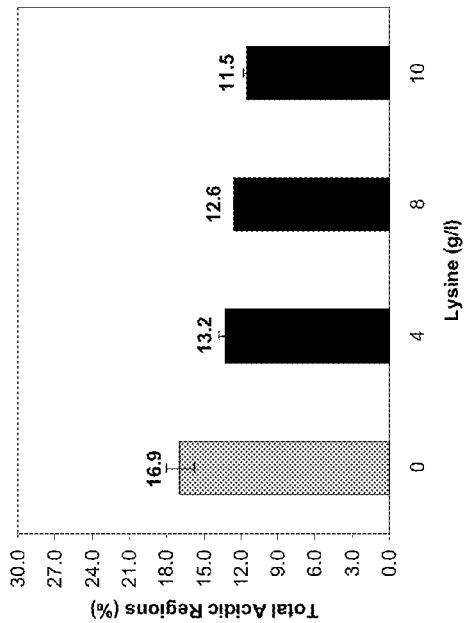
Figure 26) Effect of lysine addition to adalimumab producing cell line 1, media 2 on WCX-10 profile total acidic regions (n=2)
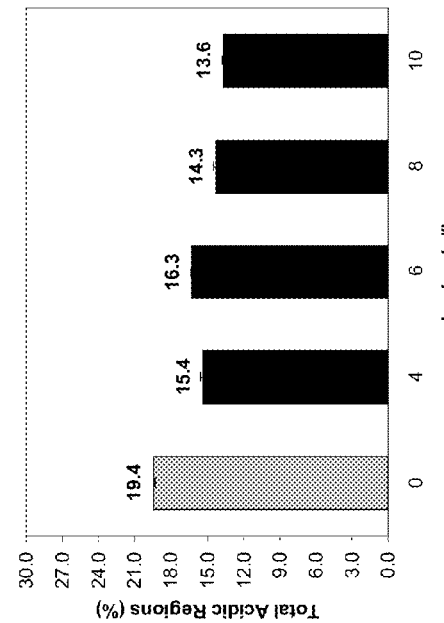
Figure 27) Effect of lysine addition to adalimumab producing cell line 2, media 3 on WCX-10 profile total acidic regions (n=2)
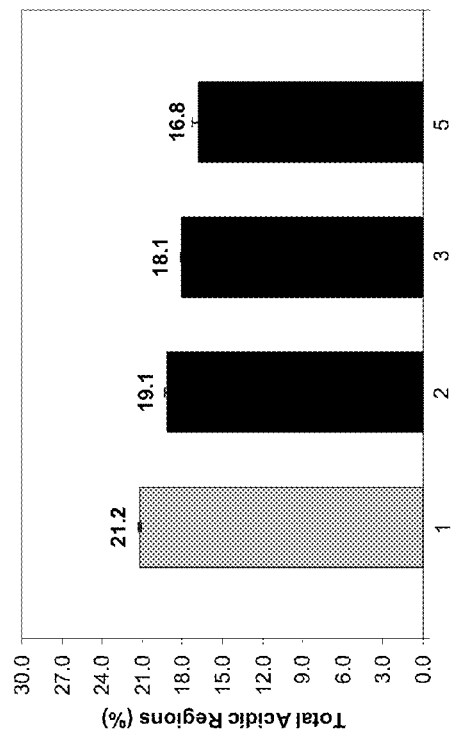
Figure 25) Effect of total lysine concentration in adalimumab producing cell line 1, media 1 on WCX 10 profile total acidic regions (n=2)

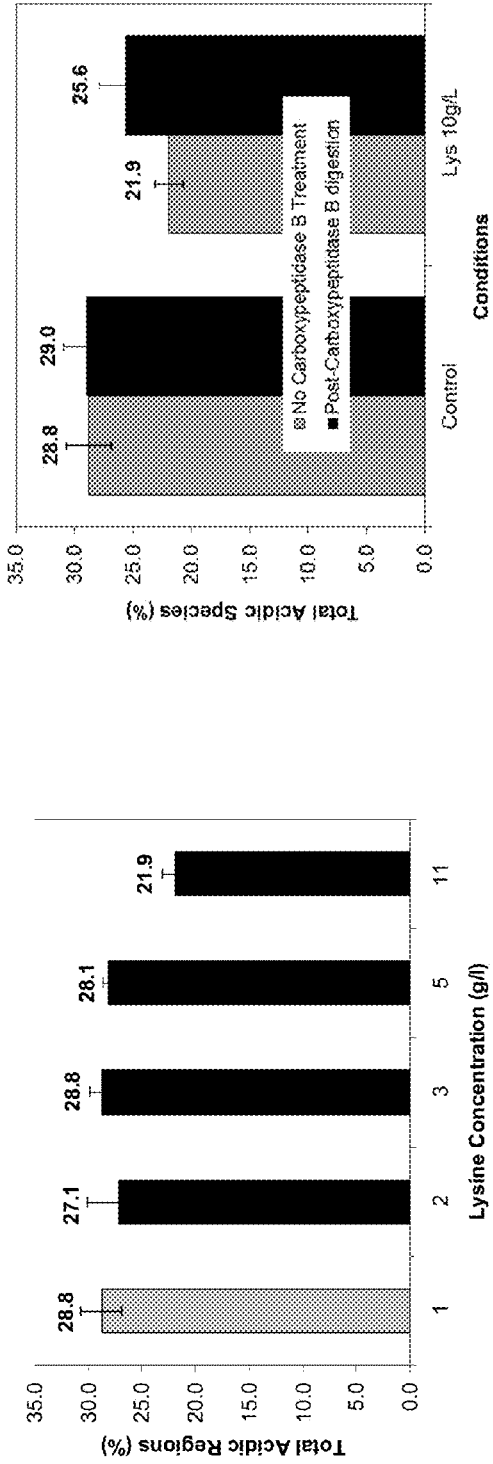

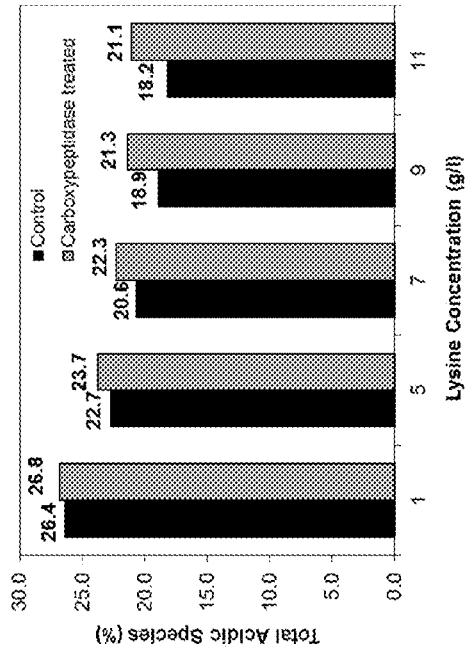

Figure 30) Effect of carboxypeptidase digestion of product from cell line 3, media 1 experiment on WCX-10 profile total acidic regions (n=1)

Figure 31) Effect of carboxypeptidase digestions of product from mAB2 producing cell line on WCX-10 profile total acidic regions (n=2)

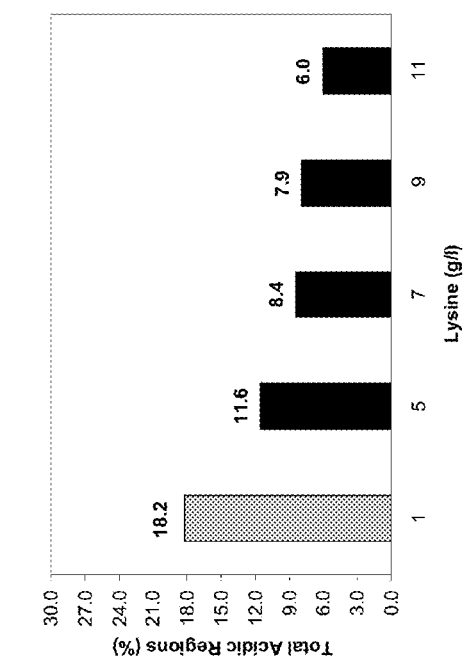

Figure 28) Effect of lysine addition to mAB1 producing cell line on WCX-10 profile total acidic regions (n=1)

Figure 29) Effect of lysine addition to mAB2 producing cell line on WCX-10 profile total acidic regions (n=2)

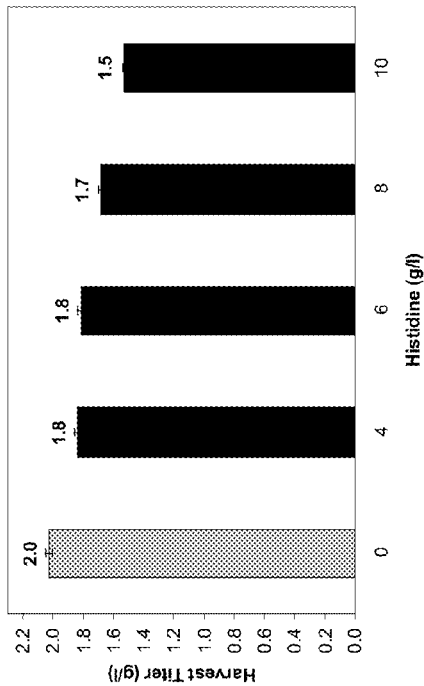

Figure 32) Effect of total histidine concentration in adalimumab producing cell line 2, media 1 on viable cell density (n=2)

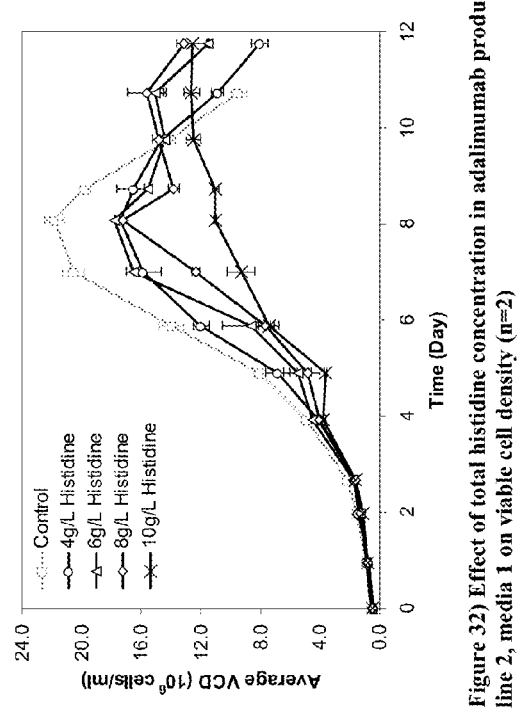

Figure 33) Effect of total histidine concentration in adalimumab producing cell line 2, media 1 on viability (n=2)

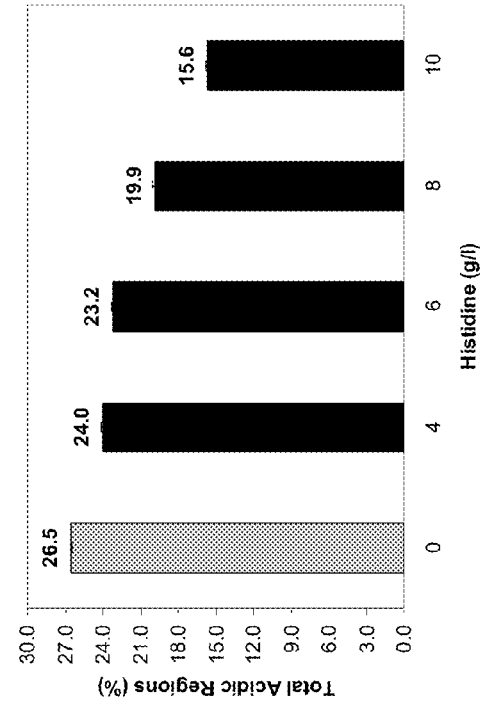

Figure 34) Effect of total histidine concentration in adalimumab producing cell line 2, media 1 on harvest titer (n=2)

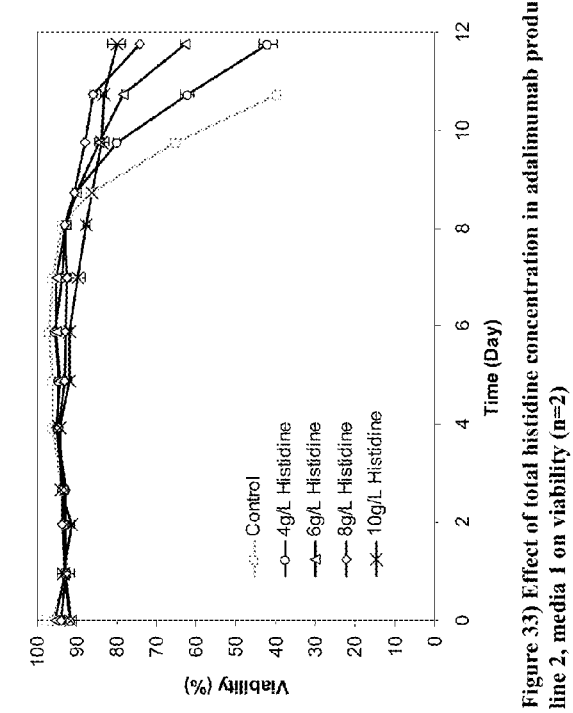

Figure 35) Effect of total histidine concentration in adalimumab producing cell line 2, media 1 on WCX 10 profile total acidic regions (n=2)

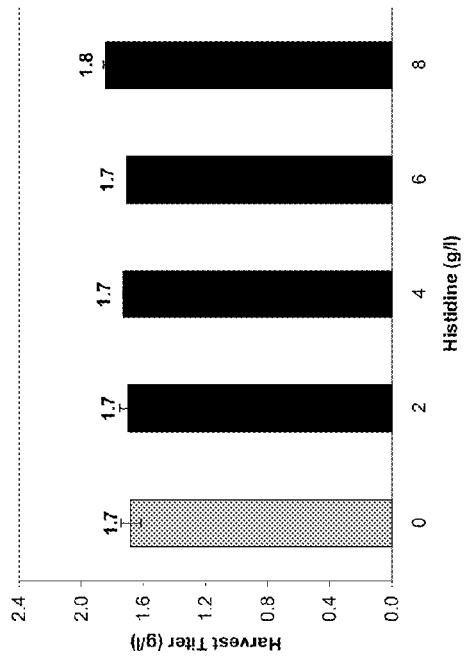

Figure 36) Effect of total histidine concentration in adalimumab producing cell line 3, media 1 on viable cell density (n=2)

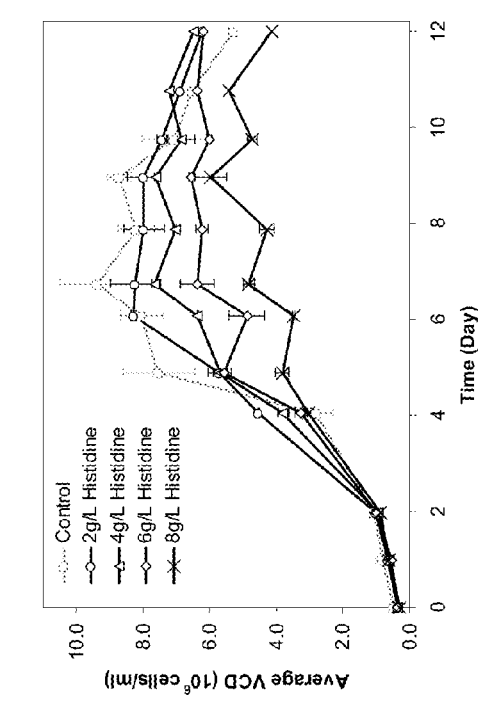

Figure 37) Effect of total histidine concentration in adalimumab producing cell line 3, media 1 on viability (n=2)

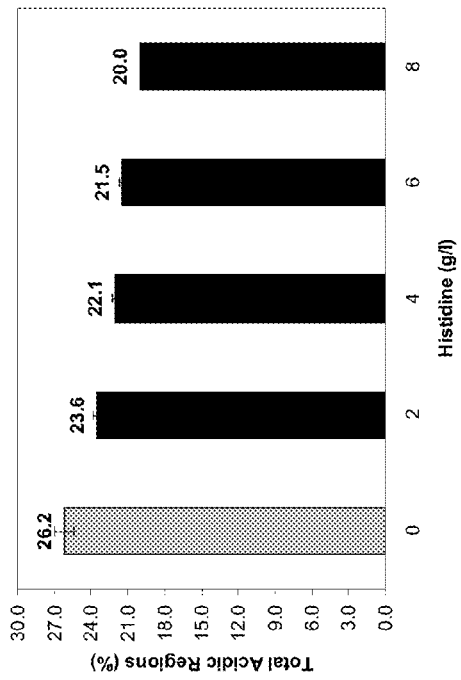

Figure 38) Effect of total histidine concentration in adalimumab producing cell line 3, media 1 on harvest titer (n=2)

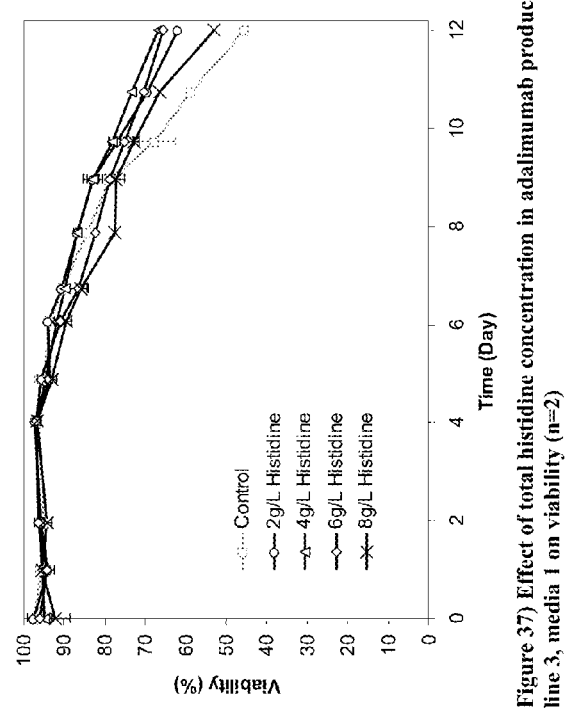

Figure 39) Effect of total histidine concentration in adalimumab producing cell line 3, media 1 on WCX 10 profile total acidic regions (n=2)

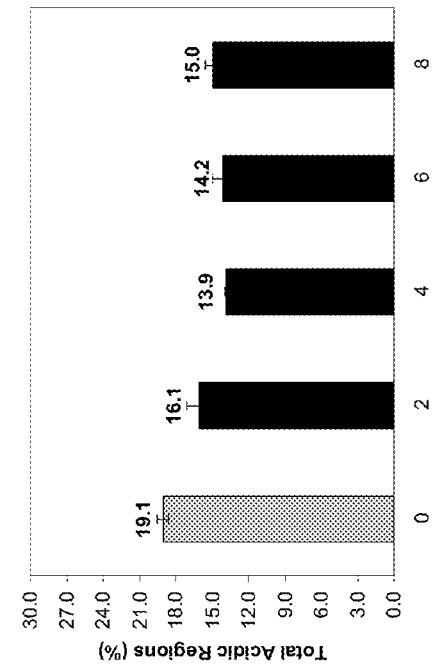

Figure 41) Effect of histidine addition to adalimumab producing cell line 1, media 2 on WCX-10 profile total acidic regions (n=2)

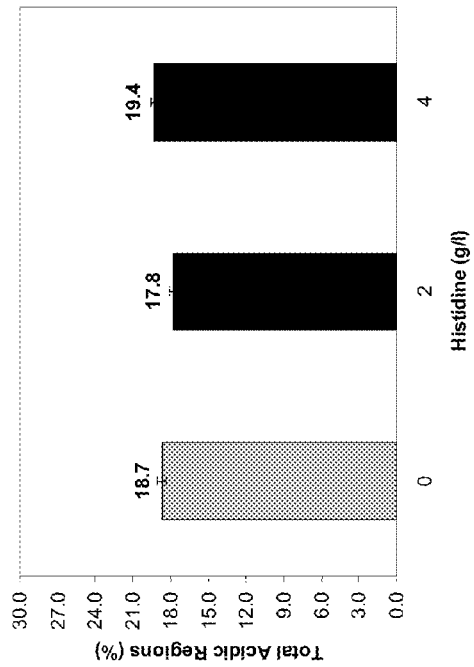

Figure 42) Effect of histidine addition to adalimumab producing cell line 2, media 3 on WCX-10 profile total acidic regions (n=2)

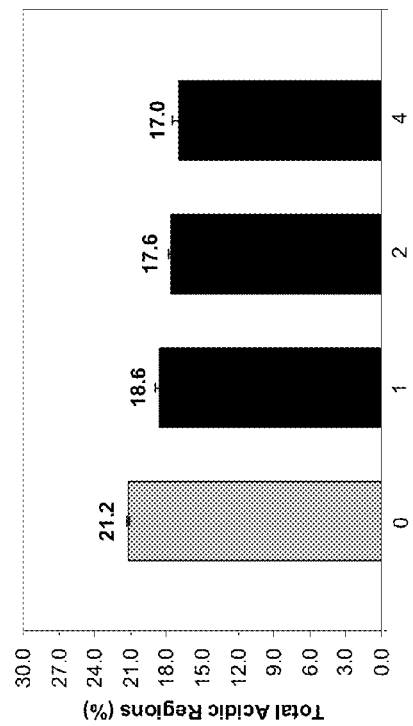

Figure 40) Effect of total histidine concentration in adalimumab producing cell line 1, media 1 on WCX 10 profile total acidic regions (n=2)

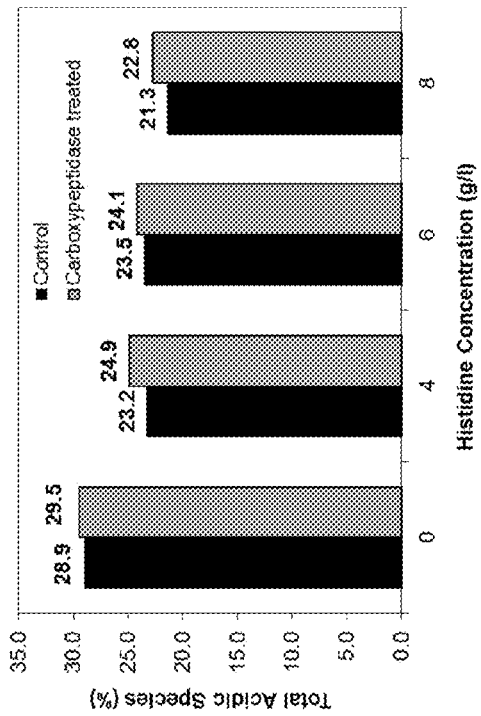

Figure 43) Effect of histidine concentration in mAB1 producing cell line on WCX-10 profile total acidic regions (n=1)

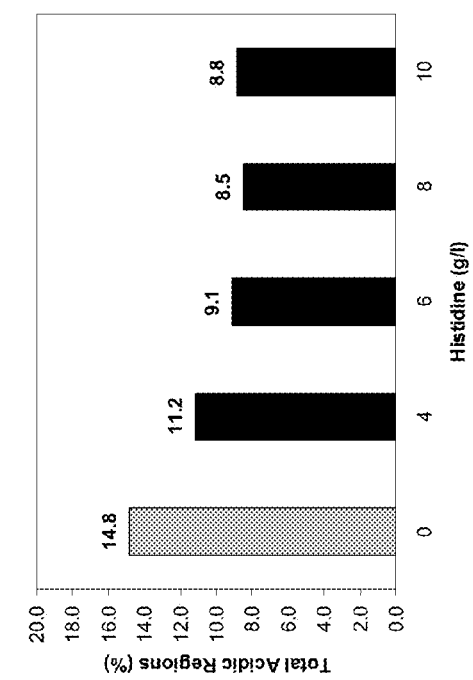

Figure 44) Effect of histidine concentration in mAB2 producing cell line on WCX-10 profile total acidic regions (n=2)

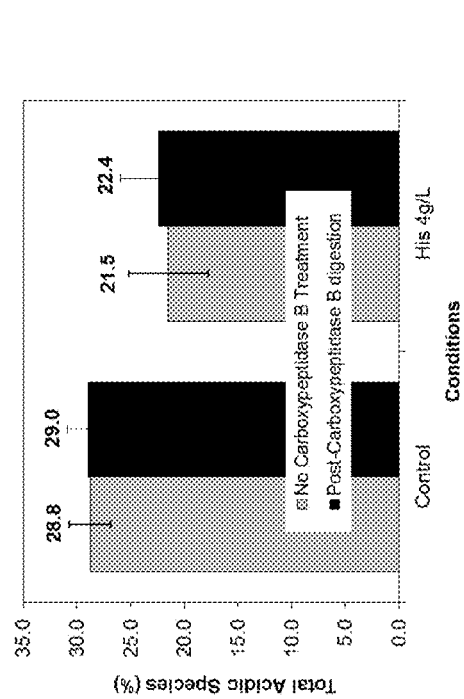

Figure 45) Effect of carboxypeptidase digestion of product from cell line 3, media 1 experiment on WCX-10 profile total acidic regions (n=1)

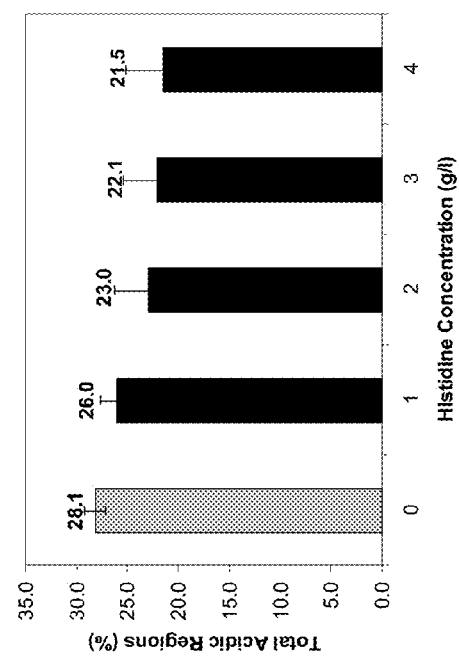

Figure 46) Effect of carboxypeptidase digestions of product from mAB2 producing cell line on WCX-10 profile total acidic regions (n=2)

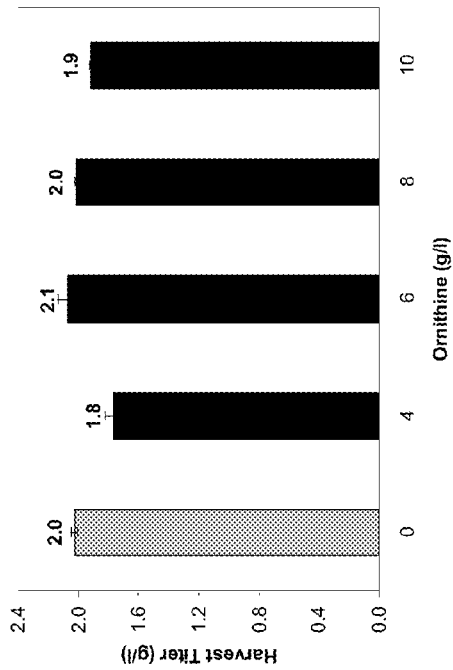

Figure 49) Effect of total ornithine concentration in adalimumab producing cell line 2, media 1 on harvest titer (n=2)

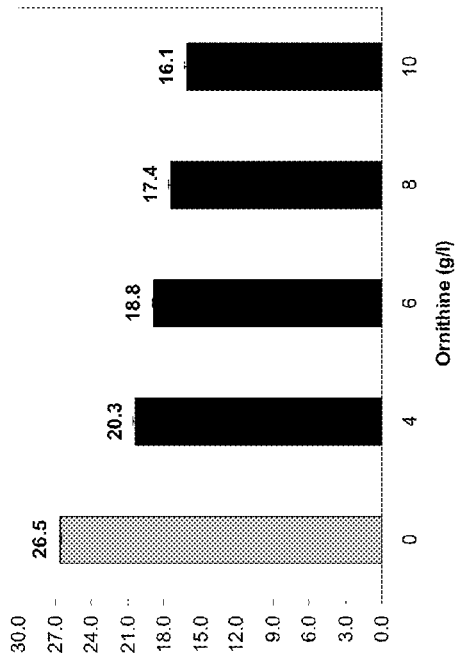

Figure 50) Effect of total ornithine concentration in adalimumab producing cell line 2, media 1 on WCX 10 profile total acidic regions (n=2)

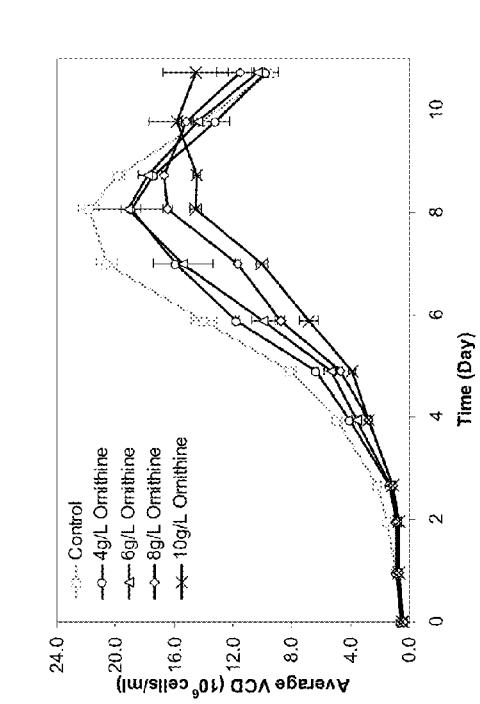

Figure 47) Effect of total ornithine concentration in adalimumab producing cell line 2, media 1 on viable cell density (n=2)

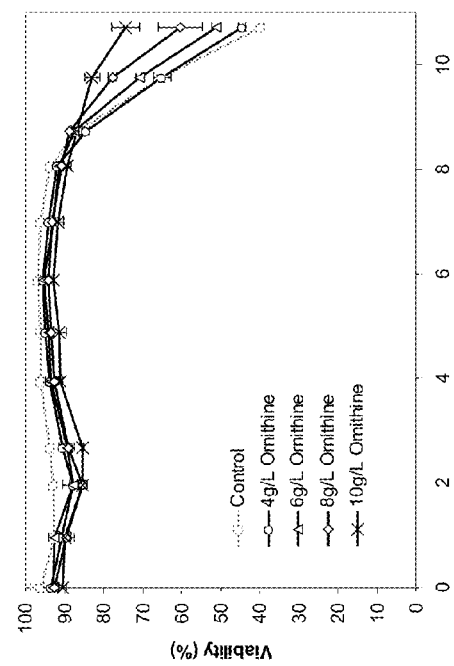

Figure 48) Effect of total ornithine concentration in adalimumab producing cell line 2, media 1 on viability (n=2)

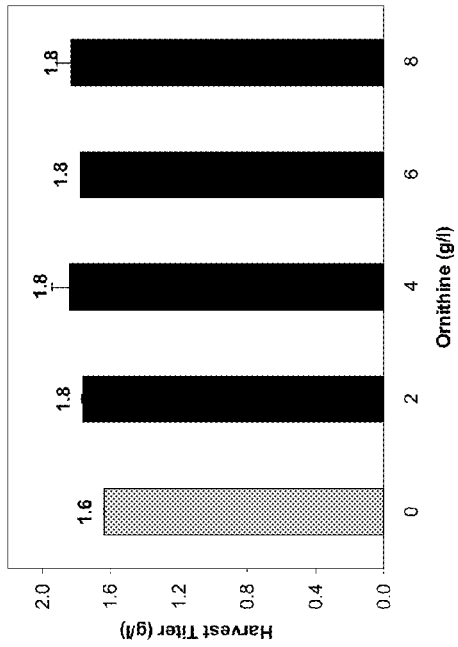

Figure 51) Effect of total ornithine concentration in adalimumab producing cell line 3, media 1 on viable cell density (n=2)

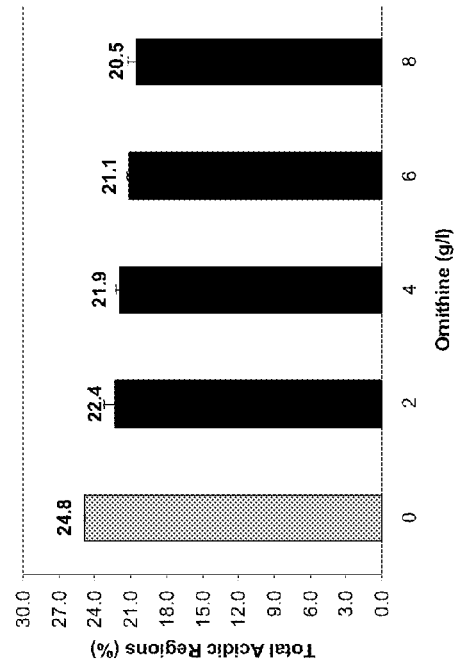

Figure 53) Effect of total ornithine concentration in adalimumab producing cell line 3, media 1 on harvest titer (n=2)

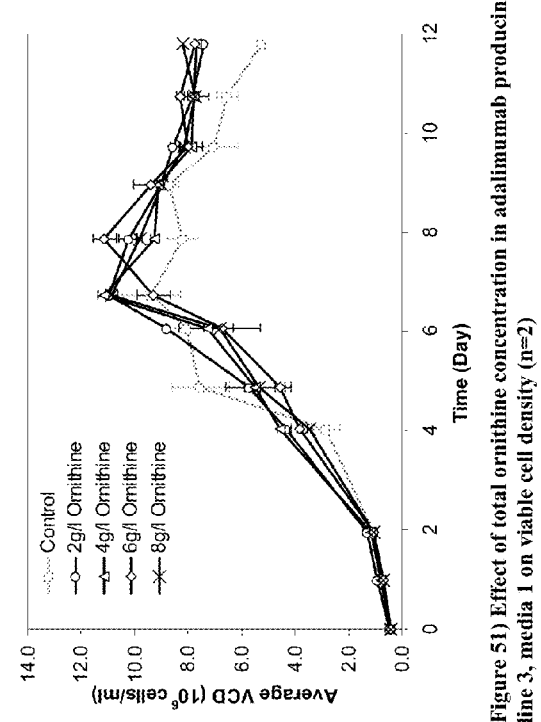

Figure 52) Effect of total ornithine concentration in adalimumab producing cell line 3, media 1 on viability (n=2)

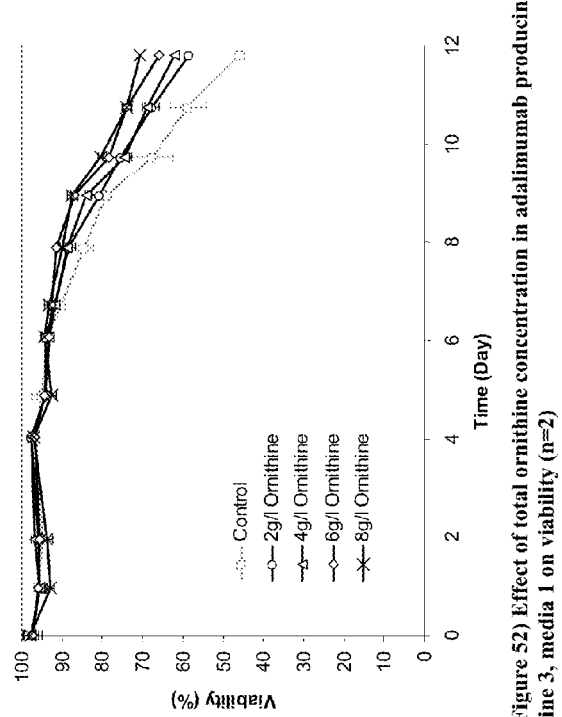

Figure 54) Effect of total ornithine concentration in adalimumab producing cell line 3, media 1 on WCX 10 profile total acidic regions (n=2)

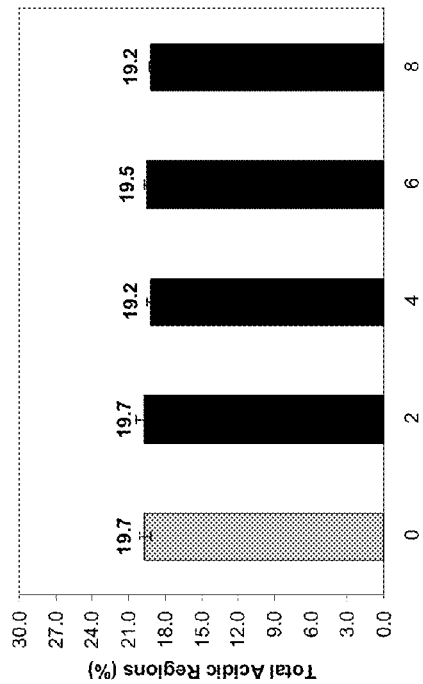

Figure 56) Effect of ornithine addition to adalimumab producing cell line 1, media 2 on WCX-10 profile total acidic regions (n=2)

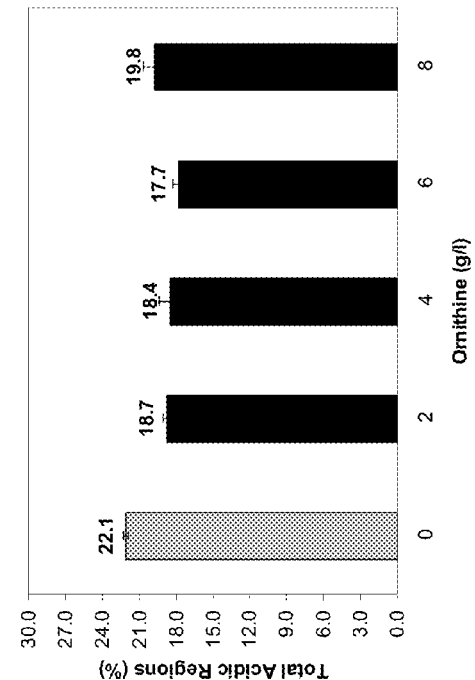

Figure 57) Effect of ornithine addition to adalimumab producing cell line 2, media 3 on WCX-10 profile total acidic regions (n=2)

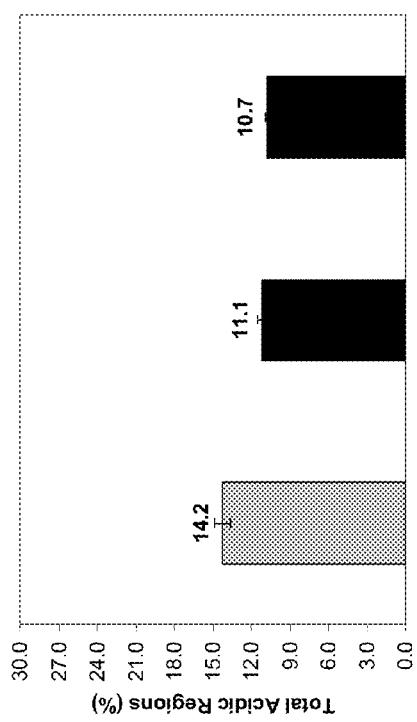

Figure 55) Effect of total ornithine concentration in adalimumab producing cell line 1, media 1 on WCX 10 profile total acidic regions (n=2)

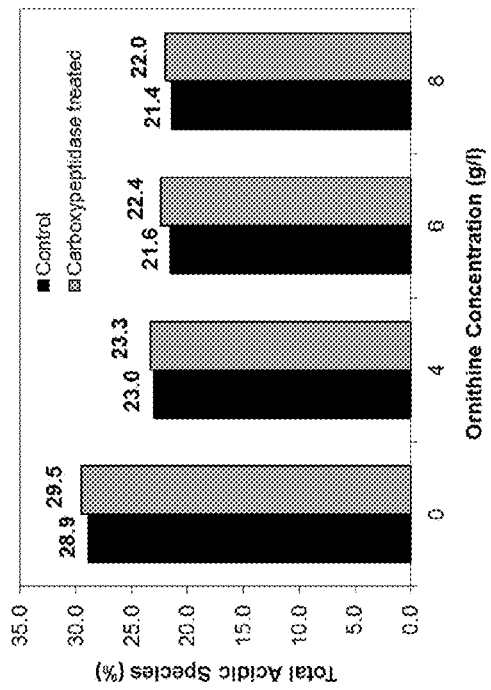

Figure 58) Effect of total ornithine concentration in mAB1 producing cell line on WCX-10 profile total acidic regions (n=1)

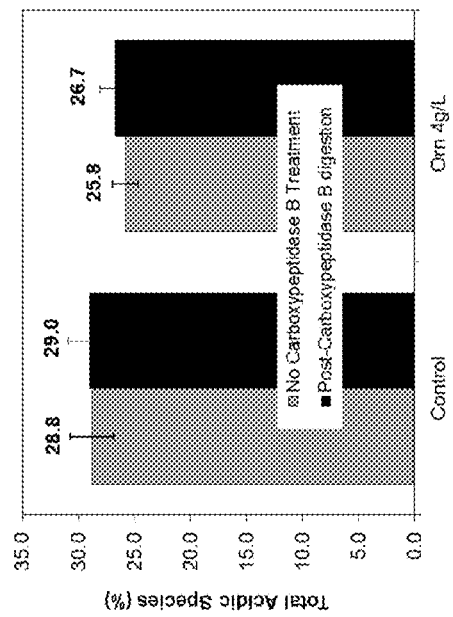

Figure 60) Effect of carboxypeptidase digestion of product from cell line 3, media 1 experiment on WCX-10 profile total acidic regions (n=1)

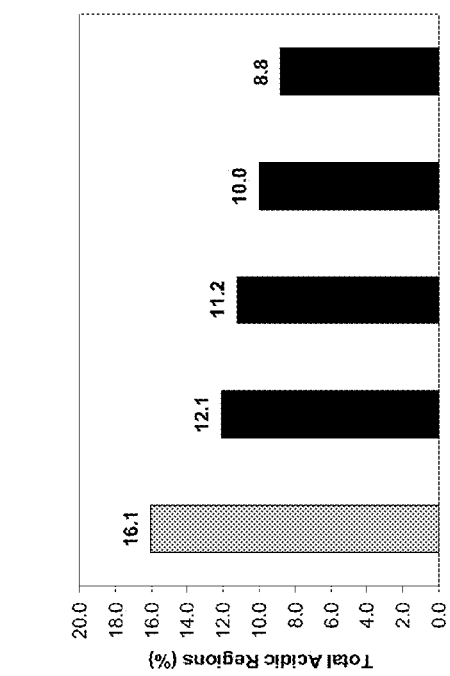

Figure 59) Effect of total ornithine concentration in mAB2 producing cell line on WCX-10 profile total acidic regions (n=2)

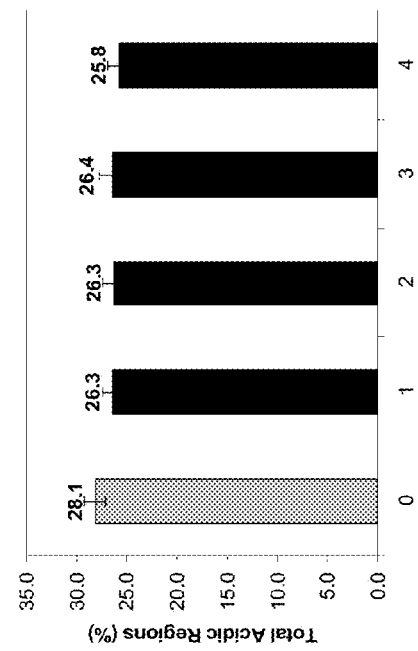

Figure 61) Effect of carboxypeptidase digestions of product from mAB2 producing cell line on WCX-10 profile total acidic regions (n=2)

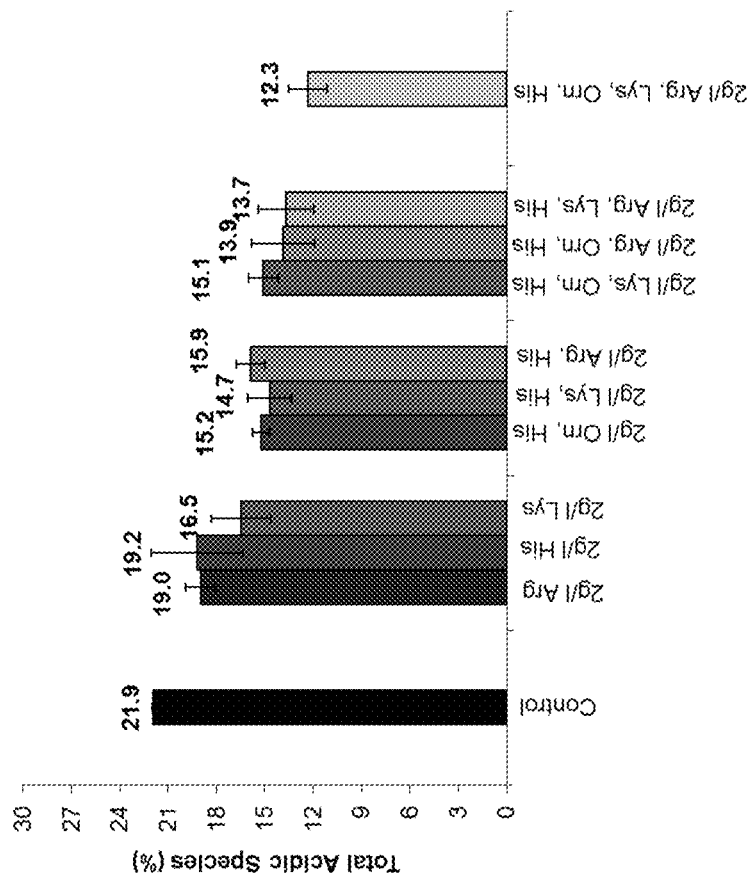
Figure 62) Effect of multiple amino acid additions to adalimumab producing cell line 2, media 1 containing 1g/l arginine and 1g/l lysine on WCX 10 profile total acidic regions (n=2)

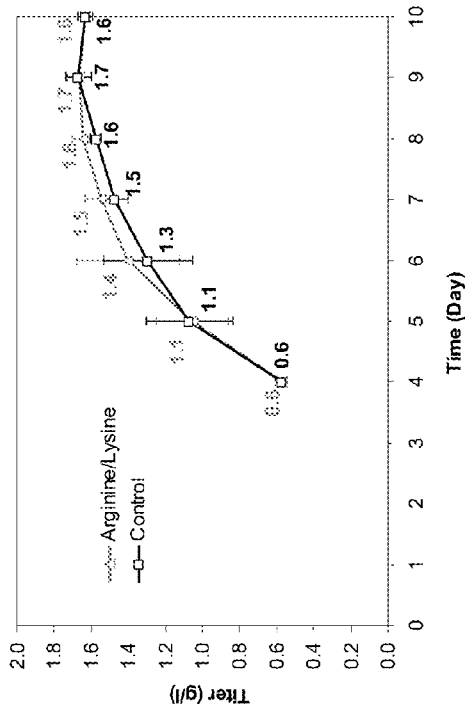

Figure 65) Effect of increased arginine and lysine concentration in adalimumab producing cell line 3, media 1 on culture titer (n=3)

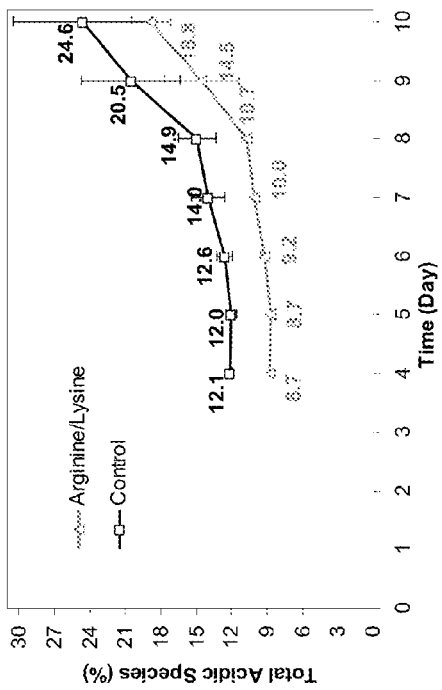

Figure 66) Effect of increased arginine and lysine concentration in adalimumab producing cell line 1, media 1 on WCX 10 profile total acidic regions (n=2)

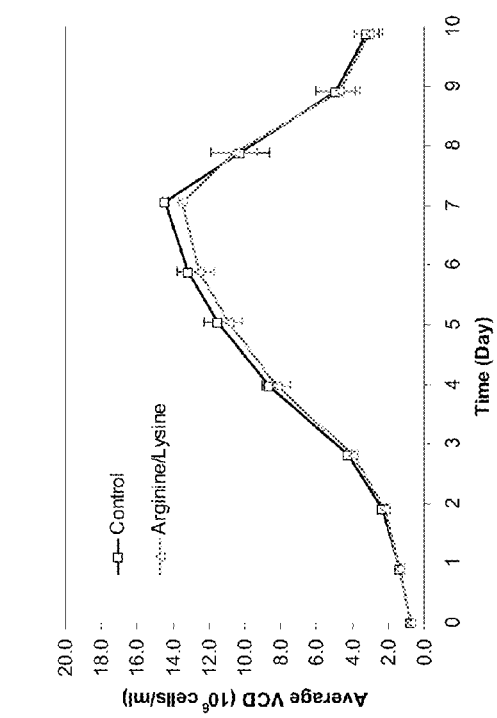

Figure 63) Effect of increased arginine and lysine concentration in adalimumab producing cell line 1, media 1 on viable cell density (n=3)

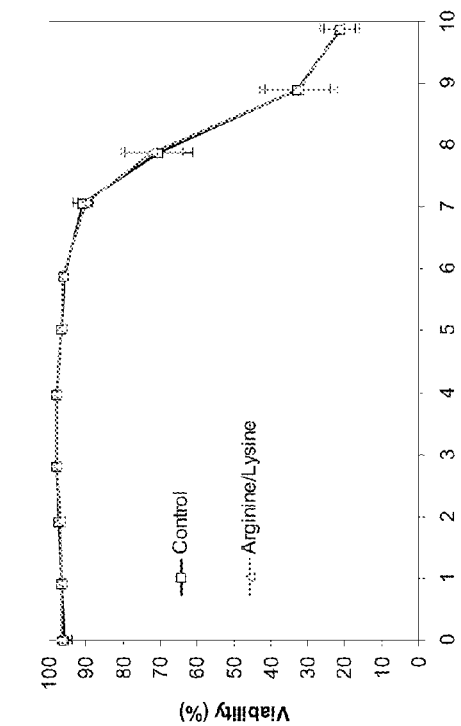

Figure 64) Effect of increased arginine and lysine concentration in adalimumab producing cell line 3, media 1 on viability (n=3)

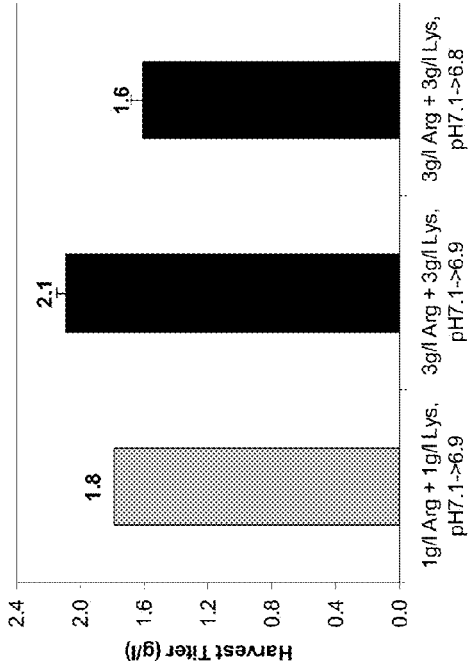

Figure 67) Effect of arginine, lysine and pH modulation to adalimumab producing cell line 1, media 1 on viable cell density (n=2)

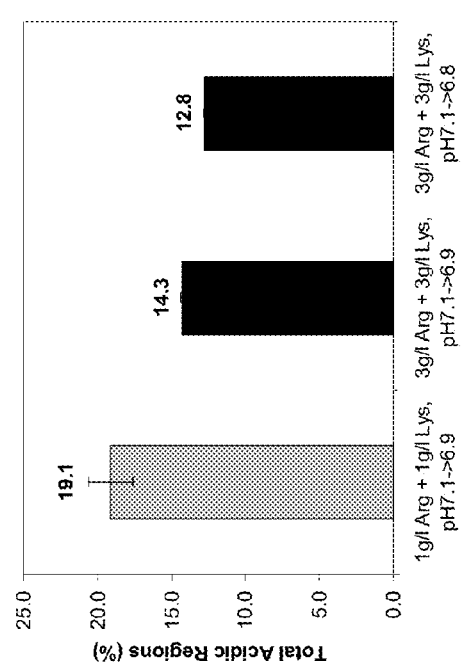

Figure 69) Effect of arginine, lysine and pH modulation to adalimumab producing cell line 3, media 1 on culture titer (n=2)

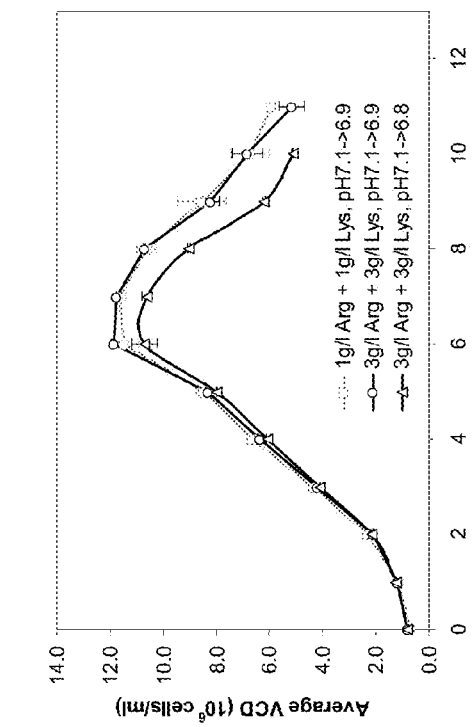

Figure 68) Effect of arginine, lysine and pH modulation to adalimumab producing cell line 3, media 1 on viability (n=2)

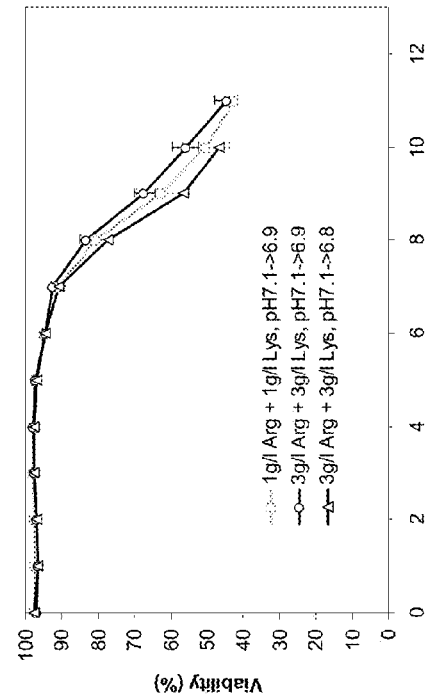

Figure 70) Effect of arginine, lysine and pH modulation to adalimumab producing cell line 1, media 1 on WCX 10 profile total acidic regions (n=2)

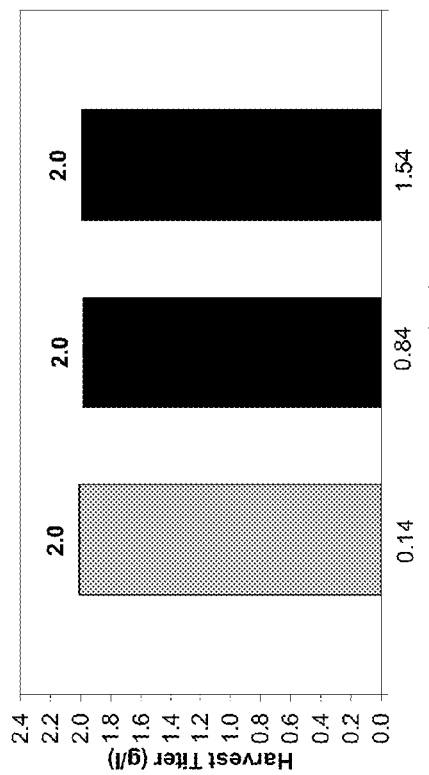

Figure 73) Effect of total calcium concentration in adalimumab producing cell line 2, media 1 on harvest titer (n=2)

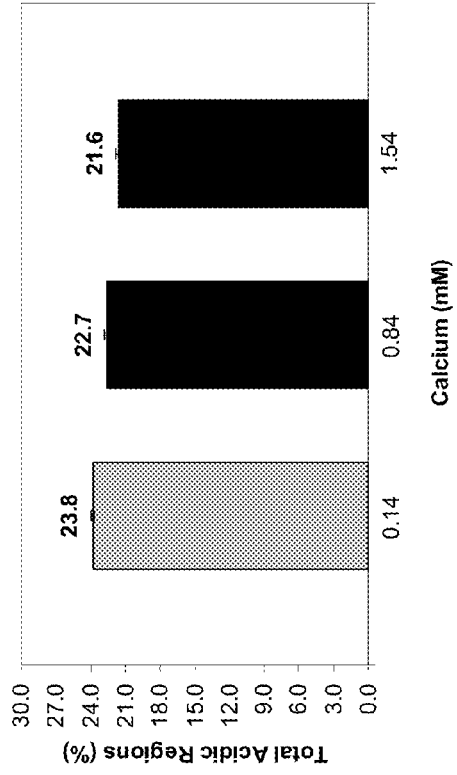

Figure 74) Effect of total calcium concentration in adalimumab producing cell line 2, media 1 on WCX 10 profile total acidic regions (n=2)

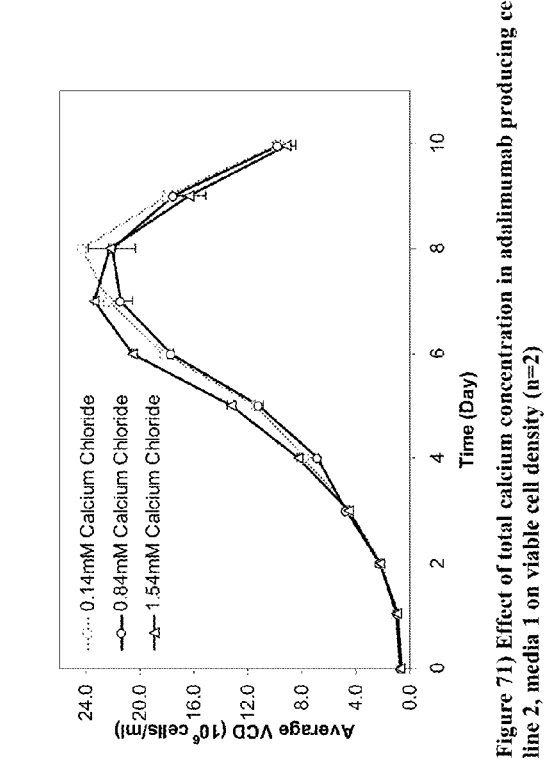

Figure 71) Effect of total calcium concentration in adalimumab producing cell line 2, media 1 on viable cell density (n=2)

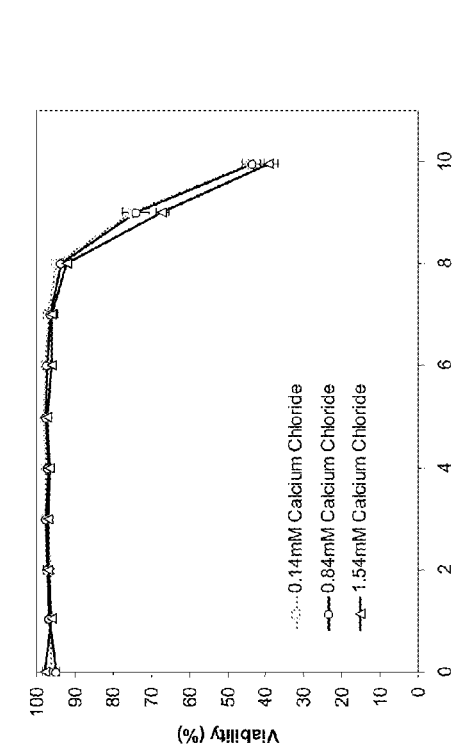

Figure 72) Effect of total calcium concentration in adalimumab producing cell line 2, media 1 on viability (n=2)

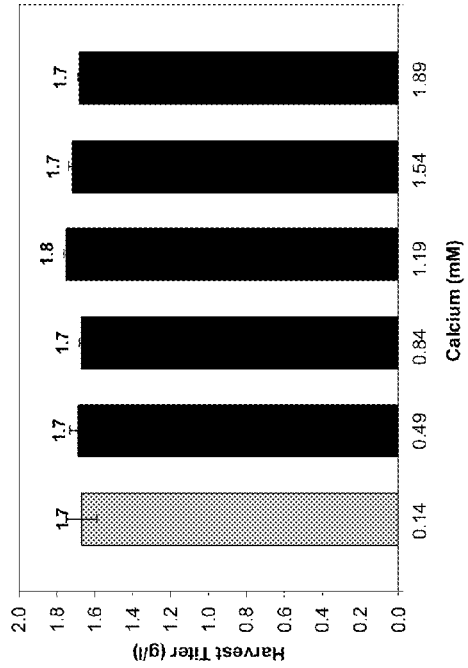

Figure 77) Effect of total calcium concentration in adalimumab producing cell line 3, media 1 on harvest titer (n=2)

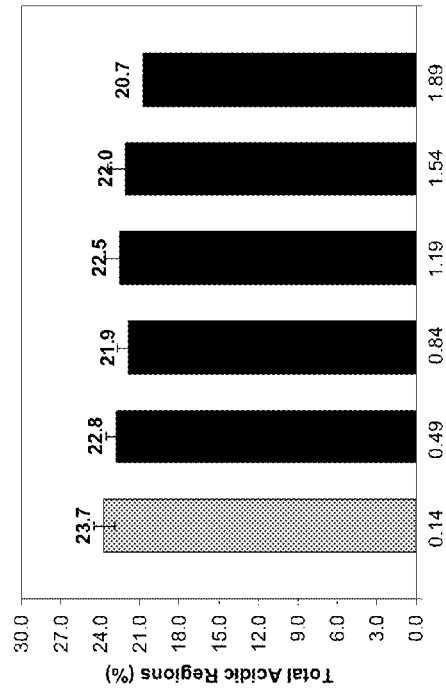

Figure 78) Effect of total calcium concentration in adalimumab producing cell line 3, media 1 on WCX 10 profile total acidic regions (n=2)

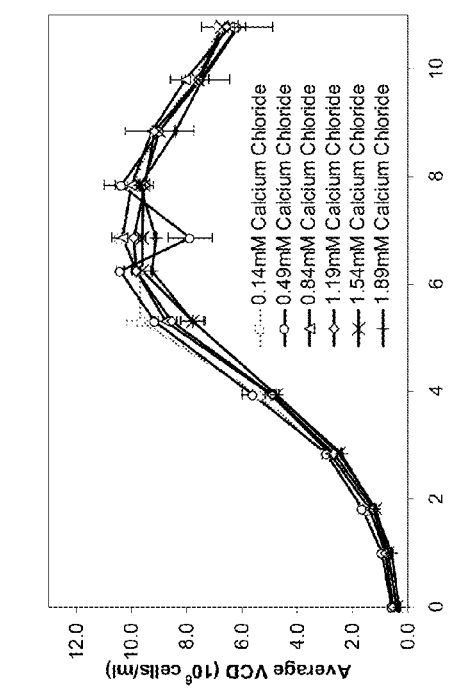

Figure 75) Effect of total calcium concentration in adalimumab producing cell line 3, media 1 on viable cell density (n=2)

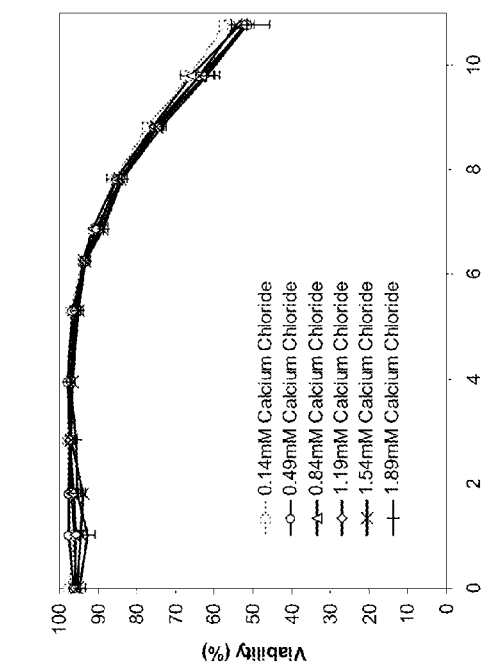

Figure 76) Effect of total calcium concentration in adalimumab producing cell line 3, media 1 on viability (n=2)

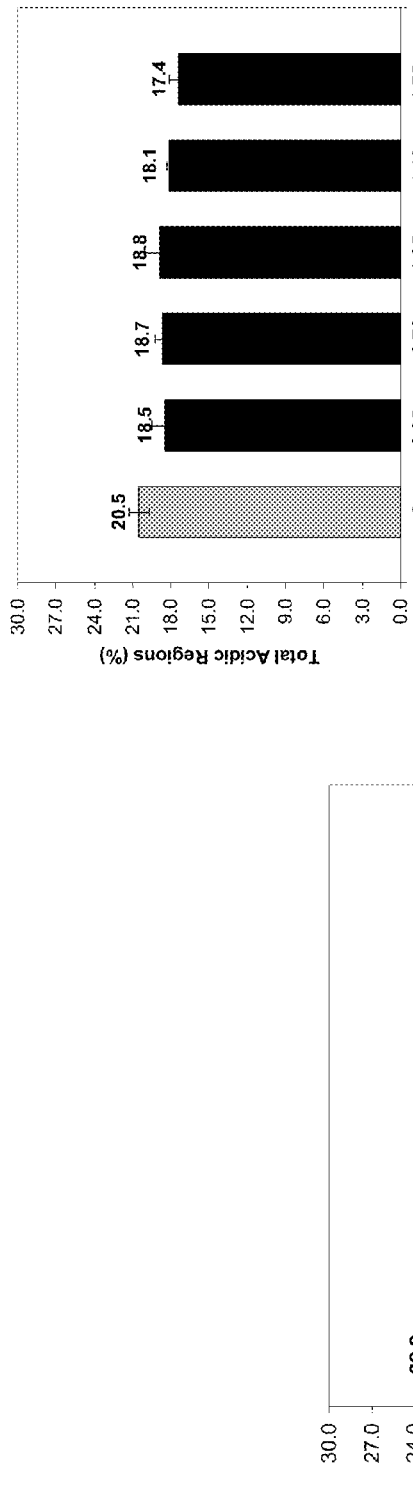

Figure 79) Effect of total calcium concentration in adalimumab producing cell line 1, media 1 on WCX 10 profile total acidic regions (n=2)

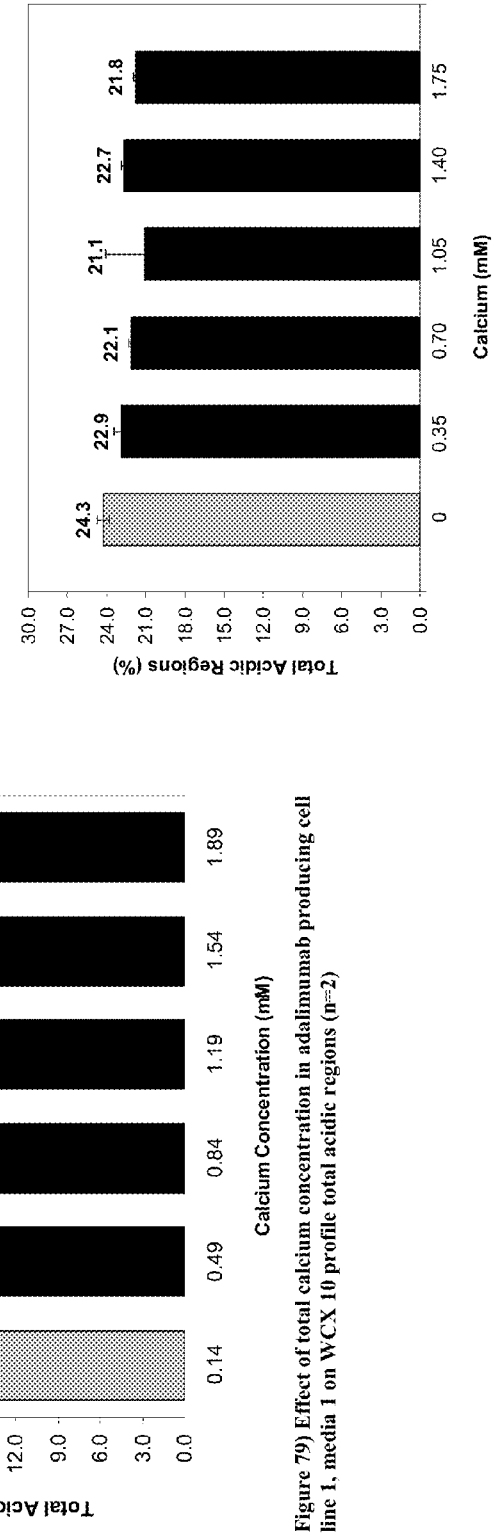

Figure 80) Effect of total calcium concentration in adalimumab producing cell line 1, media 2 on WCX-10 profile total acidic regions (n=2)

Figure 81) Effect of total calcium concentration in adalimumab producing cell line 2, media 3 on WCX-10 profile total acidic regions (n=2)

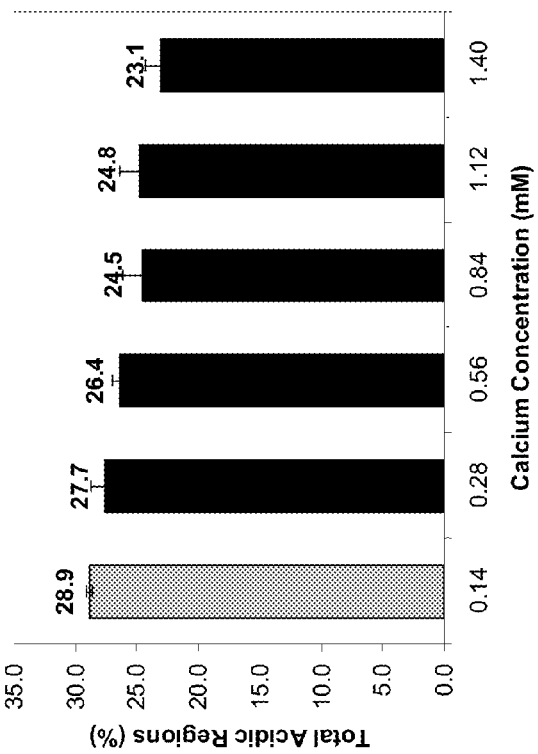
Figure 83) Effect of total calcium concentration in mAB2 producing cell line on WCX-10 profile total acidic regions (n=2)
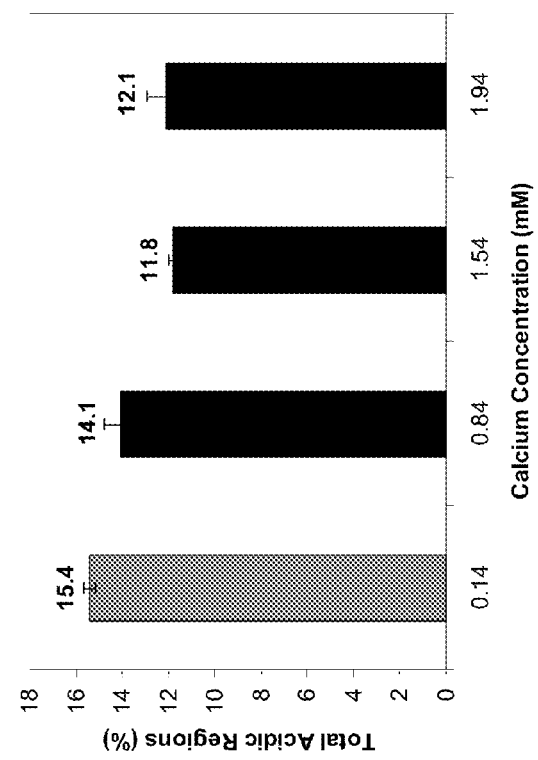
Figure 82) Effect of total calcium concentration in mAB1 producing cell line on WCX-10 profile total acidic regions (n=2)

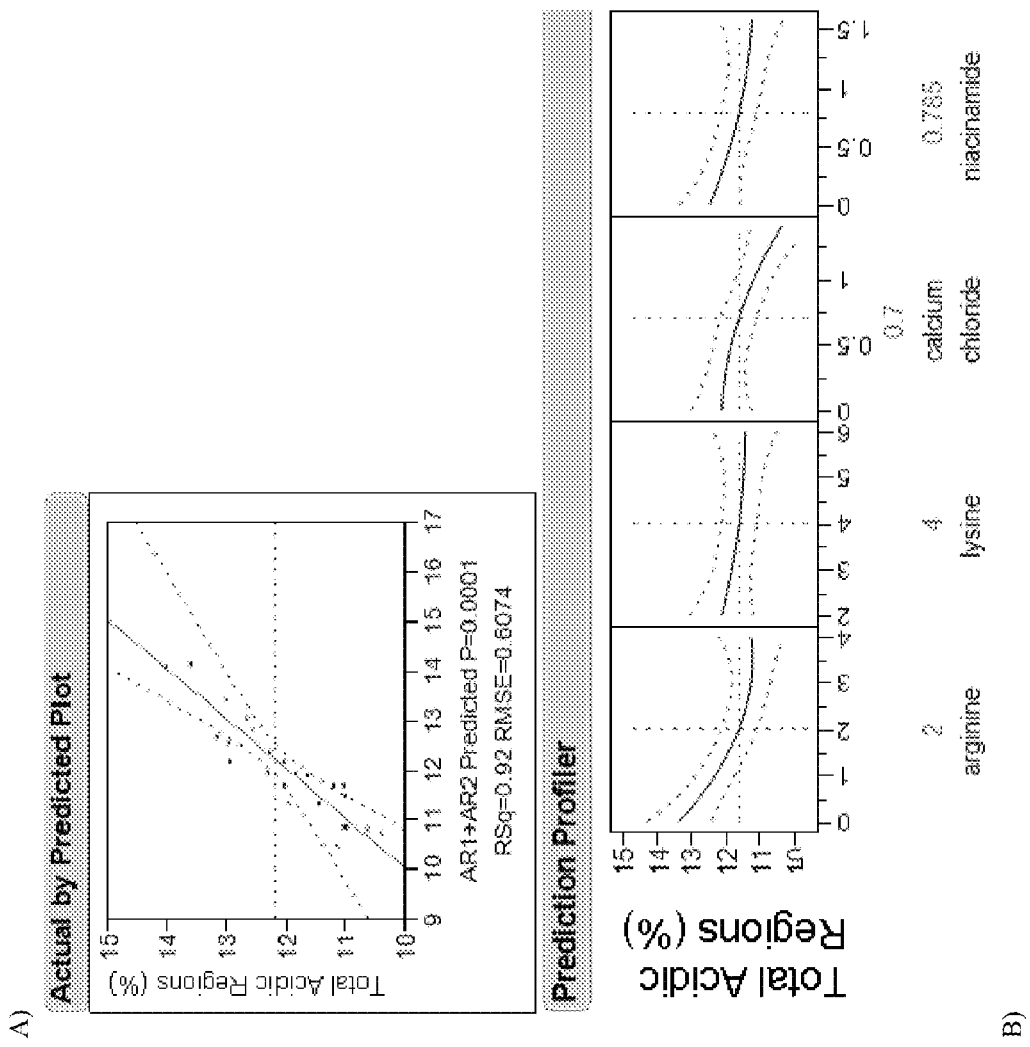
Figure 84) Effect of multiple amino acid additions to cell line 1, media 1 on WCX 10 profile total acidic regions a) overall prediction plot, b) prediction plots for each additive (n=2)

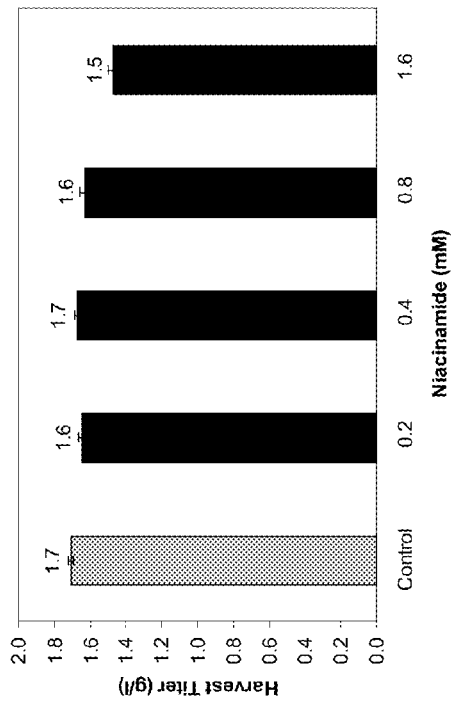

Figure 87) Effect of niacinamide addition to adalimumab producing cell line 1, media 1 on harvest titer (n=2)

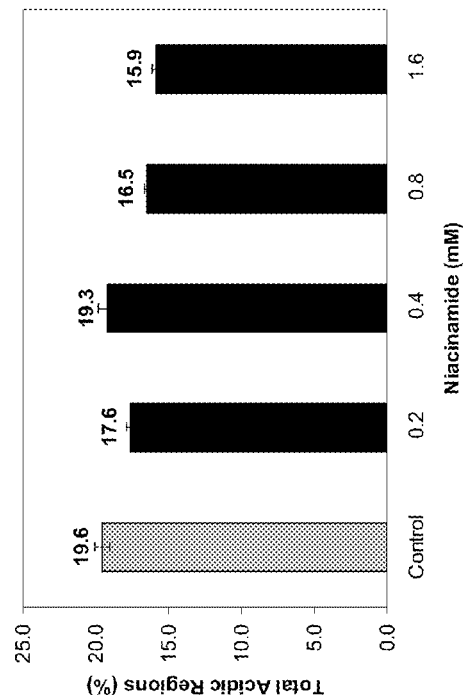

Figure 88) Effect of niacinamide addition to adalimumab producing cell line 1, media 1 on Day 11 WCX 10 profile total acidic regions (n=2)

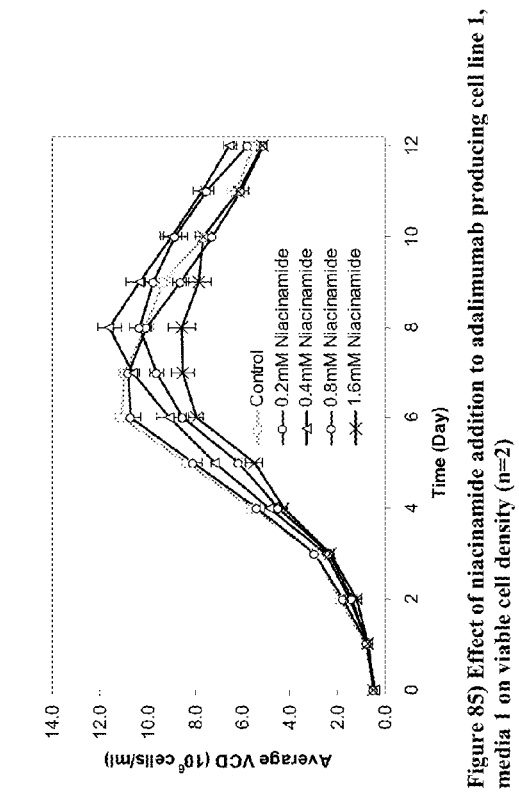

Figure 85) Effect of niacinamide addition to adalimumab producing cell line 1, media 1 on viable cell density (n=2)

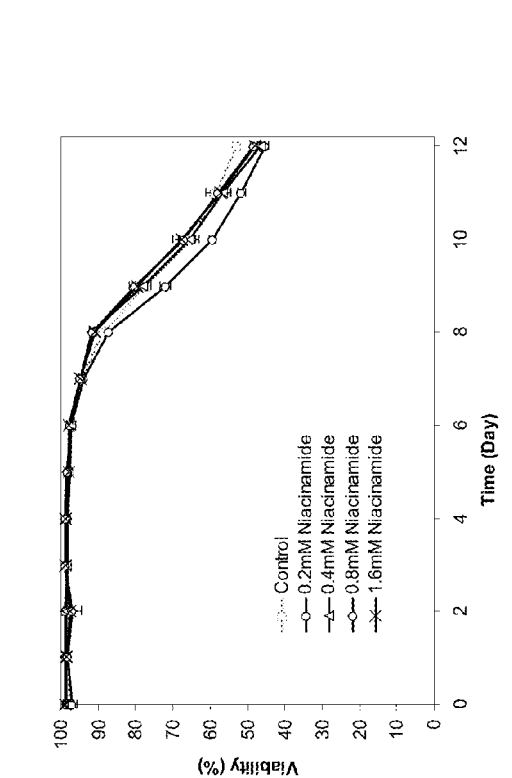

Figure 86) Effect of niacinamide addition to adalimumab producing cell line 1, media 1 on viability (n=2)

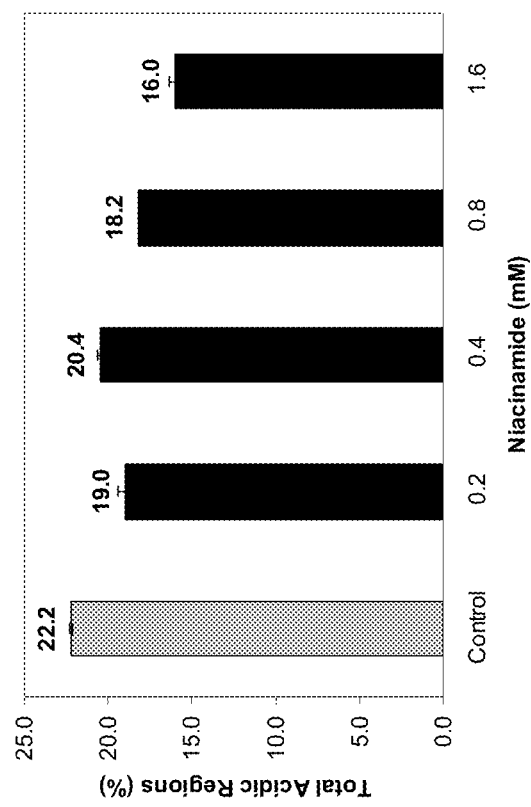
Figure 89) Effect of niacinamide addition to adalimumab producing cell line 1, media 1 on Day 12 WCX-10 profile total acidic regions (n=2)

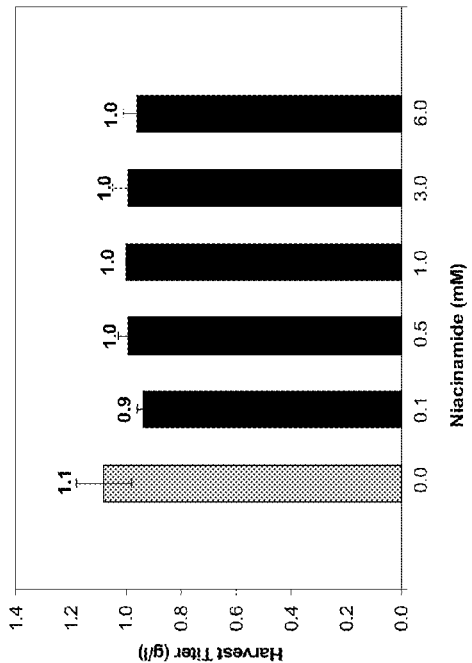

Figure 92) Effect of niacinamide addition to mAB2 producing cell line, media 1 on harvest titer (n=2)

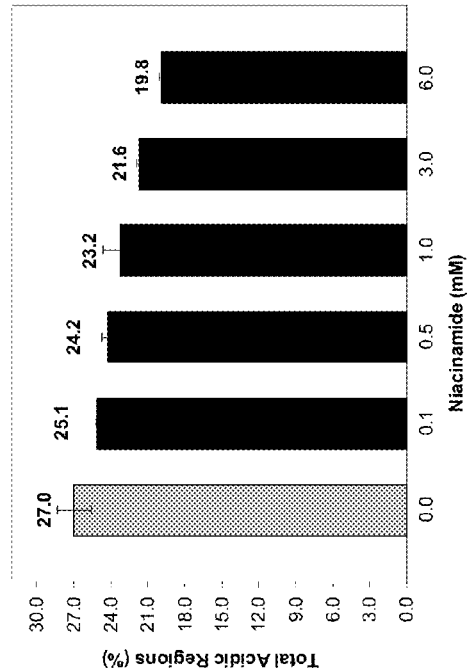

Figure 93) Effect of niacinamide addition to mAB2 producing cell line, media 1 on WCX 10 profile total acidic regions (n=2)

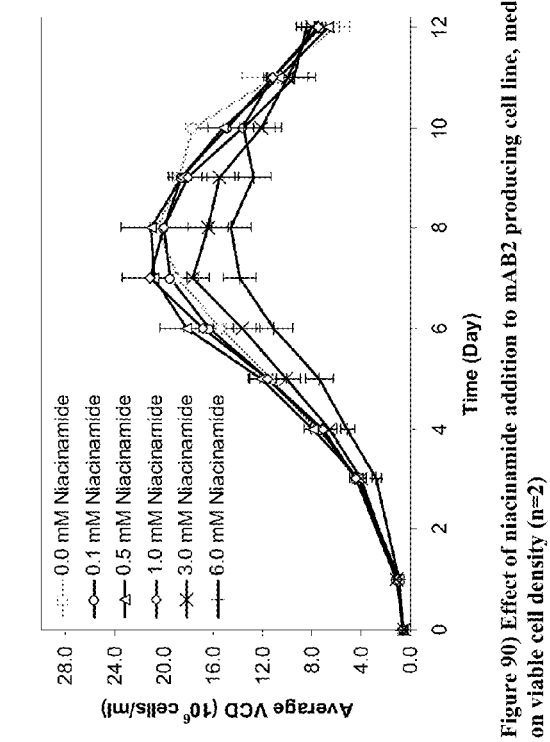

Figure 90) Effect of niacinamide addition to mAB2 producing cell line, media 1 on viable cell density (n=2)

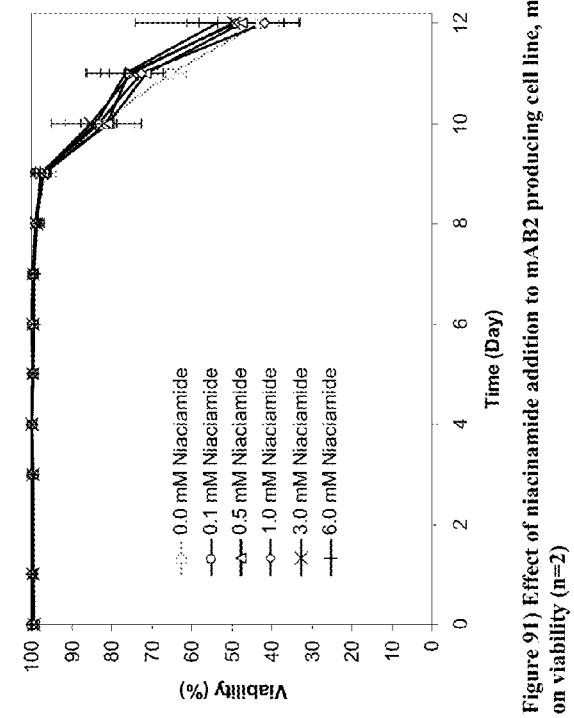

Figure 91) Effect of niacinamide addition to mAB2 producing cell line, media 1 on viability (n=2)

Figure 94A
Figure 94B
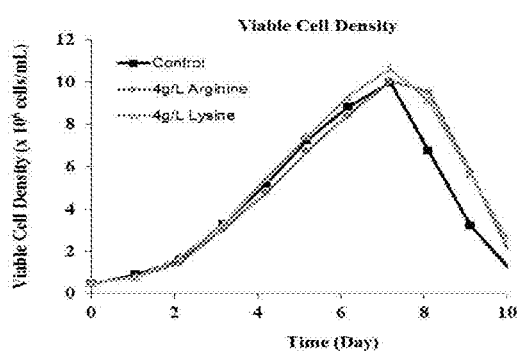
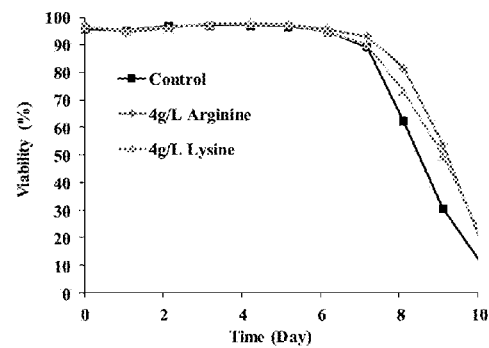
Figure 94C
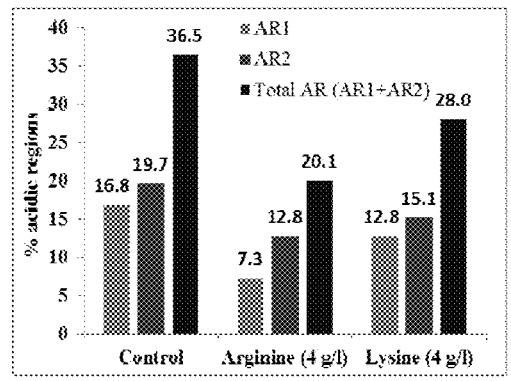
Figure 94D
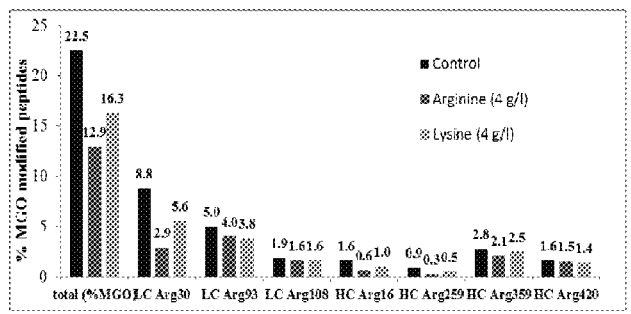

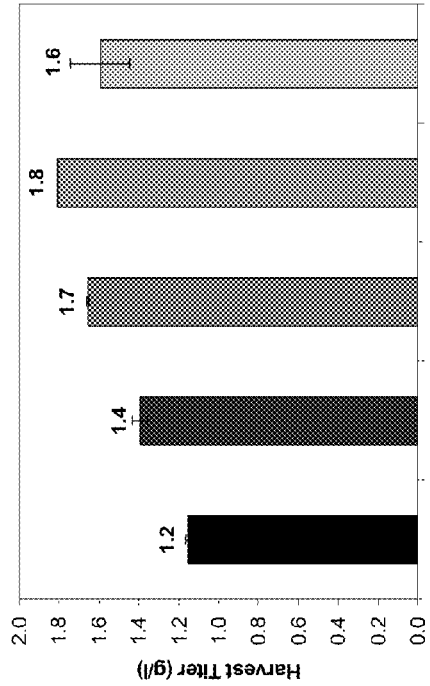

Figure 97) Effect of pH modulation of adalimumab producing cell line 1, media 1 on harvest titer

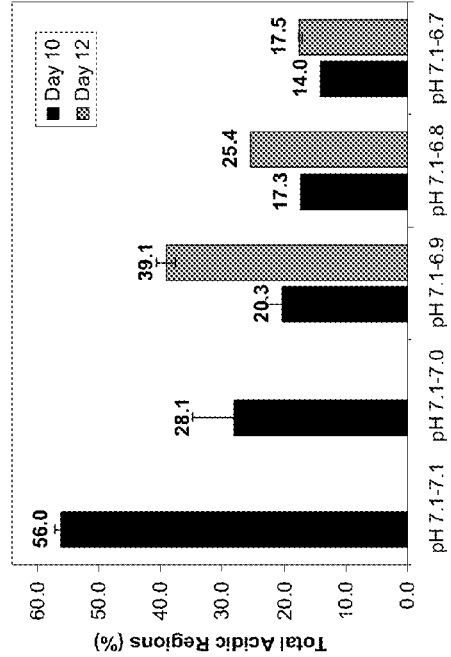

Figure 98) Effect of pH modulation of adalimumab producing cell line 1, media 1 on WCX 10 profile total acidic regions

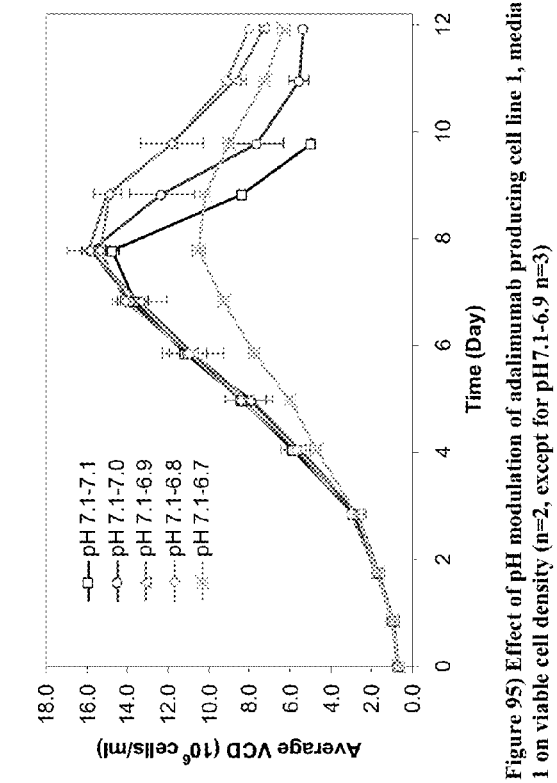

Figure 95) Effect of pH modulation of adalimumab producing cell line 1, media 1 on viable cell density (n=2, except for pH7.1-6.9 n=3)

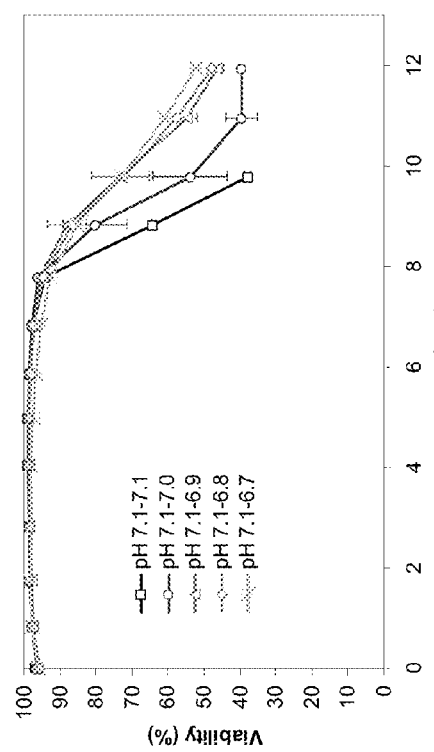

Figure 96) Effect of pH modulation adalimumab producing cell line 1, media 1 on viability (n=2, except for pH7.1-6.9 n=3)

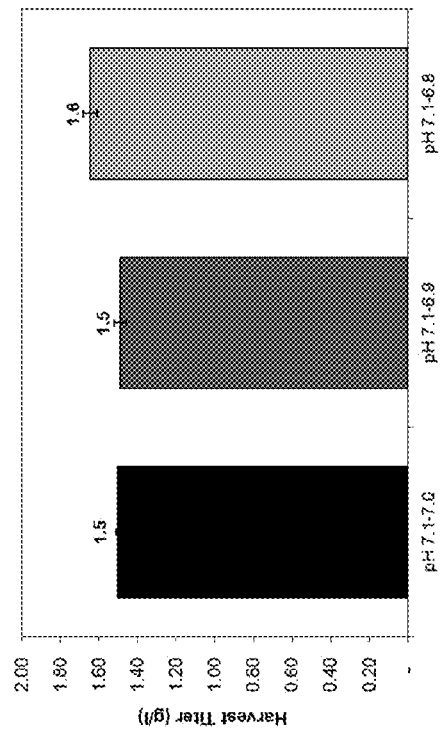

Figure 99) Effect of pH modulation of adalimumab producing cell line 1, media 2 on viable cell density (n=2, except for pH7.1-6.9 n=3)

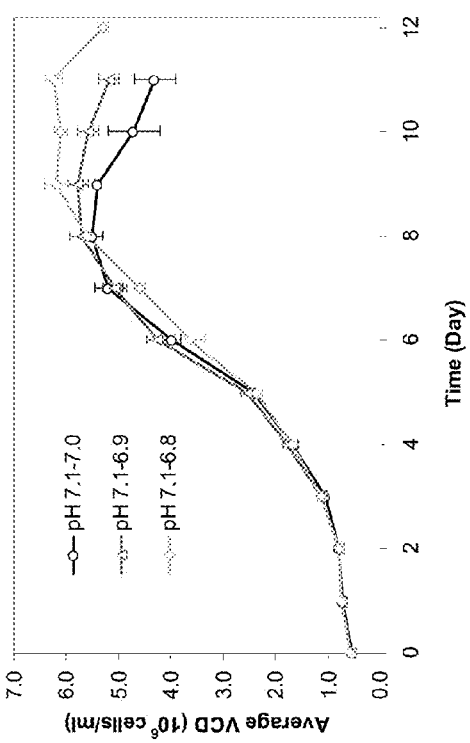

Figure 100) Effect of pH modulation of adalimumab producing cell line 1, media 2 on viability (n=2, except for pH7.1-6.9 n=3)

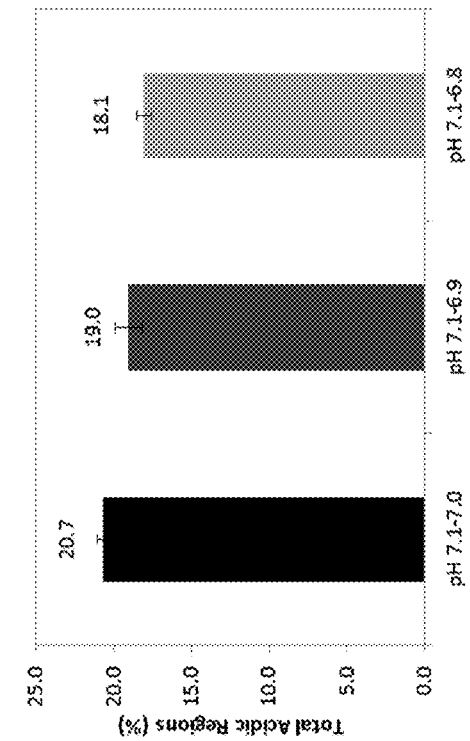

Figure 101) Effect of pH modulation of adalimumab producing cell line 1, media 2 on harvest titer

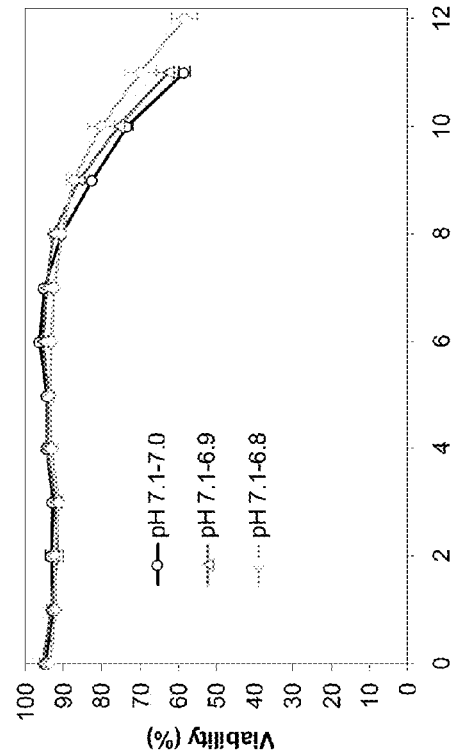

Figure 102) Effect of pH modulation of adalimumab producing cell line 1, media 2 on WCX 10 profile total acidic regions

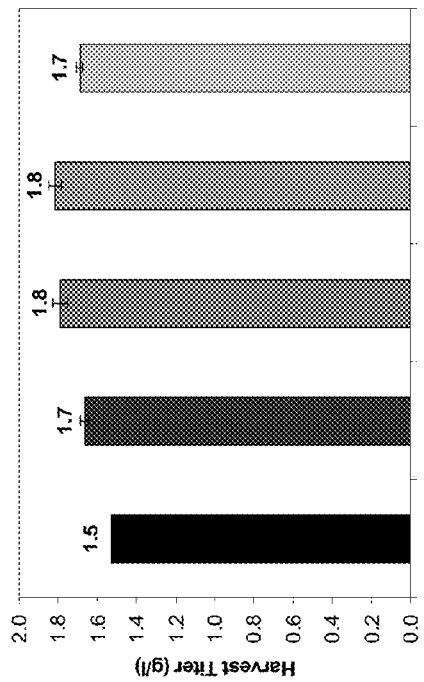

Figure 103) Effect of pH modulation of adalimumab producing cell line 3, media 1 on viable cell density (n=2, except for pH7.1-6.9 and pH7.1-6.8 n=3)

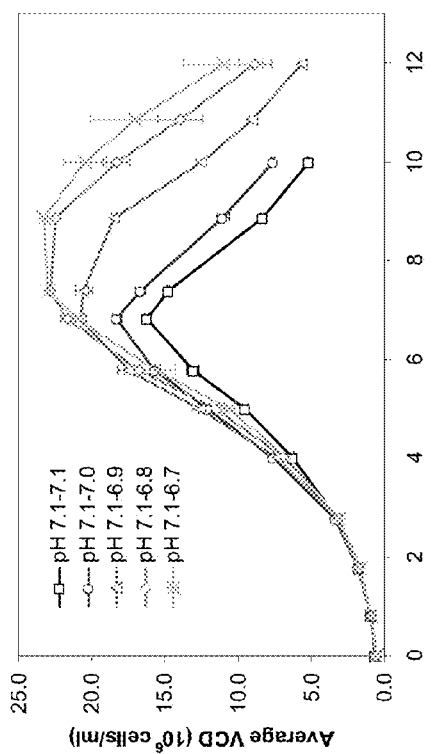

Figure 104) Effect of pH modulation of adalimumab producing cell line 3, media 1 on viability (n=2, except for pH7.1-6.9 and pH7.1-6.8 n=3)

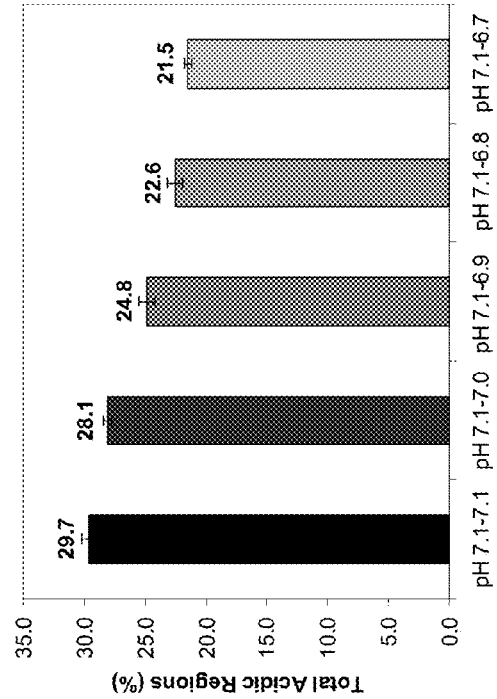

Figure 105) Effect of pH modulation of adalimumab producing cell line 3, media 1 on harvest titer

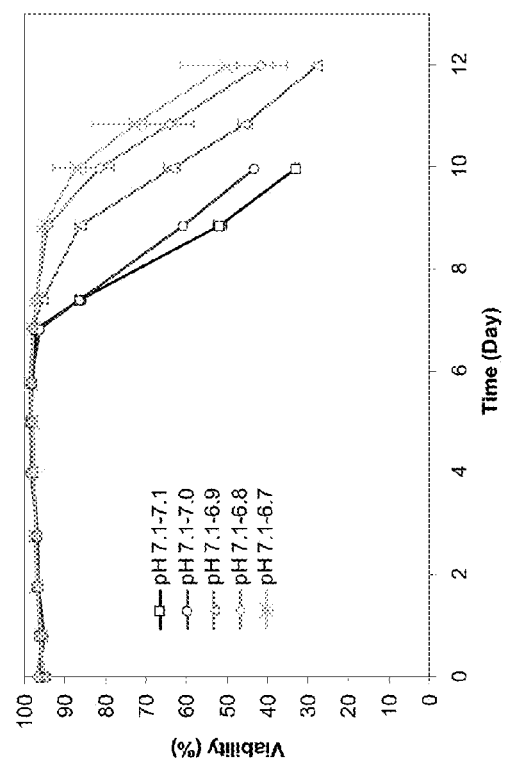

Figure 106) Effect of pH modulation of adalimumab producing cell line 3, media 1 on WCX 10 profile total acidic regions

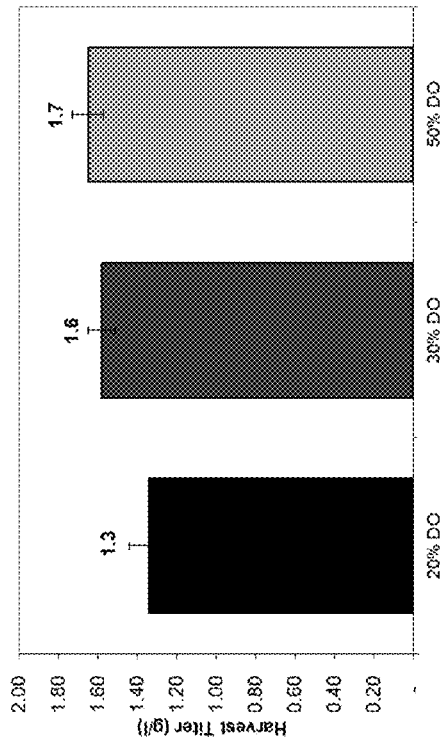

Figure 107) Effect of dissolved oxygen modulation of adalimumab producing cell line 1, media 2 at 35°C on viable cell density (n=2, except 30% DO n=3)

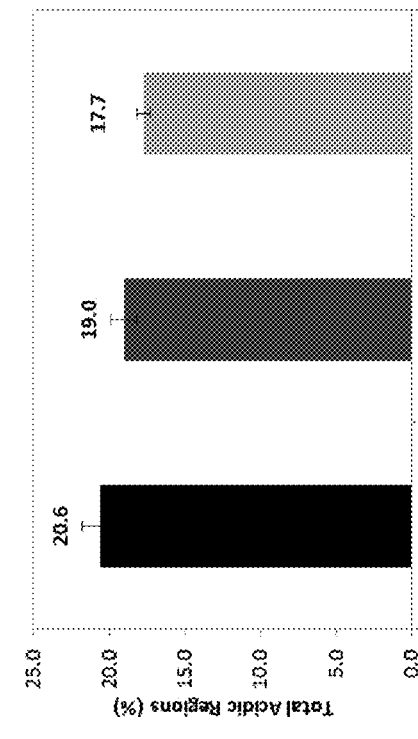

Figure 108) Effect of dissolved oxygen modulation of adalimumab producing cell line 1, media 2 at 35°C on viability (n=2, except 30% DO n=3)

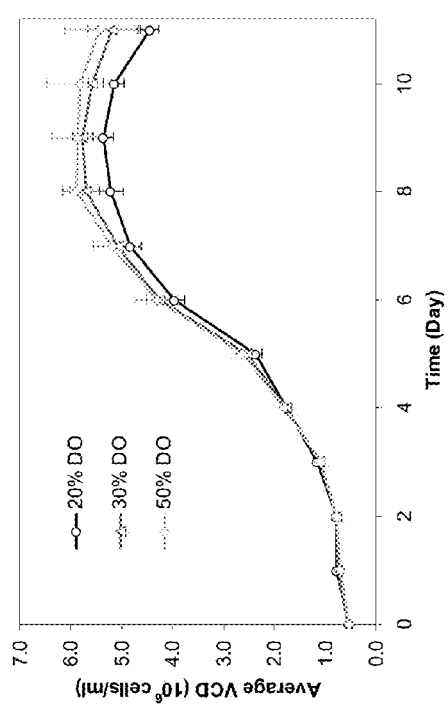

Figure 109) Effect of dissolved oxygen modulation of adalimumab producing cell line 1, media 2 at 35°C on harvest titer

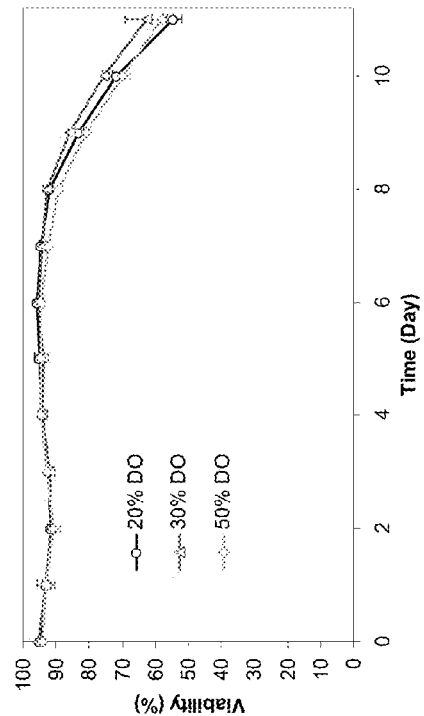

Figure 110) Effect of dissolved oxygen modulation of adalimumab producing cell line 1, media 2 at 35°C on WCX 10 profile total acidic regions

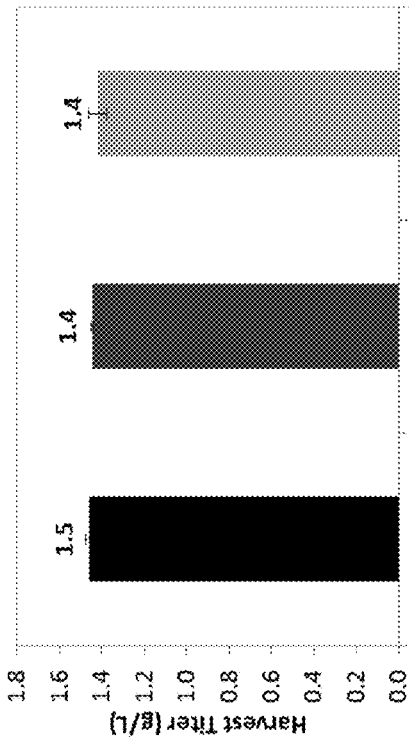

Figure 111) Effect of dissolved oxygen modulation of adalimumab producing cell line 1, media 2 at 33°C on viable cell density (n=2)

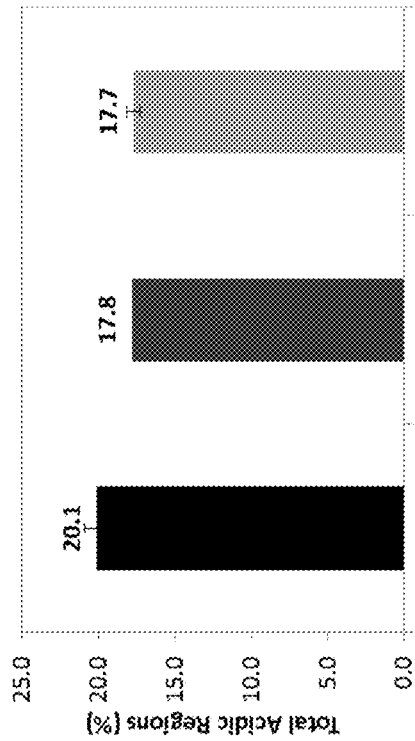

Figure 113) Effect of dissolved oxygen modulation of adalimumab producing cell line 1, media 2 at 33°C on harvest titer

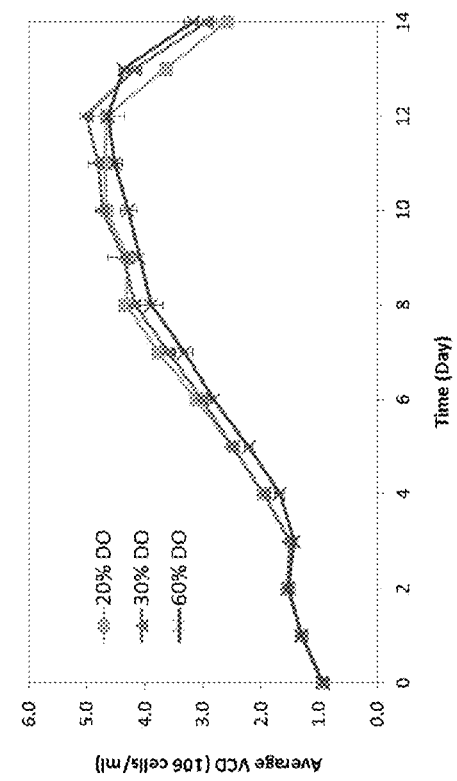

Figure 112) Effect of dissolved oxygen modulation of adalimumab producing cell line 1, media 2 at 33°C on viability (n=2)

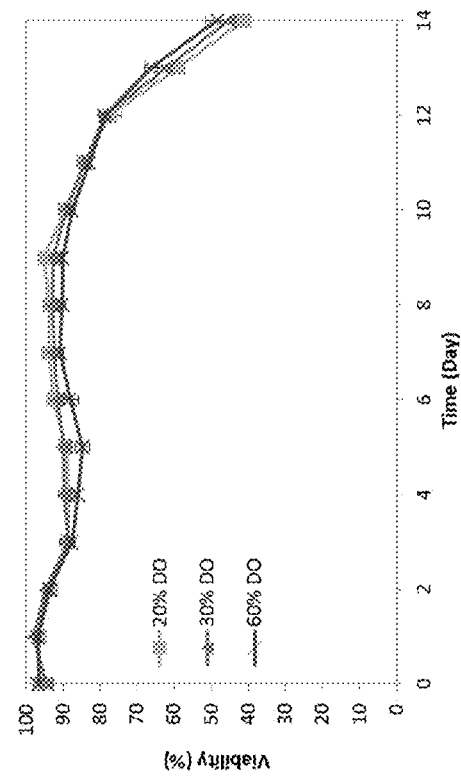

Figure 114) Effect of dissolved oxygen modulation of adalimumab producing cell line 1, media 2 at 33°C on WCX 10 profile total acidic regions

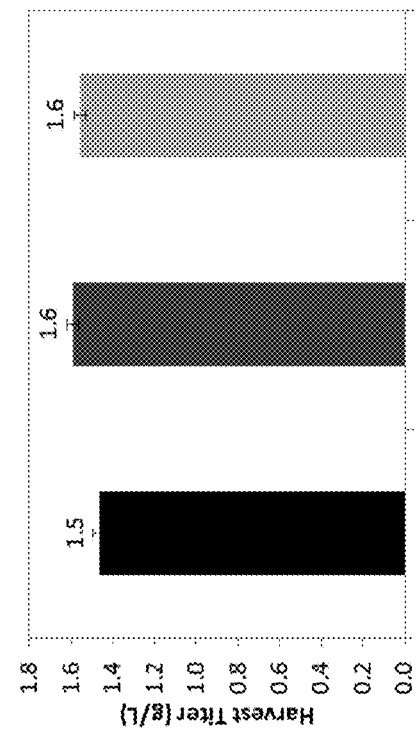

Figure 115) Effect of dissolved oxygen modulation of adalimumab producing cell line 1, media 1 at 35°C on viable cell density (n=3, except for 30% DO n=2)

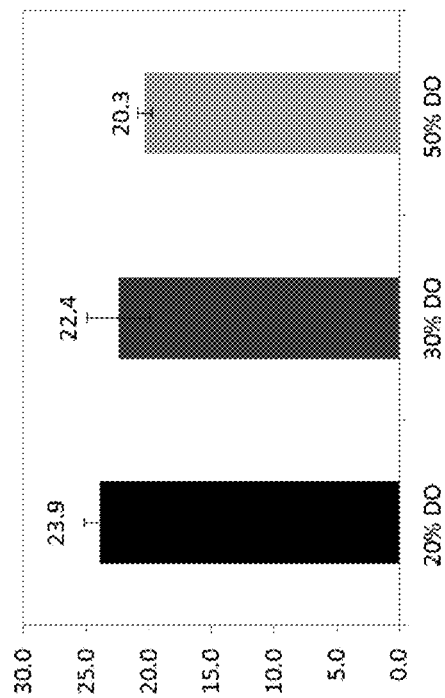

Figure 117) Effect of dissolved oxygen modulation of adalimumab producing cell line 1, media 1 at 35°C on harvest titer

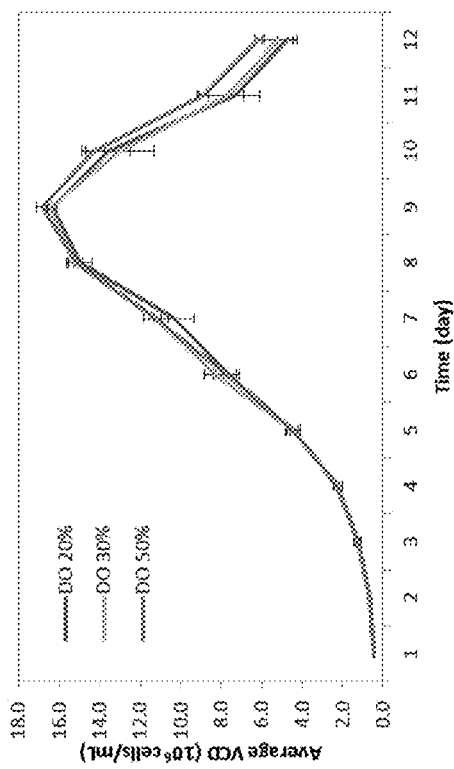

Figure 116) Effect of dissolved oxygen modulation of adalimumab producing cell line 1, media 1 at 35°C on viability (n=3, except for 30% DO n=2)

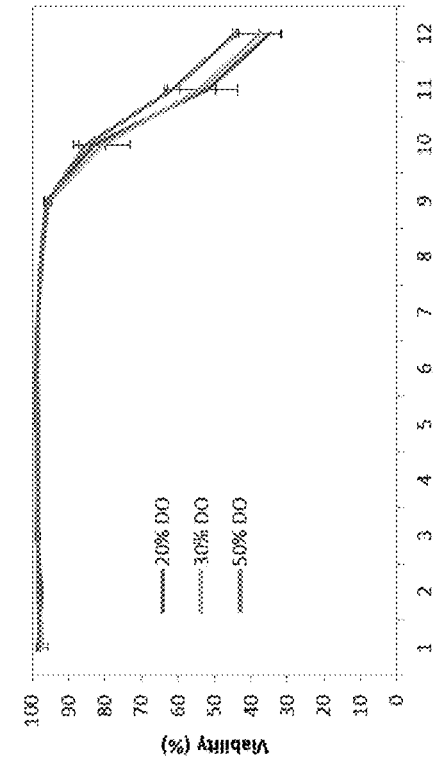

Figure 118) Effect of dissolved oxygen modulation of adalimumab producing cell line 1, media 1 on WCX 10 profile total acidic regions

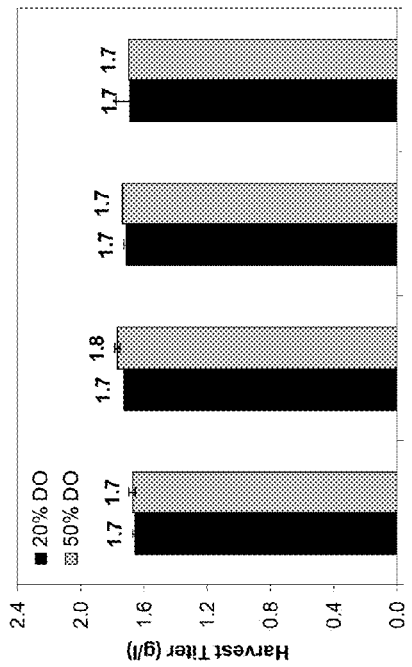

Figure 121) Effect of dissolved oxygen modulation of adalimumab producing cell line 3, media 1 on harvest titer

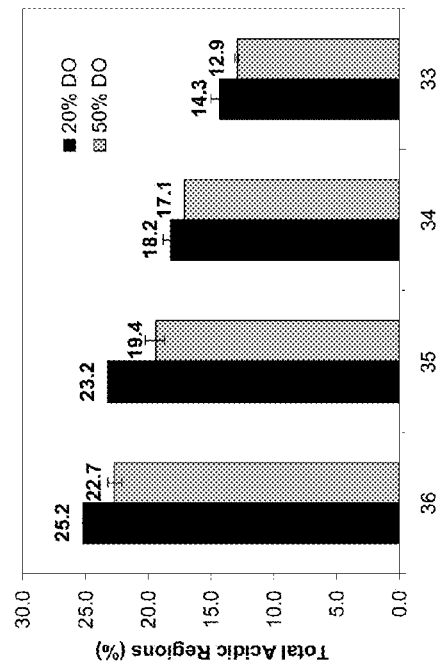

Figure 122) Effect of dissolved oxygen modulation of adalimumab producing cell line 3, media 1 on WCX 10 profile total acidic regions

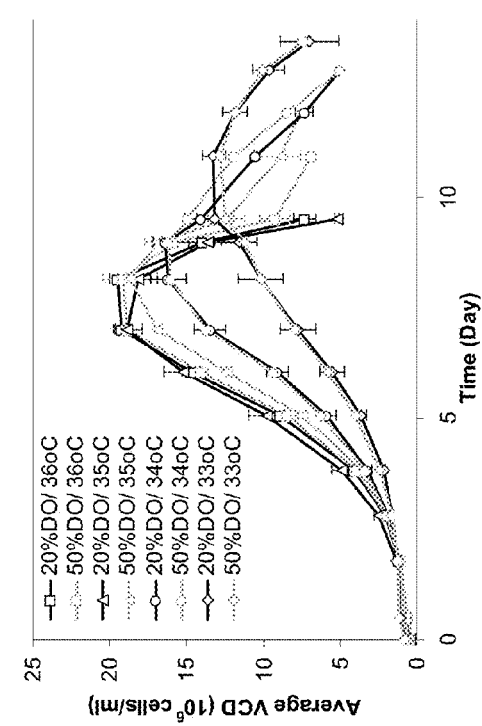

Figure 119) Effect of dissolved oxygen modulation of adalimumab producing cell line 3, media 1 on viable cell density (n=2)

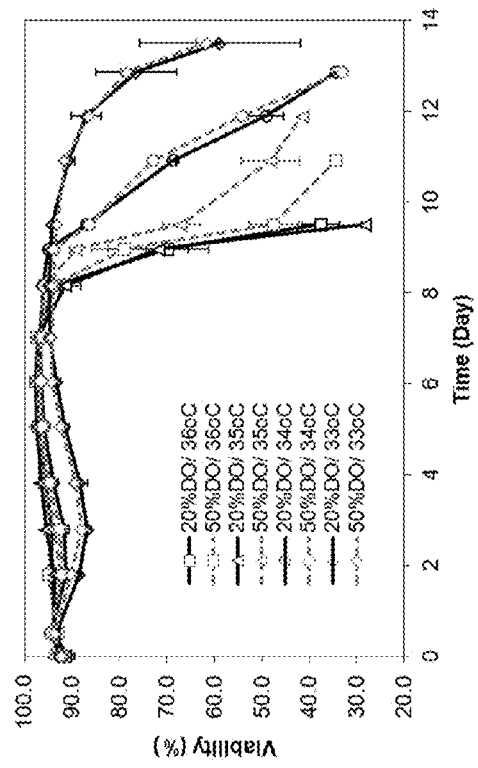

Figure 120) Effect of dissolved oxygen modulation of adalimumab producing cell line 3, media 1 on viability (n=2)

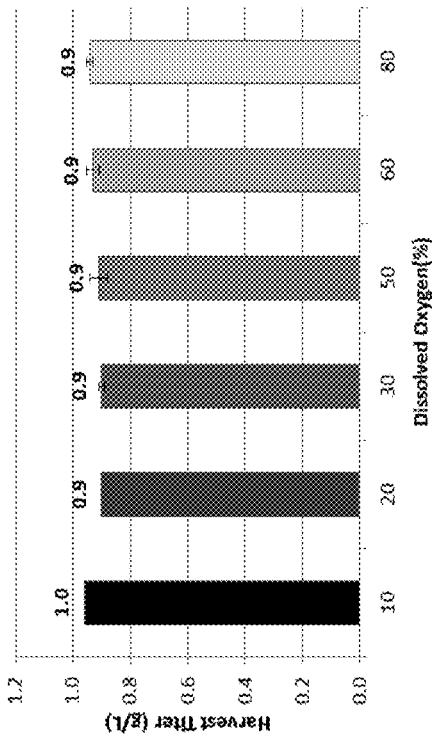

Figure 125) Effect of dissolved oxygen modulation of mAB2 producing cell line, media 1 on harvest titer

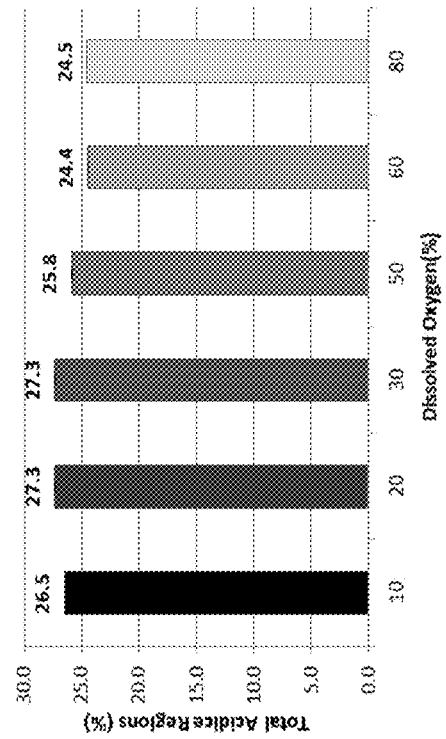

Figure 126) Effect of dissolved oxygen modulation of mAB2 producing cell line, media 1 on WCX 10 profile total acidic regions

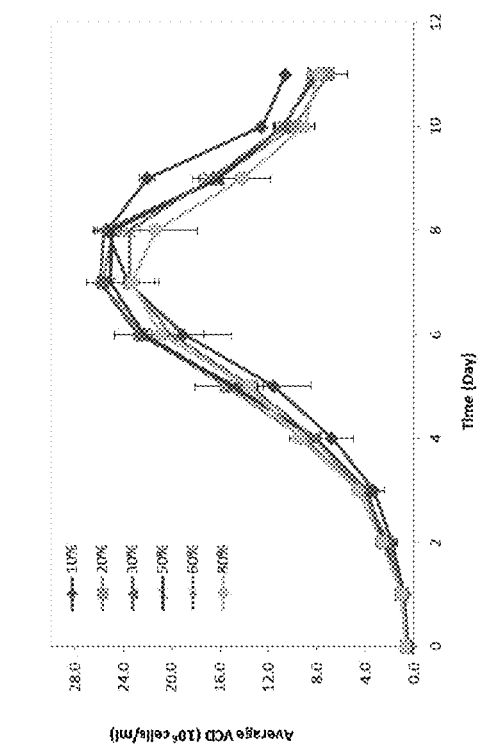

Figure 123) Effect of dissolved oxygen modulation of mAB2 producing cell line, media 1 on viable cell density (n=2)

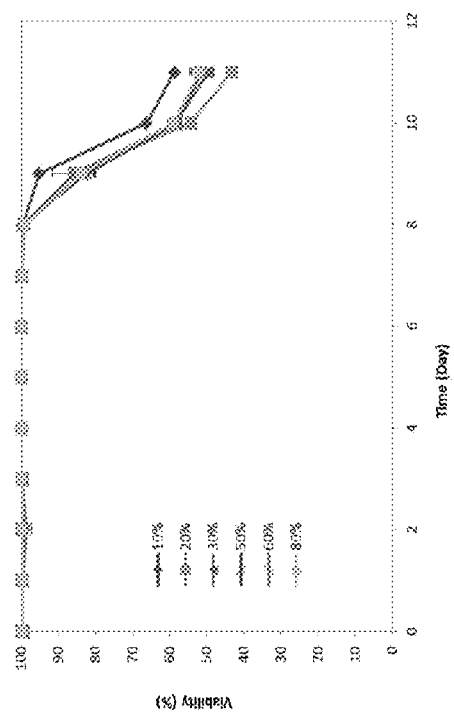

Figure 124) Effect of dissolved oxygen modulation addition of mAB2 producing cell line, media 1 on viability (n=2)

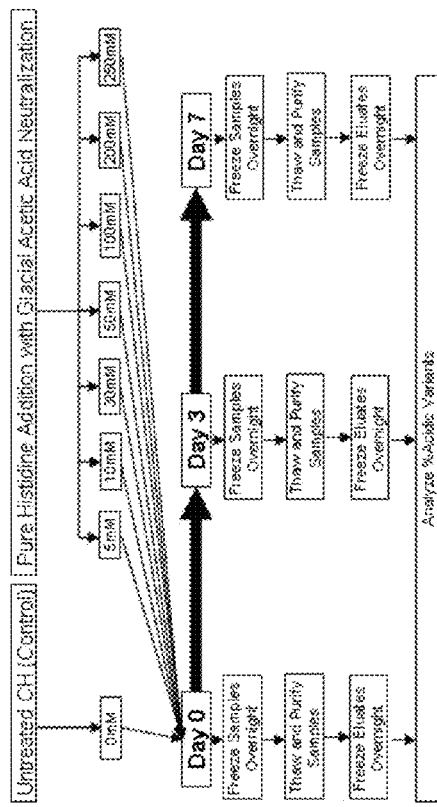
Figure 127) Acidicfication sample preparation scheme
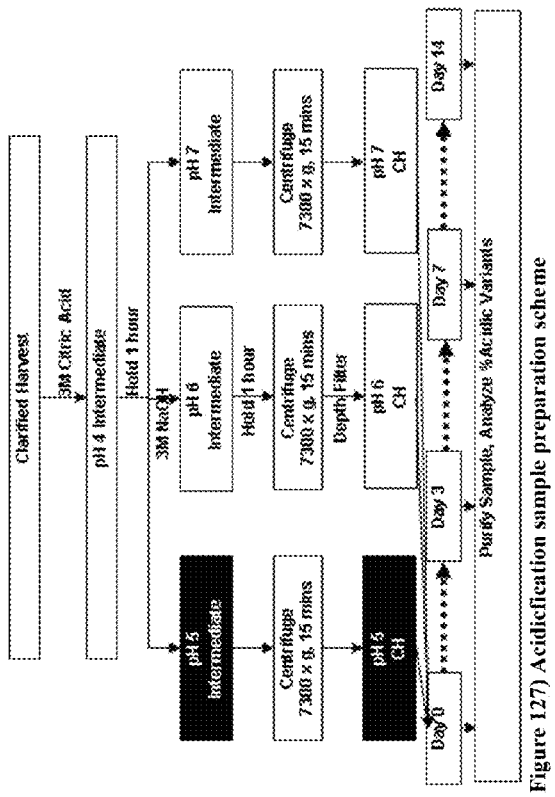
Figure 128) Arginine sample preparation scheme
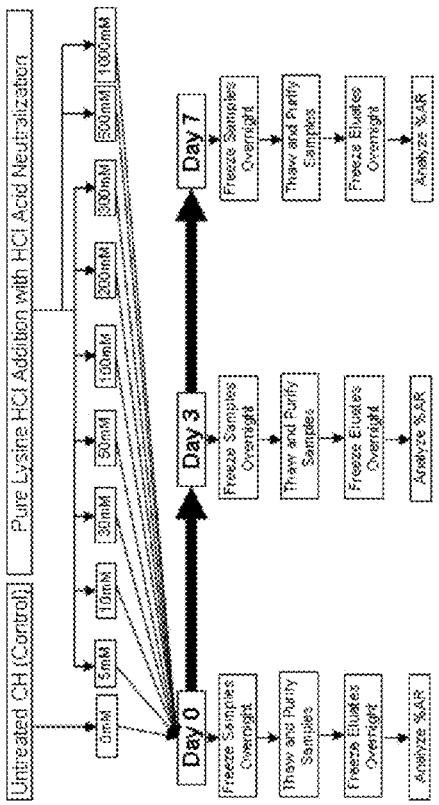
Figure 129) Histidine sample preparation scheme
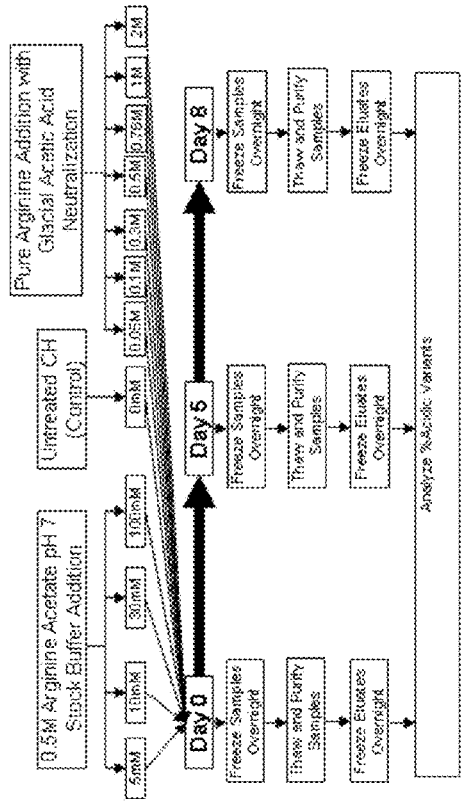
Figure 130) Lysine sample preparation scheme

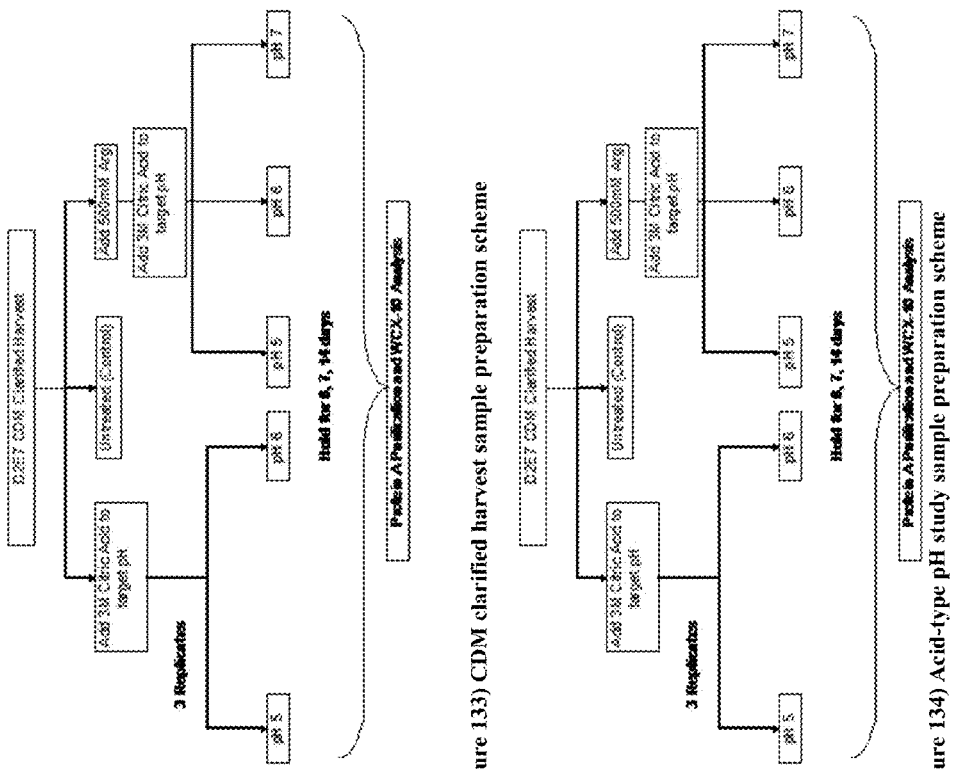
Figure 133) CDM clarified harvest sample preparation scheme
Figure 134) Acid-type pH study sample preparation scheme
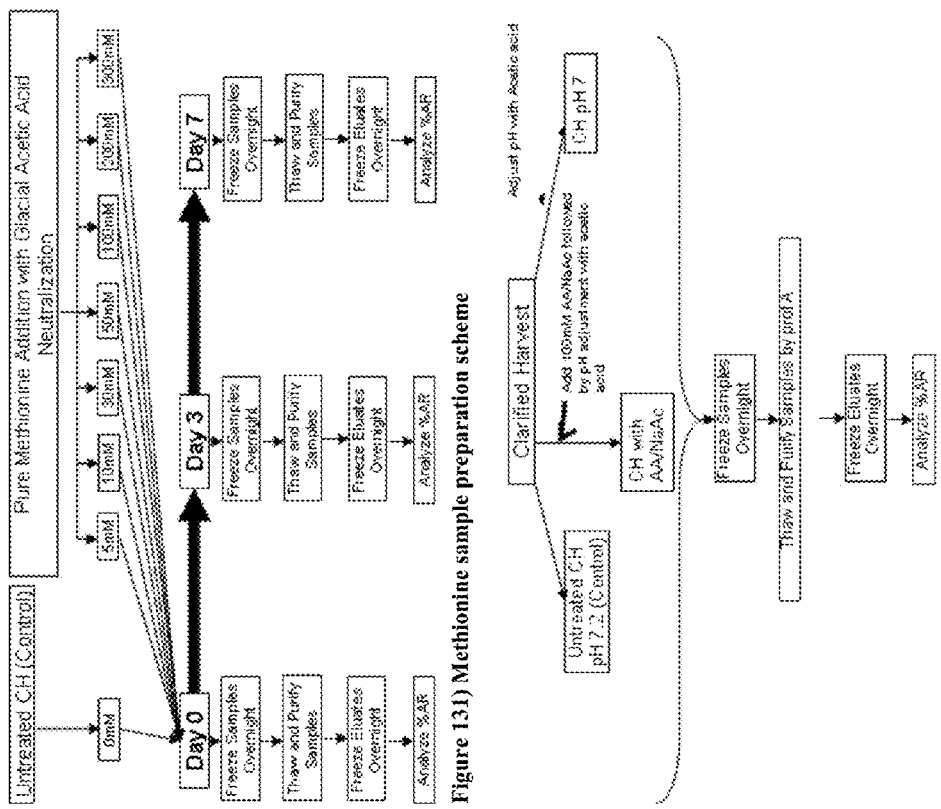
Figure 131) Methionine sample preparation scheme
Figure 132) Amino acid sample preparation scheme

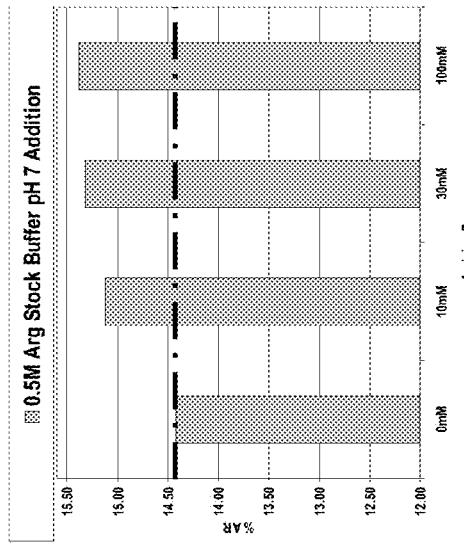

Figure 135) Effect of low pH treatment with subsequent neutralization on initial acidic variant content

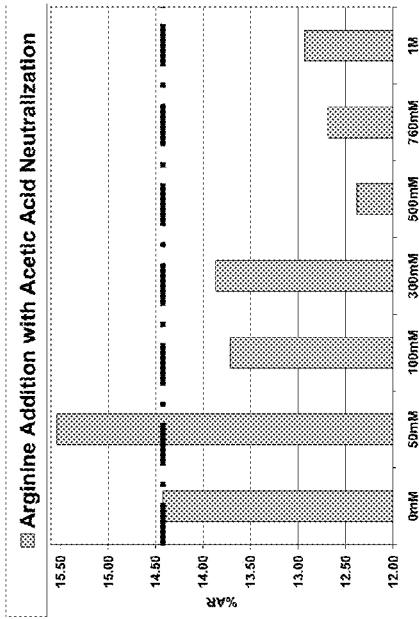

Figure 137) Effect of sample preparation method on initial acidic variant content

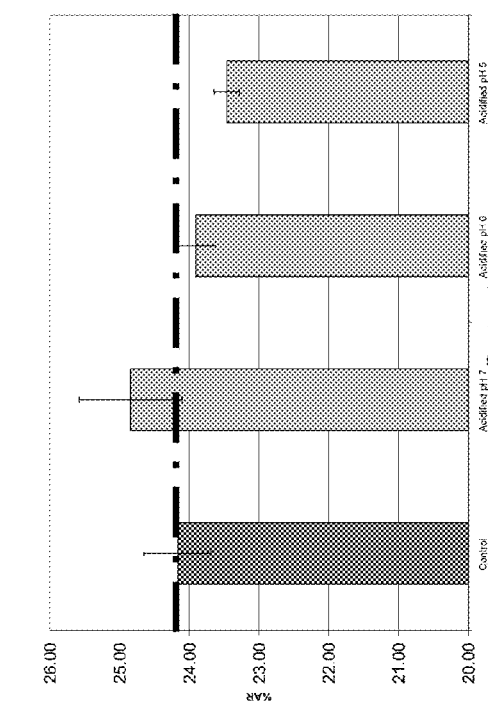

Figure 136) Effect of low pH treatment with subsequent neutralization on acidic variant formation rate

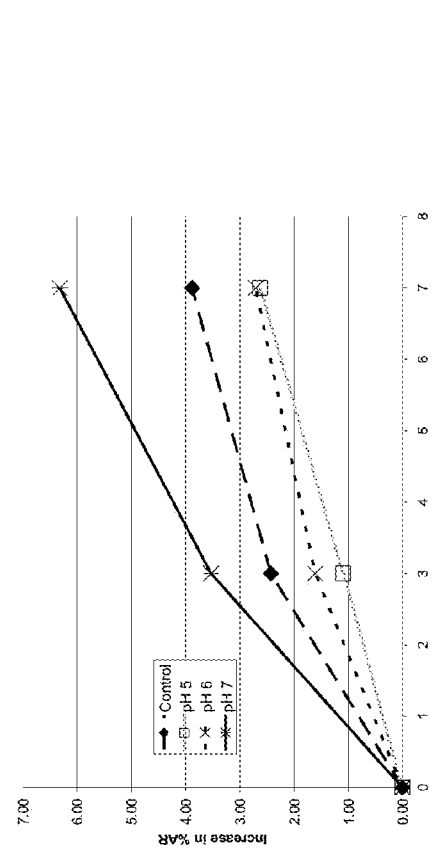

Figure 138) Effect of sample preparation method on initial acidic variant content

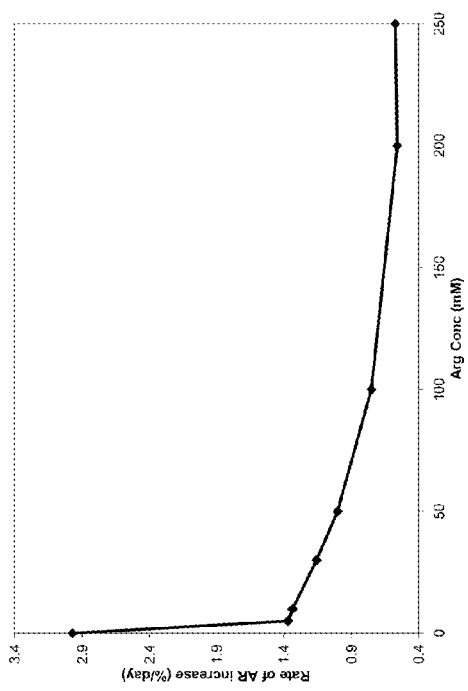
Figure 139) Dose dependent effect of arginine on reduction of acidic variant formation rate
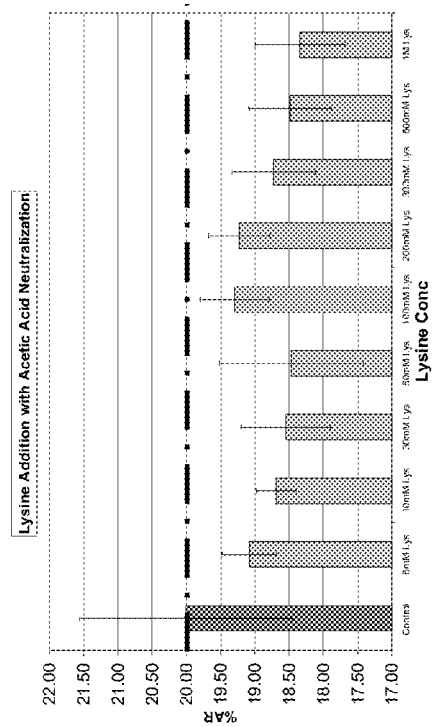
Figure 141) Effect of histidine concentration on acidic variant formation rate
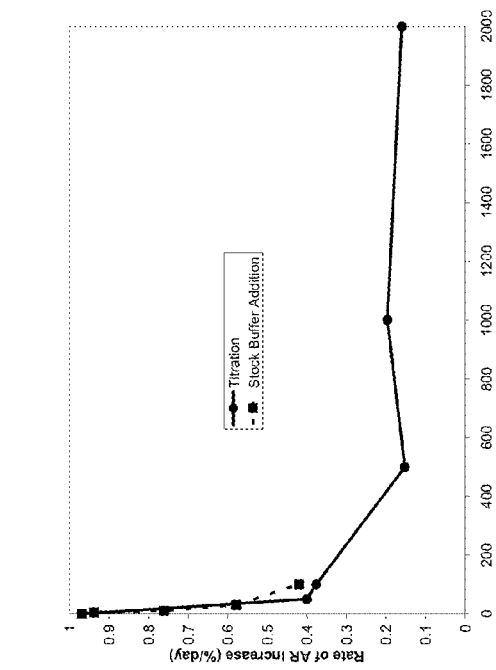
Figure 140) Effect of histidine concentration on initial acidic variant content
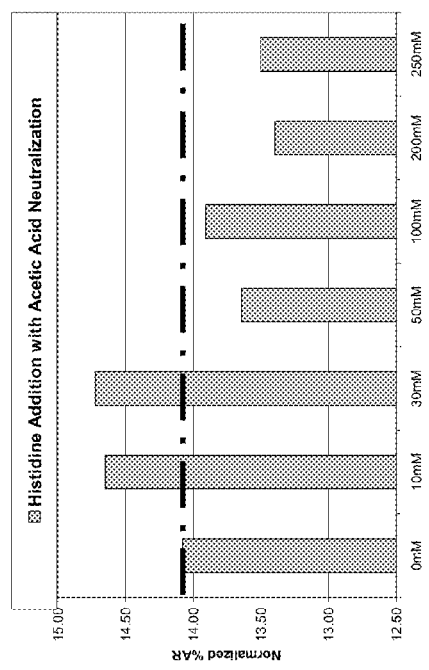
Figure 142) Effect of lysine on initial acid variant content

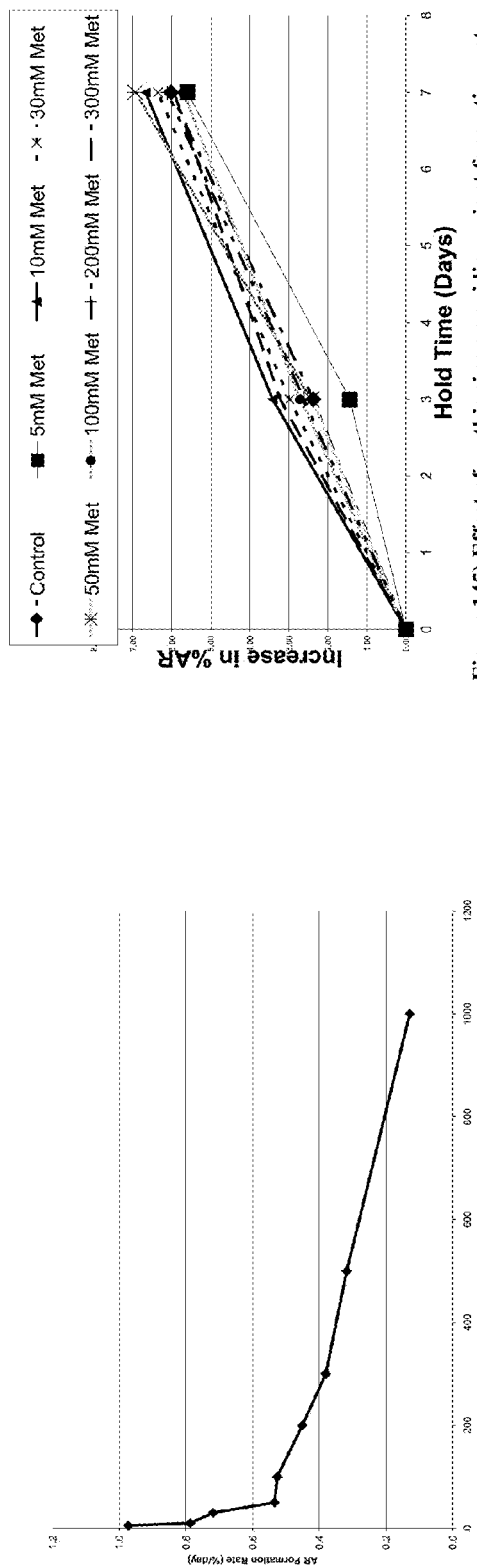
Figure 143) Effect of lysine on acidic variant formation rate
Figure 144) Effect of methionine on initial acid variant content
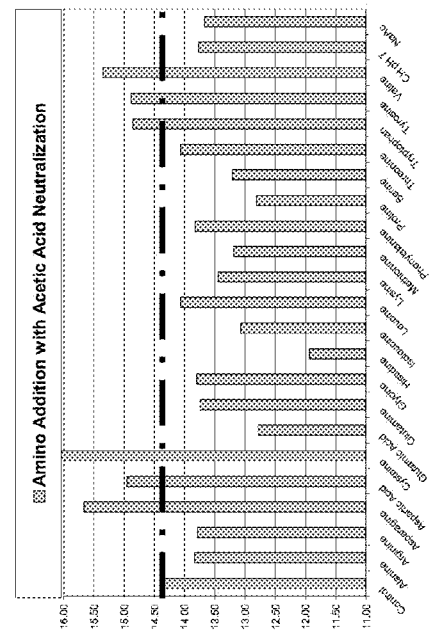
Figure 145) Effect of methionine on acidic variant formation rate
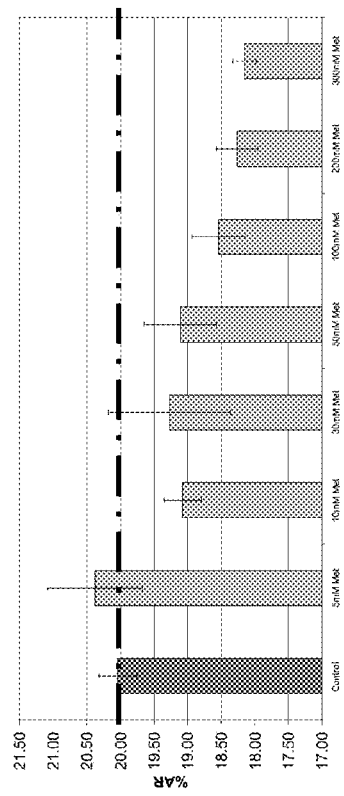
Figure 146) Effect of amino acids on initial acid variant content

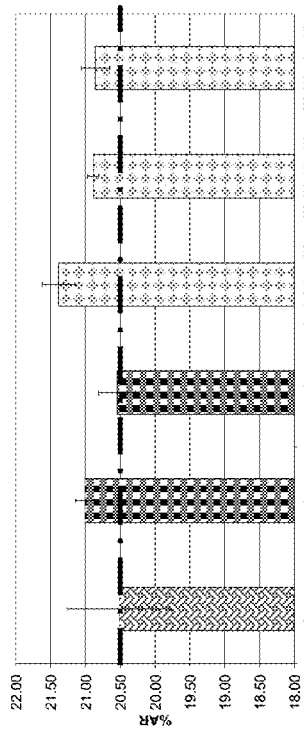
Figure 149) Effect of alternative additives on acidic variant formation rate
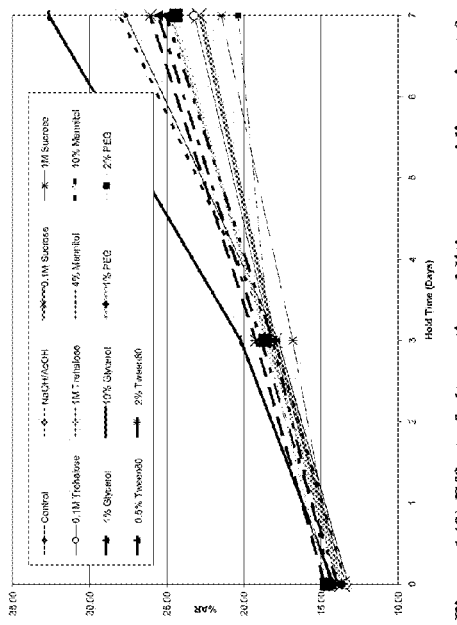
Figure 147) Effect of amino acids on acidic variant formation rate
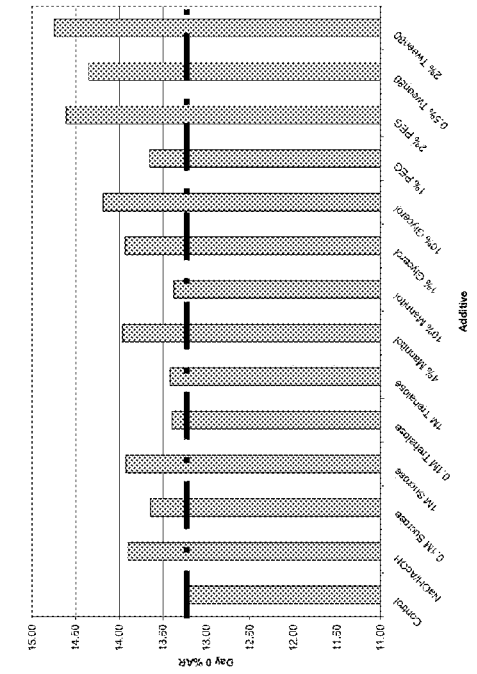
Figure 150) Effect of low pH/arginine treatment on adalimumab CDM initial acid variant content
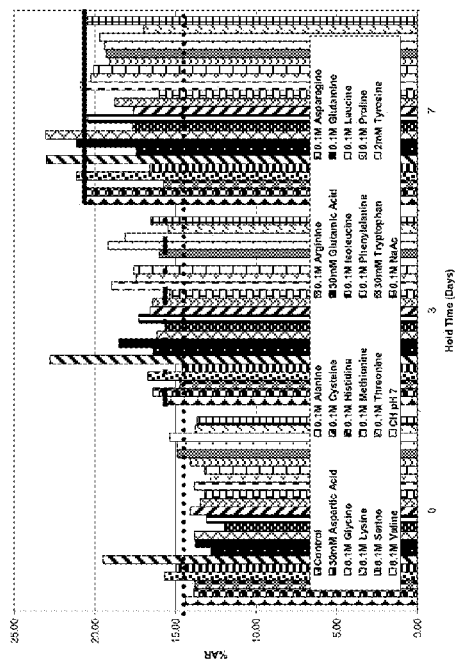
Figure 148) Effect of alternative additives on initial acid variant content

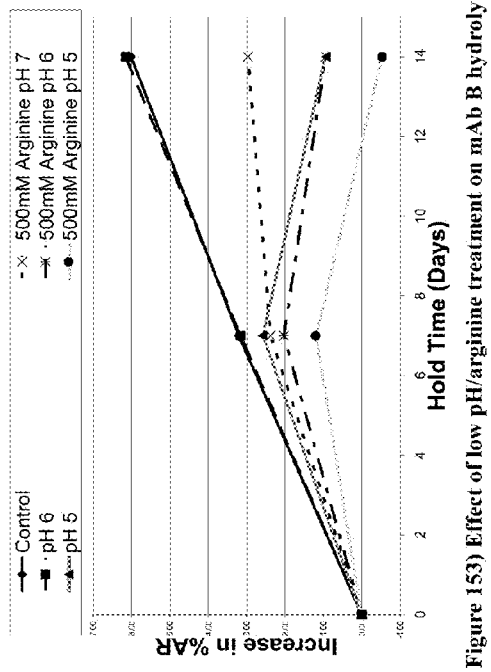

Figure 151) Effect of low pH/arginine treatment on adalimumab CDM acidic variant formation rate

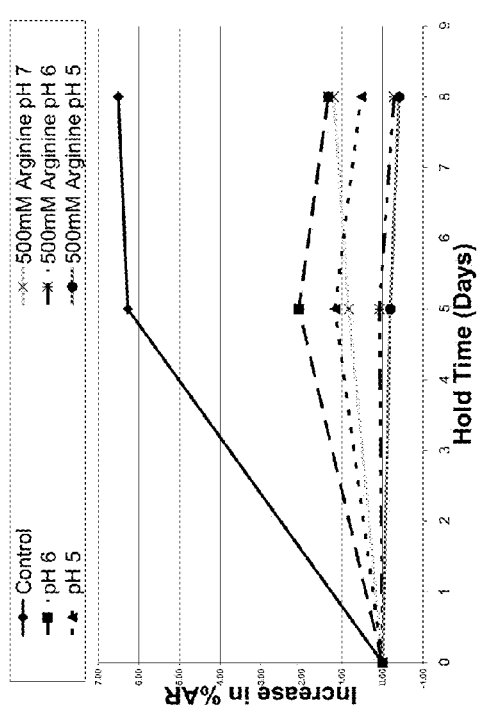

Figure 152) Effect of low pH/arginine treatment on mAb B hydrolysate initial acid variant content

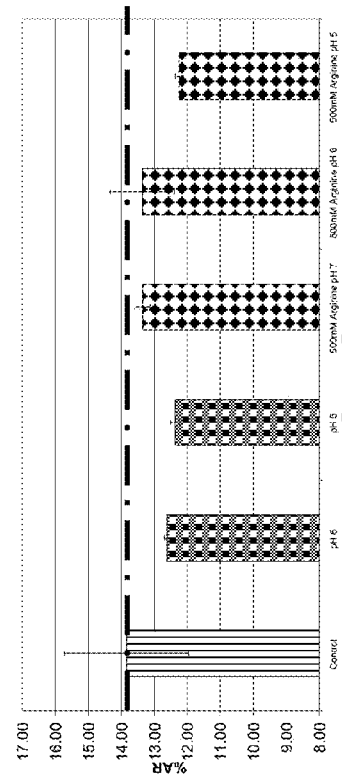

Figure 153) Effect of low pH/arginine treatment on mAb B hydrolysate acidic variant formation rate

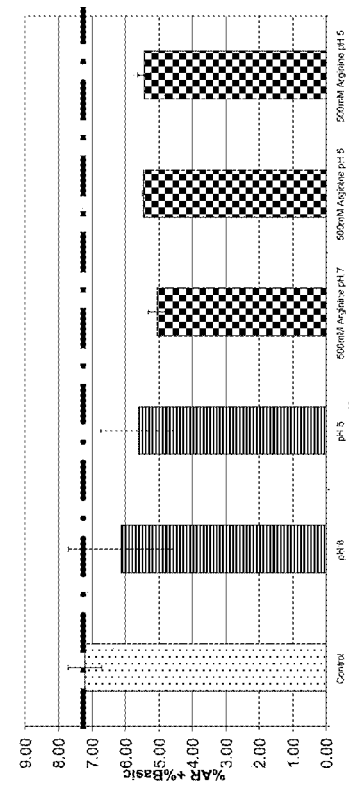

Figure 154) Effect of low pH/arginine treatment on mAb C hydrolysate initial acid variant content

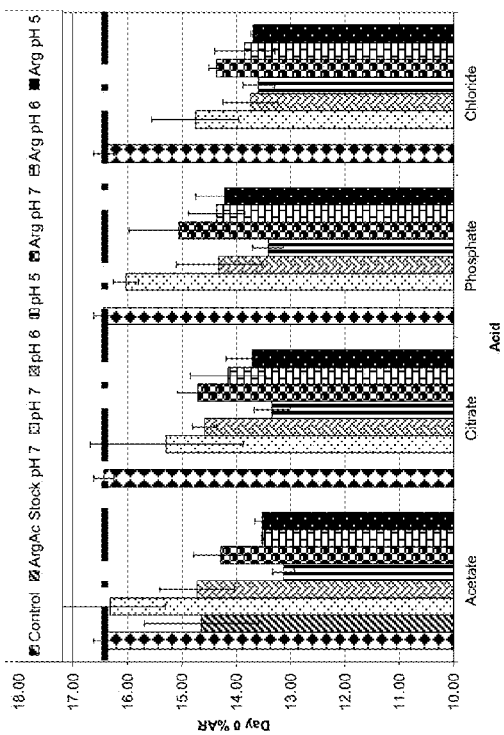
Figure 156) Effect of acid type/pH on acid variant content
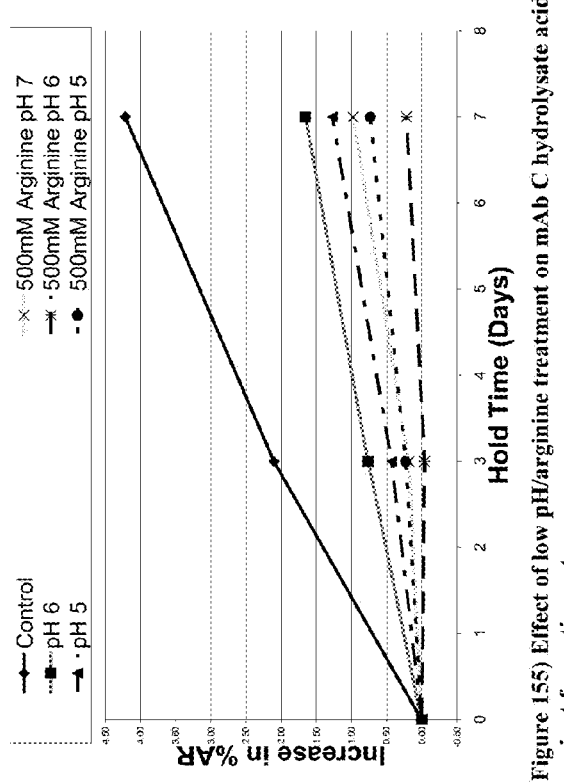
Figure 155) Effect of low pH/arginine treatment on mAb C hydrolysate acidic variant formation rate

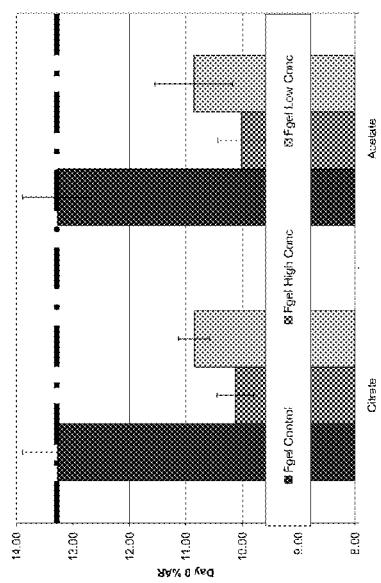
Figure 158) Effect of acid concentration on acid variant content
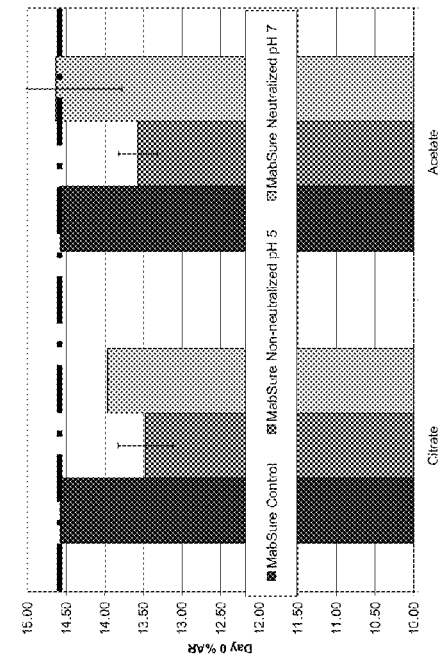
Figure 159) Effect of neutralization on acid variant content
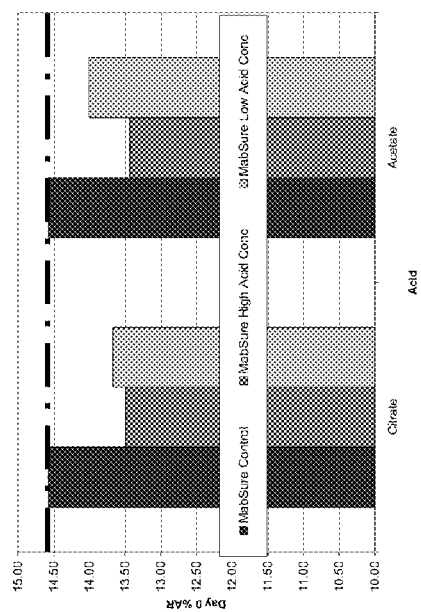
Figure 157) Effect of acid concentration on acid variant content

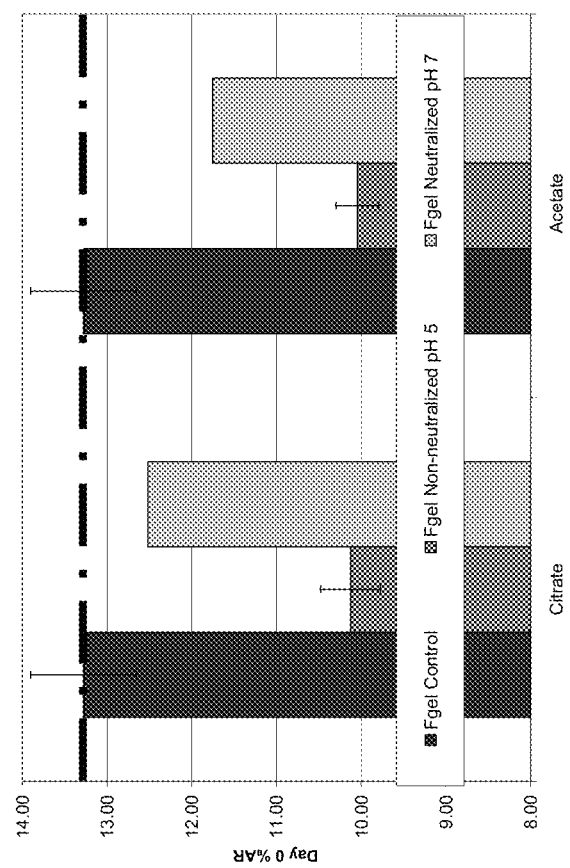
Figure 160) Effect of neutralization on acid variant content

Figure 162: Total ion current of the Lys-C peptide map and mass filter traces of a modified and non-modified peptides used for quantification. Spectra below confirm identity.

Figure 164: AR Growth at 25°C

Figure 165: Process Chromatogram of pH Gradient Elution

Figure 166: Process Chromatogram of Linear Gradient Elution by increasing Anion Concentration Figure 167: Process Chromatogram of Fractionation of 300 g/L Load and Wash Figure 168: Effect of pH on AR reduction Figure 169: Process Chromotogram at Different Salt (Cation) Concentrations Figure 170: Recovery versus AR reduction Figure 171: WCX-10 Profile of Glycated Load Material and CEX Eluate Figure 172: WCX 10 Profile of MGO Modified Load Material and Eluate from CEX Column Employing Toyo Pearl MX TRP 650M Resin Figure 173: Change in Lysine Distribution during CEX chromatography – effect of Tris concentration Figure 174: Effect of pH and conductivity on adalimumab AR reduction and recovery yield Note: AR reductions and protein recovery yields were calculated based on the Flow Through fractions at about loading 200 g protein per L of resin Figure 175: AR Reduction Achieved with the Corresponding Protein Recovery Figure 176: Total adalimumab Protein concentration levels and AR levels during Flow Through and Wash Figure 177: Total mAb B Protein concentration levels and AR levels during Flow Through and Wash Figure 178: Total mAb C Protein concentration levels and AR levels during Flow Through and Wash Figure 179: Cumulative % AR Breakthrough of mAb C on Different MM Resins Figure 180: Impact of pH-pI and Conductivity on adalimumab AR Reduction Figure 181: Impact of pH-pI and Conductivity on mAb B AR Reduction Figure 182: Impact and trend of pH-pI on mAb C AR reduction with multiple resins

Figure 183: Effect of pH and Conductivity on AR reduction and Yield

Note: AR reductions and protein recovery yields were calculated based on the Flow Through fractions at about loading 200 g protein per L of resin Figure 184: AR reduction and Protein recovery vs. pH Note: adalimumab in Protein A eluate containing 20 mM acetate was adjusted to target pH with 400 mM Arginine solution. The final conductivity was 1 mS/cm.

Figure 185: Effect of pH, conductivity and protein load amount on AR reduction and Yield

Figure 186: Effect of pH, conductivity and protein load amount on AR reduction and Yield Figure 187: Effect of AEX adsorbent pKa

Figure 188

Acidic Variants Summary

Charge — afucosylation, deamidation, citric acid, MGO, glycation

Structure — glycosylation, acetonation

Fragmentation — HC VD missing, C-terminal truncation, Fab fragment

Acidic Region 1

Acidic Region 2 — glycation, deamidation

Legend: Formed during cell culture; Formed during storage; Formed during both

SEQUENCE LISTING

```
<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
```

```
                  20                  25                  30
Ala Met His Trp Val Arg Gln Ala Pro Gly Lys Gly Leu Glu Trp Val
              35                  40                  45

Ser Ala Ile Thr Trp Asn Ser Gly His Ile Asp Tyr Ala Asp Ser Val
      50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                  85                  90                  95

Ala Lys Val Ser Tyr Leu Ser Thr Ala Ser Ser Leu Asp Tyr Trp Gly
              100                 105                 110

Gln Gly Thr Leu Val Thr Val Ser Ser
          115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15
```

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc        60
atcacttgtc gggcaagtca gggcatcaga aattacttag cctggtatca gcaaaaacca       120
gggaaagccc ctaagctcct gatctatgct gcatccactt tgcaatcagg ggtcccatct       180
cggttcagtg gcagtggatc tgggacagat ttcactctca ccatcagcag cctacagcct       240
gaagatgttg caacttatta ctgtcaaagg tataaccgtg caccgtatac ttttggccag       300
gggaccaagg tggaaatcaa a                                                 321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc        60
tcctgtgcgg cctctggatt cacctttgat gattatgcca tgcactgggt ccggcaagct       120
ccagggaagg gcctggaatg gtctcagct atcacttgga atagtggtca catagactat       180
gcggactctg tgagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                     363

<210> SEQ ID NO 11
<211> LENGTH: 214
<212> TYPE: PRT

-continued

<213> ORGANISM: Artificial Sequence
<220> FEATURE:
<223> OTHER INFORMATION: adalimumab light chain

<400> SEQUENCE: 11

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

LOW ACIDIC SPECIES COMPOSITIONS AND METHODS FOR PRODUCING AND USING THE SAME

RELATED APPLICATIONS

This application is a divisional application of U.S. patent application Ser. No. 14/077,871, filed on Nov. 12, 2013, pending, which claims priority to U.S. Provisional Patent Application Ser. No. 61/893,068, filed on Oct. 18, 2013, the contents of each of which are hereby incorporated herein by reference in their entirety.

SEQUENCE LISTING

This specification incorporates by reference the Sequence Listing submitted via EFS web on Dec. 29, 2014 identified as 73904seqlist.txt, which is 10,923 bytes, and was created on Dec. 29, 2014. The Sequence Listing, electronically filed, does not extend beyond the scope of the specification and does not contain new matter.

BACKGROUND OF THE INVENTION

The production of compositions comprising proteins for biopharmaceutical applications involves the use of upstream process technologies (e.g., cell culture) and downstream process technologies (e.g., protein purification) that are known to produce proteins exhibiting varying levels of protein variants and impurities within the composition. Such protein variants include, but are not limited to, the presence of acidic species, including process-related impurities. For example, in monoclonal antibody (mAb) preparations, acidic species can be detected by various methods, such as ion exchange chromatography, for example, WCX-10 HPLC (a weak cation exchange chromatography) or IEF (isoelectric focusing). Because of their similar chemical characteristics to the antibody product molecules of interest, reduction of acidic species is a challenge in monoclonal antibody production.

Reduction of acidic species is particularly advantageous in the context of commercially produced recombinant biotherapeutics, as they have the potential to impact numerous product characteristics, including, but not limited to, product stability, product safety and product efficacy. Accordingly, there remains a need in the art for low acidic species compositions and high-efficiency methods of producing protein compositions, e.g., antibodies, having low levels of acidic species.

SUMMARY OF THE INVENTION

The present invention is based on the identification and optimization of upstream and downstream process technologies for protein production, e.g., production of antibodies or antigen-binding portions thereof, resulting in the production of compositions comprising proteins that comprise low percentages of acidic species. As demonstrated herein, these low acidic species compositions have improved therapeutic efficacy and improved biological properties, for example, increased cartilage tissue penetration, reduced cartilage destruction, reduced synovial proliferation, reduced bone erosion, increased protection against the development of arthritis as measured by arthritic scores and/or histopathology scores, reduced cell infiltration, reduced proteoglycan loss, reduced chondrocyte death, and/or increased TNFα affinity, as compared to a non-low acidic species composition.

Accordingly, in one embodiment, the present invention provides a low acidic species (low AR) composition comprising an antibody, or antigen-binding portion thereof, where the composition comprises about 15% or less AR. In one aspect of this embodiment, the low AR composition comprises about 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. In one aspect of this embodiment, the present invention provides a low AR composition comprising an antibody, or antigen-binding portion thereof, where the composition comprises about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, about 8% to about 10% AR, or about 10% to about 15% AR, and ranges within one or more of the preceding.

In one embodiment, the low AR composition comprises a first acidic species region (AR1) and a second acidic species region (AR2). In one aspect of this embodiment, the low AR composition comprises about 0.1% or less AR1 and about 3% or less AR2, or about 0.0% AR1 and about 1.4% or less AR2. In a related embodiment, the low AR composition comprises about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. In one aspect of this embodiment, the present invention provides a low AR composition comprising an antibody, or antigen-binding portion thereof, where the composition comprises about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In one aspect of this embodiment, the low AR composition comprises about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the present invention provides a low AR composition comprising an antibody, or antigen-binding portion thereof, where the composition comprises about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

In another embodiment, the low AR composition, e.g., a low AR composition of adalimumab, comprises about 1.4% or less AR. For example, in one aspect of this embodiment, the low AR composition, e.g., a low AR composition of adalimumab comprising about 1.4% or less AR can comprise about 0.0% AR1 and about 1.4% or less AR2.

In another aspect, the present invention provides compositions comprising an antibody, or antigen-binding portion thereof, wherein the composition is substantially free of acidic species and other process-related impurities, including, for example, host cell proteins (HCPs), host nucleic acids, chromatographic materials, and/or media components, as well as product related impurities such as aggregates.

In one embodiment, the antibody, or antigen-binding portion thereof, of the compositions disclosed herein is an anti-TNFα antibody, or antigen-binding portion thereof. For example, in one aspect of this embodiment, the anti-TNFα antibody, or antigen-binding portion thereof, dissociates from human TNFα with a $K_d$ of about $1\times10^{-8}$ M or less and a $K_{off}$ rate constant of $1\times10^{-3}$ S$^{-1}$ or less. In another aspect of this embodiment, the anti-TNFα antibody, or antigen-binding portion thereof, comprises a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4.

In still another aspect of this embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2. In yet another aspect of this embodiment, the anti-TNFα antibody, or antigen-binding portion thereof, is adalimumab, or an antigen binding-portion thereof.

In one embodiment, the low AR composition of the invention comprises adalimumab, and has a percentage of AR that is not the same as the percentage of AR present in adalimumab formulated as HUMIRA® as currently approved and described in the "Highlights of Prescribing Information" for HUMIRA® (adalimumab) Injection (Revised January 2008), the contents of which are hereby incorporated herein by reference.

In another embodiment, the low AR composition of the invention comprises adalimumab, and has a percentage of AR that is lower than the percentage of AR present in adalimumab formulated as HUMIRA® as currently approved and described in the "Highlights of Prescribing Information" for HUMIRA® (adalimumab) Injection (Revised January 2008), the contents of which are hereby incorporated herein by reference.

In another embodiment, the present invention provides low AR compositions comprising an anti-TNFα antibody, or antigen-binding portion thereof, comprising a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4, wherein the composition comprises less than about 10% AR. In one aspect of this embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2, wherein the composition comprises less than about 10% AR. In another aspect of this embodiment, the anti-TNFα antibody, or antigen-binding portion thereof, is adalimumab, or an antigen binding-portion thereof, and the composition comprises less than about 10% AR. In one aspect of this embodiment, the low AR composition comprising an anti-TNFα antibody, or antigen-binding portion thereof, comprises about 0.1% or less AR1 and about 3% or less AR2, or about 0.0% AR1 and about 1.4% or less AR2.

In one embodiment, the acidic species in the low AR composition comprising an antibody, or antigen-binding portion thereof (e.g., an anti-TNFα antibody, or antigen binding portion thereof, such as adalimumab) comprise one or more variants selected from the group consisting of charge variants, structure variants and fragmentation variants (see, for example, FIG. 188).

For example, in one aspect of this embodiment, the charge variants in the low AR composition are AR1 species and comprise, for example, deamidation variants, glycation variants, afucosylation variants, methylglyoxal (MGO) variants or citric acid variants. For example, when the low AR composition comprises adalimumab, the deamidation variants can result from deamidation occurring at asparagine residues comprising Asn393 and Asn329 of adalimumab and at glutamine residues comprising Gln3 and Gln6. In another aspect of this embodiment, when the low AR composition comprises adalimumab, the glycation variants can result from glycation occurring at Lys98 and Lys151 of adalimumab.

In another aspect of this embodiment, the structure variants in the low AR composition comprising an antibody, or antigen-binding portion thereof (e.g., an anti-TNFα antibody, or antigen binding portion thereof, such as adalimumab) are AR1 species and comprise, for example, glycosylation variants or acetonation variants.

In still another aspect of this embodiment, the fragmentation variants in the low AR composition comprising an antibody, or antigen-binding portion thereof (e.g., an anti-TNFα antibody, or antigen binding portion thereof, such as adalimumab), are AR1 species and comprise, for example, Fab fragment variants, C-terminal truncation variants or variants missing a heavy chain variable domain.

In another embodiment, the acidic species in the low AR composition comprising an antibody, or antigen-binding portion thereof (e.g., an anti-TNFα antibody, or antigen binding portion thereof, such as adalimumab), are AR2 species, and comprise charge variants, such as deamidation variants or glycation variants. For example, when the low AR composition comprises adalimumab, the deamidation variants can result from deamidation occurring at asparagine residues comprising Asn393 and Asn329 of adalimumab and at glutamine residues comprising Gln3 and Gln6. In another aspect of this embodiment, when the low AR composition comprises adalimumab, the glycation variants result from glycation occurring at Lys98 and Lys151 of adalimumab.

In one embodiment, the percent of acidic species in a low AR composition is determined using ion exchange chromatography, for example WCX-10 HPLC. In another aspect of this embodiment, the percent acidic species in a low AR composition is determined using isoelectric focusing (IEF).

In one embodiment, the low AR compositions of the invention comprise product preparation-derived acidic species. For example, in one aspect of this embodiment, the acidic species are cell culture-derived acidic species. In another aspect of this embodiment, the acidic species of the low AR compositions are storage-derived acidic species which are primarily generated when stored under process, intermediate or shelf storage conditions prior to use.

In still another embodiment, the invention provides low AR compositions that further comprise a pharmaceutically acceptable carrier.

In another aspect, the present invention provides methods for treating a subject having a disorder in which TNFα is detrimental, by administering to the subject a low AR composition of the invention, e.g., a low AR adalimumab composition, thereby treating the subject having a disorder in which TNFα is detrimental. In one aspect of this embodiment, the disorder in which TNFα is detrimental is selected from the group consisting of rheumatoid arthritis (RA), psoriasis, psoriatic arthritis, ankylosing spondylitis, juvenile idiopathic arthritis (JIA), ulcerative colitis, and Crohn's Disease.

In one aspect, upstream methods for producing the low AR compositions of the invention are included. In one embodiment, a method for producing a low acidic species composition comprising an antibody, or antigen binding portion thereof, comprises culturing cells expressing the antibody, or antigen binding portion thereof, in a cell culture media comprising an increased concentration of an amino acid selected from the group consisting of arginine, lysine, ornithine and histidine, or a combination thereof, as compared to the amino acid concentration in cell culture media used to produce a non-low acidic species composition comprising the antibody, or antigen binding portion thereof. In another aspect of this embodiment, the amino acid concentration in the culture media is between about 0.025 and 20 g/L.

In another embodiment, a method for producing a low acidic species composition comprising an antibody, or antigen binding portion thereof, comprises culturing cells expressing the antibody, or antigen binding portion thereof, in a cell culture media comprising an increased concentration of calcium as compared to the calcium concentration in cell culture media used to produce a non-low acidic species composition comprising the antibody, or antigen binding portion thereof. In one aspect of this embodiment, the calcium concentration is between about 0.005 and 5 mM. In another aspect of this embodiment, the cell culture media further comprises an increased concentration of an amino acid selected from the group consisting of arginine, lysine, ornithine and histidine, or a combination thereof, as compared to the amino acid concentration in cell culture media used to produce a non-low acidic species composition comprising the antibody, or antigen binding portion thereof.

In still another embodiment, a method for producing a low acidic species composition comprising an antibody, or antigen binding portion thereof, comprises culturing cells expressing the antibody, or antigen binding portion thereof, in a cell culture media comprising an increased concentration of niacinamide, calcium, and at least one amino acid, as compared to the concentration of niacinamide, calcium, and amino acid in the cell culture media used to produce a non-low acidic species composition comprising the antibody, or antigen binding portion thereof. In one aspect of the embodiment, the at least one amino acid is selected from the group consisting of arginine, lysine, ornithine and histidine, and combinations thereof.

In yet another embodiment, a method for producing a low acidic species composition comprising an antibody, or antigen binding portion thereof, comprises culturing cells expressing the antibody, or antigen binding portion thereof, in a cell culture media having a pH of between about 7.1-about 6.8.

In still another embodiment, a method for producing a low acidic species composition comprising an antibody, or antigen binding portion thereof, comprises culturing cells expressing the antibody, or antigen binding portion thereof, in a cell culture media having an altered exchange rate as compared to the exchange rate of cell culture media used to produce a non-low acidic species composition comprising the antibody, or antigen binding portion thereof.

In another embodiment, a method for producing a low acidic species composition comprising an antibody, or antigen binding portion thereof, comprises culturing cells expressing the antibody, or antigen binding portion thereof, extracting a clarified harvest from the cell culture, and adding one or more amino acids to the clarified harvest. In one aspect of this embodiment, the one or more amino acids are selected from the group consisting of arginine, histidine, lysine, aspartic acid, glutamic acid and leucine, and combinations thereof.

In yet another embodiment, a method for producing a low acidic species composition comprising an antibody, or antigen binding portion thereof, comprises culturing cells expressing the antibody, or antigen binding portion thereof, extracting a clarified harvest from the cell culture, and adjusting the pH of the clarified harvest to between about 4.5 and 6.5.

In another aspect of the invention, upstream methods for producing the low AR compositions of the invention are included. In one embodiment, the invention includes a method for producing a low acidic species composition comprising an antibody, or antigen binding portion thereof, comprising contacting a first sample comprising the antibody, or antigen binding portion thereof, to a chromatography media, wherein the contact occurs in the context of a loading buffer; washing the chromatography media with a wash buffer that is substantially the same as the loading buffer; and collecting a chromatography sample, wherein the chromatography sample comprises a composition of the antibody, or antigen binding portion thereof, which contains less than about 10% acidic species, thereby producing a low acidic species composition comprising an antibody, or antigen binding portion thereof. In one aspect of this embodiment, the bound antibody material is eluted with a buffer having a different composition than the wash buffer. In another aspect of this embodiment, the chromatography media is selected from the group consisting of anion exchange adsorbent material, cation exchange adsorbent material, mixed mode media, cation exchange mixed mode media, and anion exchange mixed mode media. In one embodiment, the chromatography media is a mixed mode media comprising cation exchange (CEX) and hydrophobic interaction functional groups. In another embodiment, the chromatography media is a mixed mode media comprising anion exchange (AEX) and hydrophobic interaction functional groups. For example, the mixed mode media may be Capto MMC resin, the CEX resin may be the Poros XS resin, and the AEX resin may be the Poros 50HQ resin.

In one embodiment, the chromatography media is a CEX adsorbent material or a mixed mode media, and the pH of the loading and wash buffers is lower than the isoelectric point of the antibody. In another embodiment, the chromatography sample contains a reduced level of antibody fragments as compared to the first sample. In still another embodiment, the chromatography sample contains a reduced level of host cell proteins as compared to the first sample. In yet another embodiment, the chromatography sample contains a reduced level of one or more of charge variants (e.g., deamidation variants, glycation variants, afucosylation variants, MGO variants or citric acid variants), structure variants (e.g., glycosylation variants or acetonation variants), or fragmentation variants (e.g., Fab fragment variants, C-terminal truncation variants or variants missing a heavy chain variable domain) as compared to the first sample.

In one embodiment, a method for producing a low acidic species composition comprising an antibody, or antigen binding portion thereof, comprises contacting a first sample comprising the antibody, or antigen binding portion thereof, to an affinity chromatography media (e.g., a Protein A resin) in a load buffer, and eluting said sample from the affinity chromatography media as a first eluted sample; contacting the first eluted sample to an anion exchange (AEX) chromatography adsorbent material (e.g., a Poros 50HQ resin) in a load buffer, and eluting said sample from the AEX chromatography adsorbent material as a second eluted sample; and contacting the second eluted sample to a cation exchange (CEX) chromatography adsorbent material (e.g., a Poros XS resin) in a load buffer, and eluting said sample from the CEX chromatography adsorbent material as a third eluted sample, wherein the third eluted sample comprises a composition of the antibody, or antigen binding portion thereof, which contains less than about 3% acidic species, thereby producing a low acidic species composition comprising an antibody, or antigen binding portion thereof. In one embodiment, the second eluted sample is contacted to a CEX chromatography at least one additional time. In one embodiment, the method further comprises performing viral filtration on the third eluted sample resulting in a filtered sample. In another embodiment, the method further comprises filtering the filtered sample using ultrafiltration/diafilteration (UF/DF).

In another aspect, the invention provides a method for producing a low acidic species composition comprising an antibody, or antigen binding portion thereof, the method comprising contacting a sample comprising an antibody, or antigen binding portion thereof to one or more of the group consisting of: an anion exchange (AEX) chromatography adsorbent material, a cation exchange (CEX) chromatography adsorbent material, a mixed mode media, a cation exchange mixed mode media, and an anion exchange mixed mode media, in a load buffer, and eluting the sample from the AEX chromatography adsorbent material, the CEX chromatography adsorbent material, the mixed mode media, the cation exchange mixed mode media, or the anion exchange mixed mode media, wherein the eluted sample comprises a composition of the antibody, or antigen binding portion thereof, which contains less than about 3% acidic species, thereby producing a low acidic species composition comprising an antibody, or antigen binding portion thereof. In one aspect of this embodiment, the method further comprises contacting the eluted sample to a hydrophobic interaction chromatography (HIC) media.

The present invention is further illustrated by the following detailed description and claims.

BRIEF DESCRIPTION OF THE DRAWINGS

FIG. 1 depicts the effect of total arginine concentration in adalimumab producing cell line 2, media 1 on viable cell density (n=2).

FIG. 2 depicts the effect of total arginine concentration in adalimumab producing cell line 2, media 1 on viability (n=2).

FIG. 3 depicts the effect of total arginine concentration in adalimumab producing cell line 2, media 1 on harvest titer (n=2).

FIG. 4 depicts the effect of total arginine concentration in adalimumab producing cell line 2, media 1 on day 10 WCX-10 profile total acidic regions (n=2).

FIG. 5 depicts the effect of total arginine concentration in adalimumab producing cell line 2, media 1 on day 12 WCX-10 profile total acidic regions (n=2).

FIG. 6 depicts the effect of total arginine concentration in adalimumab producing cell line 3, media 1 on viable cell density (n=2).

FIG. 7 depicts the effect of total arginine concentration in adalimumab producing cell line 3, media 1 on viability (n=2).

FIG. 8 depicts the effect of total arginine concentration in adalimumab producing cell line 3, media 1 on harvest titer (n=2).

FIG. 9 depicts the effect of total arginine concentration in adalimumab producing cell line 3, media 1 on WCX-10 profile total acidic regions (n=2).

FIG. 10 depicts the effect of total arginine concentration in adalimumab producing cell line 1, media 1 on WCX-10 profile total acidic regions (n=2).

FIG. 11 depicts the effect of arginine addition to adalimumab producing cell line 1, media 2 on day 11 on WCX-10 profile total acidic regions (n=2).

FIG. 12 depicts the effect of arginine addition to adalimumab producing cell line 2, media 3 on WCX-10 profile total acidic regions (n=2).

FIG. 13 depicts the effect of total arginine concentration in mAb1 producing cell line on WCX-10 profile total acidic regions (n=1).

FIG. 14 depicts the effect of total arginine concentration in mAb2 producing cell line on WCX-10 profile total acidic regions (n=2)

FIG. 15 depicts the effect of carboxypeptidase digestion of product from adalimumab producing cell line 3, media 1 experiment on WCX-10 profile total acidic regions (n=1).

FIG. 16 depicts the effect of carboxypeptidase digestions of product from mAb2 producing cell line on WCX-10 profile total acidic regions (n=2).

FIG. 17 depicts the effect of total lysine concentration in adalimumab producing cell line 2, media 1 on viable cell density (n=2).

FIG. 18 depicts the effect of total lysine concentration in adalimumab producing cell line 2, media 1 on viability (n=2).

FIG. 19 depicts the effect of total lysine concentration in adalimumab producing cell line 2, media 1 on harvest titer (n=2).

FIG. 20 depicts the effect of total lysine concentration in adalimumab producing cell line 2, media 1 on WCX-10 profile total acidic regions (n=2).

FIG. 21 depicts the effect of total lysine concentration in adalimumab producing cell line 3, media 1 on viable cell density (n=2).

FIG. 22 depicts the effect of total lysine concentration in adalimumab producing cell line 3, media 1 on viability (n=2).

FIG. 23 depicts the effect of total lysine concentration in adalimumab producing cell line 3, media 1 on harvest titer (n=2).

FIG. 24 depicts the effect of total lysine concentration in adalimumab producing cell line 3, media 1 on WCX-10 profile total acidic regions (n=2).

FIG. 25 depicts the effect of total lysine concentration in adalimumab producing cell line 1, media 1 on WCX-10 profile total acidic regions (n=2).

FIG. 26 depicts the effect of lysine addition to adalimumab producing cell line 1, media 2 on WCX-10 profile total acidic regions (n=2).

FIG. 27 depicts the effect of lysine addition to adalimumab producing cell line 2, media 3 on WCX-10 profile total acidic regions (n=2).

FIG. 28 depicts the effect of total lysine concentration in mAb1 producing cell line on WCX-10 profile total acidic regions (n=1).

FIG. 29 depicts the effect of total lysine concentration in mAb2 producing cell line on WCX-10 profile total acidic regions (n=2).

FIG. 30 depicts the effect of carboxypeptidase digestion of product from cell line 3, media 1 experiment on WCX-10 profile total acidic regions (n=1).

FIG. 31 depicts the effect of carboxypeptidase digestions of product from mAb2 producing cell line on WCX-10 profile total acidic regions (n=2).

FIG. 32 depicts the effect of total histidine concentration in adalimumab producing cell line 2, media 1 on viable cell density (n=2).

FIG. 33 depicts the effect of total histidine concentration in adalimumab producing cell line 2, media 1 on viability (n=2).

FIG. 34 depicts the effect of total histidine concentration in adalimumab producing cell line 2, media 1 on harvest titer (n=2).

FIG. 35 depicts the effect of total histidine concentration in adalimumab producing cell line 2, media 1 on WCX-10 profile total acidic regions (n=2).

FIG. 36 depicts the effect of total histidine concentration in adalimumab producing cell line 3, media 1 on viable cell density (n=2).

FIG. 37 depicts the effect of total histidine concentration in adalimumab producing cell line 3, media 1 on viability (n=2).

FIG. 38 depicts the effect of total histidine concentration in adalimumab producing cell line 3, media 1 on harvest titer (n=2).

FIG. 39 depicts the effect of total histidine concentration in adalimumab producing cell line 3, media 1 on WCX-10 profile total acidic regions (n=2).

FIG. 40 depicts the effect of total histidine concentration in adalimumab producing cell line 1, media 1 on WCX-10 profile total acidic regions (n=2).

FIG. 41 depicts the effect of histidine addition to adalimumab producing cell line 1, media 2 on WCX-10 profile total acidic regions (n=2).

FIG. 42 depicts the effect of histidine addition to adalimumab producing cell line 2, media 3 on WCX-10 profile total acidic regions (n=2).

FIG. 43 depicts the effect of total histidine concentration in mAb1 producing cell line on WCX-10 profile total acidic regions (n=1).

FIG. 44 depicts the effect of total histidine concentration in mAb2 producing cell line on WCX-10 profile total acidic regions (n=2).

FIG. 45 depicts the effect of carboxypeptidase digestion of product from cell line 3, media 1 experiment on WCX-10 profile total acidic regions (n=1).

FIG. 46 depicts the effect of carboxypeptidase digestions of product from mAb2 producing cell line on WCX-10 profile total acidic regions (n=2).

FIG. 47 depicts the effect of total ornithine concentration in adalimumab producing cell line 2, media 1 on viable cell density (n=2).

FIG. 48 depicts the effect of total ornithine concentration in adalimumab producing cell line 2, media 1 on viability (n=2).

FIG. 49 depicts the effect of total ornithine concentration in adalimumab producing cell line 2, media 1 on harvest titer (n=2).

FIG. 50 depicts the effect of total ornithine concentration in adalimumab producing cell line 2, media 1 on WCX-10 profile total acidic regions.

FIG. 51 depicts the effect of total ornithine concentration in adalimumab producing cell line 3, media 1 on viable cell density (n=2).

FIG. 52 depicts the effect of total ornithine concentration in adalimumab producing cell line 3, media 1 on viability (n=2).

FIG. 53 depicts the effect of total ornithine concentration in adalimumab producing cell line 3, media 1 on harvest titer (n=2).

FIG. 54 depicts the effect of total ornithine concentration in adalimumab producing cell line 3, media 1 on WCX-10 profile total acidic regions (n=2).

FIG. 55 depicts the effect of total ornithine concentration in adalimumab producing cell line 1, media 1 on WCX-10 profile total acidic regions (n=2).

FIG. 56 depicts the effect of ornithine addition to adalimumab producing cell line 1, media 2 on WCX-10 profile total acidic regions (n=2).

FIG. 57 depicts the effect of ornithine addition to adalimumab producing cell line 2, media 3 on WCX-10 profile total acidic regions (n=2).

FIG. 58 depicts the effect of total ornithine concentration in mAb1 producing cell line on WCX-10 profile total acidic regions (n=1).

FIG. 59 depicts the effect of total ornithine concentration in mAb2 producing cell line on WCX-10 profile total acidic regions (n=2).

FIG. 60 depicts the effect of carboxypeptidase digestion of product from cell line 3, media 1 experiment on WCX-10 profile total acidic regions (n=1).

FIG. 61 depicts the effect of carboxypeptidase digestions of product from mAb2 producing cell line on WCX-10 profile total acidic regions (n=2).

FIG. 62 depicts the effect of multiple amino acid additions to adalimumab producing cell line 2, media 1 on WCX-10 profile total acidic regions (n=2).

FIG. 63 depicts the effect of increased arginine and lysine concentration in adalimumab producing cell line 1, media 1 on viable cell density (n=3).

FIG. 64 depicts the effect of increased arginine and lysine concentration in adalimumab producing cell line 1, media 1 on viability (n=3).

FIG. 65 depicts the effect of increased arginine and lysine concentration in adalimumab producing cell line 1, media 1 on culture titer (n=3).

FIG. 66 depicts the effect of increased arginine and lysine concentration in adalimumab producing cell line 1, media 1 on WCX-10 profile total acidic regions (n=2).

FIG. 67 depicts the effect of arginine, lysine and pH modulation to adalimumab producing cell line 1, media 1 on viable cell density (n=2).

FIG. 68 depicts the effect of arginine, lysine and pH modulation to adalimumab producing cell line 1, media 1 on viability (n=2).

FIG. 69 depicts the effect of arginine, lysine and pH modulation to adalimumab producing cell line 1, media 1 on culture titer (n=2).

FIG. 70 depicts the effect of arginine, lysine and pH modulation to adalimumab producing cell line 1, media 1 on WCX-10 profile total acidic regions (n=2).

FIG. 71 depicts the effect of total calcium concentration in adalimumab producing cell line 2, media 1 on viable cell density (n=2).

FIG. 72 depicts the effect of total calcium concentration in adalimumab producing cell line 2, media 1 on viability (n=2).

FIG. 73 depicts the effect of total calcium concentration in adalimumab producing cell line 2, media 1 on harvest titer (n=2).

FIG. 74 depicts the effect of total calcium concentration in adalimumab producing cell line 2, media 1 on WCX-10 profile total acidic regions (n=2).

FIG. 75 depicts the effect of total calcium concentration in adalimumab producing cell line 3, media 1 on viable cell density (n=2).

FIG. 76 depicts the effect of total calcium concentration in adalimumab producing cell line 3, media 1 on viability (n=2).

FIG. 77 depicts the effect of total calcium concentration in adalimumab producing cell line 3, media 1 on harvest titer (n=2)

FIG. 78 depicts the effect of total calcium concentration in adalimumab producing cell line 3, media 1 on WCX-10 profile total acidic regions (n=2).

FIG. 79 depicts the effect of total calcium concentration in adalimumab producing cell line 1, media 1 on WCX-10 profile total acidic regions (n=2).

FIG. 80 depicts the effect of calcium addition to adalimumab producing cell line 1, media 2 on WCX-10 profile total acidic regions (n=2).

FIG. 81 depicts the effect of calcium addition to adalimumab producing cell line 2, media 3 on WCX-10 profile total acidic regions (n=2).

FIG. 82 depicts the effect of total calcium concentration in mAb1 producing cell line on WCX-10 profile total acidic regions (n=2).

FIG. 83 depicts the effect of total calcium concentration in mAb2 producing cell line on WCX-10 profile total acidic regions (n=2).

FIGS. 84A-B depict the effect of multiple amino acid additions to cell line 1, media 1 on WCX-10 profile total acidic regions a) overall prediction plot, b) prediction plots for each additive (n=2).

FIG. 85 depicts the effect of niacinamide addition to adalimumab producing cell line 1, media 1 on viable cell density (n=2).

FIG. 86 depicts the effect of niacinamide addition to adalimumab producing cell line 1, media 1 on viability (n=2).

FIG. 87 depicts the effect of niacinamide addition to adalimumab producing cell line 1, media 1 on harvest titer (n=2).

FIG. 88 depicts the effect of niacinamide addition to adalimumab producing cell line 1, media 1 on Day 11 WCX-10 profile total acidic regions (n=2).

FIG. 89 depicts the effect of niacinamide addition to adalimumab producing cell line 1, media 1 on Day 12 WCX-10 profile total acidic regions (n=2).

FIG. 90 depicts the effect of niacinamide addition to mAb2 producing cell line, media 1 on viable cell density (n=2).

FIG. 91 depicts the effect of niacinamide addition to mAb2 producing cell line, media 1 on viability (n=2).

FIG. 92 depicts the effect of niacinamide addition to mAb2 producing cell line, media 1 on harvest titer (n=2).

FIG. 93 depicts the effect of niacinamide addition to mAb2 producing cell line, media 1 on WCX-10 profile total acidic regions (n=2).

FIGS. 94A-D depict the effect of amino acid supplementation to CD media GIA-1 in adalimumab-producing CHO cell line #1 on (A) culture growth, (B) culture viability, (C) acidic species, and (D) MGO modification.

FIG. 95 depicts the effect of pH modulation of adalimumab producing cell line 1, media 1 on viable cell density.

FIG. 96 depicts the effect of pH modulation of adalimumab producing cell line 1, media 1 on viability.

FIG. 97 depicts the effect of pH modulation of adalimumab producing cell line 1, media 1 on harvest titer.

FIG. 98 depicts the effect of pH modulation of adalimumab producing cell line 1, media 1 on WCX-10 profile total acidic regions.

FIG. 99 depicts the effect of pH modulation of adalimumab producing cell line 1, media 2 on viable cell density.

FIG. 100 depicts the effect of pH modulation addition of adalimumab producing adalimumab producing cell line 1, media 2 on viability.

FIG. 101 depicts the effect of pH modulation of adalimumab producing cell line 1, media 2 on harvest titer.

FIG. 102 depicts the effect of pH modulation of adalimumab producing cell line 1, media 2 on WCX-10 profile total acidic regions.

FIG. 103 depicts the effect of pH modulation of adalimumab producing cell line 3, media 1 on viable cell density.

FIG. 104 depicts the effect of pH modulation adalimumab producing cell line 3, media 1 on viability.

FIG. 105 depicts the effect of pH modulation of adalimumab producing cell line 3, media 1 on harvest titer.

FIG. 106 depicts the effect of pH modulation of adalimumab producing cell line 3, media 1 on WCX-10 profile total acidic regions.

FIG. 107 depicts the effect of dissolved oxygen modulation of adalimumab producing cell line 1, media 2 at 35° C. on viable cell density.

FIG. 108 depicts the effect of dissolved oxygen modulation of adalimumab producing cell line 1, media 2 at 35° C. on viability.

FIG. 109 depicts the effect of dissolved oxygen modulation of adalimumab producing cell line 1, media 2 at 35° C. on harvest titer.

FIG. 110 depicts the effect of dissolved oxygen modulation of adalimumab producing cell line 1, media 2 at 35° C. on WCX-10 profile total acidic regions.

FIG. 111 depicts the effect of dissolved oxygen modulation of adalimumab producing cell line 1, media 2 at 33° C. on viable cell density.

FIG. 112 depicts the effect of dissolved oxygen modulation to adalimumab producing cell line 1, media 2 at 33° C. on viability.

FIG. 113 depicts the effect of dissolved oxygen modulation of adalimumab producing cell line 1, media 2 at 33° C. on harvest titer.

FIG. 114 depicts the effect of dissolved oxygen modulation of adalimumab producing cell line 1, media 2 at 33° C. on WCX-10 profile total acidic regions.

FIG. 115 depicts the effect of dissolved oxygen modulation of adalimumab producing cell line 1, media 1 at 35° C. on viable cell density.

FIG. 116 depicts the effect of dissolved oxygen modulation to adalimumab producing cell line 1, media 1 at 35° C. on viability.

FIG. 117 depicts the effect of dissolved oxygen modulation of adalimumab producing cell line 1, media 1 at 35° C. on harvest titer.

FIG. 118 depicts the effect of dissolved oxygen modulation of adalimumab producing cell line 1, media 1 on WCX-10 profile total acidic regions.

FIG. 119 depicts the effect of dissolved oxygen modulation of adalimumab producing cell line 3, media 1 on viable cell density.

FIG. 120 depicts the effect of dissolved oxygen modulation to adalimumab producing cell line 3, media 1 on viability.

FIG. 121 depicts the effect of dissolved oxygen modulation of adalimumab producing cell line 3, media 1 on harvest titer.

FIG. 122 depicts the effect of dissolved oxygen modulation of adalimumab producing cell line 3, media 1 on WCX-10 profile total acidic regions.

FIG. 123 depicts the effect of dissolved oxygen modulation to mAb2 producing cell line, media 1 on viable cell density.

FIG. 124 depicts the effect of dissolved oxygen modulation addition to mAb2 producing cell line, media 1 on viability.

FIG. 125 depicts the effect of dissolved oxygen modulation to mAb2 producing cell line, media 1 on harvest titer.

FIG. 126 depicts the effect of dissolved oxygen modulation to mAb2 producing cell line, media 1 on WCX-10 profile total acidic regions.

FIG. 127 depicts an acidification sample preparation scheme.

FIG. 128 depicts an arginine sample preparation scheme.

FIG. 129 depicts a histidine sample preparation scheme.

FIG. 130 depicts a lysine sample preparation scheme.

FIG. 131 depicts a methionine sample preparation scheme.

FIG. 132 depicts an amino acid sample preparation scheme.

FIG. 133 depicts a CDM clarified harvest sample preparation scheme.

FIG. 134 depicts an acid-type pH study sample preparation scheme.

FIG. 135 depicts the effect of low pH treatment with subsequent neutralization on initial acidic variant content.

FIG. 136 depicts the effect of low pH treatment with subsequent neutralization on acidic variant formation rate.

FIG. 137 depicts the effect of sample preparation method on initial acidic variant content.

FIG. 138 depicts the effect of sample preparation method on initial acidic variant content.

FIG. 139 depicts the dose dependent effect of arginine on reduction of acidic variant formation rate.

FIG. 140 depicts the effect of histidine concentration on initial acidic variant content.

FIG. 141 depicts the effect of histidine concentration on acidic variant formation rate.

FIG. 142 depicts the effect of lysine on initial acid variant content.

FIG. 143 depicts the effect of lysine on acidic variant formation rate.

FIG. 144 depicts the effect of methionine on initial acid variant content.

FIG. 145 depicts the effect of methionine on acidic variant formation rate.

FIG. 146 depicts the effect of amino acids on initial acid variant content.

FIG. 147 depicts the effect of amino acids on acidic variant formation rate.

FIG. 148 depicts the effect of alternative additives on initial acid variant content.

FIG. 149 depicts the effect of alternative additives on acidic variant formation rate.

FIG. 150 depicts the effect of low pH/arginine treatment on adalimumab CDM initial acid variant content.

FIG. 151 depicts the effect of low pH/arginine treatment on adalimumab CDM acidic variant formation rate.

FIG. 152 depicts the effect of low pH/arginine treatment on mAb B hydrolysate initial acid variant content.

FIG. 153 depicts the effect of low pH/arginine treatment on mAb B hydrolysate acidic variant formation rate.

FIG. 154 depicts the effect of low pH/arginine treatment on mAb C hydrolysate initial acid variant content.

FIG. 155 depicts the effect of low pH/arginine treatment on mAb C hydrolysate acidic variant formation rate.

FIG. 156 depicts the effect of acid type/pH on acid variant content.

FIG. 157 depicts the effect of acid concentration on acid variant content.

FIG. 158 depicts the effect of acid concentration on acid variant content.

FIG. 159 depicts the effect of neutralization on acid variant content.

FIG. 160 depicts the effect of neutralization on acid variant content.

Figure 161:
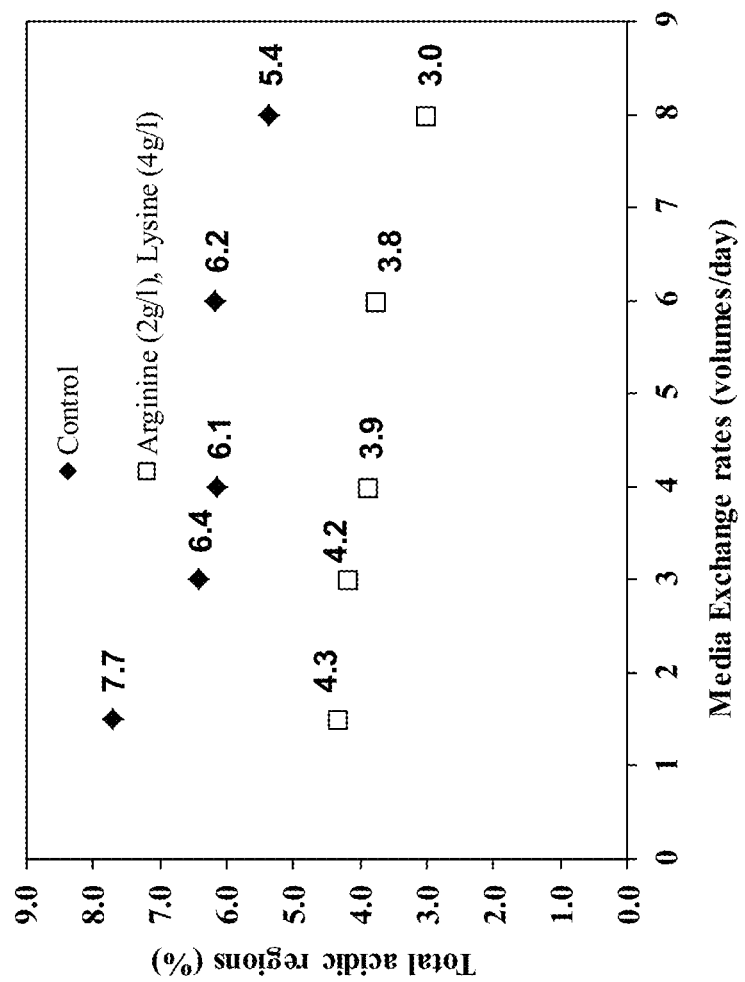

FIG. 161 depicts the effect of medium exchange rate and the supplementation of amino acids arginine and lysine on total acidic species reduction.

Figure 162:
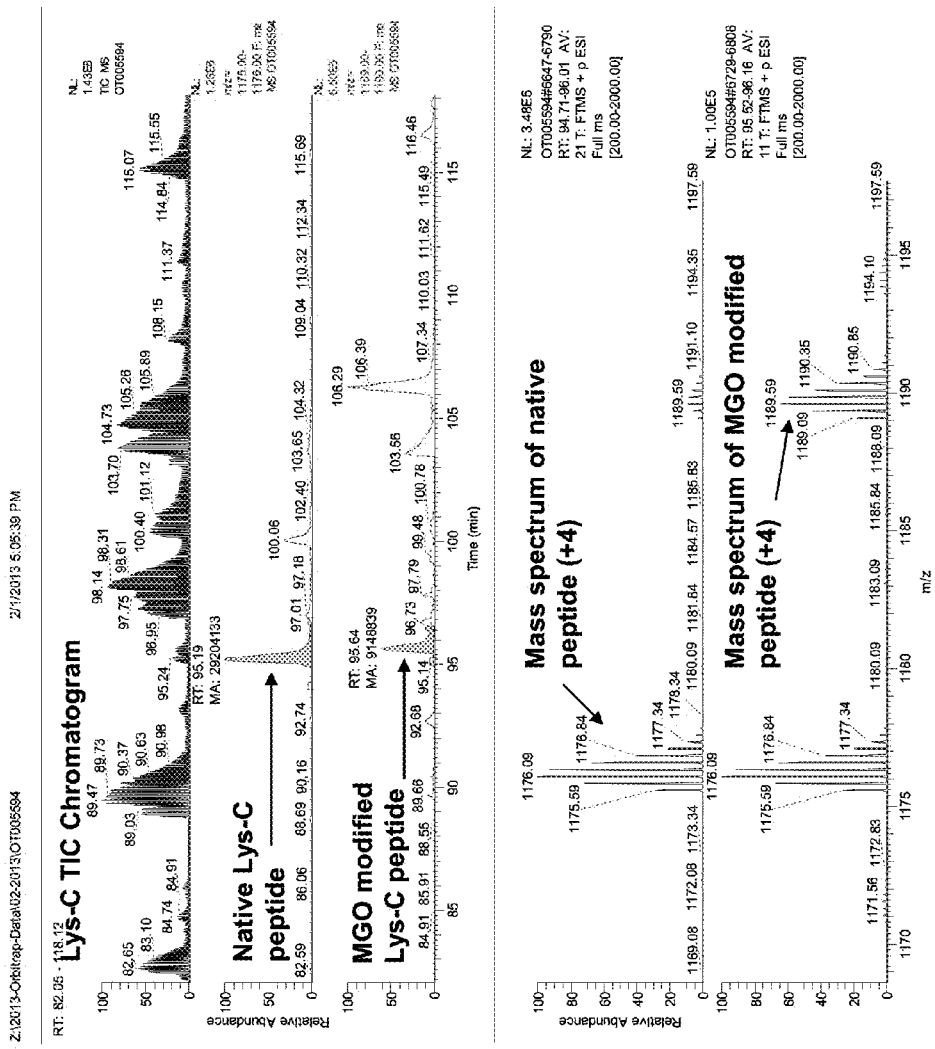

FIG. 162 depicts LC/MS peptide mapping analysis of exemplary antibodies expressed in the context of the cell culture conditions of the instant invention, including preparation of specific mass traces for both modified and non-modified peptides in order to accurately quantify the total amount of MGO modification. Mass spectra are also analyzed for the specific region of the chromatogram to confirm the peptide identity.

Figure 163:
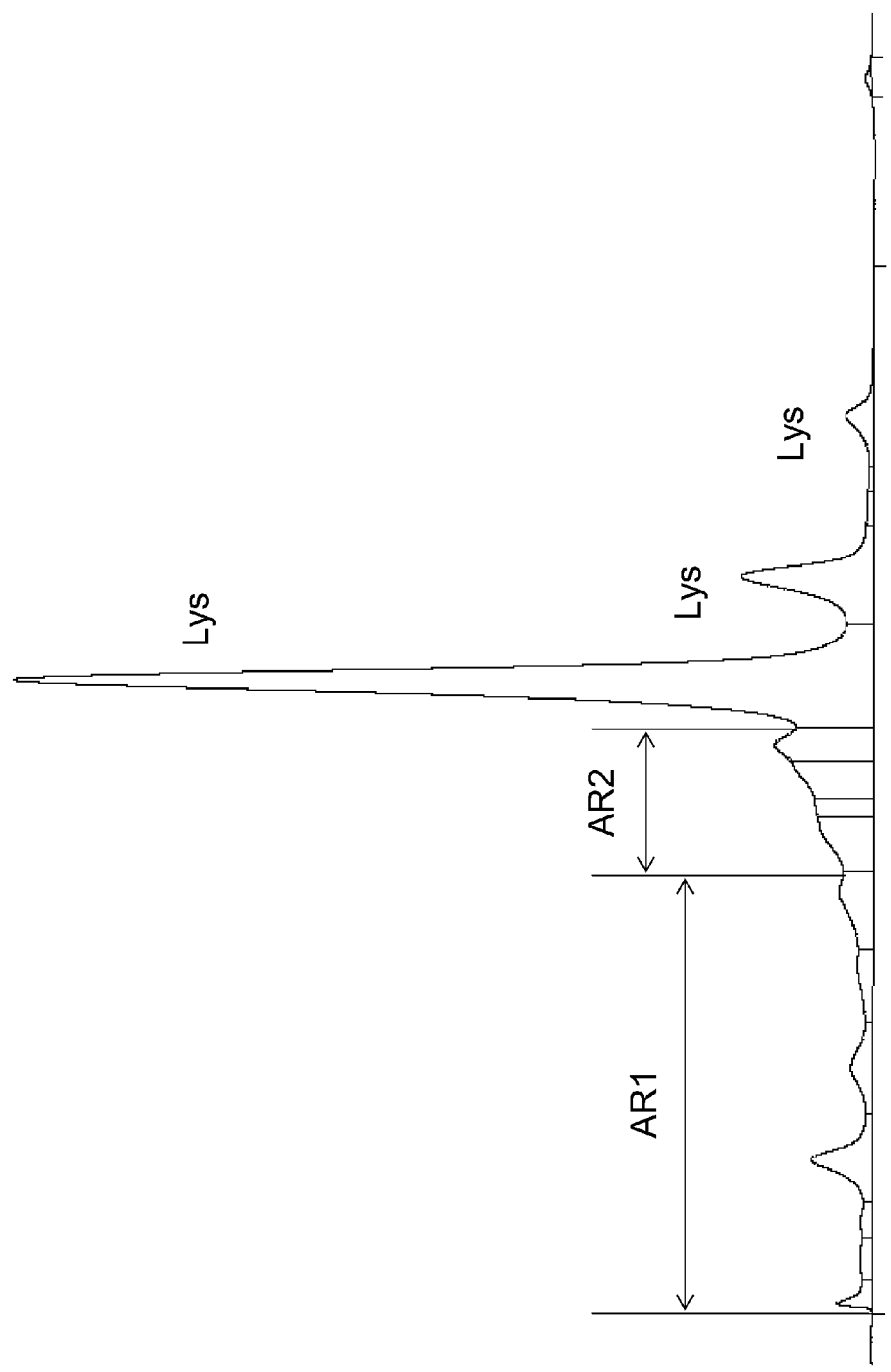

FIG. 163 depicts a chromatogram wherein the total acidic species associated with the expression of adalimumab is divided into a first acidic species region (AR1) and a second acidic species region (AR2).

Figure 164:
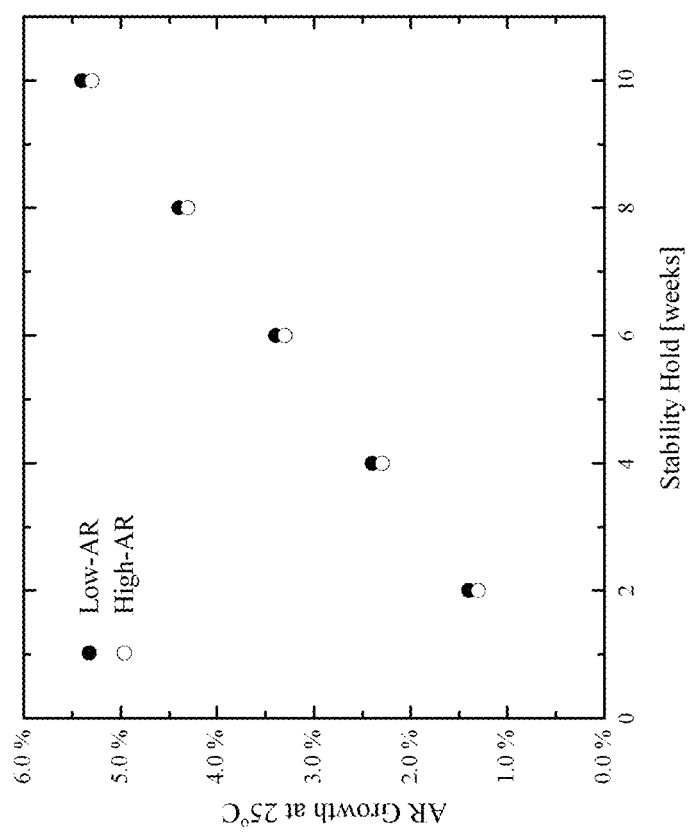

FIG. 164 depicts the AR growth at 25° C. of low and high AR containing samples.

Figure 165:
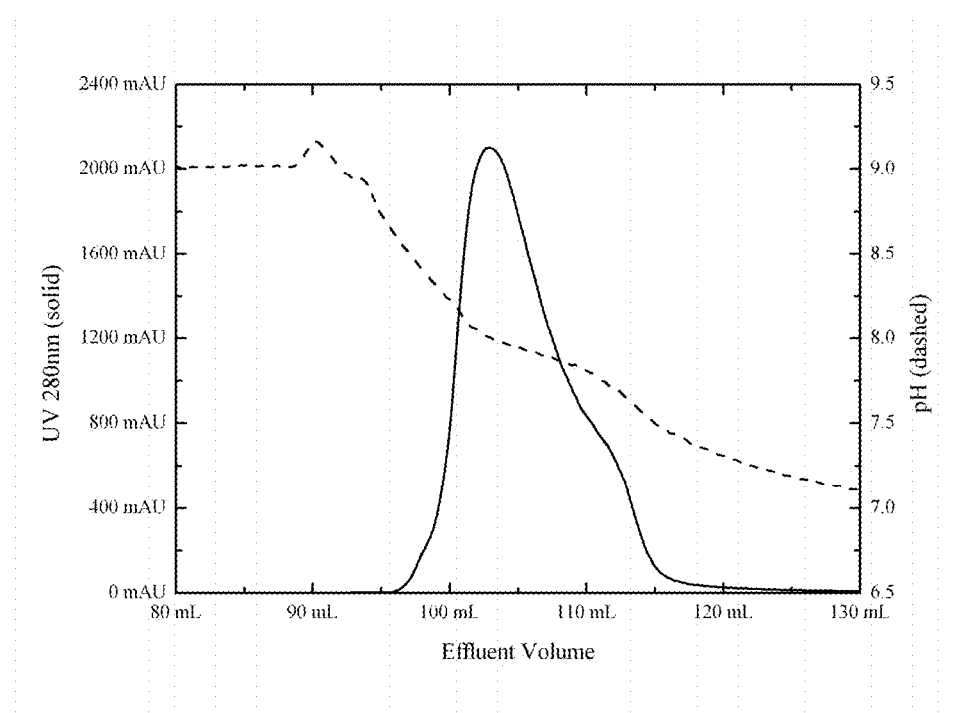

FIG. 165 depicts a process chromatogram of pH gradient elution in the context of AEX chromatography.

Figure 166:
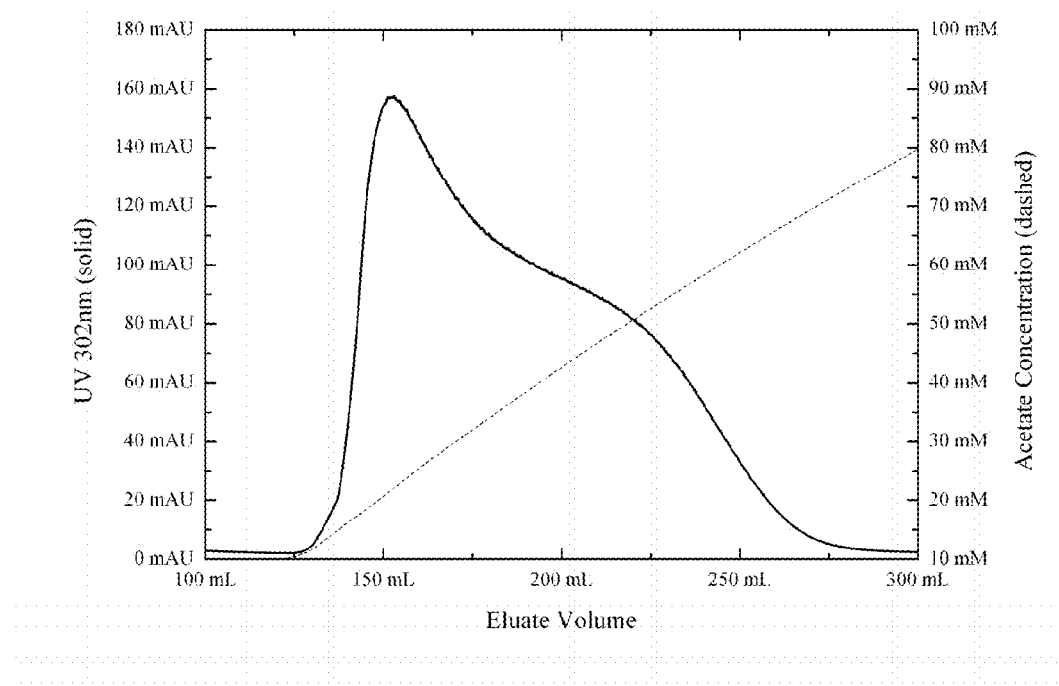

FIG. 166 depicts a process chromatogram of a linear gradient elution by increasing anion concentration in the context of AEX chromatography.

Figure 167:
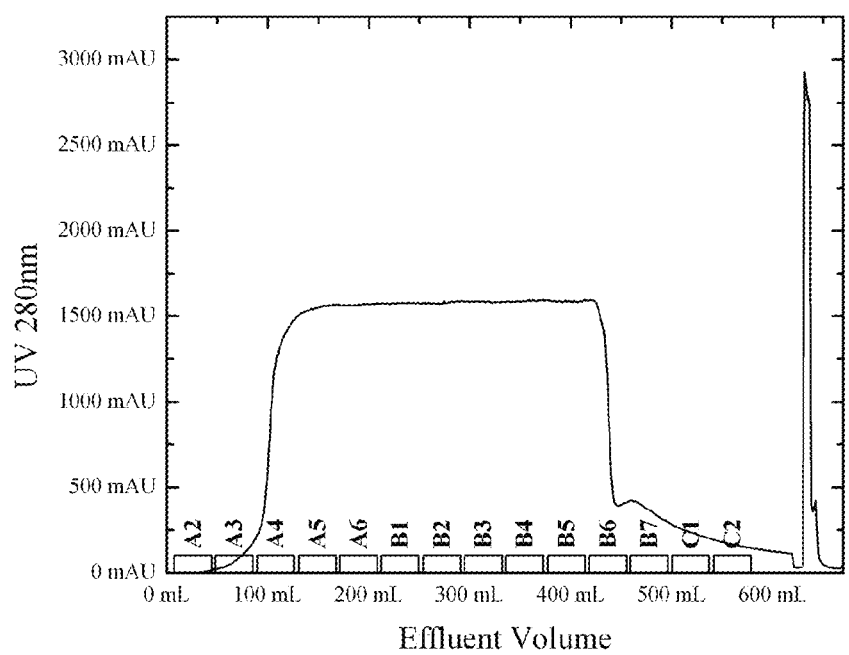

FIG. 167 depicts a process chromatogram of fractionation of 300 g/L load and wash in the context of AEX chromatography.

Figure 168:
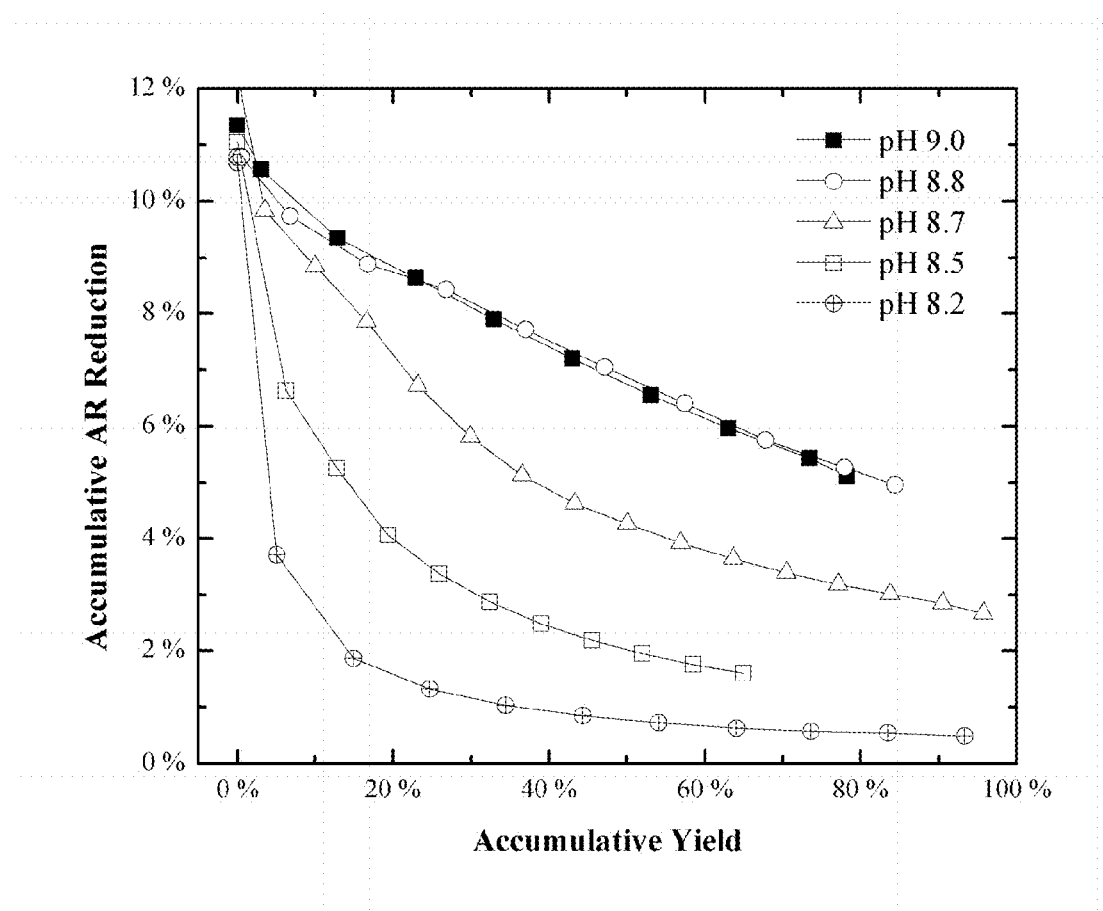

FIG. 168 depicts the effect of pH on AR reduction in the context of AEX chromatography.

Figure 169:
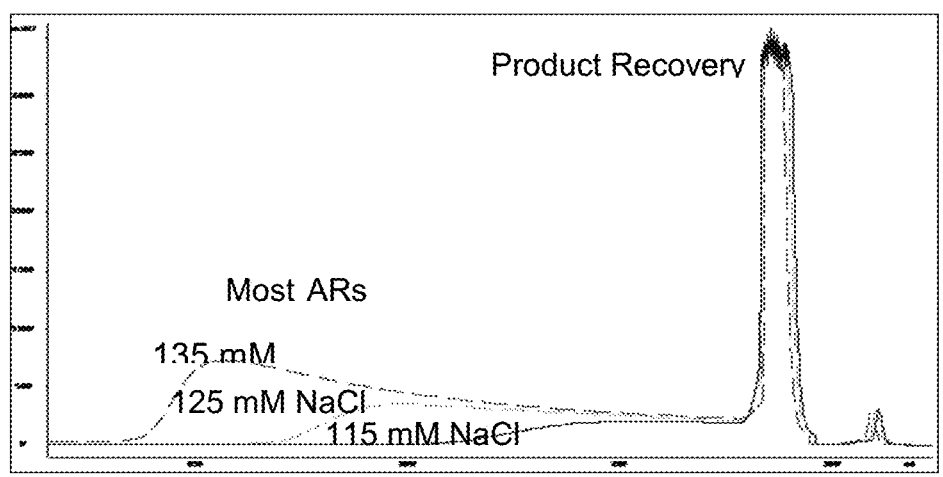

FIG. 169 depicts a process chromatogram at different salt (cation) concentrations in the context of CEX chromatography.

Figure 170:
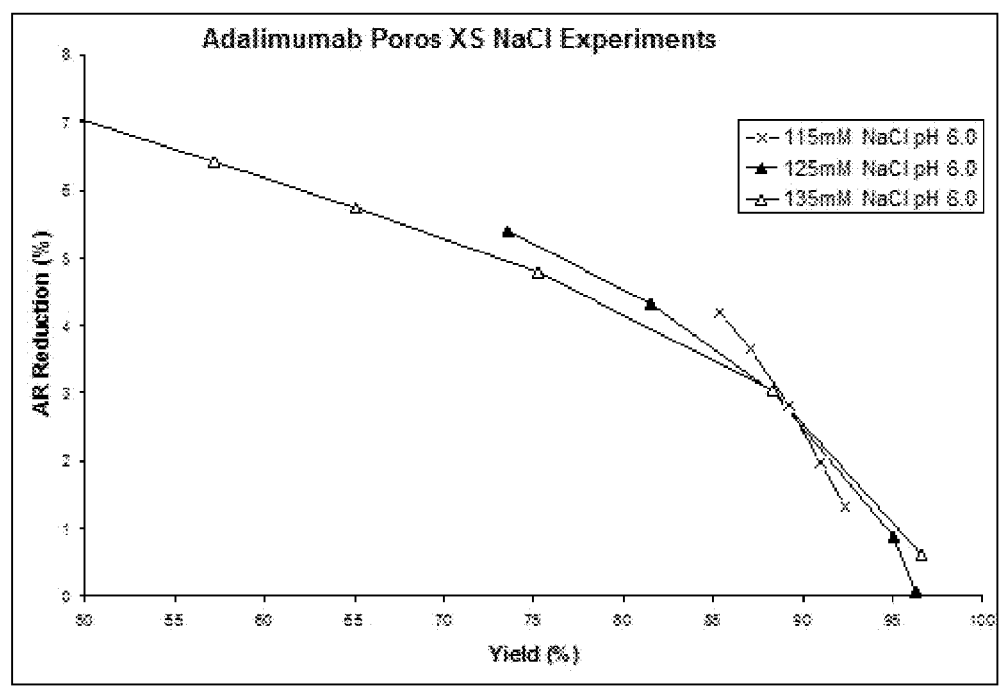

FIG. 170 depicts recovery versus AR reduction in the context of CEX purification of adalimumab.

Figure 171:
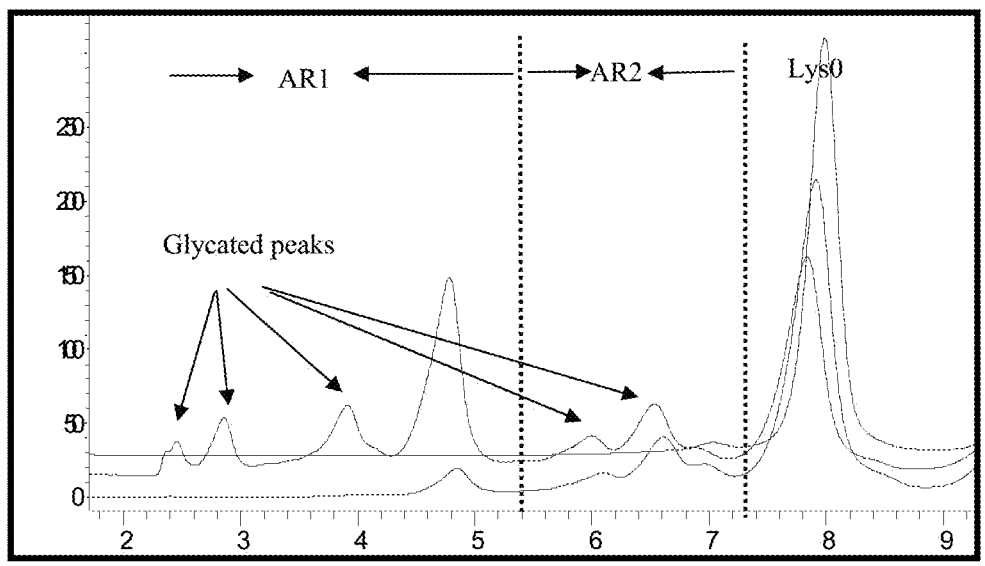

FIG. 171 depicts the WCX-10 profile of glycated load material and CEX eluate.

Figure 172:
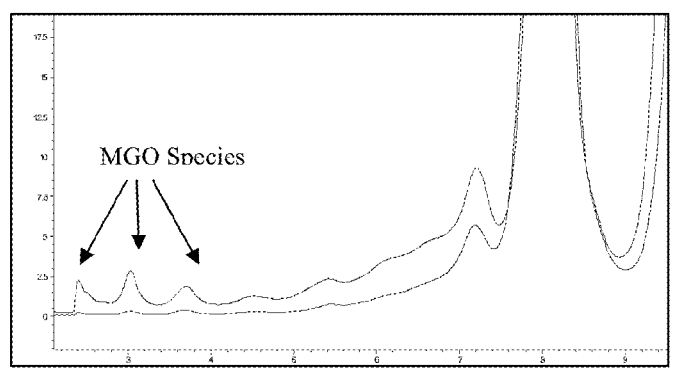

FIG. 172 depicts the WCX-10 profile of MGO modified load material and eluate from CEX column employing Toyo Pearl MX TRP 650M resin.

Figure 173:
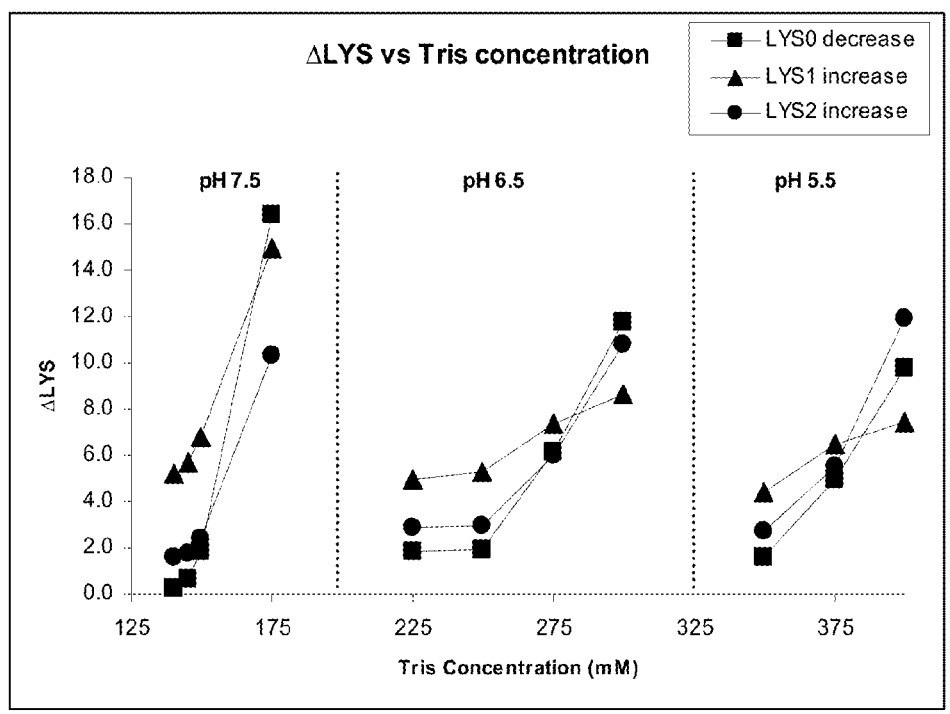

FIG. 173 depicts the change in lysine distribution during CEX chromatography, highlighting the effect of Tris concentration.

Figure 174:
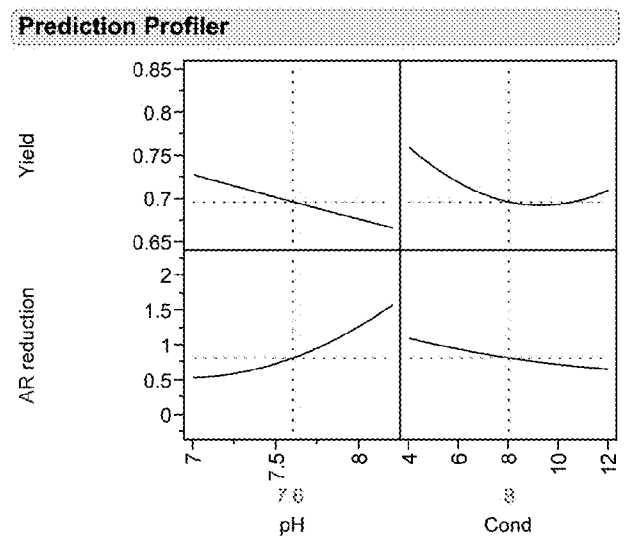

FIG. 174 depicts the effect of pH and conductivity on adalimumab AR reduction and recovery yield in the context of MM chromatography.

Figure 175:
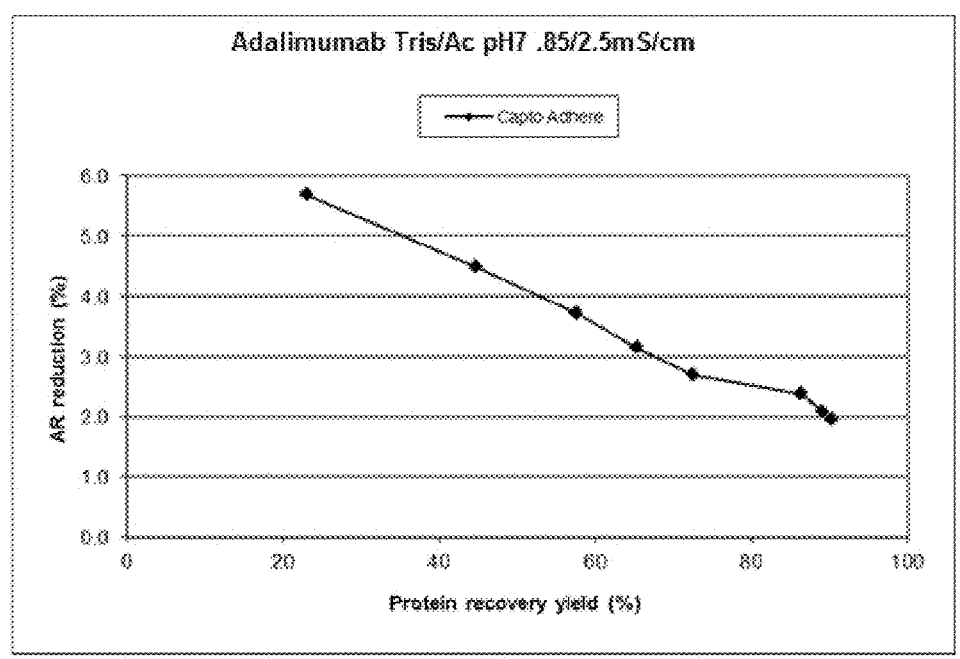

FIG. 175 depicts the AR reduction achieved with the corresponding protein recovery in the context of MM chromatography.

Figure 176:
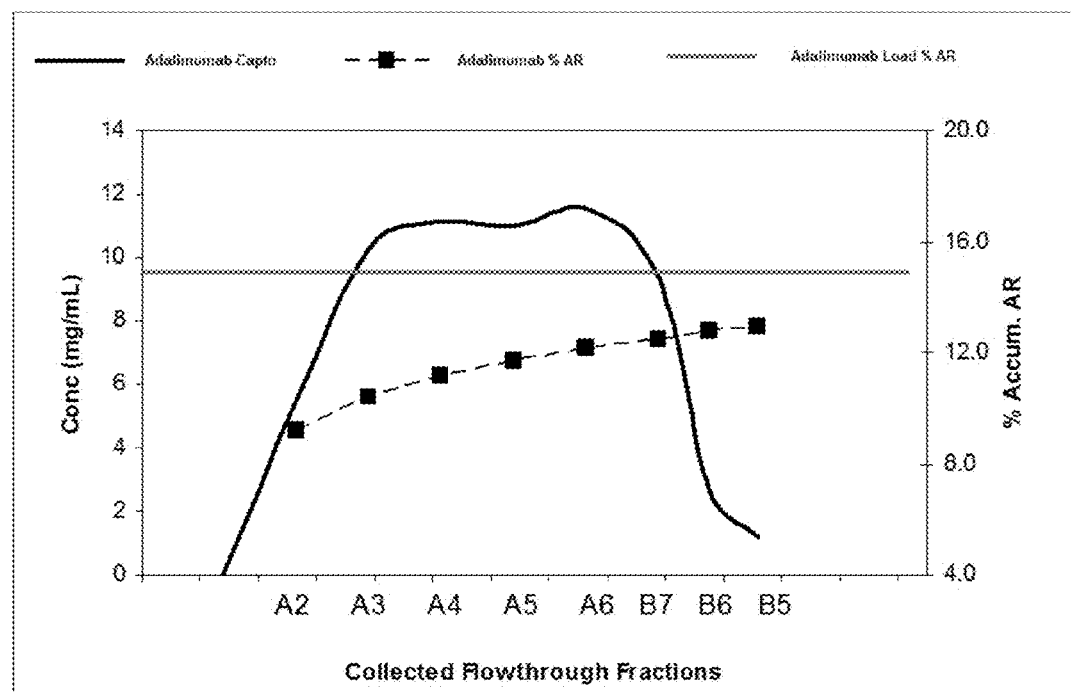

FIG. 176 depicts the total adalimumab Protein concentration levels and AR levels during Flow Through and Wash.

Figure 177:
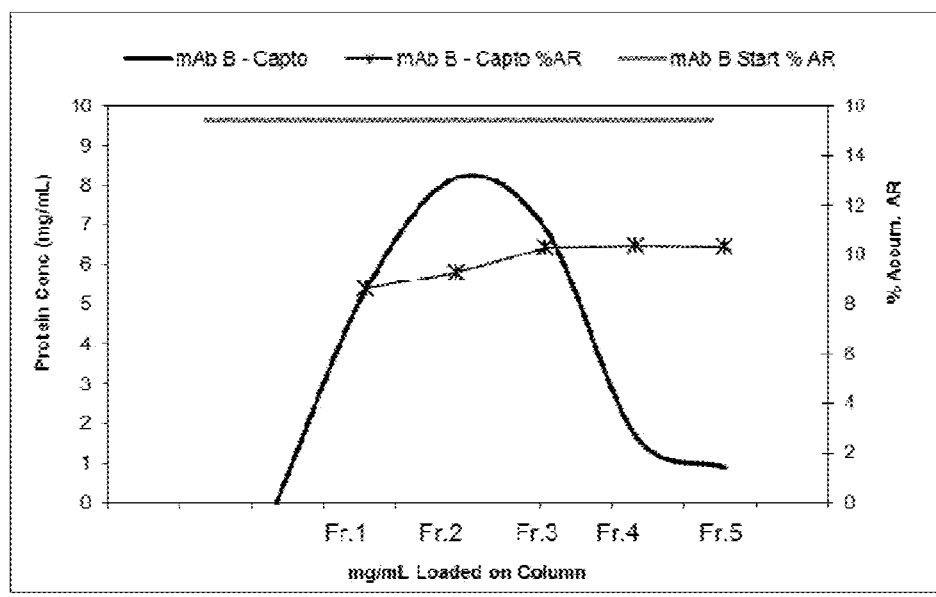

FIG. 177 depicts the total mAb B Protein concentration levels and AR levels during Flow Through and Wash in the context of MM chromatography.

Figure 178:
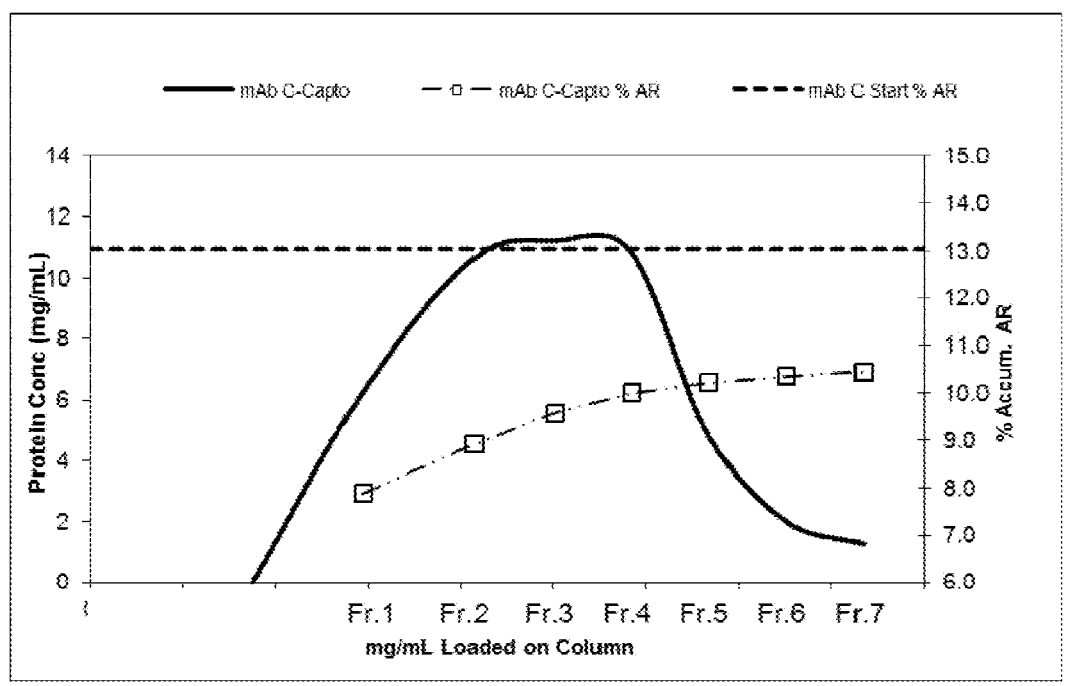

FIG. 178 depicts the total mAb C Protein concentration levels and AR levels during Flow Through and Wash in the context of MM chromatography.

Figure 179:
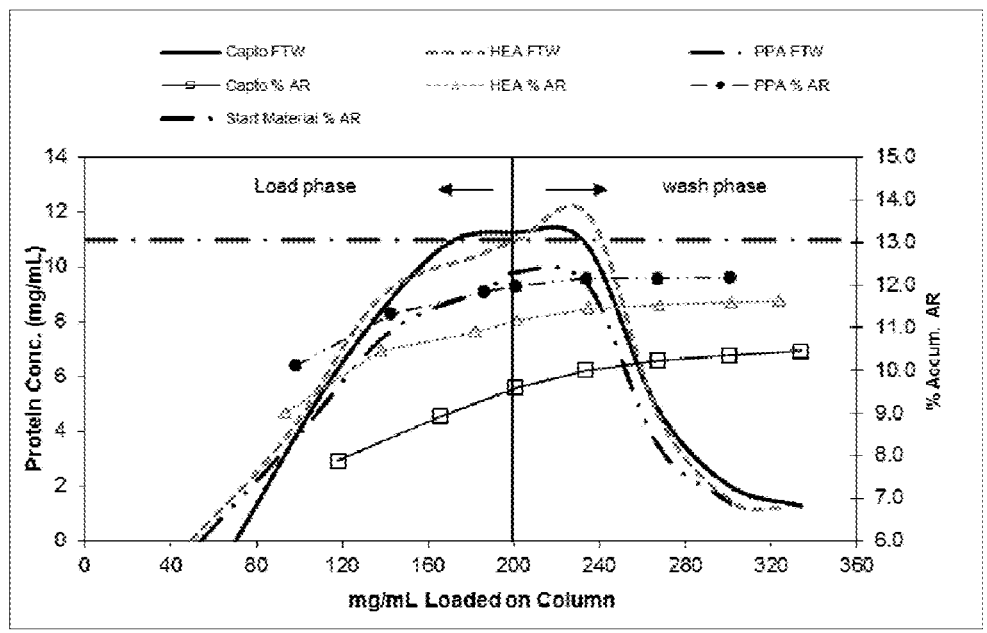

FIG. 179 depicts the Cumulative % AR breakthrough of mAb C on different MM resins.

Figure 180:
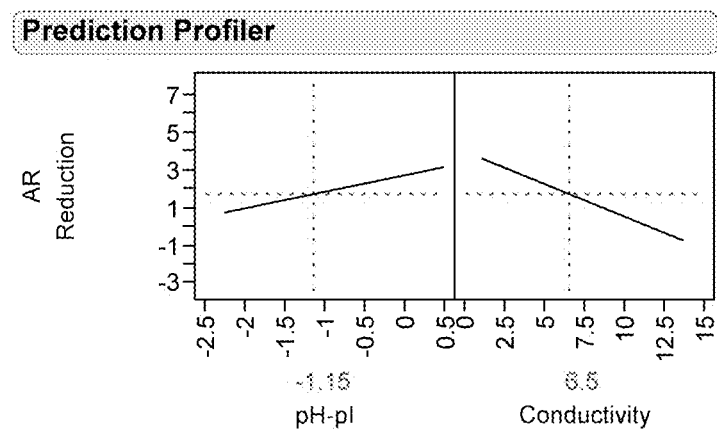

FIG. 180 depicts the impact of pH-pI and conductivity on adalimumab AR reduction in the context of MM chromatography.

Figure 181:
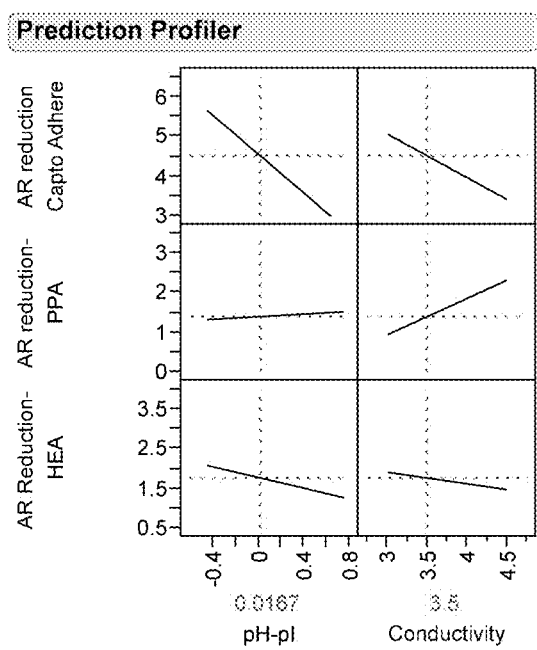

FIG. 181 depicts the impact of pH-pI and conductivity on mAb B AR reduction in the context of MM chromatography.

Figure 182:
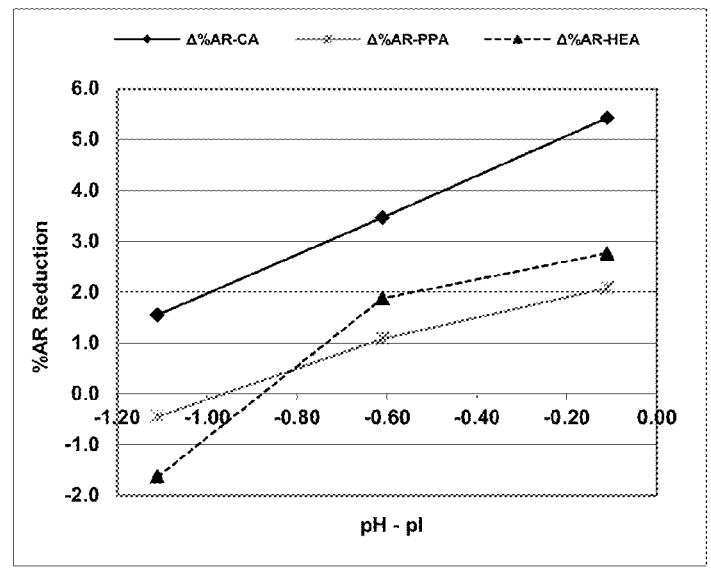

FIG. 182 depicts the impact and trend of pH-pI on mAb C AR reduction with multiple resins in the context of MM chromatography.

Figure 183:
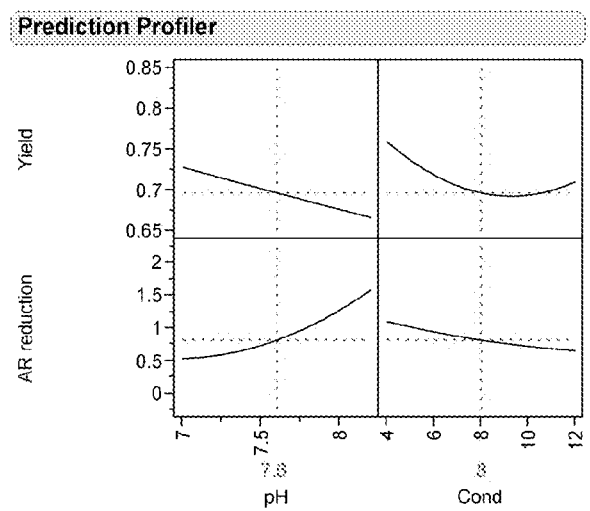

FIG. 183 depicts the effect of pH and conductivity on AR reduction and Yield in the context of MM chromatography.

Figure 184:
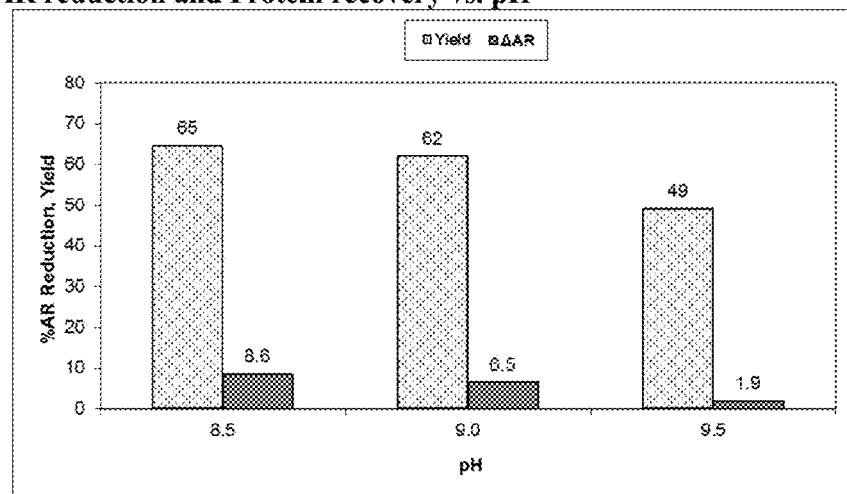

FIG. 184 depicts AR reduction and protein recovery vs. pH in the context of MM chromatography.

Figure 185:
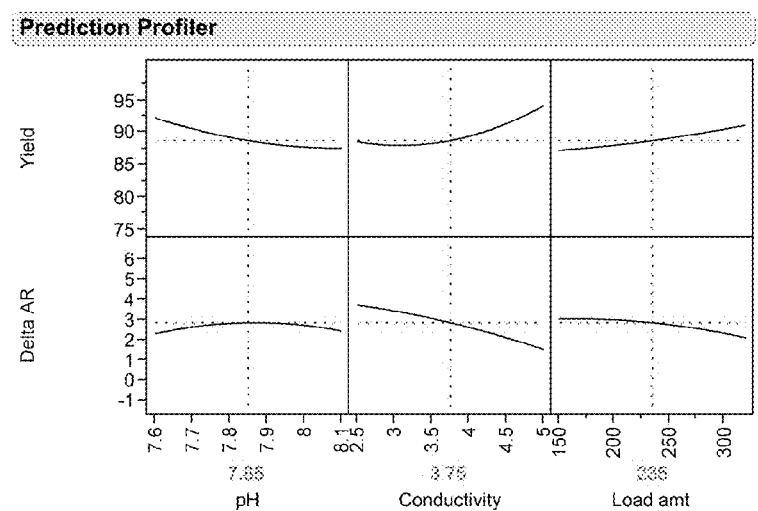

FIG. 185 depicts the effect of pH, conductivity and protein load amount on AR reduction and yield.

Figure 186:
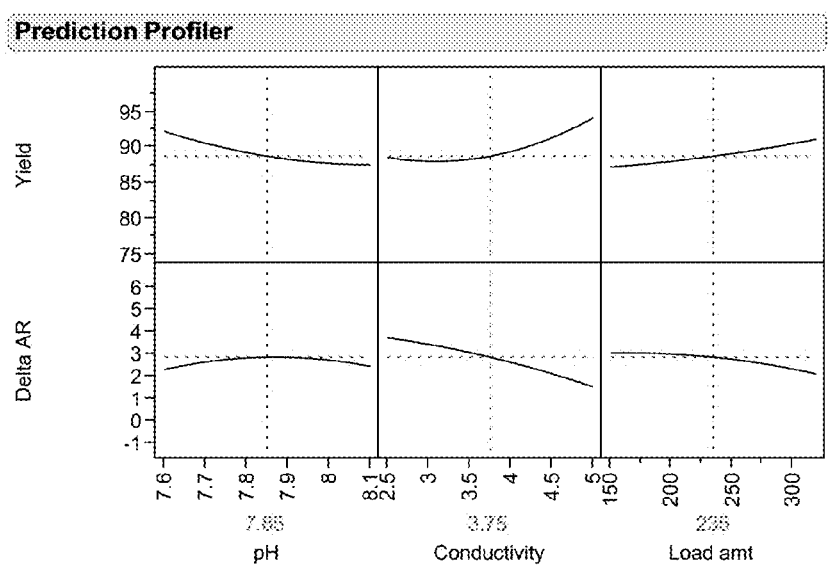

FIG. 186 depicts the effect of pH, conductivity and protein load amount on AR reduction and yield.

Figure 187:
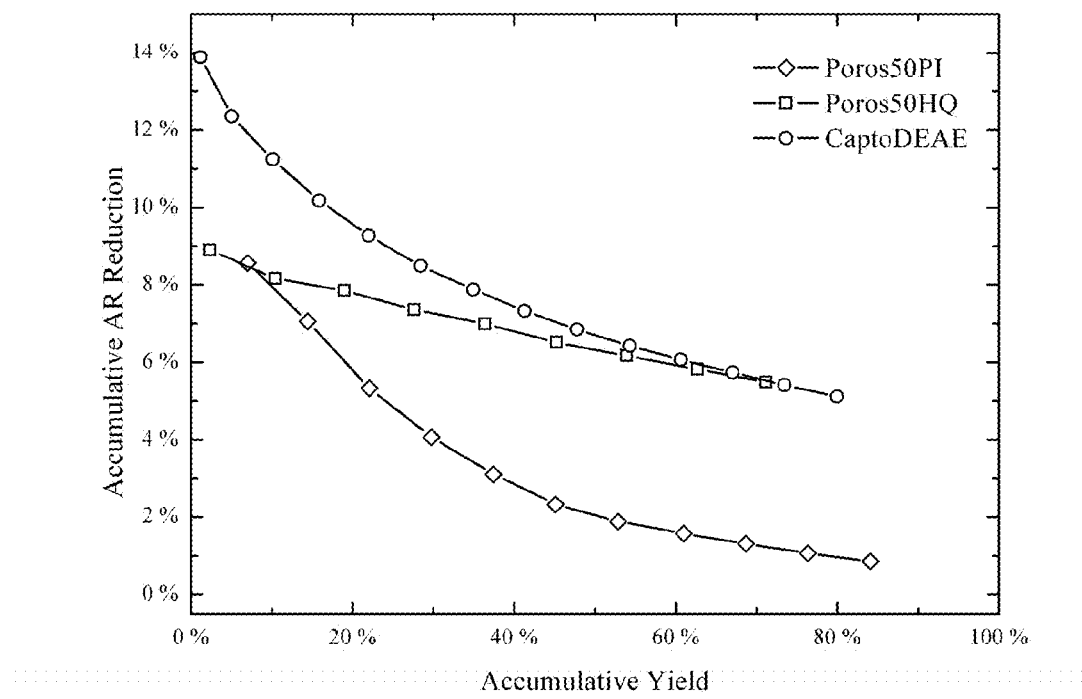

FIG. 187 depicts the effect of AEX adsorbent pKa for mAb B with several different AEX adsorbents, with different pKa values, run at with an acetate/Tris buffer at pH 9.1.

FIG. 188 is a schematic depiction of exemplary AR1 and AR2 present in a composition comprising an exemplary antibody. Preparation-derived ARs and storage-derived ARs are depicted.

Figure 189:
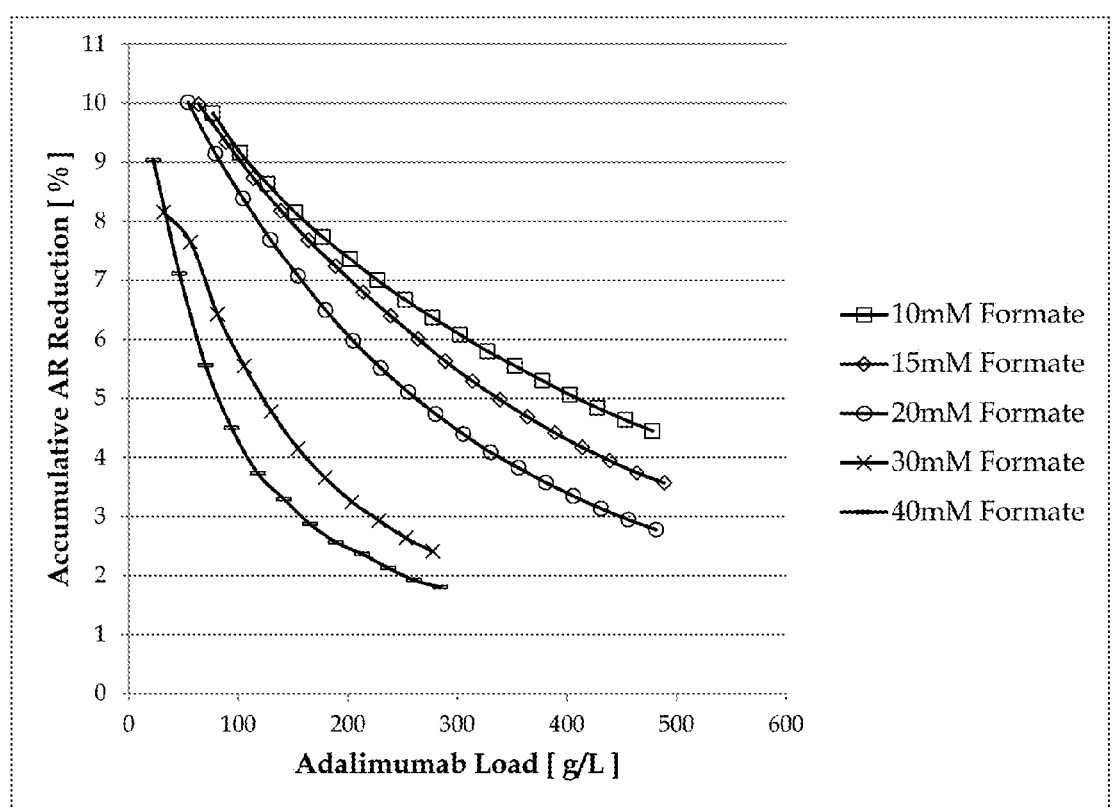

FIG. 189 depicts cumulative AR reduction as a function of yield for various formic acid concentrations.

Figure 190:
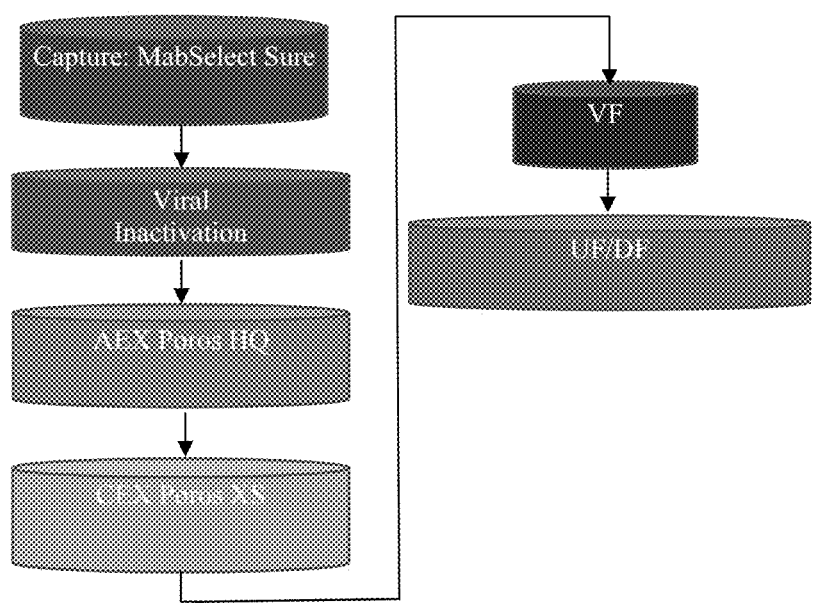

FIG. 190 depicts an exemplary flow path for the production of a low AR composition.

Figure 191:
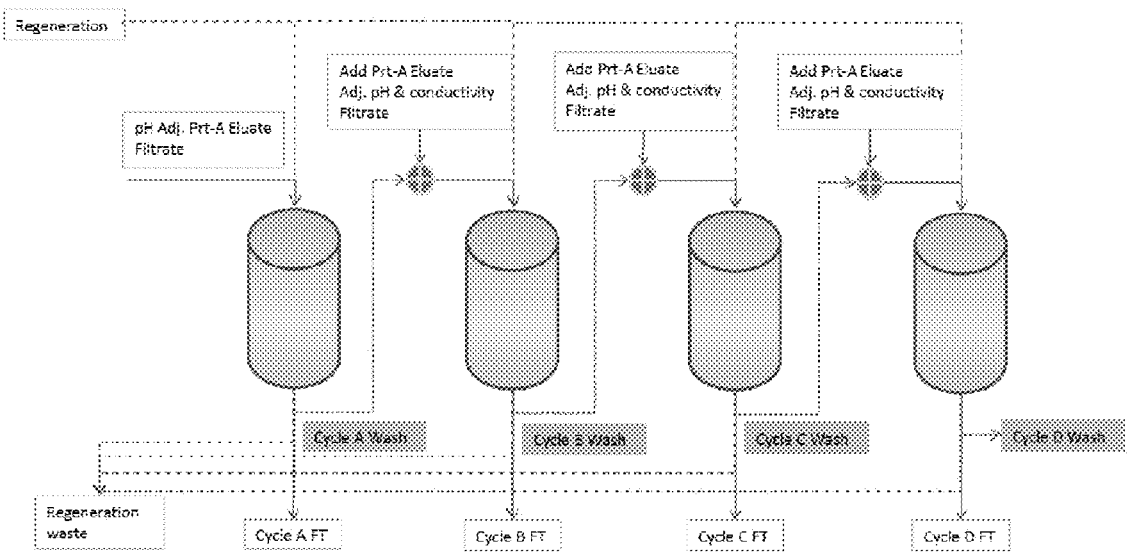

FIG. 191 depicts an experimental scheme for a "Continuous Chromatography" process of producing a low AR composition.

Figure 192:
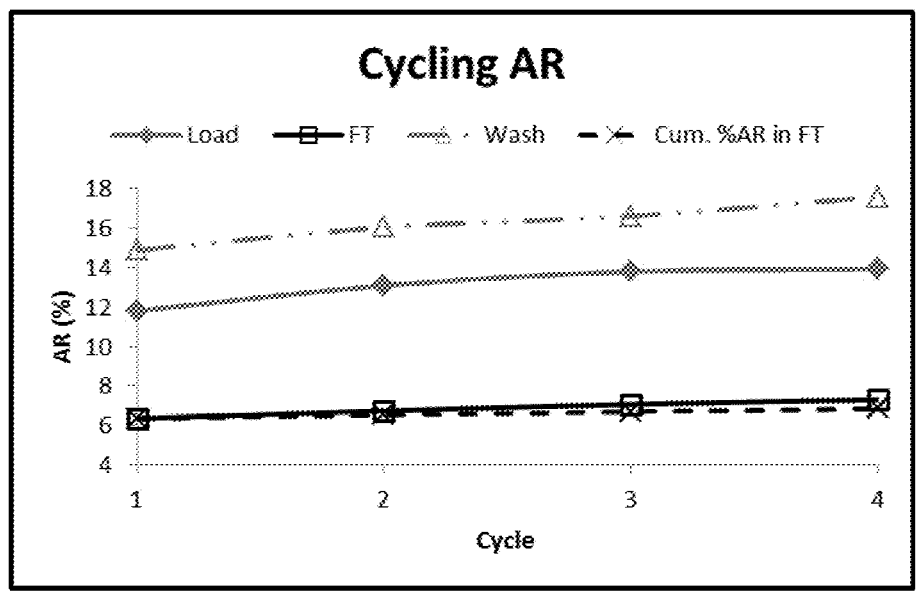

FIG. 192 depicts the percent AR in each of the cycles of the continuous MM process.

Figure 193:
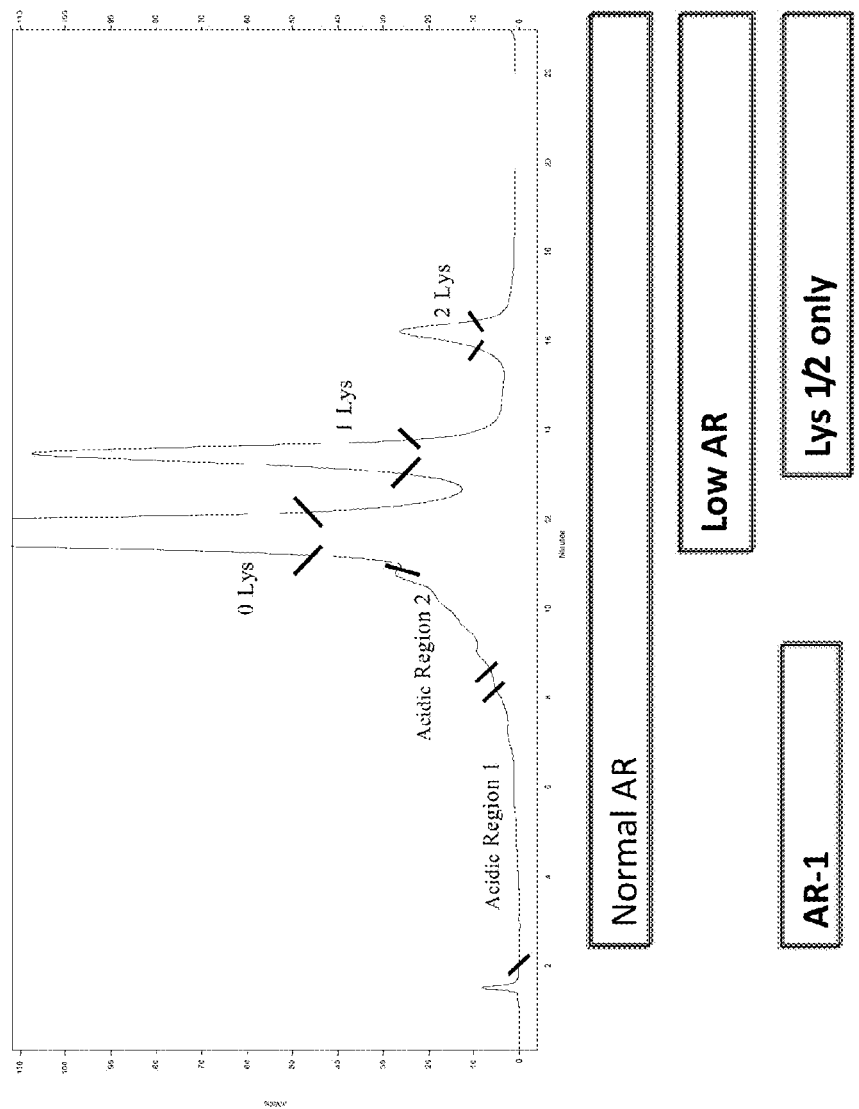

FIG. 193 depicts a chromatogram wherein acidic and basic species are identified in adalimumab and various fractions are delineated.

Figure 194A:
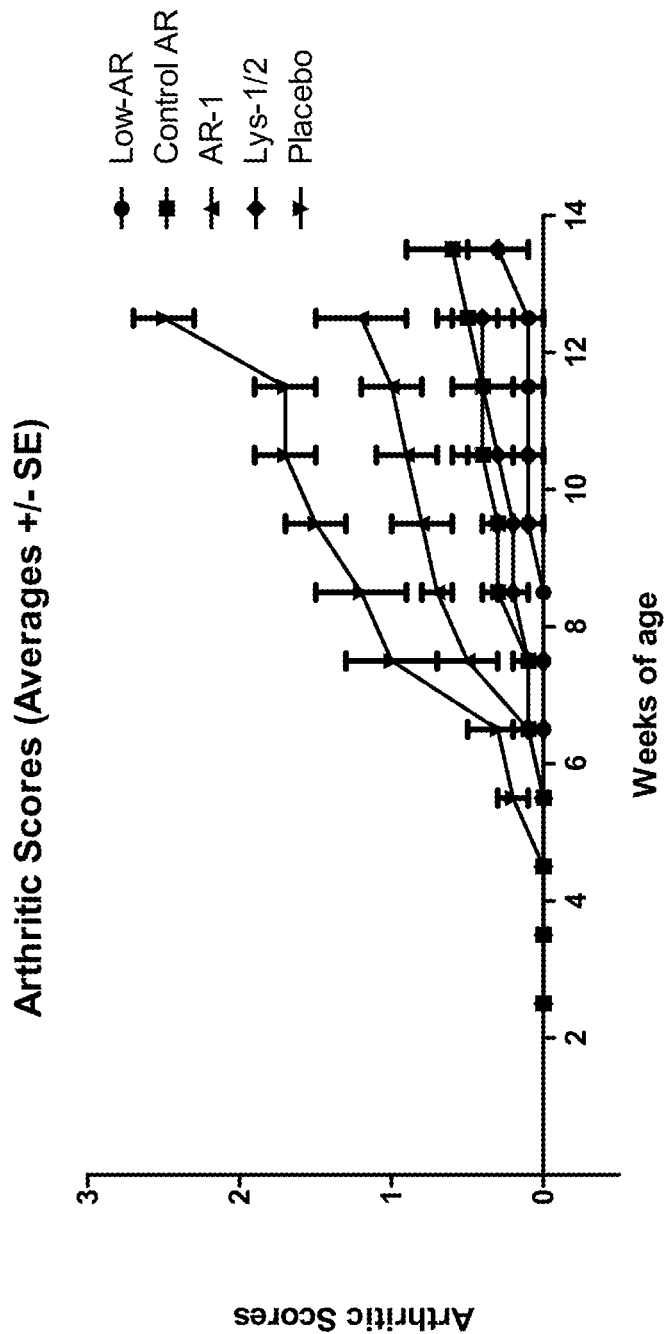
Figure 194B:
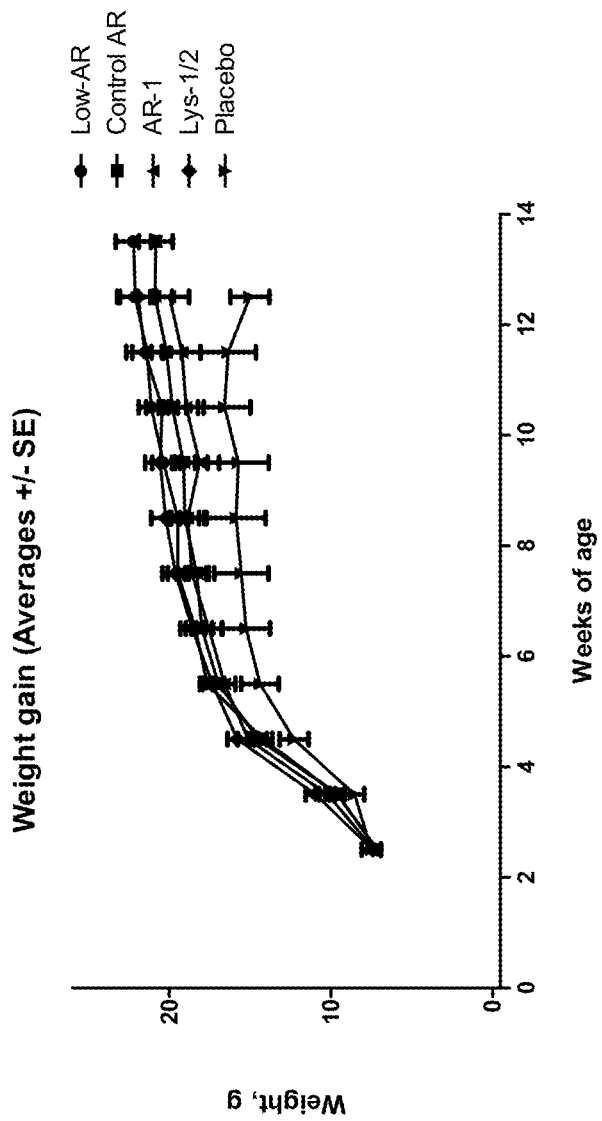

FIGS. 194A-B depict (A) the average arthritic scores and (B) growth related weight gain of mice administered low AR composition, AR1 composition, Lys-1/2 composition, and control AR composition.

Figure 195:
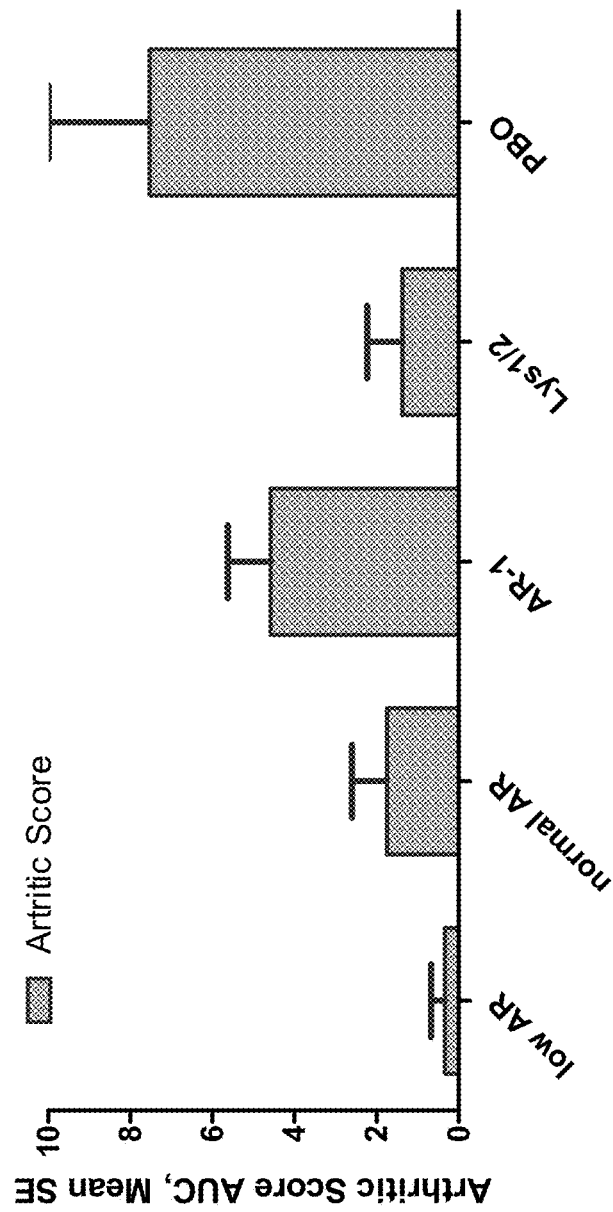

FIG. 195 depicts the average arthritic scores (area under the curve) of mice administered low AR composition, AR1 composition, Lys-1/2 composition, and control AR composition.

Figure 196A:
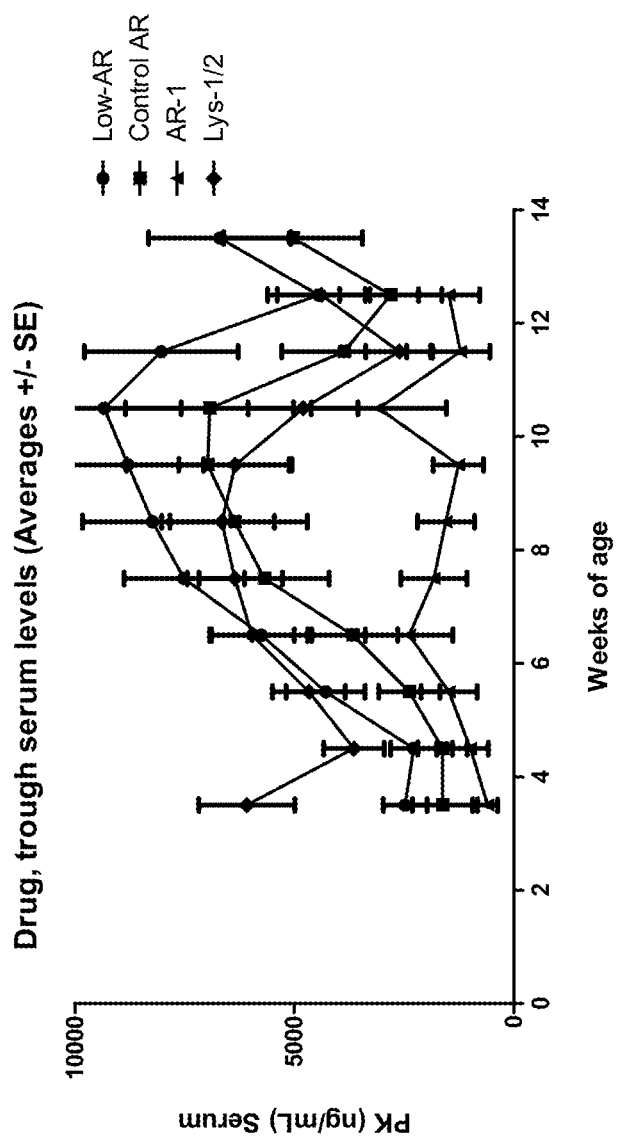
Figure 196B:
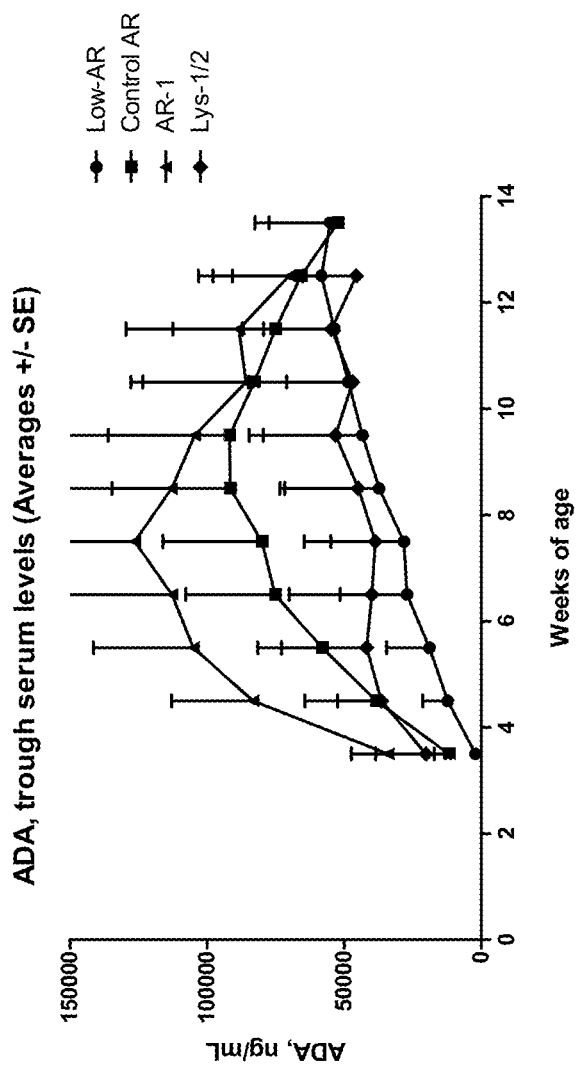

FIGS. 196A-B depict (A) the average trough serum drug levels and (B) the average trough serum ADA levels for mice administered low AR composition, AR1 composition, Lys-1/2 composition, and control AR composition.

Figure 197:
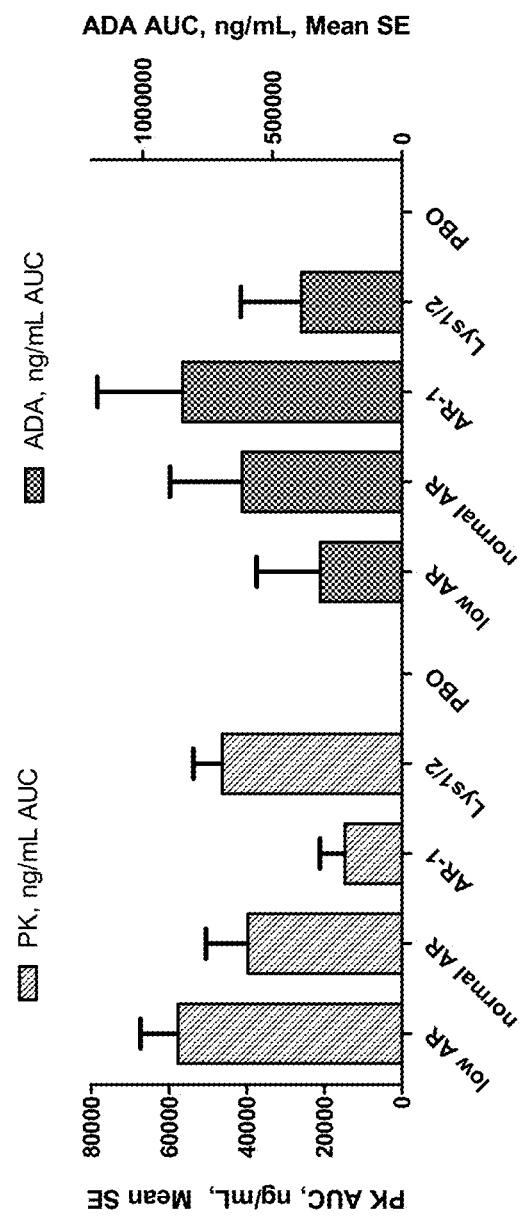

FIG. 197 depicts the average PK and ADA profiles (area under the curve) for mice administered low AR composition, AR1 composition, Lys-1/2 composition, and control AR composition.

Figure 198:
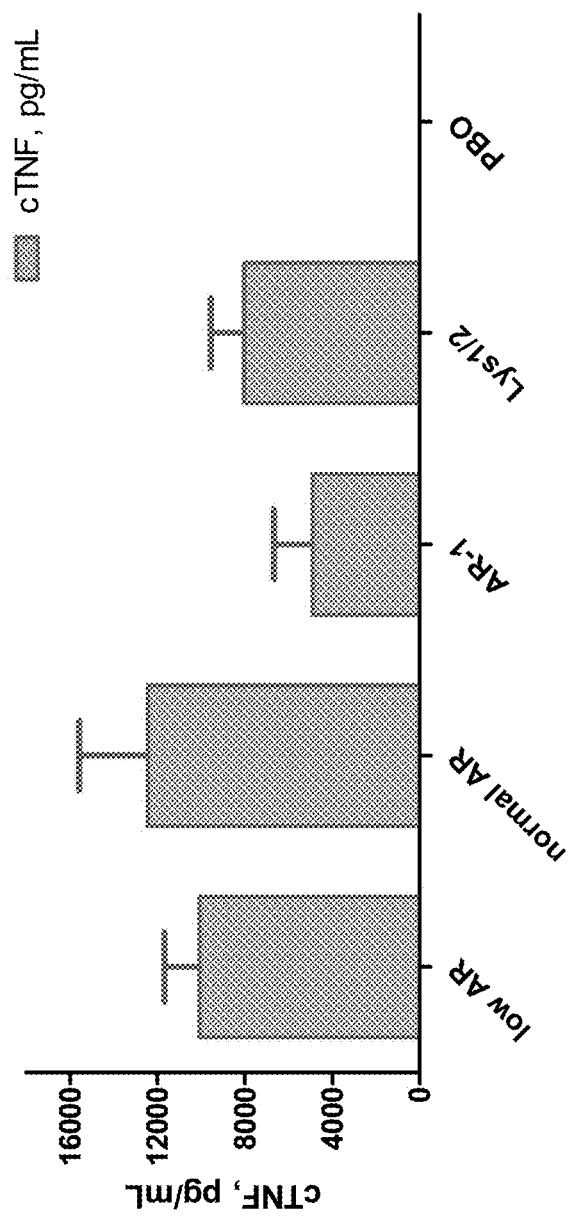

FIG. 198 depicts complexed TNF levels (area under the curve) and shows that the cumulative serum concentration values of adalimumab for mice administered low AR composition, AR1 composition, Lys-1/2 composition, and control AR composition during the ten week treatment period was highest for the low AR and the control AR compositions and lowest for the AR1 fraction.

Figure 199:
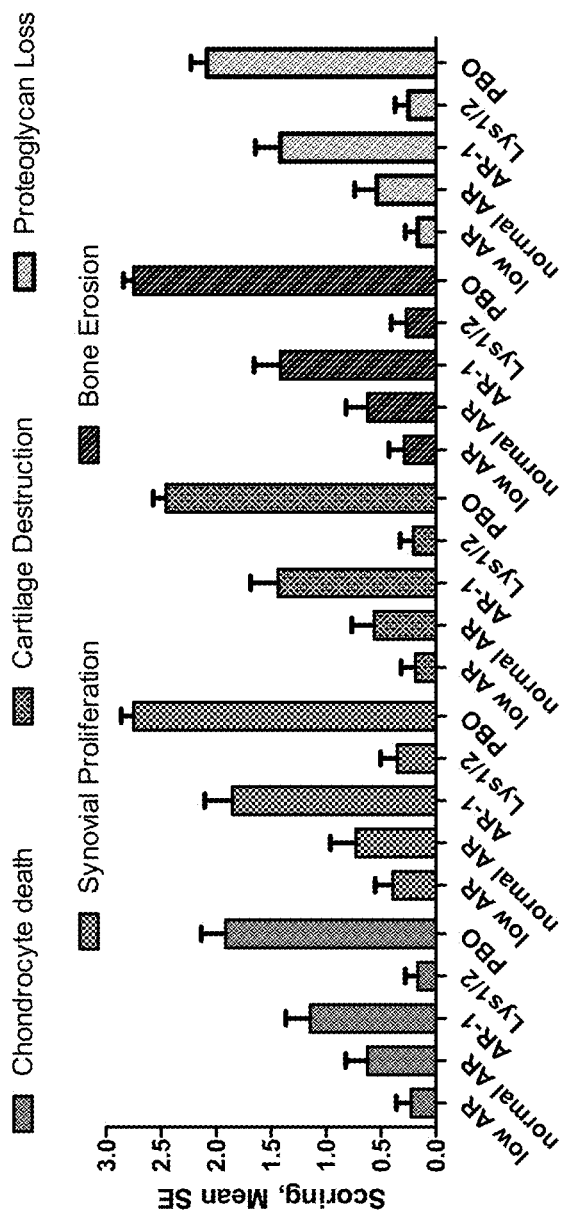
Figure 200:
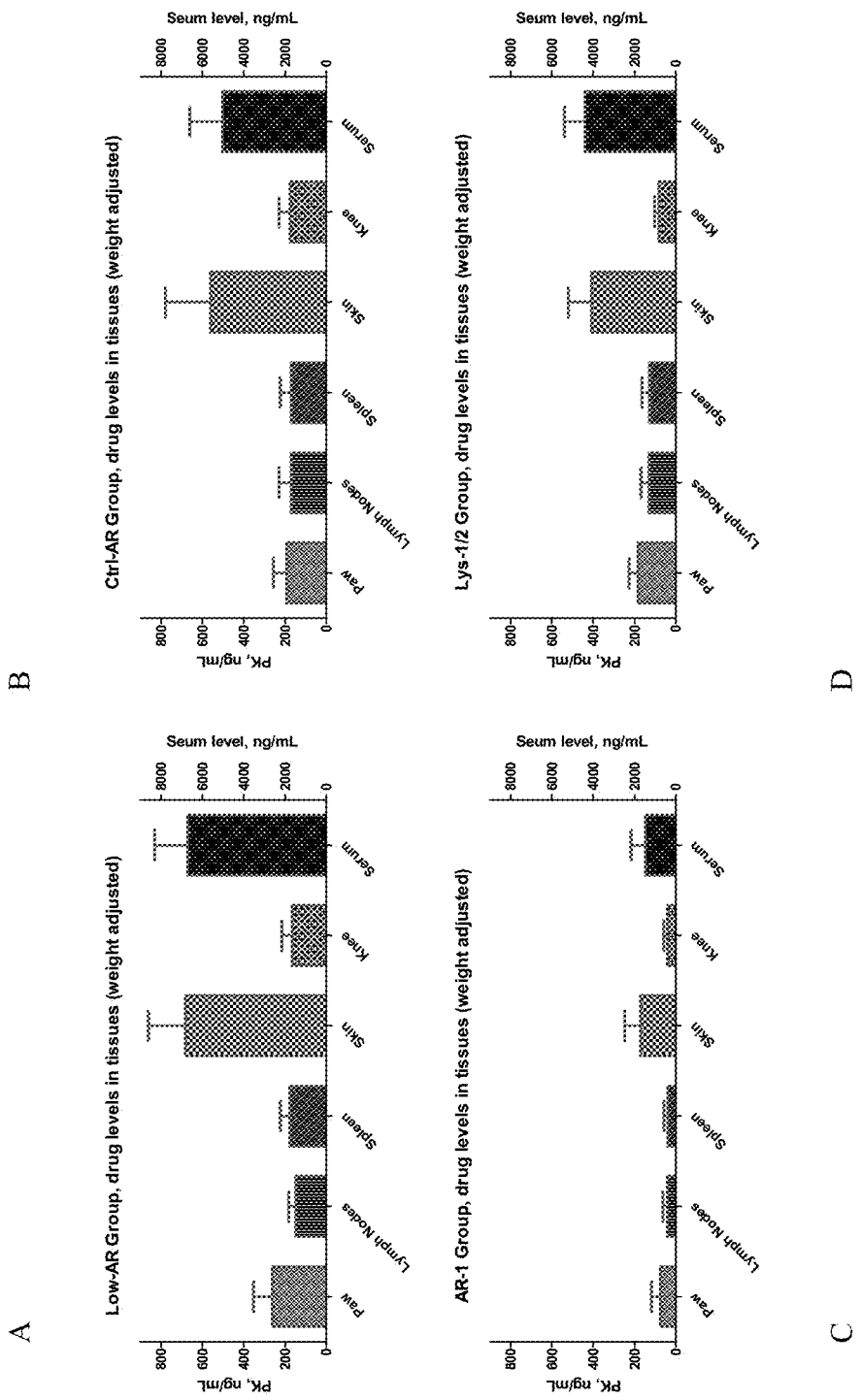
Figure 201:
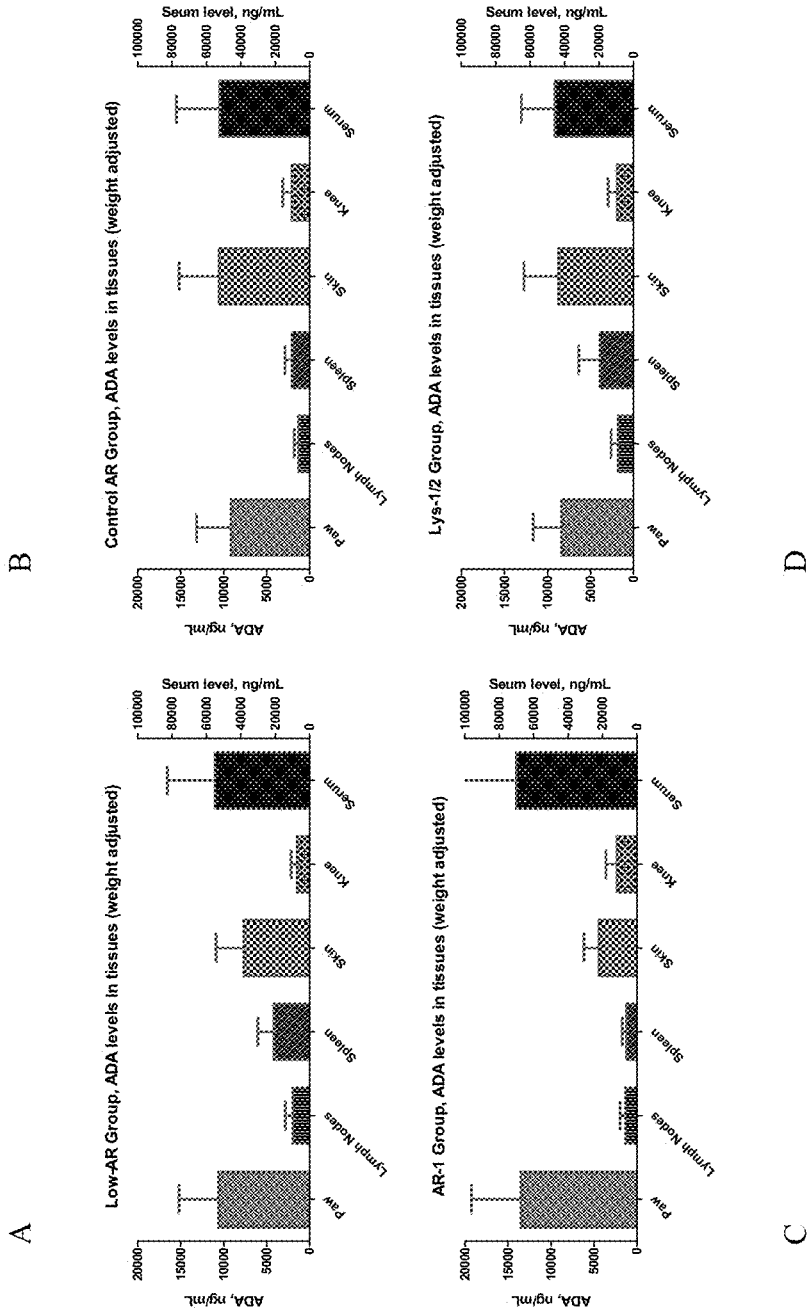
Figure 202:
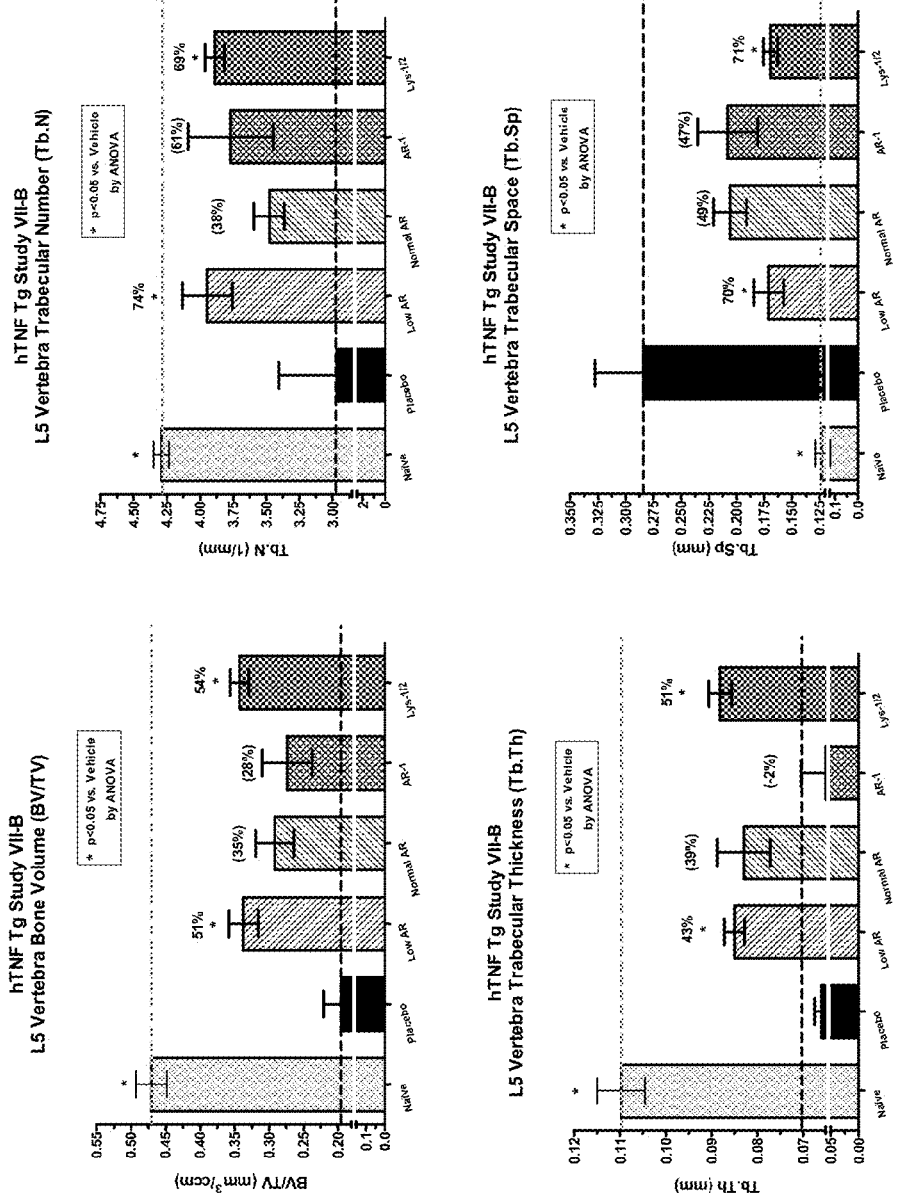
Figure 203:
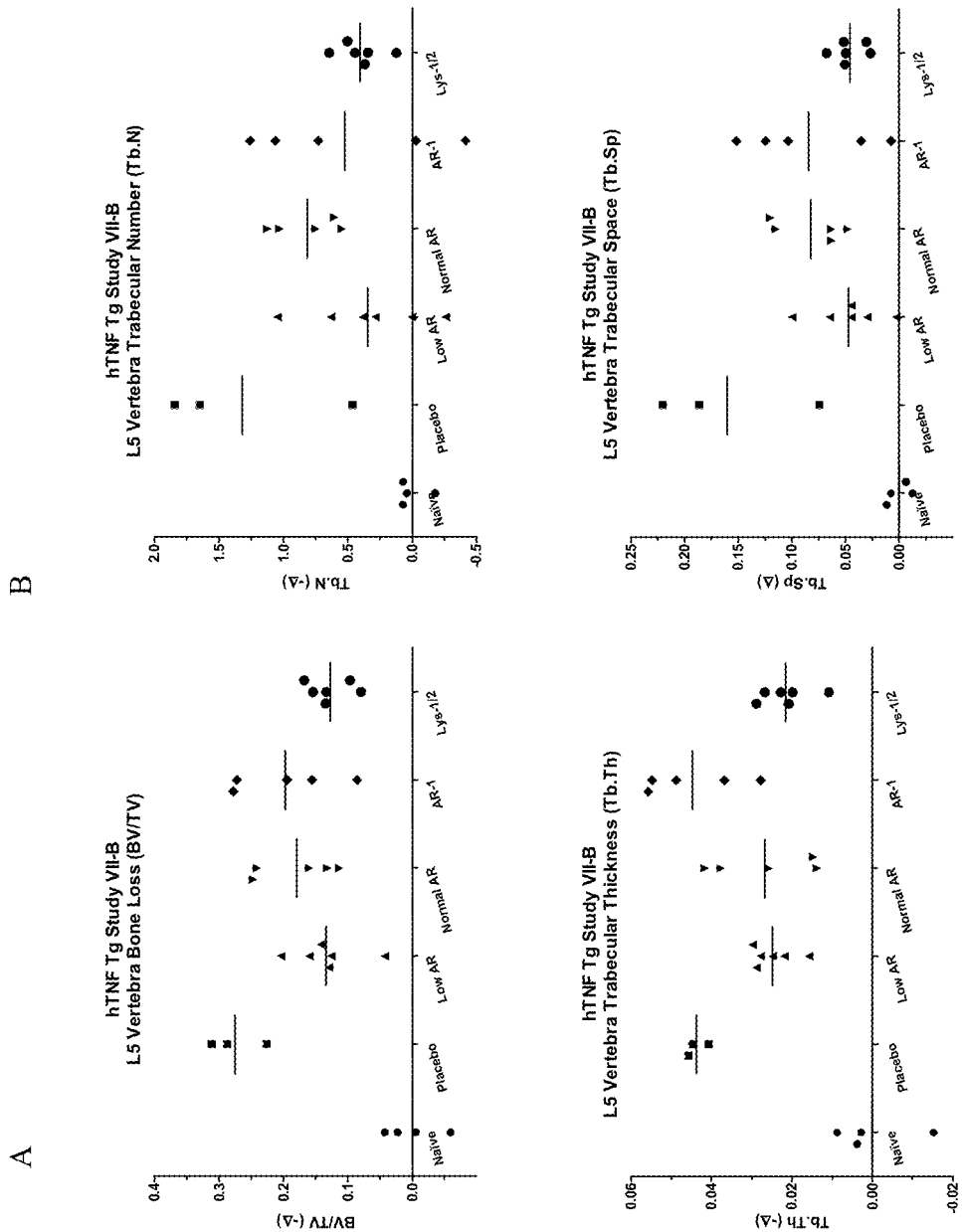
Figure 204:
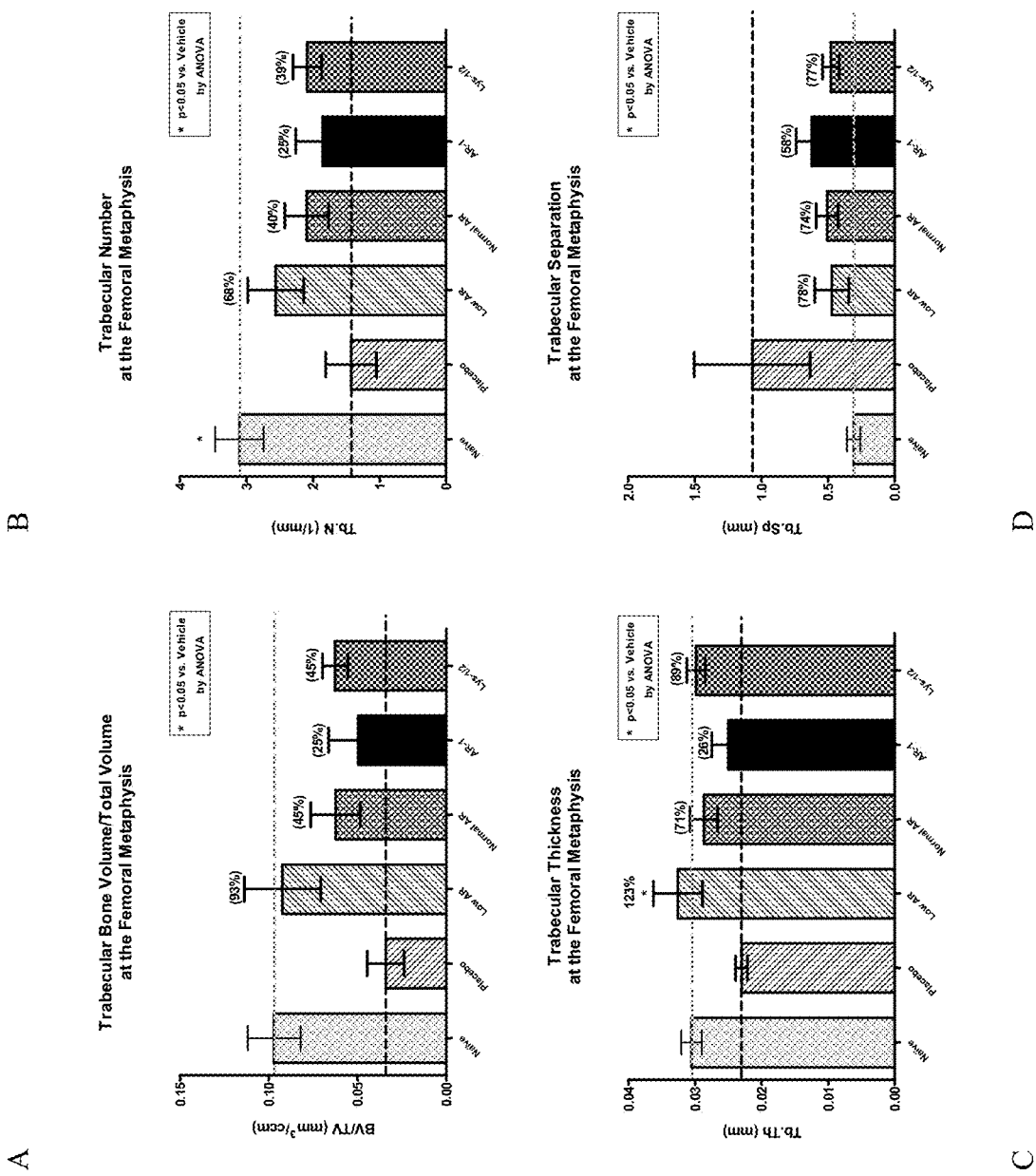

FIG. 199 depicts the chondrocyte death, synovial proliferation, proteoglycan loss, cartilage destruction, and bone erosion of mice administered low AR composition, AR1 composition, Lys-1/2 composition, and control AR composition.

FIGS. 200A-D illustrate the average drug levels for various tissues (paw, lymph node, spleen, skin, knee and serum) for mice administered (A) low AR composition; (B) control AR composition; (C) AR1 composition; and (D) Lys-1/2 composition.

FIGS. 201A-D illustrate the average ADA levels for various tissues (paw, lymph node, spleen, skin, knee and serum) for mice administered (A) low AR composition; (B) control AR composition; (C) AR1 composition; and (D) Lys-1/2 composition.

FIGS. 202A-D show the results of a micro CT analysis of spines and femurs obtained from TNF-Tg197 transgenic mice which were administered placebo, low AR composition, control (normal) AR composition, AR1 composition, and Lys-1/2 composition. The graphs depict the effect of the administered compositions on (A) vertebra bone volume; (B) vertebra trabecular number; (C) vertebra trabecular thickness; and (D) vertebra trabecular space.

FIGS. 203A-D show the results of a micro CT analysis of spines and femurs obtained from TNF-Tg197 transgenic mice which were administered placebo, low AR composition, control (normal) AR composition, AR1 composition, and Lys-1/2 composition. The graphs depict the effect of the administered compositions on (A) vertebra bone loss; (B) vertebra trabecular number; (C) vertebra trabecular thickness; and (D) vertebra trabecular space.

FIGS. 204A-D show results of a micro CT analysis of spines and femurs obtained from TNF-Tg197 transgenic mice which were administered placebo, low AR composition, control (normal) AR composition, AR1 composition, and Lys-1/2 composition. The graphs depict the effect of the administered compositions on (A) trabecular bone volume/total volume at the femoral metaphysis; (B) trabecular number at the femoral metaphysis; (C) trabecular thickness at the femoral metaphysis; and (D) trabecular separation at the femoral metaphysis.

Figure 205:
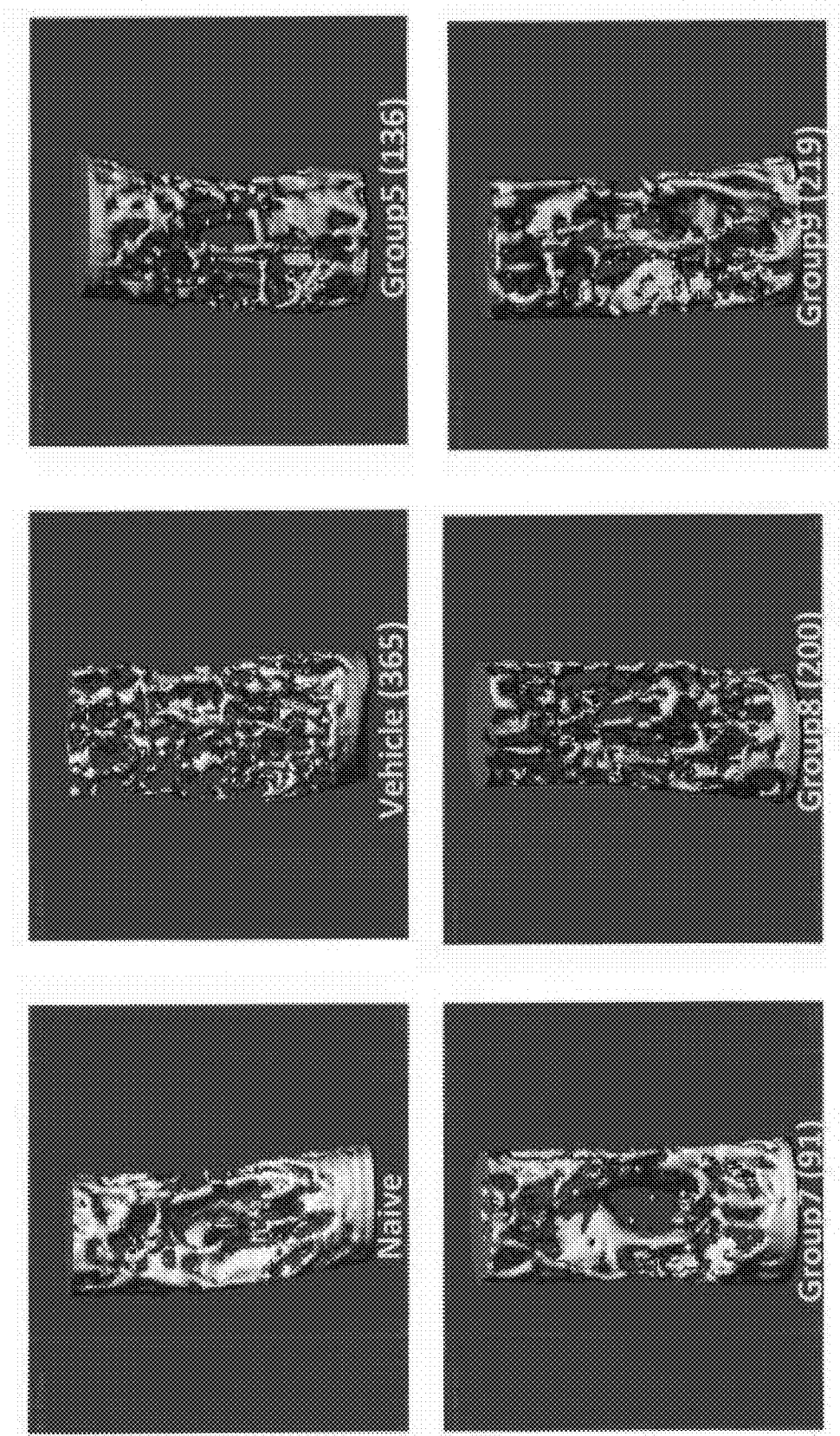

FIG. 205 depicts micro CT images of the spine from each of six groups of mice administered the following compositions: naïve, vehicle (control), low AR composition (group 5), low host cell protein (HCP) composition (group 7), AR1 composition (containing only AR1 acidic variants) (group 8), and Lys-1/2 composition (containing only Lys 1 and Lys 2 variants) (group 9).

Figure 206:
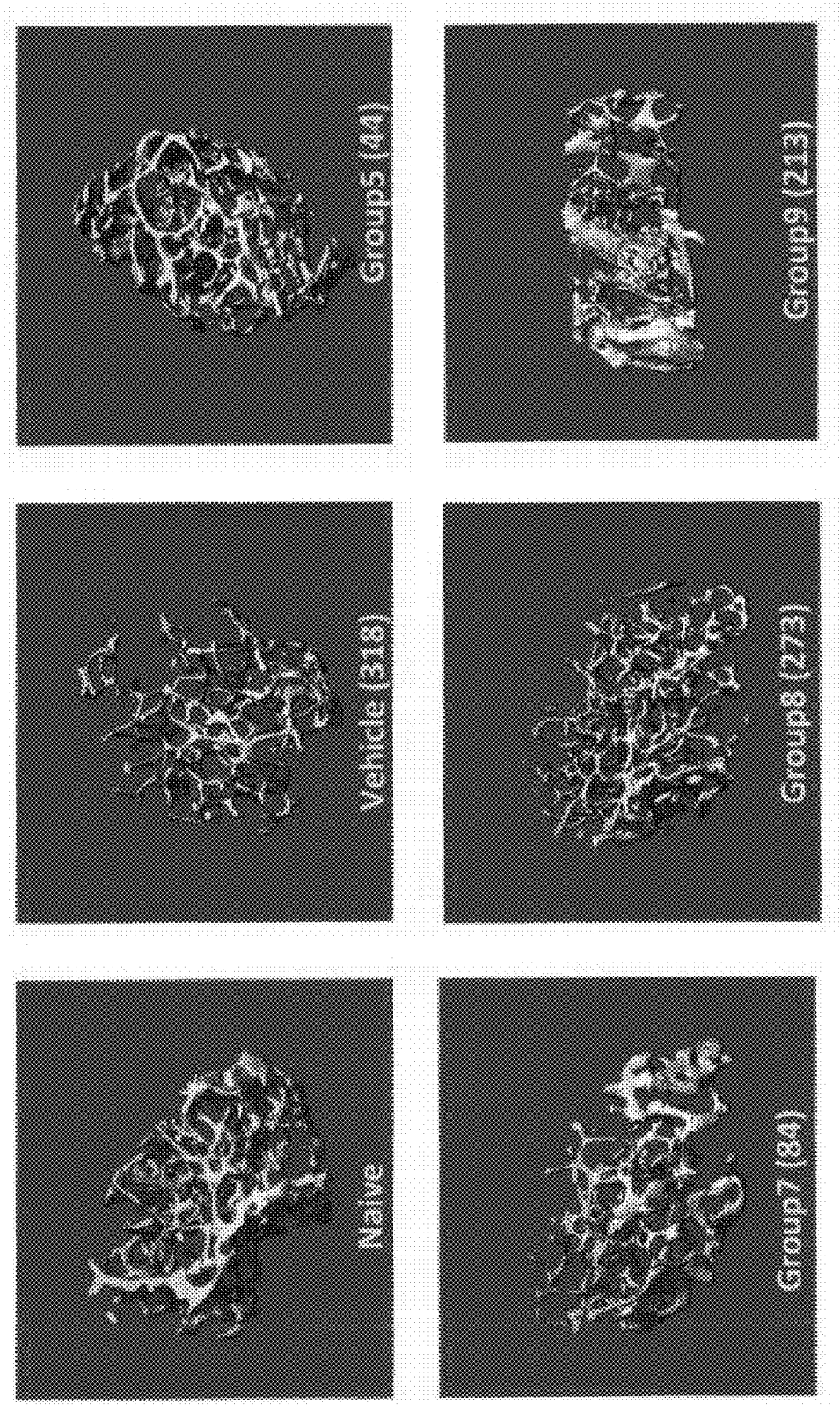

FIG. 206 depicts micro CT images of the femur from each of six groups of mice administered the following compositions: naïve, vehicle (control), low AR composition (group 5), low host cell protein (HCP) composition (group 7), AR1 composition (containing only AR1 acidic variants) (group 8), and Lys-1/2 composition (containing only Lys 1 and Lys 2 variants) (group 9).

DETAILED DESCRIPTION OF THE INVENTION

The present invention is based on the identification and optimization of upstream and downstream process technologies for protein production, e.g., production of antibodies or antigen-binding portions thereof, resulting in the production of protein compositions that comprise low percentages of acidic species (AR) and/or low levels of process-related impurities (e.g., host cell proteins and media components).

As demonstrated herein, the compositions of the present invention exhibit increased therapeutic efficacy when administered to a subject. For example, compositions comprising anti-TNFα antibodies, or antigen binding portions thereof, comprising low AR are capable of increased therapeutic efficacy in the treatment and prevention of a disorder in which TNFα is detrimental, e.g., rheumatoid arthritis (RA), juvenile idiopathic arthritis (JIA), psoriasis, psoriatic arthritis, ankylosing spondylitis, Crohn's disease, and ulcerative colitis. Accordingly, the instant invention provides compositions comprising proteins that comprise low AR and/or low levels of process-related impurities, and methods for producing and using the same.

In one embodiment, the low AR compositions of the invention comprise about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. In one aspect of this embodiment, the low AR compositions of the invention comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding. In one embodiment, the composition of the invention is not a composition, e.g., an adalimumab composition, comprising 2.4% or 2.5% AR.

In another embodiment, the low AR composition comprises a first acidic species (AR1) and a second acidic species (AR2). In one aspect of this embodiment, the low AR composition comprises about 0.1% or less AR1 and about 3% or less AR2. In another aspect of this embodiment, the low AR composition comprises about 0.0% AR1 and about 1.4% or less AR2.

In another aspect of this embodiment, the low AR composition comprises about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1 or less, 0.3% or less AR1 or less, 0.2% or less AR1 or less, 0.1% or less AR1, or 0.0% AR1, and ranges within one or more of the preceding. In one aspect of this embodiment, the low AR compositions of the invention comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding. In one embodiment, the composition of the invention is not a composition, e.g., an adalimumab composition, comprising 0.2% AR1.

In yet another aspect of this embodiment, the low AR composition comprises about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the low AR compositions of the invention comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding. In one embodiment, the composition of the invention is not a composition, e.g., an adalimumab composition, comprising 2.2% AR2.

In another embodiment, the low AR composition, e.g., a low AR composition of adalimumab, comprises about 1.4% or less AR. For example, in one aspect of this embodiment, the low AR composition, e.g., a low AR composition of adalimumab comprising about 1.4% or less AR comprises about 0.0% AR1 and about 1.4% or less AR2.

In one embodiment, the protein is an antibody or antigen binding portion thereof, such as adalimumab, or an antigen binding portion thereof.

I. Definitions

In order that the present invention may be more readily understood, certain terms are first defined.

As used herein, the terms "acidic species," "acidic region," and "AR," refer to the variants of a protein, e.g., an antibody or antigen-binding portion thereof, which are characterized by an overall acidic charge. For example, in monoclonal antibody (mAb) preparations, such acidic species can be detected by various methods, such as ion exchange, for example, WCX-10 HPLC (a weak cation exchange chromatography), or IEF (isoelectric focusing). As depicted in FIG. 188, acidic species of an antibody may include charge variants, structure variants, and/or fragmentation variants. Exemplary charge variants include, but are not limited to, deamidation variants, afucosylation variants, methylglyoxal (MGO) variants, glycation variants, and citric acid variants. Exemplary structure variants include, but are not limited to, glycosylation variants and acetonation variants. Exemplary fragmentation variants include any truncated protein species from the target molecule due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants include variants containing unpaired disulfides, host cell proteins, and host nucleic acids, chromatographic materials, and media components.

In certain embodiments, a protein composition can comprise more than one type of acidic species variant. For example, but not by way of limitation, the total acidic species can be divided based on chromatographic retention time of the peaks appearing, for example, in a WCX-10 Weak Cation Exchange HPLC of the protein preparation. FIG. 163 depicts a non-limiting example of such a division wherein the total acidic species associated with the expression of adalimumab is divided into a first acidic species region (AR1) and a second acidic species region (AR2).

As depicted schematically in FIG. 188, AR1 can comprise, for example, charge variants such as deamidation variants, MGO modified species, glycation variants, and citric acid variants, structural variants such as glycosylation variants and acetonation variants, and/or fragmentation variants. In another embodiment, AR2 can comprise, for example, charge variants such as glycation variants and deamidation variants.

With respect, in particular, to adalimumab (and antibodies sharing certain structural characteristics of adalimumab, e.g., one or more CDR and/or heavy and light chain variable regions of adalimumab), AR1 charge variants can comprise, but are not limited to, deamidation variants, glycation variants, afucosylation variants, MGO (e.g., MGO variants at the residues shown in Table 5, below) variants or citric acid variants. In one embodiment, deamidation variants result from deamidation occurring at asparagine residues comprising Asn393 and Asn329 and at glutamine residues comprising Gln3 and Gln6. In another embodiment, the glycation variants result from glycation occurring at Lys98 and Lys151. AR1 structure variants can comprise, but are not limited to, glycosylation variants or acetonation variants.

AR1 fragmentation variants can comprise Fc and Fab fragments, fragments missing a Fab, fragments missing a heavy chain variable domain, C-terminal truncation variants, variants with excision of N-terminal Asp in the light chain, and variants having N-terminal truncation of the light chain.

AR2 charge variants can comprise, but are not limited to, deamidation variants or glycation variants, wherein the deamidation variants can result from deamidation occurring at asparagine residues comprising Asn393 and Asn329 and at glutamine residues comprising Gln3 and Gln6, and the glycation variants can result from glycation occurring at Lys98 and Lys151.

The term "acidic species" does not include process-related impurities. The term "process-related impurity," as used herein, refers to impurities that are present in a composition comprising a protein but are not derived from the protein itself. Process-related impurities include, but are not limited to, host cell proteins (HCPs), host cell nucleic acids, chromatographic materials, and media components. A "low process-related impurity composition," as used herein, refers to a composition comprising reduced levels of process-related impurities as compared to a composition wherein the impurities were not reduced. For example, a low process-related impurity composition may contain about 10%, 9%, 8%, 7%, 6%, 5%, 4%, 3%, 2%, 1%, 0.5%, or less of process-related impurities. In one embodiment, a low process-related impurity composition is free of process-related impurities or is substantially free of process-related impurities.

The acidic species may be the result of product preparation (referred to herein as "preparation-derived acidic species"), or the result of storage (referred to herein as "storage-derived acidic species"). Preparation-derived acidic species are acidic species that are formed during the preparation (upstream and/or downstream processing) of the protein, e.g., the antibody or antigen-binding portion thereof. For example, preparation-derived acidic species can be formed during cell culture ("cell culture-derived acidic species"). Storage-derived acidic species are acidic species that may or may not be present in the population of proteins directly after preparation, but are formed or generated while the sample is being stored. The type and amount of storage-derived acidic species can vary based on the formulation of the sample. Formation of storage-derived acidic species can be partially or completely inhibited when the preparation is stored under particular conditions. For example, an aqueous formulation can be stored at a particular temperature to partially or completely inhibit AR formation. For example, formation or storage-derived AR can be partially inhibited in an aqueous formulation stored at between about 2° C. and 8° C., and completely inhibited when stored at −80° C. In addition, a low AR composition can be lyophilized or freeze-dried to partially or completely inhibit the formation of storage-derived AR.

The term "low acidic species composition," or "low AR composition," as used herein, refers to a composition comprising an antibody or antigen-binding portion thereof, wherein the composition contains less than about 15% acidic species. As used herein, the percent AR in the low AR composition refers to the weight of the acidic species in a sample in relation to the weight of the total antibodies contained in the sample. For example, the percent AR can be calculated using weak cation exchange chromatography such as WCX-10, as described in, for example, Example 1 below.

In one embodiment, a low AR composition of the invention may comprise about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. A low AR composition of the invention may also comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

A low AR composition of the invention may comprise about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. A low AR composition of the invention may also comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

A low AR composition of the invention may also comprise about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. A low AR composition of the invention may also comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

In one embodiment, a low AR composition comprises between about 0.0% and about 3% AR1. In another embodiment, a low AR composition comprises about between about 0.0% and about 3% AR2. In still another embodiment, a low acidic species composition comprises about 3% or less AR2.

In another embodiment, the low AR composition comprises about 1.4% or less AR. For example, in one embodiment, the composition comprises about 1.4% AR2 and about 0.0% AR1.

In one embodiment, a low AR composition of the invention may comprise about 15% or less, 14% or less, 13% or less, 12% or less, 11% or less, 10% or less, 9% or less, 8% or less, 7% or less, 6% or less, 5% or less, 4.5% or less, 4% or less, 3.5% or less, 3% or less, 2.5% or less, 2% or less, 1.9% or less, 1.8% or less, 1.7% or less, 1.6% or less, 1.5% or less, 1.4% or less, 1.3% or less, 1.2% or less, 1.1% or less, 1% or less, 0.9% or less, 0.8% or less, 0.7% or less, 0.6% or less, 0.5% or less, 0.4% or less, 0.3% or less, 0.2% or less, 0.1% or less, or 0.0% of one or more of a deamidation variant, an afucosylation variant, an MGO variant, a glycation variant, a citric acid variant, a glycosylation variant, an acetonation variant, or a fragmentation variant, and ranges within one or more of the preceding. In one aspect of this embodiment, a low AR composition of the invention may also comprise about 0.0% to about 10%, about 0.0% to about 5%, about 0.0% to about 4%, about 0.0% to about 3%, about 0.0% to about 2%, about 3% to about 5%, about 5% to about 8%, or about 8% to about 10%, or about 10% to about 15%, of one or more of a deamidation variant, an afucosylation variant, an MGO variant, a glycation variant, a citric acid variant, a glycosylation variant, an acetonation variant, or a fragmentation variant, and ranges within one or more of the preceding. For example, a low AR composition of the invention may comprise less than 15% of a deamidation variant, while each of the other acidic variants, alone or in combination, are at a percentage that is greater than 15%.

The term "non-low acidic species composition," as used herein, refers to a composition comprising an antibody or antigen-binding portion thereof, which contains more than about 16% acidic species. For example, a non-low acidic species composition may contain about 16% or more, 17% or more, 18% or more, 19% or more, 20% or more, 21% or more, 22% or more, 23% or more, 24% or more, or 25% or more acidic species. In one embodiment, a non-low acidic species composition can comprise about 16% or more, 17% or more, 18% or more, 19% or more, 20% or more, 21% or more, 22% or more, 23% or more, 24% or more, or 25% or more of AR1. In another embodiment, a non-low acidic species composition can comprise about 16% or more, 17% or more, 18% or more, 19% or more, 20% or more, 21% or more, 22% or more, 23% or more, 24% or more, or 25% or more of AR2, and ranges within one or more of the preceding.

In one embodiment, a low AR composition has improved biological and functional properties, including increased efficacy in the treatment or prevention of a disorder in a subject, e.g., a disorder in which TNFα activity is detrimental, as compared to a non-low acidic species composition. In one embodiment, the low AR composition comprises an anti-TNFα antibody, or antigen-binding portion thereof, such as adalimumab or a fragment thereof. For example, in one embodiment, a low AR composition comprising an antibody, or antigen-binding portion thereof, exhibits increased cartilage penetration, decreased bone erosion, and/or reduced cartilage destruction, as compared to a non-low acidic species composition comprising the same antibody or antigen binding portion thereof, when administered to a subject suffering from a disorder in which TNFα activity is detrimental.

As used herein, the term "increased cartilage penetration" refers to increased penetration of cartilage in vivo by a low AR composition as compared to a non-low AR composition comprising the same antibody or antigen binding portion thereof.

As used herein, the term "reduced cartilage destruction" refers to measurable decrease in destruction of cartilage tissue in vivo by a low AR composition as compared to a non-low AR composition comprising the same antibody or antigen binding portion thereof. As used herein, the term "decreased bone erosion" refers to measurable decrease, in vivo, of the erosion of bone tissue by a low AR composition as compared to a non-low acidic species composition comprising the same antibody or antigen binding portion thereof. For example, an in vivo model of a disease or disorder in which TNFα activity is detrimental, e.g., a mouse model of arthritis, can be used to measure cartilage penetration, bone erosion, and/or cartilage destruction by a composition comprising an anti-TNFα antibody or antigen binding portion thereof. One non-limiting example of an art-recognized mouse model of arthritis is the human TNF transgenic 197 mouse model of arthritis (TNF-Tg197) (see Keffer, J. et al., *EMBO J* (1991) 10:4025-4031, the contents of which are expressly incorporated herein by reference, for further description of the TNF-Tg197 model of arthritis).

In another embodiment, a low AR composition comprising an antibody, or antigen-binding portion thereof, exhibits increased protection against the development of arthritis, as measured by arthritic scores, and/or histopathology scores as compared to a non-low acidic species composition when administered to an animal model of arthritis, e.g., the TNF-Tg197 model of arthritis. As used herein, "arthritic scores" refer to signs and symptoms of arthritis in an animal model of arthritis. As used herein, "histopathology scores" refer to radiologic damage involving cartilage and bone as well as local inflammation.

In another embodiment, a low AR composition comprising an antibody, or antigen-binding portion thereof, exhibits reduced synovial proliferation, reduced cell infiltration, reduced chondrocyte death, and/or reduced proteoglycan loss as compared to a non-low acidic species composition. In another embodiment, a low AR composition comprising an anti-TNFα antibody, or antigen-binding portion thereof, exhibits increased TNFα affinity as compared to a non-low acidic species composition.

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, or synovial fluid of the subject), which can be detected, for example, using an anti-TNFα antibody as described above. There are numerous examples of disorders in which TNFα activity is detrimental. In one embodiment, the disorder in which TNFα activity is detrimental is an autoimmune disorder. In one embodiment, the autoimmune disorder is selected from the group consisting of rheumatoid arthritis, juvenile idiopathic arthritis, rheumatoid spondylitis, ankylosing spondylitis, psoriasis, osteoarthritis, gouty arthritis, an allergy, multiple sclerosis, psoriatic arthritis, autoimmune diabetes, autoimmune uveitis, nephrotic syndrome, juvenile rheumatoid arthritis, Crohn's disease, ulcerative colitis, active axial spondyloarthritis (active axSpA) and non-radiographic axial spondyloarthritis (nr-axSpA). Disorders in which TNFα activity is detrimental are set forth in U.S. Pat. No. 6,090,382 and also in the "Highlights of Prescribing Information" for HUMIRA® (adalimumab) Injection (Revised January 2008) the contents of which are hereby incorporated herein by reference. The use of TNFα antibodies and antibody portions obtained using methods of the invention for the treatment of specific disorders is discussed in further detail below.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., in the case of adalimumab, hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is adalimumab.

As used herein, the term "adalimumab," also known by its trade name HUMIRA® (AbbVie) refers to a human IgG$_1$ antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The light chain variable region of adalimumab is provided herein as SEQ ID NO:1, and the heavy chain variable region of adalimumab is provided herein as SEQ ID NO:2. Adalimumab comprises a light chain variable region comprising a CDR1 of SEQ ID NO:7, a CDR2 of SEQ ID NO:5, and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. The nucleic acid sequence of the light chain variable region is set forth in SEQ ID NO:9. The nucleic acid sequence of the heavy chain variable region is set forth in SEQ ID NO:10. The full length amino acid sequence of the light chain is set forth as SEQ ID NO:11 and the full length amino acid sequence of the heavy chain is set forth as SEQ ID NO:12. Adalimumab is described in U.S. Pat. Nos. 6,090,382; 6,258,562; 6,509,015; 7,223,394; 7,541,031; 7,588,761; 7,863,426; 7,919,264; 8,197,813; 8,206,714; 8,216,583; 8,420,081; 8,092,998; 8,093,045; 8,187,836; 8,372,400; 8,034,906; 8,436,149; 8,231,876; 8,414,894; 8,372,401, the entire contents of each of which are expressly incorporated herein by reference in their entireties. Adalimumab is also described in the "Highlights of Prescribing Information" for HUMIRA® (adalimumab) Injection (Revised January 2008) the contents of which are hereby incorporated herein by reference.

In one embodiment, adalimumab dissociates from human TNFα with a Kd of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC50 of $1 \times 10$-M or less. In another embodiment, adalimumab dissociates from human TNFα with a $K_{off}$ of $5 \times 10^4$ s$^{-1}$ or less, or with a $K_{off}$ of $1 \times 10^{-4}$ s$^{-1}$ or less. In still another embodiment, adalimumab neutralizes human TNFα cytotoxicity in a standard in vitro L929 assay with an IC50 of $1 \times 10^{-8}$ M or less, an IC50 of $1 \times 10^{-9}$ M or less or an IC50 of $1 \times 10^{-10}$ M or less.

In general, the heavy chain constant domain 2 (CH2) of the adalimumab IgG-Fc region is glycosylated through covalent attachment of oligosaccharide at asparagine 297 (Asn-297). Analysis of adalimumab has shown that it has three main basic variants (i.e., Lys 0, Lys 1, and Lys 2), referred to herein as "lysine variant species." As used herein, the term "lysine variant species" refers to an antibody, or antigen-binding portion thereof, comprising heavy chains with either zero, one or two C-terminal lysines. For example, the "Lys 0" variant comprises an antibody, or antigen-binding portion thereof, with heavy chains that do not comprise a C-terminal lysine. The "Lys 1" variant comprises an antibody, or antigen-binding portion thereof, with one heavy chain that comprises a C-terminal lysine. The "Lys 2" variant comprises an antibody with both heavy chains comprising a C-terminal lysine. Lysine variants can be detected, for example, by weak cation exchange chromatography (such as WCX-10) of the expression product of a host cell expressing the antibody, or antigen-binding portion thereof. For example, but not by way of limitation, FIGS. 163 and 193 depict WCX-10 analysis of adalimumab wherein the three lysine variants, as well as the two acidic species regions, are resolved from each other.

A composition of the invention may comprise more than one lysine variant species of an antibody, or antigen-binding portion thereof. For example, in one embodiment, the composition may comprise a Lys 2 variant of an antibody, or antigen-binding portion thereof. The composition may comprise a Lys 1 variant of an antibody, or antigen-binding portion thereof. The composition may comprise a Lys 0 variant of an antibody, or antigen-binding portion thereof. In another embodiment, the composition may comprise both Lys 1 and Lys 2 or Lys 1 and Lys 0 or Lys 2 and Lys 0 variants of an antibody, or antigen-binding portion thereof. In another embodiment, the composition may comprise all three lysine variant species, i.e., Lys 0, Lys 1 and Lys 2, of an antibody, or antigen-binding portion thereof.

As used herein, the term "upstream process technology," in the context of protein, e.g., antibody, preparation, refers to activities involving the production and collection of proteins (e.g. antibodies) from cells (e.g., during cell culture of a protein of interest). As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host, the host can be maintained under conditions suitable for expression of the relevant nucleotide coding sequences, and the collection and purification of the desired recombinant protein.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization) can be removed by a variety of means, including but not limited to, centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit.

As used herein, the term "downstream process technology" refers to one or more techniques used after the upstream process technologies to purify the protein, e.g., antibody, of interest. For example, downstream process technology includes purification of the protein product, using, for example, affinity chromatography, including Protein A affinity chromatography, ion exchange chromatography, such as anion or cation exchange chromatography, hydrophobic interaction chromatography, or displacement chromatography.

The phrase "isolated nucleic acid molecule," as used herein in reference to nucleic acids encoding antibodies or antibody portions (e.g., VH, VL, CDR3), e.g., those that bind hTNFα, includes a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, e.g., an isolated nucleic acid of the invention encoding a VH region of an anti-TNFα antibody contains no other sequences encoding other VH regions that bind antigens other than, for example, hTNFα. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant protein" refers to a protein produced as the result of the transcription and translation of a gene carried on a recombinant expression vector that has been introduced into a host cell. In certain embodiments the recombinant protein is an antibody, e.g., a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment).

The phrase "clarified harvest" refers to a liquid material containing a protein of interest, for example, an antibody of interest such as a monoclonal antibody of interest, that has been extracted from cell culture, for example, a fermentation bioreactor, after undergoing centrifugation to remove large solid particles and subsequent filtration to remove finer solid particles and impurities from the material.

The term "preparative scale," as used herein, refers to a scale of purification operation that can be readily scaled-up and implemented at large scale manufacturing while still providing desired separation. For instance, one skilled in the field may develop a process using, e.g., a 0.5 cm (i.d.)×20 cm (L) column in the lab, and transfer it to large scale production using, e.g., a 30 cm (i.d.)×20 cm (L) column packed with the same resin and operated with the same set of buffers, same linear flow rates (or residence times) and buffer volumes. In preparative scale separation, column bed height is typically ≤about 30 cm and column pressure drop ≤about 5 bar.

II. Low Acidic Species Compositions of the Invention

The present invention provides low AR compositions comprising a protein, e.g., an antibody, or antigen-binding portion thereof, such as adalimumab, where the composition comprises about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. A low AR composition of the invention may also comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In one embodiment, a low AR composition of the invention may comprise about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. A low AR composition of the invention may also comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In another embodiment, a low AR composition of the invention may also comprise about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. A low AR composition of the invention may also comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

As demonstrated herein, these low AR compositions have improved biological properties (see Example 13). For example, the low AR compositions of the invention are characterized by increased cartilage tissue penetration, reduced cartilage destruction, reduced synovial proliferation, reduced bone erosion, increased protection against the development of arthritic scores and/or histopathology scores, reduced cell infiltration, reduced proteoglycan loss, reduced chondrocyte death, and/or increased TNF affinity, as compared to non-low acidic species compositions. In addition, the compositions of the present invention exhibit increased therapeutic efficacy when administered to a subject.

In one embodiment, the protein in the low AR composition of the invention is an antibody or antigen binding portion thereof. For example, the antibody, or antigen binding portion thereof may be an anti-TNFα antibody, or antigen binding portion thereof, such as adalimumab, or an antigen binding portion thereof. In one aspect of this embodiment, the antibody, or antigen binding portion thereof, can comprise a light chain variable region comprising the sequence set forth as SEQ ID NO:1, and a heavy chain variable region comprising the sequence set forth as SEQ ID NO:2. In another aspect of this embodiment, the antibody can comprise a light chain variable region comprising a CDR1 having the sequence set forth as SEQ ID NO:7, a CDR2 having the sequence set forth as SEQ ID NO:5, and a CDR3 having the sequence set forth as SEQ ID NO:3. In another aspect of this embodiment, the antibody can comprise a heavy chain variable region comprising a CDR1 having the sequence set forth as SEQ ID NO:8, a CDR2 having the sequence set forth as SEQ ID NO:6 and a CDR3 having the sequence set forth as SEQ ID NO:4.

The antibody, or antigen binding portion thereof, used in the low AR compositions of the invention, may be a human, humanized, or chimeric antibody.

The antibodies that can be used in the low AR compositions of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Somatic cell hybridization procedures can be used. In principle, other techniques for producing monoclonal antibody can be employed as well, including viral or oncogenic transformation of B lymphocytes.

One exemplary animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody used in the low AR compositions of the invention can be a human, a chimeric, or a humanized antibody. Chimeric or humanized antibodies used in the low AR compositions of the invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies to be used in the low AR compositions of the invention are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen). The antibodies, or antigen-binding portions thereof, used in the low AR compositions of the invention can also be produced using the methods described in U.S. Pat. No. 6,090,382, the entire contents of which is expressly incorporated herein by reference.

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies to be used in the low AR compositions of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibody Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies to be used in the low AR compositions of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the human antibodies to be used in the low AR compositions of the invention are anti-TNFα antibodies and antibody portions thereof, anti-TNFα-related antibodies and antibody portions, and human antibodies and antibody portions with equivalent properties to anti-TNFα antibodies, such as high affinity binding to hTNFα with low dissociation kinetics and high neutralizing capacity. In one aspect, the invention provides low AR compositions containing an isolated human antibody, or an antigen-binding portion thereof, that dissociates from hTNFα with a Kd of about $1 \times 10^{-8}$ M or less and a Koff rate constant of $1 \times 10^{-3}$ s$^{-1}$ or less, both determined by surface plasmon resonance. In specific non-limiting embodiments, an anti-TNFα antibody to be used in the low AR compositions of the invention competitively inhibits binding of adalimumab to TNFα under physiological conditions. In one embodiment, the low AR compositions of the invention comprise adalimumab, or an antigen binding fragment thereof.

Antibodies or fragments thereof to be used in the low AR compositions of the invention can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

III. Preparation of Low AR Compositions Using Upstream Process Technologies

The low AR compositions comprising a protein, e.g., an antibody, or antigen binding portion thereof, such as adalimumab, of the invention can be produced by modulating conditions during upstream protein production, such as cell culture. In one embodiment, the methods of the invention comprise lowering the amount of acidic species variants or process-related impurities expressed by host cells producing a protein of interest including an antibody or antigen-binding portion thereof during an upstream process technology (e.g., during cell culture).

The upstream process technologies may be used alone or in combination with the downstream process technologies described in Section IV, below, and as described in Example 10.

In one embodiment, one or more of the upstream process technologies described herein produce a low AR composition comprising an antibody, or antigen binding portion thereof, which comprises 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. In one aspect of this embodiment, the low AR composition of the invention comprises about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In another embodiment, one or more of the upstream process technologies described herein produce a low AR composition comprising an antibody, or antigen binding portion thereof, which comprises 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. In one aspect of this embodiment, the low AR composition of the invention comprises about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In still another embodiment, one or more of the upstream process technologies described herein produce a low AR composition comprising an antibody, or antigen binding portion thereof, which comprises 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the low AR composition of the invention comprises about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

Some embodiments of the invention comprise culturing host cells to express a protein of interest under conditions that limit the amount of acidic species that are expressed by the cells. Some embodiments of the invention comprise culturing host cells under conditions that limit the conversion of the product to acidic species variants.

The cell culture conditions can be modified as compared to conditions during production of a non-low acidic species composition comprising the same protein. In one embodiment, the low acidic species composition is produced by culturing cells expressing the antibody, or antigen binding portion thereof, in a cell culture media comprising an increased concentration of one or more amino acids. In another embodiment, the low acidic species composition is produced by culturing cells expressing the antibody, or antigen binding portion thereof, in a cell culture media comprising an increased concentration of calcium (e.g., as calcium chloride dihydrate). In still another embodiment, the low acidic species composition is produced by culturing cells expressing the antibody, or antigen binding portion thereof, in a cell culture media comprising an increased concentration of niacinamide. In certain embodiments, the methods described herein comprise culturing cells in media supplemented with one or more amino acids, calcium (e.g., as calcium chloride dihydrate) and/or niacinamide, and combinations thereof.

In certain embodiments, the low acidic species composition is produced by culturing host cells in a culture wherein process parameters, such as pH or dissolved oxygen (DO), are modulated, e.g., lowered to decrease the amount of acidic species produced by the host cells and/or reduce the conversion of the product to the acidic species variants.

Furthermore, a continuous or perfusion technology can utilized to obtain low AR. In certain embodiments, reduction of acidic species is obtained by modulating the medium exchange rate during cell culture.

In another embodiment, one or more of the above supplements and modifications can be combined and used during cell culture of one protein, e.g., antibody, composition.

To express an antibody or antigen-binding fragment thereof to be used in the low AR compositions of the invention, DNAs encoding the protein, such as DNAs encoding partial or full-length light and heavy chains in the case of antibodies, are inserted into one or more expression vector such that the genes are operatively linked to transcriptional and translational control sequences. (See, e.g., U.S. Pat. No. 6,090,382, the entire teaching of which is incorporated herein by reference.) In this context, the term "operatively linked" is intended to mean that a gene encoding the protein of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the protein of interest will comprising multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but not limited to, antibody constant region sequences. For example, one approach to converting the anti-TNFα antibody or anti-TNFα antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

A recombinant expression vector may also carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr– host cells with methotrexate selection/amplification) and the neo gene (for G418 selection).

An antibody, or antibody portion, to be used in the low AR compositions of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), K. wickeramii (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma* reesia (EP 244,234); *Neurospora crassa*; Schwanniomyces such as Schwanniomyces occidentalis; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

Mammalian cells can be used for expression and production of the recombinant protein used in the low AR compositions of the invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601- 621, the entire teachings of which are incorporated herein by reference), NSO myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767, 704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antibody, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Some antibodies can be secreted directly from the cell into the surrounding growth media; others are made intracellularly. For antibodies made intracellularly, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

Adjusting Amino Acid Concentration to Modulate Acidic Species (AR)

In certain embodiments, the amount of one or more amino acids in the media is modulated (e.g., increased or decreased) in order to produce a low acidic species composition of the invention (see the Examples Section, below). Such increases or decreases in the amount of the one or more amino acids can be of about 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount used during cell culture where a non-low acidic species composition of the same protein is produced.

In certain embodiments, a cell culture media will include one or more of the amino acids, or other compositions described herein as lowering acidic species. Accordingly, the amount of the amino acid, or other composition, that is supplemented may be adjusted to account for the amount present in the media prior to supplementation.

In certain embodiments, the cell culture media is supplemented with one or more amino acids in an amount of between about 0.025 and 20 g/L, or between about 0.05 and 15 g/L, or between about 0.1 and 14 g/L, or between about 0.2 and 13 g/L, or between about 0.25 and 12 g/L, or between about 0.5 and 11 g/L, or between about 1 and 10 g/L, or between about 1.5 and 9.5 g/L, or between about 2 and 9 g/L, or between about 2.5 and 8.5 g/L, or between about 3 and 8 g/L, or between about 3.5 and 7.5 g/L, or between about 4 and 7 g/L, or between about 4.5 and 6.5 g/L, or between about 5 and 6 g/L. In certain embodiments, the cell culture media is supplemented with one or more amino acids in an amount of about 0.25 g/L, or about 0.5 g/L, or about 1 g/L, or about 2 g/L, or about 4 g/L, or about 8 g/L.

In certain embodiments, the cell culture media is supplemented with one or more amino acids in an amount effective to produce a low AR composition comprising about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, the cell culture media is supplemented with one or more amino acids in an amount effective to produce a low AR composition comprising about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding.

In yet another embodiment, the cell culture media is supplemented with one or more amino acids in an amount effective to produce a low AR composition comprising about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding.

In another embodiment, the cell culture media is supplemented with one or more amino acids in an amount effective to reduce the percentage of acidic species in a protein or antibody composition by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In some embodiments, the one or more amino acids used to supplement the cell culture media is a basic amino acid. In certain embodiments the one or more amino acids is arginine, lysine, histidine, ornithine, or certain combinations of arginine or lysine with ornithine or of all four amino acids. In certain embodiments, the amino acids are single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids. In certain embodiments, the amount of amino acid supplemented to the cell culture to achieve concentrations of about 0 to about 9 g/L for arginine, about 0 to about 11 g/L for lysine, about 0 to about 11 g/L histidine, and about 0 to about 11 g/L ornithine. Wider ranges are also within the scope of the instant invention, including, but not limited to: about 0 to about 30 g/L for arginine, about 0 to about 30 g/L for lysine, about 0 to about 30 g/L histidine, and about 0 to about 30 g/L ornithine.

For example, and not by way of limitation, as detailed in Example 1, below, when the production medium employed in the example was supplemented with arginine to achieve a total concentration of 9 g/L arginine, the total amount of acidic species of adalimumab present in a cell culture sample after purification was reduced from 19.7% of a control sample to 12.2% of the sample purified from the cells cultured with the arginine supplemented media. Similarly, when the production medium employed in the example was supplemented with lysine, or histidine, or ornithine to achieve total concentrations of 11 g/L lysine, 10 g/L ornithine or 10 g/L histidine, respectively, the total amount of acidic species of adalimumab present in a cell culture sample after purification was reduced by 11.5%, 10.4% and 10.9%, respectively, compared to a control sample.

In certain embodiments, the cell culture media is supplemented, for example, at the start of culture, or in a fed-batch or in a continuous manner. The feed amounts may be calculated to achieve a certain concentration based on offline or online measurements. The supplements may be added as multimers, e.g., arg-arg, his-his, arg-his-orn, etc., and/or as chemical variants, e.g., of amino acids or analogs of amino acids, salt forms of amino acids, controlled release of amino acids by immobilizing in gels, etc, and/or in fully or partially dissolved form. The addition of one or more supplements may be based on measured amount of acidic species. The resulting media can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. In addition, the harvest criterion for these cultures may be chosen, for example, based on choice of harvest viability or culture duration, to further optimize a certain targeted acidic species profile.

Adjusting $CaCl_2$ and/or Niacinamide Concentration to Modulate Acidic Species (AR)

In certain embodiments, the cell culture media is supplemented with calcium (e.g., as calcium chloride dihydrate) to achieve a calcium concentration of between about 0.05 and 2.5 mM, or between about 0.05 and 1 mM, or between about 0.1 and 0.8 mM, or between about 0.15 and 0.7 mM, or between about 0.2 and 0.6 mM, or between about 0.25 and 0.5 mM, or between about 0.3 and 0.4 mM calcium.

In certain embodiments, the cell culture media is supplemented with calcium (e.g., as calcium chloride dihydrate) in an amount effective to produce a low AR composition comprising about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, the cell culture media is supplemented with calcium (e.g., as calcium chloride dihydrate) in an amount effective to produce a low AR composition comprising about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding.

In yet another embodiment, the cell culture media is supplemented with calcium (e.g., as calcium chloride dihydrate) in an amount effective to produce a low AR composition comprising about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding.

In another embodiment, the cell culture media is supplemented with calcium (e.g., as calcium chloride dihydrate) in an amount effective to reduce the amount of acidic species in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

For example, and not by way of limitation, as detailed in Example 1, below, when the production medium employed in the example was supplemented with calcium (e.g., as calcium chloride dihydrate) at a concentration of 1.05 mM, the total amount of acidic species of adalimumab present in a cell culture sample after purification was reduced from 23.2% of a control sample to 16.5% of the sample purified from the cells cultured with the calcium supplemented media.

In certain embodiments, the cell culture can be supplemented with a combination of calcium, e.g., $CaCl_2$, and one or more a basic amino acids, as described above. In certain embodiments, the amount of basic amino acid concentrations in combination with calcium in the cell culture is between about 0 to about 9 g/L for arginine, about 0 to about 11 g/L for lysine, about 0 to about 11 g/L histidine, and about 0 to about 11 g/L ornithine. Wider ranges are also within the scope of the instant invention, including, but not limited to: about 0 to about 30 g/L for arginine, about 0 to about 30 g/L for lysine, about 0 to about 30 g/L histidine, and about 0 to about 30 g/L ornithine.

In certain embodiments, the cell culture media is supplemented with niacinamide to achieve a niacinamide concentration of between about 0.2 and 3.0 mM, or between about 0.4 and 3.0 mM, or between about 0.8 and 3.0 mM.

In some embodiments, the cell culture media is supplemented with niacinamide in an amount effective to reduce the amount of acidic species heterogeneity in a protein or antibody sample by about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, the cell culture media is supplemented with niacinamide in an amount effective to produce a low AR composition comprising about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding.

In yet another embodiment, the cell culture media is supplemented with niacinamide in an amount effective to produce a low AR composition comprising about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding.

For example, and not by way of limitation, as detailed in Example 1, below, when the production medium employed in the example was supplemented with niacinamide at a concentration of 1.6 mM, the total amount of acidic species of adalimumab present in a cell culture sample after purification was reduced from 19.9% of a control sample to 15.9% of the sample purified from the cells cultured with the niacinamide supplemented media. In a separate example, where the media was supplemented with 3 mM niacinamide, the total amount of acidic species of adalimumab present in a cell culture sample after purification was reduced from 27.0% of a control sample to 19.8% of the sample purified from the cells cultured with the niacinamide supplemented media.

In certain embodiments, the cell culture can be supplemented with a combination of niacinamide, calcium, e.g., $CaCl_2$, and/or one or more basic amino acids. In certain embodiments, the amount of basic amino acid concentrations (after supplementation) in combination with calcium in the cell culture is between about 0 to about 9 g/L for arginine, about 0 to about 11 g/L for lysine, about 0 to about 11 g/L histidine, and about 0 to about 11 g/L ornithine. Although wider ranges are also within the scope of the instant invention, including, but not limited to: about 0 to about 30 g/L for arginine, about 0 to about 30 g/L for lysine, about 0 to about 30 g/L histidine, and about 0 to about 30 g/L ornithine.

In certain embodiments, the one or more amino acids, calcium, and/or niacinamide can be included in the medium at the start of culture, or can be added in a fed-batch or in a continuous manner. The feed amounts may be calculated to achieve a certain concentration based on offline or online measurements. The addition of the supplement may be based on measured amount of acidic species. Other salts of particular supplements, e.g., calcium, may also be used, for example calcium nitrate. The resulting media can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line.

In certain embodiments, a low AR composition is produced by supplementing a clarified harvest. For example, but not by way of limitation, such clarified harvests can be supplemented as described above (e.g., with calcium, niacinamide, and/or basic amino acids or combinations thereof) to reduce AR formation (see Example 3).

Adjusting Process Parameters to Modulate Acidic Species (AR)

In certain embodiments, a low AR composition is produced by adjustment of the dissolved oxygen (DO) concentration, and/or pH of the cell culture run. In certain embodiments, such adjustment includes increasing the DO concentration of the cell culture, or decreasing the pH of the cell culture. Such increases in the DO concentration or decreases in the pH can be of a magnitude of about 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, cell cultures are run in DO concentrations maintained above about 15%, above about 20%, above about 30%, or between about 15% and about 80%, between about 30% and about 50%, or at about 80%, and ranges within one or more of the preceding, to achieve the desired reduction in acidic species.

In certain embodiments, pH is either increased or decreased in order to increase or decrease the amount of acidic species and/or the rate at which such acidic species form. For example, but not by way of limitation, a reduction in pH to about 6.7 from a control pH of about 7.1 can be employed to decrease the acidic species during cell culture and the rate of acidic species formation in the context of a clarified harvest.

In certain embodiments, the DO concentration, and/or pH is maintained in such a manner as to produce a low AR composition comprising about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, the DO concentration, and/or pH is maintained in such a manner as to produce a low AR composition comprising about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding.

In yet another embodiment, the DO concentration, and/or pH is maintained in such a manner as to produce a low AR composition comprising about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding.

In certain embodiments, the pH and/or DO is maintained in such a manner as to reduce the amount of acidic species in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

For example, and not by way of limitation, as detailed in Example 2, below, when five different pH conditions were assessed during cell culture: 7.1 7.0, 6.9, 6.8, and 6.7, the percent acidic species decreased with a decrease in pH from 29.7% in the pH 7.1 condition to 21.5% in the pH 6.7 condition, for a total reduction of 8.2%.

In addition, as detailed in Example 2, below (and not by way of limitation), three different DO concentrations were assessed during cell culture: 20% DO concentration, 30% DO concentration and 50% DO concentration, at 35° C. The percentage of acidic species was overall lower at higher DO concentrations. In particular, the percentage of acidic species decreased with an increase in DO concentration from 23.9% in the 20% DO concentration sample to 20.3% in the 50% DO concentration sample, for a total reduction of 3.6%.

In certain embodiments, a low AR composition is produced by cell culture can be exerted by maintaining the DO concentration, and/or pH of the cell culture expressing the protein of interest as described herein along with choice of suitable temperature or temperature shift strategies, for example, but not limited to, lower process temperature of operation, temperature shift to a lower temperature or a temperature shift at an earlier culture time point. These culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. These methods of modulating pH and/or DO and/or temperature may also be used in combination with supplementation of culture media with additives such as one or more amino acids, niacinamide, and/or calcium, or combinations thereof, as described above to maintain or achieve a target level of AR or to reduce the formation of AR during cell culture.

Continuous/Perfusion Cell Culture Technology to Modulate Acidic Species (AR)

In certain embodiments, a low AR composition is produced by the choice of cell culture methodology. In certain embodiments, use of a continuous or perfusion technology may be utilized to achieve the desired lowering of acidic species in combination. In certain embodiments, this may be attained by modulation of medium exchange rate (where the exchange rate is the rate of exchange of medium in/out of a reactor).

In certain, non-limiting, embodiments, maintenance of the medium exchange rates (working volumes/day) of a cell culture run between about 0 and about 20, or between about 0.5 and about 12 or between about 1 and about 8 or between about 1.5 and about 6 can be used to achieve the desired reduction in acidic species.

For example, and not by way of limitation, as detailed in Example 4, below, when the medium exchange rate was chosen to be 1.5, the acidic species was 8.1%. With further increase in exchange rates to 6, a further reduction in acidic species to 6% was obtained.

In certain embodiments, continuous or perfusion technology (e.g., modulation of exchange rate) may result in a low AR composition comprising about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, continuous or perfusion technology (e.g., modulation of exchange rate) may result in a low AR composition comprising about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding.

In yet another embodiment, continuous or perfusion technology (e.g., modulation of exchange rate) may result in a low AR composition comprising about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding.

In certain embodiments, continuous or perfusion technology (e.g., modulation of exchange rate) may result in a low AR composition comprising about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In one embodiment, media containing additives, such as, for example, one or more amino acids, calcium, and/or niacinamide, or combinations thereof, as described above, may be used as the perfusion media to maintain or achieve a target level of AR or to reduce the formation of AR during cell culture.

In certain embodiments, a low AR composition is produced by, for example, employment of an intermittent harvest strategy or through use of cell retention device technology.

IV. Preparation of Low AR Compositions Using Downstream Process Technologies

In certain embodiments, the low AR compositions of the present invention may be produced using downstream process technologies (e.g., purification), following cell culture of a protein. The downstream process technologies may be used alone or in combination with the upstream process technologies described in Section III, above, and as described in Example 10.

The methods described herein for the production of compositions comprising low AR and/or low process-related impurities comprise the purification of a protein, such as an antibody or antigen-binding portion thereof, by, for example, chromatography, such as multimodal (MM) chromatography, wherein the MM media comprises both ion exchange and hydrophobic interaction functional groups, and an aqueous salt solution. In one embodiment, the same or substantially the same aqueous salt solution is used as a loading buffer and a wash buffer.

In further embodiments, the methods described herein for the production of compositions comprising low AR and/or low process-related impurities comprise the purification of a protein, such as an antibody or antigen-binding portion thereof, by chromatography comprising an anion exchange (AEX) resin and an aqueous salt solution. In one embodiment, the same or substantially the same aqueous salt solution is used as a loading buffer and a wash buffer.

In yet further embodiments, the methods described herein for the production of compositions comprising low AR and/or low process-related impurities comprise the purification of a protein, such as an antibody or antigen-binding portion thereof, by chromatography comprising a cation exchange (CEX) adsorbent resin and an aqueous salt solution. In one embodiment, the same or substantially the same aqueous salt solution is used as a loading buffer and a wash buffer, and the target protein bound to the CEX adsorbent resin is eluted with a buffer having a higher conductivity and/or pH than the loading/wash buffer.

In still further embodiments, the methods described herein for production of compositions comprising low AR and/or low process-related impurities comprise the purification of a protein, such as an antibody or antigen-binding portion thereof, by a combination of several media, for example by using an anion exchange (AEX) resin, and chromatography using a cation exchange (CEX) adsorbent resin, in a suitable buffer, such as, for example, a Tris/Formate buffer system. In one embodiment, the sample is purified affinity chromatography media, e.g., Protein A, prior to the ion chromatography resins. For example, in one embodiment, the methods described herein for production of compositions comprising low AR comprise the exemplary process reflected in FIG. 190.

In one embodiment, the method for producing a low AR composition comprising an antibody, or antigen binding portion thereof, comprises contacting a first sample comprising the antibody, or antigen binding portion thereof, to affinity chromatography media in a load buffer (for example a low concentration Tris/Formate buffer), and eluting the sample from the affinity chromatography media as a first eluted sample, contacting the first eluted sample to a first chromatography media, such as an AEX chromatography resin, in a load buffer, and eluting the sample from the AEX chromatography resin as a second eluted sample. The second eluted sample is then contacted with a second chromatography media, such as a CEX chromatography resin, in a load buffer, and the sample is eluted from the CEX chromatography resin as a third eluted sample. In one embodiment, the CEX chromatography resin is eluted one, two, three or more times. In one embodiment, the process optionally includes one or more intermediate filtration steps, pH adjustment steps and/or inactivation steps.

In one embodiment, the downstream process technologies described herein, alone or in combination with other downstream process technologies or with one or more upstream process technology, produce a low AR composition comprising an antibody, or antigen binding portion thereof, which contains 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% AR, 0.3% or less AR, 0.2% or less AR, 0.1% or less AR, or 0.0% AR, and ranges within one or more of the preceding. In one aspect of this embodiment, the low AR composition of the invention comprises about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In one embodiment, the downstream process technologies described herein, alone or in combination with other downstream process technologies or with one or more upstream process technology, produce a low AR composition comprising an antibody, or antigen binding portion thereof, which contains 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. In one aspect of this embodiment, the low AR composition of the invention comprises about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In one embodiment, the downstream process technologies described herein, alone or in combination with other downstream process technologies or with one or more upstream process technology, produce a low AR composition comprising an antibody, or antigen binding portion thereof, which contains 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the low AR composition of the invention comprises about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

Protein Purification Generally

Following upstream processing of a protein of interest, downstream process technologies can be used to purify the protein. For example, but not by way of limitation, once a clarified solution or mixture comprising the protein of interest, for example, an antibody or antigen binding fragment thereof, has been obtained, separation of the protein of interest from the acidic species can be effected using a combination of different purification techniques, including, but not limited to, affinity separation steps, ion exchange separation steps, mixed mode separation steps, and hydrophobic interaction separation steps singularly or in combination. The separation steps separate mixtures of proteins on the basis of their charge, degree of hydrophobicity, or size, or any combination thereof, depending on the particular form of separation, including chromatographic separation. In one aspect of the invention, separation is performed using chromatography, including cationic, anionic, and hydrophobic interaction. Several different chromatography resins are available for each of these techniques, allowing accurate tailoring of the purification scheme to the particular protein involved. Each of the separation methods result in the protein traversing at different rates through a column, to achieve a physical separation that increases as they pass further through the column, or adhere selectively to the separation medium. The proteins are then differentially eluted by different elution buffers. In some cases, the antibody is separated from impurities when the impurities preferentially adhere to the column and the antibody less so, i.e., the desired antibody variant is present in the Flow Through.

In certain embodiments, a low AR composition is produced using chromatographic separation to identify the particular conditions, e.g., salt concentration, pH, DO concentration, temperature, load amount and conditions, and washing conditions, sufficient to elicit the desired fractionation profile, e.g., fractionation of acidic species and lysine variants, of a sample comprising the protein of interest and at least one process-related impurity. In certain embodiments, the method further comprises pooling the resulting fractions comprising the desired low AR composition compositions.

The purification process may begin at the separation step after the antibody has been produced using upstream production methods described above and/or by alternative production methods conventional in the art. Once a clarified solution or mixture comprising the protein of interest, e.g., an antibody, has been obtained, separation of the protein of interest from process-related impurities, such as the other proteins produced by the cell, as well as product-related substances, such acidic or basic variants, is performed. In certain non-limiting embodiments, such separation is performed using CEX, AEX, and/or MM chromatography. In certain embodiments, a combination of one or more different purification techniques, including affinity separation step(s), ion exchange separation step(s), mixed-mode step(s), and/or hydrophobic interaction separation step(s) can also be employed. Such additional purification steps separate mixtures of proteins on the basis of their charge, degree of hydrophobicity, and/or size. In one aspect of the invention, such additional separation steps are performed using chromatography, including hydrophobic, anionic or cationic interaction (or a combination thereof). Numerous chromatography resins are commercially available for each of these techniques, allowing accurate tailoring of the purification scheme to the particular protein involved. Each of the separation methods allow proteins to either traverse at different rates through a column, achieving a physical separation that increases as they pass further through the column, or to adhere selectively to a separation resin (or medium). The proteins are then differentially eluted using different eluents. In some cases, the protein of interest is separated from impurities when the impurities specifically adhere to the column's resin and the protein of interest does not, i.e., the protein of interest is contained in the effluent, while in other cases the protein of interest will adhere to the column's resin, while the impurities and/or product-related substances are extruded from the column's resin during a wash cycle.

Primary Recovery and Virus Inactivation

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be performed at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+ X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 µm filter such as Sartorius's 0.45/0.2 µm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, buffer/detergent treatment, UV and γ-ray irradiation and the addition of certain chemical inactivating agents such as β-propiolactone or e.g., copper phenanthroline as described in U.S. Pat. No. 4,534,972. In certain embodiments of the present invention, the sample matrix is exposed to detergent viral inactivation during the primary recovery phase. In other embodiments, the sample matrix may be exposed to low pH inactivation during the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, prior to continuing the purification process. Additionally, the mixture may be diluted with water for injection (WFI) to obtain a desired conductivity.

Additives to the Clarified Harvest

In certain embodiments, a low AR composition is produced by supplementing a clarified harvest containing antibodies or antigen binding portions thereof. A clarified harvest can be extracted from a cell culture, for example, a fermentation bioreactor, after undergoing centrifugation to remove large solid particles and subsequent filtration to remove finer solid particles and impurities from the material. Such clarified harvests can be supplemented as described above (e.g., with calcium, niacinamide, and/or basic amino acids, or combinations thereof) or modulation, e.g., lowering, of pH, to reduce AR formation (see Example 3).

Affinity Chromatography

In certain embodiments, it will be advantageous to subject a sample produced by the techniques of the instant invention to affinity chromatography to further purify the protein of interest away from acidic species. In certain embodiments the chromatographic material is capable of selectively or specifically binding to the protein of interest ("capture"). Non-limiting examples of such chromatographic material include: Protein A, Protein G, chromatographic material comprising, for example, an antigen bound by an antibody of interest, and chromatographic material comprising an Fc binding protein.

In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five $IgG_1$ binding domains as well as other domains of unknown function.

There are several commercial sources for Protein A resin. One suitable resin is MabSelect™ from GE Healthcare. Suitable resins include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies. A non-limiting example of a suitable column packed with MabSelect™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™

The Protein A column can be equilibrated with a suitable buffer prior to sample loading. Following the loading of the column, the column can be washed one or multiple times using a suitable set of buffers. The Protein A column can then be eluted using an appropriate elution buffer. For example, glycine-HCL or citric acid can be used as an elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

The invention is not limited to capture of the protein of interest using Protein A chromatography. A non-Protein A chromatography capture step can also be carried out. For example, cation exchange capture and non-chromatographic methods, such as aqueous two phase extraction or precipitation, or other methods known in the art, can be used.

Anion Exchange Chromatography

In certain embodiments, the low AR compositions are produced by subjecting the primary recovery sample to at least one anion exchange separation step. In certain embodiments, the anion exchange step will occur after the above-described affinity chromatography, e.g., Protein A affinity, step.

The use of an anionic exchange material versus a cationic exchange material, such as those cation exchange materials discussed in detail below, is based on the local charges of the protein of interest in a given solution. Therefore, it is within the scope of this invention to employ an anionic exchange step prior to the use of a cationic exchange step, or a cationic exchange step prior to the use of an anionic exchange step. Furthermore, it is within the scope of this invention to employ only an anionic exchange step, only an cationic exchange step, or any serial combination of the two (including serial combinations of one or both ion exchange steps with the other chromatographic separation technologies described herein).

In performing the separation, the initial protein composition can be contacted with the anion exchange material by using any of a variety of techniques, e.g., using a batch purification technique or a chromatographic technique.

For example, in the context of batch purification, anion exchange material is prepared in, or equilibrated to, the desired starting buffer. Upon preparation, or equilibration, a slurry of the anion exchange material is obtained. The protein of interest, e.g., antibody, solution is contacted with the slurry to allow for protein adsorption to the anion exchange material. The solution comprising the acidic species that do not bind to the AEX material is separated from the slurry, e.g., by allowing the slurry to settle and removing the supernatant. The slurry can be subjected to one or more washing steps and/or elution steps.

In the context of chromatographic separation, a chromatographic apparatus, commonly cylindrical in shape, is employed to contain the chromatographic support material (e.g., AEX material) prepared in an appropriate buffer solution. The chromatographic apparatus, if cylindrical, can have a diameter of about 5 mm to about 2 meters, and a height of 5 cm to 50 cm, and in certain embodiments, particularly for large scale processing, a height of ≤30 cm is employed. Once the chromatographic material is added to the chromatographic apparatus, a sample containing the protein of interest, e.g., an antibody, is contacted to the chromatographic material to induce the separation. Any portion of the solution that does not bind to the chromatographic material, e.g., which may comprise, depending on the AEX material being employed, the protein of interest, acidic species, is separated from the chromatographic material by washing the material and collecting fractions from column. The chromatographic material can be subjected to one or more wash steps. If desired, the chromatographic material can then be contacted with a solution designed to desorb any components of the solution that have bound to the chromatographic material.

In certain embodiments, a wash step can be performed in the context of AEX chromatography using conditions similar to the load conditions or alternatively by decreasing the pH and/or increasing the ionic strength/conductivity of the wash in a step wise or linear gradient manner. The resulting Flow Through and wash fractions can be analyzed and appropriate fractions pooled to achieve the desired reduction in charged variant species. In certain embodiments, the aqueous salt solution used as both the loading and wash buffer has a pH that at or near the isoelectric point (pI) of the protein of interest. In certain embodiments the pH is about 0 to 2 units higher or lower than the pI of the protein of interest. In certain embodiments, it will be in the range of 0 to 0.5 units higher or lower. In certain embodiments, it will be at the pI of the antibody.

In certain non-limiting embodiments, the anionic agent is selected from the group consisting of acetate, formate, or combinations thereof. In certain non-limiting embodiments, the cationic agent is selected from the group consisting of Tris, arginine, or combinations thereof. In one embodiment, the buffer solution is a Tris/formate buffer. In another embodiment, the buffer is selected from the group consisting of pyridine, piperazine, L-histidine, Bis-tris, Bis-tris propane, imidazole, N-Ethylmorpholine, TEA (triethanolamine), Tris, Morpholine, N-Methyldiethanolamine, AMPD (2-amino-2-methyl-1,3-propanediol), diethanolamine, ethanolamine, AMP (2-amino-2-methyl-1-propaol), piperazine, 1,3-Diaminopropane, piperidine A packed anion-exchange chromatography column, anion-exchange membrane device, anion-exchange monolithic device, or depth filter media can be operated either in bind-elute mode, flow-through mode, or a hybrid mode wherein the product exhibits binding to the chromatographic material, yet can be washed from the column using a buffer that is the same or substantially similar to the loading buffer. In the bind-elute mode, the column or the membrane device is first conditioned with a buffer with appropriate ionic strength and pH under conditions where certain proteins will be immobilized on the resin based matrix. For example, in certain embodiments, during the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or step-wise (step elution). In the flow-through mode, the column or the membrane device is operated at selected pH and conductivity such that the protein of interest does not bind to the resin or the membrane while the acidic species will either be retained on the column or will have a distinct elution profile as compared to the protein of interest. In the context of this hybrid strategy, acidic species will bind to the chromatographic material (or Flow Through) in a manner distinct from the protein of interest, e.g., while the protein of interest and certain aggregates and/or fragments of the protein of interest may bind the chromatographic material, washes that preferentially remove the protein of interest can be applied. The column is then regenerated before next use.

Non-limiting examples of anionic exchange substituents include diethylaminoethyl (DEAE), quaternary aminoethyl (QAE) and quaternary amine (Q) groups. Additional non-limiting examples include: Poros 50PI and Poros 50HQ, which are a rigid polymeric bead with a backbone consisting of cross-linked poly[styrene-divinylbenzene]; Capto Q Impres and Capto DEAE, which are a high flow agarose bead; Toyopearl QAE-550, Toyopearl DEAE-650, and Toyopearl GigaCap Q-650, which are a polymeric base bead; Fractogel® EMD TMAE Hicap, which is a synthetic polymeric resin with a tentacle ion exchanger; Sartobind STIC® PA nano, which is a salt-tolerant chromatographic membrane with a primary amine ligand; Sartobind Q nano; which is a strong anion exchange chromatographic membrane; CUNO BioCap; which is a zeta-plus depth filter media constructed from inorganic filter aids, refined cellulose, and an ion exchange resin; and X0HC, which is a depth-filter media constructed from inorganic filter aid, cellulose, and mixed cellulose esters. The detailed information is listed in Table 1.

TABLE 1

List of AEX Adsorbent Properties

| AEX Adsorbent | Vendor | Media Type | Ligand Type | Particle/Pore Size | Catalog Number |
|---|---|---|---|---|---|
| Poros PI | Applied Biosystems | Resin | Weak | ~50 μm | 1-2459-11 |
| Poros HQ | | | Strong | ~50 μm | 1-2559-11 |
| Capto DEAE | GE | | Weak | ~90 μm | 17-5443-10 |
| CaptoQ Impres | | | Strong | ~90 μm | 17-5316-10 |
| QAE-550 | Tosoh | | Strong | ~100 μm | 43271 |
| DEAE-650 | | | Weak | ~65 μm | 43201 |
| GigaCap Q-650 | | | Strong | ~75 μm | 21854 |
| TMAE HiCap | EMD/Millipore | | Strong | ~40-90 μm | 1.16881.0013 |
| Sartobind STIC ® PA Nano | Sartorius | Membrane | Weak | 3-5 μm | 92STPA42DN-11-A |
| Sartobind Q Nano | | | Strong | 3-5 μm | 92IEXQ42DN-11 |
| CUNO BioCap 25 | 3M | Depth Filter | NA | NA | BC0025L60ZA05A |
| X0HC | Millipore | | NA | NA | MX0HC23CL3 |

In certain embodiments, the protein load of the mixture comprising protein of interest is adjusted to a total protein load to the column of between about 50 and 500 g/L, or between about 75 and 350 g/L, or between about 200 and 300 g/L. In certain embodiments, the protein concentration of the load protein mixture is adjusted to a protein concentration of the material loaded to the column of about 0.5 and 50 g/L, between about 1 and 20 g/L, or between 3 and 10 g/L. In certain embodiments, the protein concentration of the load protein mixture is adjusted to a protein centration of the material to the column of about 37 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the methods of the instant invention can be used to selectively remove, significantly reduce, or essentially remove all of AR in the Flow Through and wash fractions while enriching for the same in the flow elution fraction, thereby producing protein compositions that have reduced AR or are free of AR. In certain embodiments relating to but not limited to adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments relating to but not limited to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including but not limited to those relating to adalimumab, the methods of the instant invention can be used to selectively remove, significantly reduce, or essentially remove all of the MGO variants in the Flow Through and wash fractions while enriching for the same in the elution fraction, thereby producing protein compositions that have reduced MGO or are free of MGO variants (for example, see U.S. Patent Application Ser. No. 61/777,883, filed on Mar. 12, 2013). In certain embodiments, including, but not limited to those relating to adalimumab, the methods of the instant invention can be used to selectively remove, significantly reduce, or essentially remove all of the glycated variants (Schiff's base and permanently glycated forms) in the Flow Through and wash fractions while enriching for the same in the elution fraction, thereby producing protein preparations with reduced or free of glycated variants.

In certain embodiments, the loading, pH, conductivity of the AEX chromatography step, as well as elution pH conductivity, can be modified to achieve a desired distribution of product-relates substances (AR or lysine variants) For example, but not by way of limitation, certain embodiments are directed to the modulation of the lysine distribution of purified sample of a protein of interest, e.g., increasing Lys 0 and decreasing Lys 1 and Lys 2. In certain embodiments, the methods of the present invention allow for the preparation of samples wherein the amount of Lys 0 is decreased, while the amount of Lys 1 and/or Lys 2 is increased.

In certain embodiments, an AEX chromatographic separation can be performed and combinations of fractions can be pooled to achieve a combination of desired process-related impurity and/or product-relates substance levels, in addition to, or in place of merely modulating charge variant concentration.

Spectroscopy methods such as UV, NIR, FTIR, Fluorescence, and Raman may be used to monitor levels of AR species in an on-line, at-line or in-line mode, which can then be used to control the level of charge variants, e.g., acidic species, in the pooled material collected from the AEX effluent.

In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of AEX, CEX and/or MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, and/or UF/DF steps so as to achieve the desired AR, product quality, ion concentration, and/or viral reduction.

As described below and in Example 11, AEX chromatography can be used in conjunction with recycle chromatography modes and continuous chromatography modes.

Cation Exchange Chromatography

The low AR compositions of the present invention can be produced by subjecting the composition, e.g., a primary recovery sample, to at least one cation exchange separation step. In certain embodiments, the CEX step will occur after the above-described affinity chromatography, e.g., Protein A affinity, step.

The use of a cationic exchange material versus an anionic exchange material, such as those anionic exchange materials discussed in detail above, is based on the local charges of the protein of interest in a given solution. Therefore, it is within the scope of this invention to employ a cationic exchange step prior to the use of an anionic exchange step, or an anionic exchange step prior to the use of a cationic exchange step. Furthermore, it is within the scope of this invention to employ only a cationic exchange step, only an anionic exchange step, or any serial combination of the two (including serial combinations of one or both ion exchange steps with the other chromatographic separation technologies described herein).

In performing the separation, the initial protein mixture can be contacted with the cation exchange material by using any of a variety of techniques, e.g., using a batch purification technique or a chromatographic technique, as described above in connection with Protein A or AEX.

In certain embodiments, the aqueous salt solution used as both the loading and wash buffer has a pH that is lower than the isoelectric point (pI) of the protein of interest. In certain embodiments, the pH is about 0 to 5 units lower than the pI of the protein. In certain embodiments, it is in the range of 1 to 2 units lower. In certain embodiments, it is in the range of 1 to 1.5 units lower.

In certain embodiments, the concentration of the anionic agent in aqueous salt solution is increased or decreased to achieve a pH of between about 3.5 and 10.5, or between about 4 and 10, or between about 4.5 and 9.5, or between about 5 and 9, or between about 5.5 and 8.5, or between about 6 and 8, or between about 6.5 and 7.5. In certain embodiments, the concentration of anionic agent is increased or decreased in the aqueous salt solution to achieve a pH of 5, or 5.5, or 6, or 6.5, or 6.8, or 7.5. Buffer systems suitable for use in the CEX methods include, but are not limited to tris formate, tris acetate, ammonium sulfate, sodium chloride, and sodium sulfate.

In certain embodiments, the conductivity and pH of the aqueous salt solution is adjusted by increasing or decreasing the concentration of a cationic agent. In certain embodiments, the cationic agent is maintained at a concentration of between about range of 20 mM to 500 mM, or between about 50 to 350 mM or between about 100 to 300 mM or between about 100 to 200 mM.

In certain non-limiting embodiments, the cationic agent is selected from the group consisting of sodium, Tris, tromethalmine, ammonium, arginine, or combinations thereof. In certain non-limiting embodiments, the anionic agent is selected from the group consisting of formate, acetate, citrate, chloride anion, sulphate, phosphate or combinations thereof.

A packed cation-exchange chromatography column or a cation-exchange membrane device can be operated either in bind-elute mode, flow-through mode, or a hybrid mode wherein the product exhibits binding to the chromatographic material, yet can be washed from the column using a buffer that is the same or substantially similar to the loading buffer. The details of these modes are outlined above.

Cationic substituents include carboxymethyl (CM), sulfoethyl (SE), sulfopropyl (SP), phosphate (P) and sulfonate (S). Additional cationic materials include, but are not limited to: Capto SP ImpRes, which is a high flow agarose bead; CM Hyper D grade F; which is a ceramic bead coated and permeated with a functionalized hydrogel, 250-400 ionic groups µeq/mL; Eshmuno S, which is a hydrophilic polyvinyl ether base matrix with 50-100 µeq/mL ionic capacity; Nuvia C Prime, which is a hydrophobic cation exchange media composed of a macroporous highly crosslinked hydrophilic polymer matrix 55-75 µeq/mL; Nuvia S, which has a UNOsphere base matrix with 90-150 µeq/mL ionic groups; Poros HS; which is a rigid polymetic bead with a backbone consisting of cross-linked poly[styrene-divinylbenzene]; Poros XS; which is a rigid polymetic bead with a backbone consisting of cross-linked poly[styrene-divinylbenzene]; Toyo Pearl Giga Cap CM 650M, which is a polymeric base bead with 0.225 meq/mL ionic capacity; Toyo Pearl Giga Cap S 650M which is a polymeric base bead; Toyo Pearl MX TRP, which is a polymeric base bead. Detailed information concerning the aforementioned materials is listed in Table 2. It is noted that CEX chromatography can be used with MM resins, described herein.

TABLE 2

Cationic Materials

| Resin | Vendor | type | particle size | Catalog Number |
|---|---|---|---|---|
| Capto SP ImpRes | GE | Strong | ~40 µm | 17-5468-10 |
| CM Hyper D | Pall | Weak | ~50 µm | 20050-027 |
| Eshmuno S | Millipore | Strong | ~85 µm | 1.20078 |
| Nuvia C Prime | Biorad | Mix Mode | ~70 µm | 156-3401 |
| Nuvia S | Biorad | Strong | ~85 µm | 156-0315 |
| Poros HS | Applied Biosystems | Weak | ~50 µm | 13359-06 |
| Poros XS | Applied Biosystems | Strong | ~50 µm | 4404337 |
| Toyo Pearl Giga Cap CM 650M | Tosoh | Weak | ~75 µm | 21946 |
| Toyo Pearl Giga Cap S 650M | Tosoh | Strong | ~75 µm | 21833 |
| Toyo Pearl MX Trp 650M | Tosoh | Mix Mode | ~75 µm | 22817 |

In certain embodiments, the protein load of the mixture comprising protein of interest is adjusted to a total protein load to the column of between about 5 and 150 g/L, or between about 10 and 100 g/L, between about 20 and 80 g/L, between about 30 and 50 g/L, or between about 40 and 50 g/L. In certain embodiments, the protein concentration of the load protein mixture is adjusted to a protein concentration of the material loaded to the column of about 0.5 and 50 g/L, or between about 1 and 20 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the methods of the instant invention can be used to selectively remove, significantly reduce, or essentially remove all of AR in the Flow Through and wash fractions while enriching for the same in the elution fraction, thereby producing protein compositions that have reduced AR or are free of AR. In certain embodiments relating to but not limited to adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments relating to but not limited to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including, but not limited to those relating to adalimumab, the methods of the instant invention can be used to selectively remove, significantly reduce, or essentially remove all of the MGO variants in the elution fractions while enriching for the same in the Flow Through and wash fractions, thereby producing protein preparations with reduced or free of MGO variants. In certain embodiments, including, but not limited to those relating to adalimumab, the methods of the instant invention can be used to selectively remove, significantly reduce, or essentially remove all of the glycated variants (Schiff's base and permanently glycated forms) in the elution fractions while enriching for the same in the Flow Through and wash fractions, thereby producing protein preparations with reduced or free of glycated variants.

In certain embodiments, the loading, pH, conductivity of the CEX chromatography step, as well as elution pH conductivity, can be modified to achieve a desired distribution of acidic species. For example, but not by way of limitation, certain embodiments are directed to the modulation of the lysine distribution of a purified sample of a protein of interest, e.g., increasing Lys 0 and decreasing Lys 1 and Lys 2. In certain embodiments, the methods of the present invention allow for the preparation of samples wherein the amount of Lys 0 is decreased, while the amount of Lys 1 and/or Lys 2 is increased.

In certain embodiments, a CEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of product-related charge variants, aggregates, low molecular weight variants (e.g., fragments of the protein of interest) in an on-line, at-line or in-line mode, which can then be used to control the level of charge variants, e.g., acidic species, in the pooled material collected from the CEX effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of CEX and AEX and/or MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional chromatography, filtration, pH adjustment, UF/DF steps so as to achieve the desired product quality, AR, ion concentration, and/or viral reduction.

As described below and in Example 11, CEX chromatography can be used in conjunction with recycle chromatography and continuous chromatography modes.

Mixed Mode Chromatography

Mixed mode ("MM") chromatography may also be used to prepare the low AR compositions of the invention. MM chromatography, also referred to herein as "multimodal chromatography", is a chromatographic strategy that utilizes a support comprising a ligand that is capable of providing at least two different, and in certain embodiments co-operative, sites that interact with the substance to be bound. In certain embodiments, one of these sites gives an attractive type of charge-charge interaction between the ligand and the substance of interest and the other site provides for electron acceptor-donor interaction and/or hydrophobic and/or hydrophilic interactions. Electron donor-acceptor interactions include interactions such as hydrogen-bonding, $\pi$-$\pi$, cation-$\pi$, charge transfer, dipole-dipole, induced dipole etc.

In certain embodiments, the resin employed for a mixed mode separation is Capto Adhere. Capto Adhere is a strong anion exchanger with multimodal functionality. Its base matrix is a highly cross-linked agarose with a ligand (N-Benzyl-N-methyl ethanol amine) that exhibits many functionalities for interaction, such as ionic interaction, hydrogen bonding and hydrophobic interaction. In certain embodiments, the resin employed for a mixed mode separation is selected from PPA-HyperCel and HEA-HyperCel. The base matrices of PPA-HyperCel and HEA-HyperCel are high porosity cross-linked cellulose. Their ligands are Phenylpropylamine and Hexylamine, respectively. Phenylpropylamine and Hexylamine offer different selectivity and hydrophobicity options for protein separations. Additional mixed mode chromatographic supports include, but are not limited to, Nuvia C Prime, Toyo Pearl MX Trp 650M, and Eshmuno® HCX.

In certain embodiments, the mixed mode chromatography resin is comprised of ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

In certain embodiments, the protein load of the mixture comprising protein of interest is adjusted to a total protein load to the column of between about 50 and 750 g/L, or between about 75 and 500 g/L, or between about 100 and 300 g/L. In certain embodiments, the protein concentration of the load protein mixture is adjusted to a protein concentration of the material loaded to the column of about 1 and 50 g/L, or between about 9 and 25 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the MM methods of the instant invention can be used to selectively remove, significantly reduce, or essentially remove all of AR in the Flow Through and wash fractions while enriching for the same in the flow elution fraction, thereby producing protein compositions that have reduced AR or are free of AR. In certain embodiments including, but not limited to those relating to adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments including, but not limited to those relating to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including, but not limited to those relating to adalimumab, the MM methods of the instant invention can be used to selectively remove, significantly reduce, or essentially remove all of the MGO variants in the Flow Through and wash fractions while enriching for the same in the elution fraction, thereby producing protein preparations with reduced or free of MGO variants. In certain embodiments, including, but not limited to those relating to adalimumab, the methods of the instant invention can be used to selectively remove, significantly reduce, or essentially remove all of the glycated variants (Schiff's base and permanently glycated forms) in the Flow Through and wash fractions while enriching for the same in the elution fraction, thereby producing protein preparations with reduced or free of glycated variants.

In certain embodiments, the loading, pH, conductivity of the MM chromatography step, wash pH and conductivity, as well as elution pH conductivity, can be modified to achieve a desired distribution of acidic species. For example, but not by way of limitation, certain embodiments are directed to the modulation of the lysine distribution of a purified sample of a protein of interest, e.g., increasing Lys 0 and decreasing Lys 1 and Lys 2. In certain embodiments, the methods of the present invention allow for the preparation of samples wherein the amount of Lys0 is decreased, while the amount of Lys 1 and/or Lys 2 is increased.

In certain embodiments, a MM chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of AR species in an on-line, at-line or in-line mode, which can then be used to control the level of charge variants, e.g., acidic species, in the pooled material collected from the MM effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of MM and AEX and/or CEX methods can be used to prepare the low AR compositions of the invention, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, AR, ion concentration, and/or viral reduction.

As described below and in Example 11, MM chromatography can be used in conjunction with recycle chromatography and continuous chromatography modes.

Continuous and Recycle Chromatography

Continuous and recycle chromatography modes can be used to produce the low AR compositions of the invention, and are described below and Iin Example 11. These methods result in significant improvements in recovery of the protein, e.g., antibody, of interest while maintaining the AR reduction levels. These continuous and recycle chromatography modes are applicable to chromatography methods where (a) the low acidic species component of interest is collected in the unbound fraction during the chromatography (Flow Through/wash chromatography) or (b) where the low acidic species component of interest is first bound to the media and subsequently recovered by washing the media with conditions that elute the bound component.

Continuous and Recycle Chromatography—Flow Through/Wash Chromatography

In the case where the low acidic species component of interest is collected in the unbound fraction, the following approach may be employed which prevents loss of the material loaded on the column.

In one embodiment, a recycle chromatography mode may be used wherein the column is loaded and the unbound fractions that result in the target AR level are collected. Subsequently, instead of regenerating the column and losing the product, the column may be washed under conditions that result in recovery of the product remaining bound to the column. In one embodiment, the product recovered under these conditions contains significantly higher AR levels than the original feed material. In one embodiment, this wash fraction may be adjusted to the appropriate conditions to achieve the separation desired on subsequent processing (typically similar conditions to the initial preparation) and combined with the original feed material and loaded on the column again (after preparing the column appropriately for the next cycle). In one embodiment, the amount of material prepared for the next cycle, combining the wash fraction from the first cycle and the fresh material, may be adjusted to the target loading capacity for the column to achieve the desired separation (typically similar to the capacity targeted for the first cycle).

In one embodiment, in performing the second cycle, a similar strategy may be employed, collecting the unbound fraction so as to achieve the target AR level and then subsequently washing the column under conditions to recover the product remaining on the column.

In one embodiment, this recycle chromatography mode is continued until all the load materials are used. The number of cycles can be controlled by designing the column size appropriately.

In employing the recycle chromatography mode, the recovery of the product loaded on the column may be significantly improved while achieving the target AR levels.

Several variations of the recycle chromatography mode can be employed. In one embodiment, the fractions that are collected targeting a certain AR level can be determined based on predetermined criteria or based on at-line, off-line or on-line analysis of the effluent of the column or the collected pool.

In another embodiment, the wash conditions used for the first cycle can be adjusted to recover the desired amount of product at the desired product quality, only limited by the feasibility of preparing an appropriate load mixture for the subsequent step. In one aspect of this embodiment, the wash condition may be similar to the load condition. In another aspect of this embodiment, the wash condition can be stringent to recover all of the product species (desired and undesired) remaining on the column.

In still another embodiment, the loading amount, the loading conditions and the washing conditions used for the subsequent cycles can be modified to achieve the desired purity, given that that loading material for the subsequent cycles are likely to contain higher levels of AR.

In another embodiment, the last cycle of the operation can be performed under different conditions such that the target purity and target recovery can be achieved to optimize overall recovery and purity.

The methods for producing the low AR composition of the invention can also be implemented in a continuous chromatography mode. In this mode, at least two columns may be employed (referred to as a "first" column and a "second" column). In one embodiment, the feed material may be loaded onto the first column, and the unbound fraction from the first column may be collected such that the pool material contains the target AR level. In one embodiment, the column may be then washed under conditions that recover the remaining product. In one embodiment, this material may be then dynamically diluted with appropriate solutions to achieve the desired loading conditions, mixed with fresh feed material and directed to the second column. In one embodiment, the unbound fraction from the second column may be collected to achieve the target AR level. The second column may be then washed under conditions to recover the product and diluted with appropriate solutions, mixed with fresh materials dynamically and directed to the first column (which is prepared to receive the load after regeneration/cleaning). In one embodiment, this cycling is continued until all the load material is used. The last cycle can be operated in a "typical" mode, with appropriate adjustments to the load and wash conditions as necessary.

In certain embodiments, this continuous chromatography mode can be carried out such that the wash material containing the higher AR levels can be directed back into the load tank after appropriate dilution. This material can then be loaded subsequently or concurrently onto the second column, such that the operation of the two columns are not in tandem, reducing complexity of the operation.

This continuous chromatography mode, while similar to the recycle chromatography mode, can be carried out more efficiently, and therefore has a reduced processing time in some embodiments.

For this continuous chromatography mode, several variations can be employed. In one embodiment, the fractions that are collected targeting a certain AR level can be determined based on predetermined criteria or based on at-line, off-line or on-line analysis of the effluent of the column or the collected pool.

In another embodiment, the wash conditions used for the first cycle can be adjusted to recover the desired amount of product at the desired product quality, only limited by the feasibility of preparing an appropriate load mixture for the subsequent step. In one aspect of this embodiment, the wash conditions may be similar to the load conditions. In another aspect of the embodiment, the wash conditions can be stringent to recover all of the product species (desired and undesired) remaining on the column.

In still another embodiment, the loading amount, the loading conditions and the washing conditions used for the subsequent cycles can be modified to achieve the desired purity, given that that loading material for the subsequent cycles are likely to contain higher levels of AR.

In another embodiment, the last cycle of the operation can be performed under different conditions such that the target purity/recovery can be achieved to optimize overall recovery and and/or purity.

In one embodiment, the media choice for the recycle or continuous modes can be one of many chromatographic resins with pendant hydrophobic and anion exchange functional groups, monolithic media, membrane adsorbent media or depth filtration media.

In certain embodiments, membrane or depth filter based media ("convective media") can be used in the recycle or continuous chromatography modes because selectivity of separation is not required to be high given the fact that the less enriched portions of the product are "recycled" while the pure fractions are selectively pooled.

Continuous and Recycle Chromatography—Elution Chromatography

In the elution mode of chromatography or separation, as exemplified by the CEX technology for AR reduction, the conditions are chosen for the load and wash steps such that the AR enriched material is collected in the Flow Through and/or wash fractions, while the AR reduced material is collected in the elution fraction. In the typical implementation of the CEX technology, about 10 to 40% of the product (the desired charge variant) may be lost in the Flow Through/Wash fractions. Two modes of operation, namely the recycle chromatography mode and the continuous chromatography mode, provide improved recovery, while maintaining the target AR levels.

In one embodiment, in the recycle chromatography mode, the load material is, in general, processed over multiple cycles. In implementing the recycle chromatography mode, the load material may be prepared such that the eluate contains the target product purity or AR level. Under these conditions, the AR enriched material may be collected in the Flow Through/wash fractions. This material may be pooled and additional fresh load material is added to achieve the appropriate loading capacity for the next cycle of chromatography on the same column. In particular, in one embodiment, the column is eluted under conditions where the bound product (having low AR levels) is recovered, and subsequently regenerated and equilibrated to prepare for the next cycle.

In the next cycle, the combined load (Flow Through/wash from cycle 1 above, as well as fresh material) may be loaded to the target capacity. The Flow Through/wash fractions are collected and pooled. The column may be then eluted to obtain the second eluate, again containing the target low AR composition. In one embodiment, this sequence is continued until all the load materials are processed.

In another embodiment, by implementing the recycle chromatography mode, the material that would otherwise be discarded as AR enriched material is further purified to "recover" pure protein product, thereby improving the overall recovery of the protein. In one embodiment, the level of recovery depends on the number of cycles employed.

For the recycle chromatography mode, several variations can be employed. In one embodiment, the entire pool of the Flow Through/wash fractions are typically combined with fresh materials to maximize recovery of the entire operation. However, a portion of the flow through wash can be discarded to achieve higher purity or efficiency. For example, in one embodiment, certain fractions containing very high levels of AR species can be discarded. To enable such selective pooling, off-line, in-line or at line methods can be used to directly or indirectly measure the levels of AR.

In another embodiment, the loading amount and the conditions for loading, washing and eluting can be modified for the second and subsequent cycles to accommodate the higher levels of AR that will be present in the loading pool.

In still another embodiment, the last cycle of the method can be performed under conditions such that the target purity and recovery can be achieved to optimize overall recovery and purity.

A continuous chromatography mode provides additional advantages in terms of time efficiency. In one embodiment, in this mode of operation, two or more columns are used. Specifically, as with the recycle mode, an appropriate condition for the load capacity, load, wash and elution conditions are chosen for the operation. In one embodiment, the Flow Through and wash fractions (or a portion thereof) may be directed to the load tank containing the fresh material. After completion of the load and wash steps, the first column may be eluted and subsequently regenerated. Meanwhile, the second column may be loaded with the material that is a mix of fresh material and the wash and Flow Through from the previous cycle. In one embodiment, the wash and Flow Through from the second column may be again directed back to the load tank. The second column may be then eluted and regenerated. In one embodiment, the first column is then ready to be loaded and the cycle continues. This continuous chromatography mode is efficient as the product is processed continuously and the purified product is obtained in a semi-continuous manner.

Several variations of the continuous chromatography mode can be employed. In one embodiment, the entire pool of the Flow Through/wash fractions is combined with fresh materials to maximize recovery of the entire operation. However, a portion of the Flow Through wash can be discarded to achieve higher purity or efficiency. For example, certain fractions containing very high levels of AR species can be discarded. To enable such selective pooling, off-line, in-line or at line methods can be used to measure directly or indirectly the levels of acidic species.

In another embodiment, the loading amount, conditions for loading, washing and eluting can be modified for the second and subsequent cycles to accommodate the higher levels of AR that will be present in the loading pool. In still another embodiment, the last cycle of the operation can be performed under different conditions to optimize overall recover and purity.

The recycle chromatography mode and the continuous chromatography mode are not limited to use with any particular chromatography resin. The media used for the recycle or continuous modes can be, for example, one of many chromatographic resins with pendant hydrophobic and anion exchange functional groups, monolithic media, membrane adsorber media or depth filtration media.

In certain embodiments, membrane depth filter-based media ("convective media") can be used with the recycle or continuous modes as the selectivity of separation is not required to be high given the fact that the less enriched portions of the product are "recycled" while the pure fractions are selectively pooled.

Recycle chromatography mode and the continuous chromatography mode can be used inconjunction with AEX, CEX, or MM chromatography methods, as described herein, to produce the low AR compositions of the invention. For example, Example 11, below, describes the recycle mode of chromatography for AR reduction using AEX, CEX, and MM technologies.

Hydrophobic Interaction Chromatography

The low AR compositions of the invention may also be prepared using a hydrophobic interaction chromatography (HIC) step in addition to the displacement chromatography step.

In performing the separation, the sample mixture is contacted with the HIC material, e.g., using a batch purification technique or using a column or membrane chromatography. Prior to HIC purification it may be desirable to adjust the concentration of the salt buffer to achieve desired protein binding to the resin or the membrane.

Whereas ion exchange chromatography relies on the local charge of the protein of interest for selective separation, hydrophobic interaction chromatography employs the hydrophobic properties of the proteins to achieve selective separation. Hydrophobic groups on the protein interact with hydrophobic groups of the resin or the membrane. The more hydrophobic a protein is the stronger it will interact with the column or the membrane. Thus the HIC step removes process-related impurities (e.g., HCPs) as well as product-related substances (e.g., aggregates and fragments).

Like ion exchange chromatography, a HIC column or membrane device can also be operated in product a bind-elute mode, a flow-through, or a hybrid mode wherein the product exhibits binding to the chromatographic material, yet can be washed from the column using a buffer that is the same or substantially similar to the loading buffer. The details of these modes are outlined above in connection with AEX purification.

As hydrophobic interactions are strongest at high ionic strength, this form of separation is conveniently performed following salt elution step, such as those that are typically used in connection with ion exchange chromatography. Alternatively, salts can be added into a low salt level feed stream before this step. Adsorption of the antibody to a HIC column is favored by high salt concentrations, but the actual concentrations can vary over a wide range depending on the nature of the protein of interest, salt type and the particular HIC ligand chosen. Various ions can be arranged in a so-called solupho-bic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4 > Na_2SO_4 > NaCl > NH_4Cl > NaBr > NaSCN$. In general, salt concentrations of between about 0.75 M and about 2 M ammonium sulfate or between about 1 and 4 M NaCl are useful.

HIC media normally comprise a base matrix (e.g., cross-linked agarose or synthetic copolymer material) to which hydrophobic ligands (e.g., alkyl or aryl groups) are coupled. A suitable HIC media comprises an agarose resin or a membrane functionalized with phenyl groups (e.g., a Phenyl Sepharose™ from GE Healthcare or a Phenyl Membrane from Sartorius). Many HIC resins are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, N.J.); and Toyopearl™ ether, phenyl or butyl (Toso-Haas, Pa.).

Viral Filtration

Viral filtration is a dedicated viral reduction step in the entire purification process. This step is usually performed post chromatographic polishing steps. Viral reduction can be achieved via the use of suitable filters including, but not limited to, Planova 20N™, 50 N or BioEx from Asahi Kasei Pharma, Viresolve™ filters from EMD Millipore, ViroS art CPV from Sartorius, or Ultipor DV20 or DV50™ filter from Pall Corporation. It will be apparent to one of ordinary skill in the art to select a suitable filter to obtain desired filtration performance.

Ultrafiltration/Diafiltration

Certain embodiments of the present invention employ ultrafiltration and diafiltration steps to further concentrate and formulate the protein of interest, e.g., an antibody product. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter membrane pores while proteins, such as antibodies, are retained above the membrane surface.

Diafiltration is a method of using membrane filters to remove and exchange salts, sugars, and non-aqueous solvents, to separate free from bound species, to remove low molecular-weight species, and/or to cause the rapid change of ionic and/or pH environments. Microsolutes are removed most efficiently by adding solvent to the solution being diafiltered at a rate approximately equal to the permeate flow rate. This washes away microspecies from the solution at a constant volume, effectively purifying the retained protein of interest. In certain embodiments of the present invention, a diafiltration step is employed to exchange the various buffers used in connection with the instant invention, optionally prior to further chromatography or other purification steps, as well as to remove impurities from the protein preparations.

One of ordinary skill in the art can select appropriate membrane filter device for the UF/DF operation. Examples of membrane cassettes suitable for the present invention include, but not limited to, Pellicon 2 or Pellicon 3 cassettes with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

Exemplary Purification Strategies

In certain embodiments, primary recovery can proceed by sequentially employing pH reduction, centrifugation, and filtration steps to remove cells and cell debris (including HCPs) from the production bioreactor harvest. In certain embodiments, the present invention is directed to subjecting a sample mixture from said primary recovery to one or more AEX, CEX, and/or MM purification steps. Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

Specific examples of such combinations of strategies is presented below, with specific data relating to particular combinations useful in the context of the instant invention included in Tables 80-87 and 76-78.

In certain embodiments the unbound Flow Through and wash fractions can be further fractionated and a combination of fractions providing a target product purity can be pooled.

In certain embodiments the protein concentration can be adjusted to achieve a differential partitioning behavior between the antibody product and the product-related substances such that the purity and/or yield can be further improved. In certain embodiments the loading can be performed at different protein concentrations during the loading operation to improve the product quality/yield of any particular purification step.

In certain embodiments the column temperature can be independently varied to improve the separation efficiency and/or yield of any particular purification step.

In certain embodiments, the loading and washing buffer matrices can be different or composed of mixtures of chemicals, while achieving similar "resin interaction" behavior such that the above novel separation can be effected. For example, but not by way of limitation, the loading and washing buffers can be different, in terms of ionic strength or pH, while remaining substantially similar in function in terms of the washout of the product achieved during the wash step. In certain embodiments, additives such as amino acids, sugars, PEG, etc can be added to the load or wash steps to modulate the partitioning behavior to achieve the separation efficiency and/or yield.

In certain embodiments, the loading & washing steps can be controlled by in-line, at-line or off-line measurement of the product related impurity/substance levels, either in the column effluent, or the collected pool or both, so as to achieve the target product quality and/or yield. In certain embodiments, the loading concentration can be dynamically controlled by in-line or batch or continuous dilutions with buffers or other solutions to achieve the partitioning necessary to improve the separation efficiency and/or yield.

V. Methods of Assaying Sample Purity

Assaying Host Cell Protein

The present invention also provides methods for determining the residual levels of host cell protein (HCP) concentration in the low AR compositions of the invention. As described above, HCPs are desirably excluded from the final target substance product. Exemplary HCPs include proteins originating from the source of the antibody production. Failure to identify and sufficiently remove HCPs from the target antibody may lead to reduced efficacy and/or adverse reactions in a subject.

As used herein, the term "HCP ELISA" refers to an ELISA where the second antibody used in the assay is specific to the HCPs produced from cells, e.g., CHO cells, used to generate the antibody of interest. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HCPs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (*Cygnus*). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

Assaying Acidic Species (AR)

The levels of acidic species in the chromatographic samples produced using the techniques described herein may be analyzed as described in the Examples section. In certain embodiments a CEX-HPLC method is employed. For example, but not by way of limitation, cation exchange chromatography can be performed on a Dionex ProPac WCX-10, Analytical column 4 mm×250 mm (Dionex, Calif.). An Agilent 1200 HPLC system can then be used as the HPLC. In certain embodiments, mobile phases such as 10 mM Sodium Phosphate dibasic pH 7.5 (Mobile phase A) and 10 mM Sodium Phosphate dibasic, 500 mM Sodium Chloride pH 5.5 (Mobile phase B) can be used. In certain embodiments, a binary gradient (94% A, 6% B: 0-20 min; 84% A, 16% B: 20-22 min; 0% A, 100% B: 22-28 min; 94% A, 6% B: 28-34 min) can be used with detection at 280 nm. In certain embodiments, quantitation is based on the relative area percent of detected peaks. In certain embodiments, the peaks that elute at relative residence time less than a certain time are together represented as the acidic peaks.

Assaying Size Variants

In certain embodiments, the levels of aggregates, monomer, and fragments in the chromatographic samples produced using the techniques described herein are analyzed. In certain embodiments, the aggregates, monomer, and fragments are measured using a size exclusion chromatographic (SEC) method for each molecule. For example, but not by way of limitation, a TSK-gel G3000SW×L, 5 µm, 125 Å, 7.8×300 mm column (Tosoh Bioscience) can be used in connection with certain embodiments, while a TSK-gel Super SW3000, 4 µm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

Any additional technique, such as mass spectroscopy, can be used for assaying size variants.

VI. Methods of Treatment Using the Low AR Compositions of the Invention

The low AR compositions of the invention may be used to treat any disorder in a subject for which the therapeutic protein comprised in the composition is appropriate for treating.

A "disorder" is any condition that would benefit from treatment with the protein. This includes chronic and acute disorders or diseases including those pathological conditions which predispose the subject to the disorder in question. In the case of an anti-TNFα antibody, or antigen binding portion thereof, such as adalimumab, a therapeutically effective amount of the low AR composition may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the low AR compositions or a low process-related impurity compositions of the invention may be used to treat an autoimmune disease, such as rheumatoid arthritis, juvenile idiopathic arthritis, or psoriatic arthritis, an intestinal disorder, such as Crohn's disease or ulcerative colitis, a spondyloarthropathy, such as ankylosing spondylitis, or a skin disorder, such as psoriasis.

Disorders in which TNFα activity is detrimental are well known in the art and described in detail in U.S. Pat. No. 8,231,876 and U.S. Pat. No. 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), active axial spondyloarthritis (active axSpA) and non-radiographic axial spondyloarthritis (nr-axSpA), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina, and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, cardiomyopathy, coronary artery spasm, coronary artery disease, valvular disease, arrhythmias, and cardiomyopathies), spondyloarthropathies (including ankylosing spondylitis, psoriatic arthritis/spondylitis, enteropathic arthritis, reactive arthritis or Reiter's syndrome, and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis), hepatic disorders (including hepatitis, alcoholic hepatitis, viral hepatitis, alcoholic cirrhosis, a1 antitypsin deficiency, autoimmune cirrhosis, cryptogenic cirrhosis, fulminant hepatitis, hepatitis B and C, and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), *pemphigus vulgaris, scleroderma*, atopic dermatitis (eczema), sarcoidosis, erythema nodosum, hidradenitis suppurative, lichen planus, Sweet's syndrome, *scleroderma* and vitiligo), vasculitides (including Behcet's disease), and other disorders, such as juvenile rheumatoid arthritis (JRA), endometriosis, prostatitis, choroidal neovascularization, sciatica, Sjogren's syndrome, uveitis, wet macular degeneration, osteoporosis and osteoarthritis.

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering a low AR composition comprising an anti-TNFα antibody, or antigen binding portion thereof, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab, also referred to as HUMIRA®.

The low AR compositions can be administered by a variety of methods known in the art. Exemplary routes/modes of administration include subcutaneous injection, intravenous injection or infusion. In certain aspects, a low AR compositions may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a low AR composition of the invention is 0.01-20 mg/kg, or 1-10 mg/kg, or 0.3-1 mg/kg. With respect to low AR compositions comprising an anti-TNFα antibody, or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg, and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

VII. Pharmaceutical Formulations Containing the Low AR Compositions of the Invention The present invention further provides preparations and formulations comprising the low AR compositions of the invention. It should be understood that any of the antibodies and antibody fragments described herein, including antibodies and antibody fragments having any one or more of the structural and functional features described in detail throughout the application, may be formulated or prepared as described below. When various formulations are described in this section as including an antibody, it is understood that such an antibody may be an antibody or an antibody fragment having any one or more of the characteristics of the antibodies and antibody fragments described herein. In one embodiment, the antibody is an anti-TNFα antibody, or antigen-binding portion thereof.

In certain embodiments, the low AR compositions of the invention may be formulated with a pharmaceutically acceptable carrier as pharmaceutical (therapeutic) compositions, and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

The low AR compositions of the invention are present in a form known in the art and acceptable for therapeutic uses. In one embodiment, a formulation of the low AR compositions of the invention is a liquid formulation. In another embodiment, a formulation of the low AR compositions of the invention is a lyophilized formulation. In a further embodiment, a formulation of the low AR compositions of the invention is a reconstituted liquid formulation. In one embodiment, a formulation of the low AR compositions of the invention is a stable liquid formulation. In one embodiment, a liquid formulation of the low AR compositions of the invention is an aqueous formulation. In another embodiment, the liquid formulation is non-aqueous. In a specific embodiment, a liquid formulation of the low AR compositions of the invention is an aqueous formulation wherein the aqueous carrier is distilled water.

The formulations of the low AR compositions of the invention comprise an antibody in a concentration resulting in a w/v appropriate for a desired dose. The antibody may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In a specific embodiment, a formulation of the low AR compositions of the invention comprises at least about 100 mg/ml, at least about 125 mg/ml, at least 130 mg/ml, or at least about 150 mg/ml of an antibody of the invention.

In one embodiment, the concentration of antibody, which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml, or between about 25 mg/ml and about 50 mg/ml.

In a specific embodiment, a formulation of the low AR compositions of the invention comprises between about 90 mg/ml and about 110 mg/ml or between about 100 mg/ml and about 210 mg/ml of an antibody.

The formulations of the low AR compositions of the invention comprising an antibody may further comprise one or more active compounds as necessary for the particular indication being treated, typically those with complementary activities that do not adversely affect each other. Such additional active compounds are suitably present in combination in amounts that are effective for the purpose intended.

The formulations of the low AR compositions of the invention may be prepared for storage by mixing the antibody having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solutions, amino acids, chelators, preservatives, or the like (Goodman and Gilman's The Pharmacological Basis of Therapeutics, $12^{th}$ edition, L. Brunton, et al. and *Remington's Pharmaceutical Sciences,* 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, $MgCl_2$, or $CaCl_2$ The formulations of the low AR compositions of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0. One of skill in the art understands that the pH of a formulation generally should not be equal to the isoelectric point of the particular antibody to be used in the formulation.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, $13^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, $2^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the low AR compositions of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a formulation may comprise about 10 mM, about 25 mM, or no histidine.

The formulations of the low AR compositions of the invention may comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In a specific embodiment, the formulations of the low AR compositions of the invention may comprise trehalose. In one embodiment, a formulation of the invention comprises at least about 1%, at least about 2%, at least about 4%, at least about 8%, at least about 20%, at least about 30%, or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a formulation of the invention comprises about 1%, about 2%, about 4%, about 6%, about 8%, about 15%, about 20%, about 30%, or about 40% trehalose. In a specific embodiment, a formulation of the invention comprises about 4%, about 6% or about 15% trehalose.

In certain embodiments, a formulation of the low AR compositions of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, CaCl$_2$, and MgCl$_2$. In a specific embodiment, the formulation comprises NaCl.

A formulation of the low AR compositions of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM, or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM, or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM, or about 300 mM sodium chloride.

A formulation of the low AR compositions of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM, or about 400 mM of an amino acid.

The formulations of the low AR compositions of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc.), can optionally be added to the formulations of the invention to reduce aggregation. In one embodiment, a formulation of the invention comprises Polysorbate 20, Polysorbate 40, Polysorbate 60, or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

The formulations of the low AR compositions of the invention may optionally further comprise other common excipients and/or additives including, but not limited to, diluents, binders, stabilizers, lipophilic solutions, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of an antibody, as well known those in the art or as described herein.

In one embodiment, the low AR compositions of the invention are formulated with the same or similar excipients and buffers as are present in the commercial adalimumab (HUMIRA®) formulation, as described in the "Highlights of Prescribing Information" for HUMIRA® (adalimumab) Injection (Revised January 2008) the contents of which are hereby incorporated herein by reference. For example, each prefilled syringe of HUMIRA®, which is administered subcutaneously, delivers 0.8 mL (40 mg) of drug product to the subject. Each 0.8 mL of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for Injection, USP. Sodium hydroxide is added as necessary to adjust pH.

It will be understood by one skilled in the art that the formulations of the low AR compositions of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonity of the formulation. Tonicity modifiers suitable for this invention include, but are not limited to, saccharides, salts and amino acids.

In certain embodiments, the formulations of the low AR compositions of the invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

The concentration of any one component or any combination of various components, of the formulations of the low AR compositions of the invention is adjusted to achieve the desired tonicity of the final formulation. For example, the ratio of the carbohydrate excipient to antibody may be adjusted according to methods known in the art (e.g., U.S. Pat. No. 6,685,940). In certain embodiments, the molar ratio of the carbohydrate excipient to antibody may be from about 100 moles to about 1000 moles of carbohydrate excipient to about 1 mole of antibody, or from about 200 moles to about 6000 moles of carbohydrate excipient to about 1 mole of antibody, or from about 100 moles to about 510 moles of carbohydrate excipient to about 1 mole of antibody, or from about 100 moles to about 600 moles of carbohydrate excipient to about 1 mole of antibody.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate, and calcium chloride. In specific embodiments, formulations of the invention comprise NaCl, $MgCl_2$, and/or $CaCl_2$. In one embodiment, concentration of NaCl is between about 75 mM and about 150 mM. In another embodiment, concentration of $MgCl_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine, and histidine.

In one embodiment the formulations of the low AR compositions of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the low AR compositions of the invention should be sterile. The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the low AR compositions of the invention is a lyophilized formulation. The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein of interest (such as an antibody of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS™; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and antibody molecules of a formulation of the invention is at least about 10, at least about 50, at least about 100, at least about 200, or at least about 300. In another embodiment, the molar ratio of a lyoprotectant (e.g., trehalose) and antibody molecules of a formulation of the invention is about 1, is about 2, is about 5, is about 10, about 50, about 100, about 200, or about 300.

A "reconstituted" formulation is one which has been prepared by dissolving a lyophilized antibody formulation in a diluent such that the antibody is dispersed in the reconstituted formulation. The reconstituted formulation is suitable for administration (e.g., parenteral administration) to a patient to be treated with the antibody and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the low AR compositions of the invention is a lyophilized formulation comprising an antibody of the invention, wherein at least about 90%, at least about 95%, at least about 97%, at least about 98%, or at least about 99% of said antibody may be recovered from a vial upon shaking said vial for 4 hours at a speed of 400 shakes per minute wherein the vial is filled to half of its volume with the formulation. In another embodiment, a formulation of the invention is a lyophilized formulation comprising an antibody of the invention, wherein at least about 90%, at least about 95%, at least about 97%, at least about 98%, or at least about 99% of the antibody may be recovered from a vial upon subjecting the formulation to three freeze/thaw cycles wherein the vial is filled to half of its volume with said formulation. In a further embodiment, a formulation of the invention is a lyophilized formulation comprising an antibody of the invention, wherein at least about 90%, at least about 95%, at least about 97%, at least about 98%, or at least about 99% of the antibody may be recovered by reconstituting a lyophilized cake generated from said formulation.

In one embodiment, a reconstituted liquid formulation may comprise an antibody at the same concentration as the pre-lyophilized liquid formulation.

In another embodiment, a reconstituted liquid formulation may comprise an antibody at a higher concentration than the pre-lyophilized liquid formulation, e.g., .about 2 fold, about 3 fold, about 4 fold, about 5 fold, about 6 fold, about 7 fold, about 8 fold, about 9 fold, or about 10 fold higher concentration of an antibody than the pre-lyophilized liquid formulation.

In yet another embodiment, a reconstituted liquid formulation may comprise an antibody of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of an antibody than the pre-lyophilized liquid formulation.

The pharmaceutical formulations of the low AR compositions of the invention are typically stable formulations, e.g., stable at room temperature.

The terms "stability" and "stable" as used herein in the context of a formulation comprising an antibody of the invention refer to the resistance of the antibody in the formulation to aggregation, degradation or fragmentation under given manufacture, preparation, transportation and storage conditions. The "stable" formulations of the invention retain biological activity under given manufacture, preparation, transportation and storage conditions. The stability of the antibody can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of an antibody of the invention in PBS.

Therapeutic formulations of the low AR compositions of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic effect to be achieved, and (b) the limitations inherent in the art of compounding such an antibody for the treatment of sensitivity in individuals.

Therapeutic compositions of the low AR compositions of the invention can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. By way of example, in certain embodiments, the antibodies (including antibody fragments) are formulated for intravenous administration. In certain other embodiments, the antibodies (including antibody fragments) are formulated for local delivery to the cardiovascular system, for example, via catheter, stent, wire, intramyocardial delivery, intrapericardial delivery, or intraendocardial delivery.

Formulations of the low AR compositions of the invention which are suitable for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required (U.S. Pat. Nos. 7,378,110; 7,258,873; 7,135,180; 7,923,029; and US Publication No. 20040042972).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the low AR compositions of the invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In certain embodiments, antibodies of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant Protein A receptor (Briscoe et al. (1995) *Am. J. Physiol.* 1233:134), different species of which may comprise the formulations of the invention, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the antibodies of the invention may be delivered locally to the brain to mitigate the risk that the blood brain barrier slows effective delivery.

In certain embodiments, the low AR compositions of the invention may be administered with medical devices known in the art. For example, in certain embodiments an antibody or antibody fragment is administered locally via a catheter, stent, wire, or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The efficient dosages and the dosage regimens for the low AR compositions of the invention depend on the disease or condition to be treated and can be determined by the persons skilled in the art. One of ordinary skill in the art would be able to determine such amounts based on such factors as the subject's size, the severity of the subject's symptoms, and the particular composition or route of administration selected.

VIII. Alternative Formulations Containing the Low AR Compositions of the Invention Alternative Aqueous Formulations The invention also provides a low AR composition formulated as an aqueous formulation comprising a protein and water, as described in U.S. Pat. No. 8,420,081 and WO2012/065072, the contents of which are hereby incorporated by reference. In these aqueous formulations, the protein is stable without the need for additional agents. This aqueous formulation has a number of advantages over conventional formulations in the art, including stability of the protein in water without the requirement for additional excipients, increased concentrations of protein without the need for additional excipients to maintain solubility of the protein, and low osmolality. These also have advantageous storage properties, as the proteins in the formulation remain stable during storage, e.g., stored as a liquid form for more than 3 months at 7° C. or freeze/thaw conditions, even at high protein concentrations and repeated freeze/thaw processing steps. In one embodiment, formulations described herein include high concentrations of proteins such that the aqueous formulation does not show significant opalescence, aggregation, or precipitation.

In one embodiment, an aqueous low AR composition comprising a protein, e.g., an antibody, e.g., an anti-TNFα antibody or antigen biding portion thereof, and water is provided, wherein the formulation has certain characteristics, such as, but not limited to, low conductivity, e.g., a conductivity of less than about 2.5 mS/cm, a protein concentration of at least about 10 µg/mL, an osmolality of no more than about 30 mOsmol/kg, and/or the protein has a molecular weight (Mw) greater than about 47 kDa. In one embodiment, the formulation has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized, or spray-dried.

In one embodiment, the formulation has a low conductivity, including, for example, a conductivity of less than about 2.5 mS/cm, a conductivity of less than about 2 mS/cm, a conductivity of less than about 1.5 mS/cm, a conductivity of less than about 1 mS/cm, or a conductivity of less than about 0.5 mS/cm.

In another embodiment, low AR compositions included in the formulation have a given concentration, including, for example, a concentration of at least about 1 mg/mL, at least about 10 mg/mL, at least about 50 mg/mL, at least about 100 mg/mL, at least about 150 mg/mL, at least about 200 mg/mL, or greater than about 200 mg/mL. In another embodiment, the formulation of the invention has an osmolality of no more than about 15 mOsmol/kg.

The aqueous formulations described herein do not rely on standard excipients, e.g., a tonicity modifier, a stabilizing agent, a surfactant, an anti-oxidant, a cryoprotectant, a bulking agent, a lyroprotectant, a basic component, and an acidic component. In other embodiments of the invention, the formulation contains water, one or more proteins, and no ionic excipients (e.g., salts, free amino acids).

In certain embodiments, the aqueous formulation as described herein comprise a low AR composition comprising a protein concentration of at least 50 mg/mL and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg, and also have a high protein concentration, e.g., the concentration of the protein is at least 100 mg/mL, and may be as much as 200 mg/mL or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation as described herein is not limited by the protein size and the formulation may include any size range of proteins. Included within the scope of the invention is an aqueous formulation comprising at least 40 mg/mL and as much as 200 mg/mL or more of a protein, for example, 40 mg/mL, 65 mg/mL, 130 mg/mL, or 195 mg/ml, which may range in size from 5 kDa to 150 kDa or more. In one embodiment, the protein in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation as described herein may be characterized by the hydrodynamic diameter ($D_h$) of the proteins in solution. The hydrodynamic diameter of the protein in solution may be measured using dynamic light scattering (DLS), which is an established analytical method for determining the $D_h$ of proteins. Typical values for monoclonal antibodies, e.g., IgG, are about 10 nm. Low-ionic formulations may be characterized in that the $D_h$ of the proteins are notably lower than protein formulations comprising ionic excipients. It has been discovered that the $D_h$ values of antibodies in aqueous formulations made using the disfiltration/ultrafiltration (DF/UF) process, as described in U.S. Pat. No. 8,420,081, using pure water as an exchange medium, are notably lower than the $D_h$ of antibodies in conventional formulations independent of protein concentration. In one embodiment, antibodies in the aqueous formulation as described herein have a $D_h$ of less than 4 nm, or less than 3 nm.

In one embodiment, the $D_h$ of the protein in the aqueous formulation is smaller relative to the $D_h$ of the same protein in a buffered solution, irrespective of protein concentration. Thus, in certain embodiments, protein in an aqueous formulation made in accordance with the methods described herein, will have a $D_h$ which is at least 25% less than the $D_h$ of the protein in a buffered solution at the same given concentration. Examples of buffered solutions include, but are not limited to phosphate buffered saline (PBS). In certain embodiments, proteins in the aqueous formulation of the invention have a $D_h$ that is at least 50% less than the $D_h$ of the protein in PBS in at the given concentration; at least 60% less than the $D_h$ of the protein in PBS at the given concentration; at least 70% less than the $D_h$ of the protein in PBS at the given concentration; or more than 70% less than the $D_h$ of the protein in PBS at the given concentration. Ranges intermediate to the above recited percentages are also intended to be part of this invention, e.g., about 55%, 56%, 57%, 64%, 68%, and so forth. In addition, ranges of values using a combination of any of the above recited values as upper and/or lower limits are intended to be included, e.g., about 50% to about 80%.

In one aspect, the aqueous formulation includes the protein at a dosage of about 0.01 mg/kg-10 mg/kg. In another aspect, the dosages of the protein include approximately 1 mg/kg administered every other week, or approximately 0.3 mg/kg administered weekly. A skilled practitioner can ascertain the proper dosage and regime for administering to a subject.

Alternative Solid Unit Formulations

The invention also provides a low AR composition of the invention formulated as a stable solid composition of a protein (preferably a therapeutic protein) and a stabilizer, referred to herein as solid units, as described in Attorney Docket No. 117813-31001 (U.S. Provisional Patent Application 61/893, 123), the contents of which are hereby incorporated by reference herein. Specifically, it has been discovered that despite having a high proportion of sugar relative to the protein, the solid units of the invention maintain structural rigidity and resist changes in shape and/or volume when stored under ambient conditions, e.g., room temperature and humidity, for extended periods of time. The solid units of the invention remain free-flowing and are able to maintain long-term physical and chemical stability of the protein without significant degradation and/or aggregate formation. The solid units of the invention have many advantages over the art, including that they can be formulated for oral delivery and are easily reconstituted in a diluent, such as water. Because the solid units are readily dissolved, they may be used in dual chamber delivery devices and may be prepared directly in a device for patient use.

As used herein, the term "solid unit," refers to a composition which is suitable for pharmaceutical administration and comprises a protein, e.g., an antibody or peptide, and a stabilizer, e.g., a sugar. The solid unit has a structural rigidity and resistance to changes in shape and/or volume. In a preferred embodiment, the solid unit is obtained by lyophilizing a pharmaceutical formulation of a therapeutic protein. The solid unit may be any shape, e.g., geometric shape, including, but not limited to, a sphere, a cube, a pyramid, a hemisphere, a cylinder, a teardrop, and so forth, including irregularly shaped units. In one embodiment, the solid unit has a volume ranging from about 1 µl to about 20 µl. In one embodiment, the solid unit is not obtained using spray drying techniques, e.g., the solid unit is not a powder or granule. As used herein, the phrase "a plurality of solid units" refers to a collection or population of solid units, wherein the collection comprises two or more solid units having a substantially uniform shape, e.g., sphere, and/or volume distribution. In one embodiment, the plurality of solid units is free-flowing.

IX. Kits and Articles of Manufacture Comprising the Low AR Compositions of the Invention Also within the scope of the present invention are kits comprising the low AR compositions of the invention and instructions for use. The term "kit" as used herein refers to a packaged product comprising components with which to administer the antibody, or antigen-binding portion thereof, of the invention for treatment of a disease or disorder. The kit may comprise a box or container that holds the components of the kit. The box or container is affixed with a label or a Food and Drug Administration approved protocol. The box or container holds components of the invention which may be contained within plastic, polyethylene, polypropylene, ethylene, or propylene vessels. The vessels can be capped-tubes or bottles. The kit can also include instructions for administering an antibody of the invention.

The kit can further contain one more additional reagents, such as an immunosuppressive reagent, a cytotoxic agent or a radiotoxic agent or one or more additional antibodies of the invention (e.g., an antibody having a complementary activity which binds to an epitope in the TNFα antigen distinct from a first anti-TNFα antibody). Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation or lyophilized formulation of an antibody or antibody fragment thereof of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. No. 6,792,743, U.S. Pat. No. 5,607,400, U.S. Pat. No. 5,893,842, U.S. Pat. No. 7,081,107, U.S. Pat. No. 7,041,087, U.S. Pat. No. 5,989,227, U.S. Pat. No. 6,807,797, U.S. Pat. No. 6,142,976, U.S. Pat. No. 5,899,889, U.S. Pat. No. 7,699,811, U.S. Pat. No. 7,540,382, U.S. Pat. No. 7,998,120, U.S. Pat. No. 7,645,267, and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising antibodies of the invention are also provided that are useful for various purposes, e.g., research and diagnostic including for purification or immunoprecipitation of protein of interest from cells, detection of the protein of interest in vitro or in vivo. For isolation and purification of a protein of interest, the kit may contain an antibody coupled to beads (e.g., sepharose beads). Kits may be provided which contain the antibodies for detection and quantitation of a protein of interest in vitro, e.g., in an ELISA or a Western blot. As with the article of manufacture, the kit comprises a container and a label or package insert on or associated with the container. The container holds a composition comprising at least one antibody of the invention. Additional containers may be included that contain, e.g., diluents and buffers, control antibodies. The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising an antibody that is suitable for parenteral administration. In another embodiment, the unit dosage form is provided as a sterile lyophilized powder comprising an antibody that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within said packaging material, wherein said pharmaceutical agent comprises a liquid formulation containing an antibody. The packaging material includes instruction means which indicate how that said antibody can be used to prevent, treat and/or manage one or more symptoms associated with a disease or disorder.

The present invention is further illustrated by the following examples which should not be construed as limiting in any way.

X. EXAMPLES

Example 1

Method for Reducing the Extent of Acidic Species in Cell Culture by the Addition of Medium Components Production of recombinant proteins by host cells can result in product-related charge heterogeneities present in the population of proteins produced by the cells. The presence of acidic species in the population of proteins is an example of a product-related charge heterogeneity. Control of the amount of acidic species present in the population of proteins produced by the host cells can be accomplished by modifying the culture conditions of the host cells.

The experiments in this Example demonstrate that supplementation of cell culture medium with supplemental amounts of amino acids, calcium chloride and niacinamide enhances product quality by decreasing the amount of acidic species in the culture harvest. The amino acids included in the study were arginine, lysine, ornithine and histidine, which belong to the group of amino acids that are basic. The study includes examples from multiple cell lines and antibodies, in shake flasks and bioreactors and in batch and fed-batch culture formats. A dose dependent effect in the extent of reduction of acidic species with increasing concentrations of the supplements was observed. In addition, the possibility to supplement these medium additives individually or in suitable combinations for acidic species reduction was also demonstrated.

Materials and Methods

Cell Source and Adaptation Cultures

Three adalimumab producing cell lines (cell line 1, cell line 2, and cell line 3), one mAb1 producing cell line and one mAb2 producing cell line were employed in the studies covered below. For adalimumab producing cell lines, cells were cultured in their respective growth media (chemically defined media (media 1) or a hydrolysate based media (media 2 or media 3)) in a combination of vented non-baffled shake flasks (Corning) on a shaker platform at 110 RPM (cell line 1), 180 RPM (cell line 2), 140 RPM (cell line 3) and 10 L or 20 L wave bags (GE). For experiments with cells in the hydrolysate based media (media 3), cells were thawed in media 1 and then adapted to media 3 over a few passages. Cultures were propagated in a 35° C., 5% $CO_2$ incubator for cell line 1 and 2 and in a 36° C., 5% $CO_2$ incubator for cell line 3 in order to obtain the required number of cells to be able to initiate production stage cultures.

For the mAb1 producing cell line, cells were cultured in chemically defined growth media (media 1) in a combination of vented non-baffled shake flasks (Corning) on a shaker platform at 130 RPM and 20 L wave bags (GE). Cultures were propagated in a 36° C., 5% $CO_2$ incubator to obtain the required number of cells to be able to initiate production stage cultures.

For the mAb2 producing cell line, cells were cultured in chemically defined growth media (media 1) in a combination of vented non-baffled shake flasks (Corning) on a shaker platform at 140 RPM and 20 L wave bags (GE). Cultures were propagated in a 35° C., 5% $CO_2$ incubator to obtain the required number of cells to be able to initiate production stage cultures.

Cell Culture Media

Growth and production media were prepared from either a chemically defined media formulation (media 1) or hydrolysate-based medium formulations (media 2 and media 3). For preparation of the media 1, the media (IVGN GIA-1, a proprietary basal media formulation from Invitrogen) was supplemented with L-glutamine, sodium bicarbonate, sodium chloride, and methotrexate solution. Production media consisted of all the components in the growth medium, excluding methotrexate. For cell line 1, both growth and production medium were also supplemented with insulin. For mAb1 and mAb2 producing cell lines, the growth medium were also supplemented with insulin.

For the hydrolysate-based formulation (media 2), the growth media was composed of PFCHO (proprietary chemically defined formulation from SAFC), Dextrose, L-Glutamine, L-Asparagine, HEPES, Poloxamer 188, Ferric Citrate, Recombinant Human Insulin, Yeastolate (BD), Phytone Peptone (BD), Mono- and Di-basic Sodium Phosphate, Sodium Bicarbonate, Sodium Chloride and methotrexate. Production media consisted of all the components listed in the growth medium, excluding methotrexate.

For the hydrolysate-based formulation (media 3), the growth media was composed of OptiCHO (Invitrogen), L-Glutamine, Yeastolate (BD), Phytone Peptone (BD) and methotrexate. Production media consisted of all the components listed in the growth medium, excluding methotrexate.

Amino acids used for the experiments were reconstituted in Milli-Q water to make a 100 g/L stock solution, which was subsequently supplemented to both growth and production basal media. After addition of amino acids, media was brought to a pH similar to unsupplemented (control) media using 5N hydrochloric acid/5N NaOH, and it was brought to an osmolality similar to unsupplemented (control) media by adjusting the concentration of sodium chloride.

Calcium Chloride Dihydrate (Sigma or Fluka) used for the experiments were reconstituted in Milli-Q water to make a stock solution, which was subsequently supplemented to the production basal media. After addition of calcium chloride, media was brought to a pH similar to non-supplemented (control) media using 6N hydrochloric acid/5N NaOH, and it was brought to an osmolality similar to non-supplemented (control) media by adjusting the concentration of sodium chloride.

Niacinamide (Sigma or Calbiochem) used for the experiments were reconstituted in Milli-Q water to make a stock solution, which was subsequently supplemented to the production basal media. After addition of niacinamide, media was brought to a pH similar to non-supplemented (control) media using 6N hydrochloric acid/5N NaOH, and it was brought to an osmolality similar to non-supplemented (control) media by adjusting the concentration of sodium chloride.

All media was filtered through Corning 1 L filter systems (0.22 μm PES) and stored at 4° C. until usage.

TABLE 3

List of medium additives supplemented to culture media

| Medium additive | Catalog No./Source of medium supplements |
|---|---|
| Arginine | Sigma, A8094 |
| Lysine | Calbiochem, 4400 |
| Histidine | Sigma, H5659 |
| Ornithine | Sigma, 06503 |
| Calcium Chloride | Fulka, 21097 Sigma, C8106 |
| Niacinamide | Calbiochem, 481907 Sigma, N0636 |

Production Cultures

Production cultures were initiated either in 500 ml shake flasks (Corning) or in 3 L Bioreactors (Applikon). For shake flask experiments, duplicate 500 mL Corning vented non-baffled shake flasks (200 mL working volume) were used for each condition. The shake flasks were kept in incubators either maintained at 35° C. or 36° C. and 5% $CO_2$ on shaker platforms that were either set at 110 rpm for adalimumab producing cell line 1, 180 rpm for adalimumab producing cell line 2, 140 rpm for adalimumab producing cell line 3, for 130 rpm for mAb1 producing cell line, or 140 rpm for mAb2 producing cell line. For the bioreactor experiments, 3 L bioreactors (1.5 L working volume) were run at 35° C., 30% dissolved oxygen (DO), 200 rpm, pH profile from 7.1 to 6.9 in three days and pH 6.9 thereafter. In all experiments, the cells were transferred from the seed train to the production stage at a split ratio of 1:5.

Cultures were run in either batch or fed-batch mode. In the batch mode, cells were cultured in the respective production medium. 1.25% (v/v) of 40% glucose stock solution was fed when the media glucose concentration reduced to less than 3 g/L. In the fed-batch mode, cultures were run with either the IVGN feed (proprietary chemically defined feed formulation from Invitrogen) as per the following feed schedule—(4% (v/v)—day 6, day 7, and day 8, respectively) along with 10× Ex-Cell PFCHO feed (proprietary chemically defined formulation)—3% (v/v) on day 3. The cultures were also fed with 1.25% (v/v) of 40% glucose stock solution when the glucose concentration was below 3.0 g/L.

Retention samples for titer analysis, of 2×1.5 mL, were collected daily for the bioreactor experiments beginning on Day 8, and frozen at −80° C. The samples taken from each were later submitted for titer analysis.

The harvest procedure of the shake flasks and reactors involved centrifugation of the culture sample at 3,000 RPM for 30 min and storage of supernatant in PETG bottles at −80°

C. before submission for Protein A purification and WCX-10 analysis.

WCX-10 Assay

This method is employed towards the quantification of the acidic species and other variants present in cell culture harvest samples. Cation exchange chromatography was performed on a Dionex ProPac WCX-10, Analytical column (Dionex, Calif.).

For adalimumab and mAb1 samples, the mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

For mAb2 samples, the mobile phases used were 20 mM (4-Morpholino)ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak corresponding to the drug product are together represented as the acidic peaks (FIG. 1).

Lysine-C Peptide Mapping for Methylglyoxal (MGO) Quantification

Typical trypsin digestion employed almost universally for peptide mapping cleaves a denatured, reduced and alkylated protein at the carboxyl side of the two basic amino acids, lysine and arginine. Methylglyoxal (MGO) is a small molecule metabolite derived as a glycolysis byproduct which can modify arginine residues. A modification of an arginine prevents trypsin from cutting this site and results in a mis-cleavage. The challenge of quantifying the amount of MGO modified peptide is that it is not compared to an equivalent non-modified peptide but rather two parental cleaved peptides which will likely have different ionization potential than the modified peptide. In order to determine a truly accurate direct measurement of an MGO-modified peptide, it must be compared to its non-modified counterpart and expressed as a percent. Using endoproteinase lysine-C as an alternative enzyme, cleavages only occur at lysine residues. The result is a direct comparison of the same peptide with and without an MGO modification which provides a high degree of accuracy in quantifying even trace levels of the modified species.

Procedure: Samples were diluted to a nominal concentration of 4 mg/mL. 8 M guanidine-HCl was added to the sample in a 3:1 ratio resulting in a 1 mg/mL concentration in 6M guanidine-HCl. The samples were reduced with 10 mM final conc. DTT for 30 minutes at 37° C. followed by an alkylation with 25 mM final concentration iodoacetic acid for 30 minutes at 37° C. in the dark. The samples were then buffer exchanged into 10 mM Tris pH 8.0 using NAP-5 columns. The samples were then digested for 4 hours at 37° C. using endoproteinase Lys-C at an enzyme to protein ratio of 1:20. The digest was quenched by adding 5 μL of formic acid to each sample. Samples ere analyzed by LC/MS peptide mapping. Briefly, 50 μL of sample was loaded onto a Waters BEH C18 1.7μ 1.0×150 mm UPLC column with 98% 0.08% formic acid, 0.02% TFA in water and 2% 0.08% formic acid, 0.02% TFA in acetonitrile. The composition was changed to 65% 0.08% formic acid, 0.02% TFA in water and 35% 0.08% formic acid, 0.02% TFA in acetonitrile in 135 minutes using a Waters Acquity UPLC system. Eluting peaks were monitored using a Thermo Scientific LTQ-Orbitrap Mass Spectrometer. Specific mass traces were extracted for both modified and non-modified peptides in order to accurately quantify the total amount of MGO modification at each site. Mass spectra were also analyzed for the specific region of the chromatogram to confirm the peptide identity. An example data set is shown in FIG. 162.

Results

Effect of Arginine Supplementation to Cell Culture Media

The addition of arginine was tested in several experimental systems covering multiple cell lines, media and monoclonal antibodies. The following is a detailed description of two representative experiments where two different adalimumab producing cell lines (cell line 2 and cell line 3) were cultured in a chemically defined media (media 1).

Cell line 2 was cultured in media 1 with different total amounts of arginine (1 (control), 1.25, 1.5, 2, 3, 5, 9 g/L). The cultures were performed in shake flasks in batch format with only glucose feed as described in the materials and methods. The cells grew to maximum viable cell densities (VCD) in the range of $18-22 \times 10^6$ cells/ml for the different conditions tested. The growth and viability profiles were comparable between the different test conditions, although a slight decrease in viable cell density profile was observed in samples with the 9 g/L arginine test condition (FIGS. 1 and 2). The harvest titers were comparable between the conditions (FIG. 3). On Day 10 and Day 12 of culture, duplicate shake flasks for each of the conditions were harvested and then subsequently analyzed using WCX-10 post Protein A purification and the percentages of total peak(s) area corresponding to the acidic species were quantified (FIGS. 4 and 5). The percentage of acidic species in the control sample was as high as 19.7% on day 10. In the sample with the highest total concentration of arginine in this experiment (9 g/L), the percentage of acidic species was reduced to 12.2%. A dose dependent decrease in acidic species was observed in test conditions with arginine concentrations beyond 2 g/L (FIG. 4). A similar trend in reduction of acidic species with arginine increase was also observed in the day 12 harvest samples (FIG. 5). Further, while the extent of acidic species in the 1 g/L arginine samples increased from 19.7% (day 10 harvest) to 25.5% (day 12 harvest), this increase in the 9 g/L arginine test condition was significantly smaller from 12.2% (day 10 harvest) to 13.9% (day 12 harvest). Thus, the increase of total arginine led to a reduction in the extent of total acidic species at a particular time point in culture as well the rate of increase of acidic species with time of culture.

Cell line 3 was cultured in media 1 with different total amounts of arginine (1 (control), 3, 5, 7, 9 g/L). The cultures were performed in shake flasks in batch format with only glucose feed as described in the materials and methods. The cells grew to maximum VCD in the range of $7-10 \times 10^6$ cells/ml for the different conditions tested. The growth and viability profiles were comparable between the different test conditions, although a slight decrease in viable cell density and viability profiles was observed in samples with the 9 g/L arginine condition (FIGS. 6 and 7). The product titer was also comparable between all conditions (FIG. 8). On Day 10 of culture, duplicate shake flasks for each of the conditions were harvested and then subsequently analyzed using WCX-10 post Protein A purification and the percentages of total peak(s) area corresponding to the acidic species were quantified (FIG. 9). The percentage of acidic species in the control sample was as high as 23.3% on day 10. In the sample with the highest total concentration of arginine in this experiment (9 g/L), the percentage of acidic species was reduced to 17.0%. A dose dependent decrease in acidic species was observed in conditions with higher concentrations of arginine.

Additional experiments were performed with multiple cell lines in chemically defined or hydrolysate based media to demonstrate the wide range of applicability of this method. The experimental setup for each of these experiments was similar to that described above. The summaries of results of the different experiments performed for adalimumab are summarized in FIGS. 10, 11, and 12. A reduction in acidic species with increased arginine concentration was also observed in each case.

In addition to adalimumab, the utility of this method for acidic species reduction was also demonstrated for processes involving two other mAb producing cell lines (cell lines producing mAb1 and mAb2). The experimental setup for each of these experiments was similar to that described in section above and in the materials and methods. The reduction of acidic species with increased arginine concentration for experiments corresponding to each mAb is summarized in FIGS. 13 and 14. For mAb2, a significant reduction in acidic species was observed at arginine concentration of 9 g/L.

In U.S. Application Ser. No. 61/893,088, (the contents of which are incorporated herein by reference), we describe the utility of arginine supplementation to culture media towards modulation of the lysine variant distribution. It is possible that a fraction of acidic species also shifted along with shift in lysine variants (from Lys 0 to Lys1 and Lys2), in addition to the fraction of acidic species that is completely removed from the entire protein population. To estimate the acidic species reduction that is independent of this redistribution of lysine variants, Protein A eluate samples from a representative set of arginine supplementation experiments were pre-treated with the enzyme carboxypeptidase before WCX-10. One set of samples from adalimumab experiment and another set of samples from a mAb2 experiment were used for this analysis. The carboxypeptidase treatment of the samples resulted in the cleavage of the C-terminal lysine residues as demonstrated by the complete conversion of Lys1/Lys2 to Lys 0 in each of these samples (data not shown here). As a result of this conversion, the acidic species quantified in these samples corresponded to an aggregate sum of acidic species that would be expected to also include those species that may have previously shifted corresponding to the lysine variant shift and perhaps gone unaccounted for in the samples that were not treated with carboxypeptidase prior to WCX-10. A dose dependent reduction in acidic species was observed in the carboxypeptidase treated samples with increasing concentration arginine (FIGS. 15 and 16). This suggests that the acidic species reduction described here is not completely attributed to a probable shift of the acidic species corresponding to the lysine variant redistribution.

Effect of Lysine Supplementation to Cell Culture Media

The addition of lysine was tested in several experimental systems covering multiple cell lines, media and monoclonal antibodies. The following is a detailed description of two representative experiments where two different cell lines (cell line 2 and cell line 3) were cultured in a chemically defined media (media 1) for the production of adalimumab.

Cell line 2 was cultured in media 1 with different total concentrations of lysine (1 (control), 5, 7, 9, 11 g/L). The cultures were performed in shake flasks in batch format with only glucose feed as described in the materials and methods. The cells grew to maximum viable cell densities (VCD) in the range of $17\text{-}23 \times 10^6$ cells/ml for the different conditions tested. A slight dose dependent decrease in viable cell density profile was observed in all samples with respect to the control sample (FIG. 17). The viability profiles were comparable between the conditions (FIG. 18). On Days 10 and 11 of culture samples were collected for titer analysis (FIG. 19). The titers for all conditions were comparable. On Day 11 of culture, duplicate shake flasks for each of the conditions were harvested and then subsequently analyzed using WCX-10 post Protein A purification and the percentages of total peak(s) area corresponding to the acidic species were quantified (FIG. 20). The percentage of acidic species in the control was as high as 26.5%. In the sample with the highest tested concentration of lysine in this experiment (11 g/L), the percentage of acidic species was reduced to 15.0%. A dose dependent decrease in acidic species was observed in test conditions with higher total concentrations of lysine.

Cell line 3 was cultured in media 1 with different total concentrations of lysine (1 (control), 3, 5, 7, 9, 11 g/L). The cultures were performed in shake flasks in batch format with only glucose feed as described in the materials and methods. The cells grew to maximum VCD in the range of $9.5\text{-}11.5 \times 10^6$ cells/ml for the different conditions tested. The growth and viability profiles were comparable between the different test conditions, although a slight decrease in viable cell density and viability profiles was observed in samples with higher lysine concentrations than that in the control sample (FIGS. 21 and 22). On Days 10, 11 and 12 of culture samples were collected for titer analysis (FIG. 23). The titers for all conditions were comparable. On Day 12 of culture, duplicate shake flasks for each of the conditions were harvested and then subsequently analyzed using WCX-10 post Protein A purification and the percentages of total peak(s) area corresponding to the acidic species were quantified (FIG. 24). The percentage of acidic species in the control sample was as high as 26.6%. In the sample with the highest tested concentration of lysine in this experiment (11 g/L) the percentage of acidic species was reduced to 18.1%. A dose dependent decrease in acidic species was observed in test conditions with higher total concentrations of lysine.

Additional experiments were performed with multiple cell lines in chemically defined or hydrolysate based media to demonstrate the wide range of applicability of this method. The experimental setup for each of these experiments was similar to that described above and in materials and methods section. The summaries of results of the different experiments performed for adalimumab are summarized in FIGS. 25, 26, and 27. A reduction in acidic species with increased lysine concentration was also observed in each case.

In addition to adalimumab, the utility of this method for acidic species reduction was also demonstrated for processes involving two other mAbs. The experimental setup for each of these experiments was similar to that described above and in the materials and methods section. The reduction of acidic species with lysine addition for experiments corresponding to each mAb is summarized in FIGS. 28, 29. For mAb2, a significant reduction in acidic species was observed at lysine concentration of 11 g/L.

In U.S. Application Ser. No. 61/893,088, (the contents of which are incorporated herein by reference), the utility of lysine supplementation to culture media for the modulation of the lysine variant distribution is described. To estimate the acidic species reduction that is independent of this redistribution of lysine variants, Protein A eluate samples from a representative set of lysine supplementation experiments were pre-treated with the enzyme carboxypeptidase before WCX-10. One set of samples from an adalimumab experiment and another set of samples from a mAb2 experiment were used for this analysis. The carboxypeptidase treatment of the samples resulted in the cleavage of the C-terminal lysine residues as demonstrated by the conversion of Lys1/Lys2 to Lys 0 in each of these samples. As a result of this conversion, the acidic species quantified in these samples corresponded to an aggregate sum of acidic species that would be expected to also include those species that may have previously shifted corresponding to the lysine variant shift and perhaps gone unaccounted for in the samples that were not treated with carboxypeptidase prior to WCX-10. A dose dependent reduction in acidic species was observed in the carboxypeptidase treated samples with increasing concentration of lysine for the adalimumab samples from 26.8% in the non-supplemented sample to 21.1% in the 10 g/L lysine supplemented sample, a reduction of 5.7% in total acidic species (FIG. 30). Similar results were also observed for the mAb2 samples (FIG. 31). This suggests that the acidic species reduction described here is not completely attributed to a probable shift of the acidic species corresponding to the lysine redistribution.

Effect of Histidine Supplementation to Cell Culture Media

The addition of histidine was tested in several experimental systems covering multiple cell lines, media and monoclonal antibodies. The following is a detailed description of two representative experiments where two different cell lines (cell line 2 and cell line 3) were cultured in a chemically defined media (media 1) for the production of adalimumab.

Cell line 2 was cultured in media 1 with different total concentrations of histidine (0 (control), 4, 6, 8, 10 g/L). The cultures were performed in shake flasks in batch format with only glucose feed as described in the materials and methods. The cells grew to maximum VCD in the range of 12-22×10$^6$ cells/ml for the different conditions tested. A dose dependent decrease in viable cell density profile was observed with the 10 g/L histidine condition having significant reduction in growth (FIG. 32). A corresponding effect on viability was also observed (FIG. 33). On Days 10, 11 and 12 of culture samples were collected for titer analysis and reported for the harvest day for each sample (FIG. 34). There was a small dose dependent decrease in titers for conditions with histidine supplementation. On Days 11-12, duplicate shake flasks were harvested and then subsequently analyzed using WCX-10 post Protein A purification and the percentages of total peak(s) area corresponding to the acidic species were quantified (FIG. 35). The percentage of acidic species in the control sample was as high as 26.5%. In the sample with the highest tested concentration of histidine in this experiment (10 g/L), the percentage of acidic species was reduced to 15.6%. A dose dependent decrease in acidic species was observed in test conditions with increased histidine concentrations.

Cell line 3 was cultured in media 1 with different total concentrations of histidine (0 (control), 2, 4, 6, 8 g/L). The cultures were performed in shake flasks in batch format with only glucose feed as described in the materials and methods. The cells grew to maximum viable cell densities (VCD) in the range of 6-10×10$^6$ cells/ml for the different conditions tested. A dose dependent decrease in viable cell density profile was observed in all conditions with histidine concentrations higher than that in the control (FIG. 36). The viability profiles were more comparable between conditions with this cell line (FIG. 37). On Day 12 of culture, samples were collected for titer analysis (FIG. 38). The titers for all conditions were comparable. On Day 12 of culture, duplicate shake flasks for each of the conditions were harvested and then subsequently analyzed using WCX-10 post Protein A purification and the percentages of total peak(s) area corresponding to the acidic species were quantified (FIG. 39). The percentage of acidic species in the control sample was 26.2%. In the sample with the highest tested concentration of histidine in this experiment (8 g/L), the percentage of acidic species was reduced to 20.0%. A dose dependent decrease in acidic species was observed in test conditions with increased histidine concentration.

Additional experiments were performed with multiple cell lines in chemically defined or hydrolysate based media to evaluate the wide range of applicability of this method. The experimental setup for each of these experiments was similar to that described above and in the materials and methods section. The summaries of results of the different experiments performed for adalimumab are set forth in FIGS. 40, 41, and 42. A reduction in acidic species with increased histidine concentration was observed with cell line 1 in media 1 (FIG. 40) and with cell line 2 in media 3 (FIG. 42). For cell line 2 in media 3, a dose dependent reduction in acidic species was observed up to 4 g/L histidine, with no further significant reduction at higher concentrations of histidine (FIG. 42). For cell line 1, media 2, no significant reduction of acidic species was observed within the histidine concentration range (0-4 g/L) (FIG. 41).

In addition to adalimumab, the utility of this method for acidic species reduction was also demonstrated for processes involving two other mAbs. The experimental setup for each of these experiments was similar to that described above and in the materials and methods section. The reduction of acidic species with increased histidine concentration for experiments corresponding to each mAb is summarized in FIGS. 43 and 44. For mAb2, in contrast with the results reported with arginine and lysine supplementation shown previously, a clear significant dose dependent reduction in total acidic species from 28.1% in the control to 21.5% in 4 g/L histidine sample was observed.

In U.S. Application Ser. No. 61/893,088, (the contents of which are hereby incorporated herein by reference), the utility of increased histidine to culture media towards modulation of the lysine variant distribution is described. To estimate the acidic species reduction that is independent of this redistribution of lysine variants, Protein A eluate samples from a representative set of histidine supplementation experiments were also pre-treated with the enzyme carboxypeptidase before WCX-10. One set of samples from adalimumab experiment and another set of samples from a mAb2 experiment were used for this analysis. The carboxypeptidase treatment of the samples resulted in the cleavage of the C-terminal lysine residues as demonstrated by the complete conversion of Lys 1/Lys2 to Lys 0 in each of these samples (data not shown here). A dose dependent reduction in acidic species was observed in the carboxypeptidase treated samples with increasing concentration of histidine (FIGS. 45 and 46). This indicates that the acidic species reduction described here is not completely attributed to a probable shift of the acidic species corresponding to the lysine redistribution.

Effect of Ornithine Supplementation to Cell Culture Media

The addition of ornithine was tested in several experimental systems covering multiple cell lines, media and monoclonal antibodies. The following is a detailed description of two representative experiments where two different cell lines (cell line 2 and cell line 3) were employed in a chemically defined media (media 1) for the production of adalimumab.

Cell line 2 was cultured in media 1 with different total concentrations of ornithine (0 (control), 4, 6, 8, 10 g/L). The cultures were performed in shake flasks in batch format with only glucose feed as described in the materials and methods. The cells grew to maximum VCD in the range of 15-22×10$^6$ cells/ml for the different conditions tested. A slight decrease in viable cell density with ornithine supplementation was observed (FIG. 47). Corresponding differences in the viability profiles were also observed (FIG. 48). On Day 11 of culture, samples were collected for titer analysis (FIG. 49). The titers for all conditions were comparable. On Day 11, duplicate shake flasks were harvested for each condition and then subsequently analyzed using WCX-10 post Protein A purification and the percentages of total peak(s) area corresponding to the acidic species were quantified (FIG. 50). The percentage of acidic species in the control sample was 26.5%. In the sample with the highest tested concentration of ornithine in this experiment (10 g/L), the percentage of acidic species was reduced to 16.1%. A dose dependent decrease in acidic species was observed in test conditions with increased ornithine concentration.

Cell line 3 was cultured in media 1 supplemented with different total concentrations of ornithine (0 (control), 2, 4, 6, 8 g/L). The cultures were performed in shake flasks in batch format with only glucose feed as described in the materials and methods. The cells grew to maximum viable cell densities (VCD) in the range of 9.5-11.5×10$^6$ cells/ml for the different conditions tested. The viable cell density and viability profiles were comparable (FIGS. 51 and 52). On Day 12 of culture, samples were collected for titer analysis (FIG. 53). The titers for all conditions were comparable. On Day 12 of culture, duplicate shake flasks for each of the conditions were harvested and then subsequently analyzed using WCX-10 post Protein A purification and the percentages of total peak(s) area corresponding to the acidic species were quantified (FIG. 54). The percentage of acidic species in the control sample was 24.8%. In the sample with the highest tested concentration of ornithine in this experiment (8 g/L), the percentage of acidic species was reduced to 20.5%. A dose dependent decrease in acidic species was observed in test conditions with increased ornithine concentration.

Additional experiments were performed with multiple cell lines in chemically defined or hydrolysate based media to evaluate the wide range of applicability of this method. The experimental setup for each of these experiments was similar to that described above and in the materials and methods section. The summaries of results of the different experiments performed for adalimumab are summarized in FIGS. 55, 56 and 57. For cell line 1 in media 1, a dose dependent reduction was observed (FIG. 55). However, for cell line 1 in media 2, a hydrolysate media, no significant reduction in acidic species was observed across the conditions (FIG. 56). For cell line 2 in media 3, a reduction in acidic species from 22.1% in the control sample to 18.7% in the 2 g/L ornithine sample with no further reduction at higher ornithine concentrations was observed (FIG. 57).

In addition to adalimumab, the utility of this method for acidic species reduction was also demonstrated for processes involving two other mAbs. The experimental setup for each of these experiments was similar to that described in the section above and in the materials and method section. The reduction of acidic species with ornithine addition for experiments corresponding to each mAb is summarized in FIGS. 58 and 59. In the case of mAb1, a 7.3% dose dependent reduction in total acidic species was observed within the concentration range tested. For mAb2, about 2% reduction was observed in the 1 g/L ornithine concentration sample with minimum further reduction at higher ornithine concentrations.

Similar to the analysis conducted with the other amino acids, Protein A eluate samples from a representative set of ornithine experiments were also pre-treated with the enzyme carboxypeptidase before WCX-10. One set of samples from adalimumab experiment and another set of samples from a mAb2 experiment were used for this analysis. A dose dependent reduction in acidic species was observed in the carboxypeptidase treated samples with increasing concentration of ornithine (FIGS. 60 and 61). The percentage of acidic species was also comparable between an untreated and a carboxypeptidase treated sample for a particular concentration of ornithine. This indicates that the acidic species reduction is independent of any probable shift of the acidic species that may be corresponding to any lysine redistribution.

Effect of Increasing a Combination of Arginine, Lysine, Histidine, Ornithine to Cell Culture Media In this experiment, the combined use of the four amino acids arginine, lysine, histidine and ornithine for acidic species reduction is demonstrated. The experiment described here was performed using adalimumab producing cell line 2 in chemically defined media (media 1). The concentration range for arginine and lysine in this experiment was 1-3 g/L while the concentration range for histidine and ornithine in this experiment was between 0-2 g/L. In comparison to the lower concentrations, or conditions where a single amino acid concentration was increased, a further reduction in total acidic species was observed in conditions where combinations of amino acids were increased in the media (FIG. 62). A progressive decrease was observed in total acidic species when more amino acids were increased in combination. The percentage of acidic species was reduced from 21.9% in the lowest concentration sample to 12.3% in the sample with high concentrations of all four amino acids.

Control of Acidic Species Through Cell Culture with Increased Arginine and Lysine and Choice of Harvest Criterion and/or Modulation of pH The increase of the amino acid (arginine, lysine) concentration in basal media may also be combined with choice of when to harvest a culture to achieve optimal reduction in total acidic species. In this example, a study was carried out in 3 L bioreactors with cell line 1 (producing adalimumab) in media 1. Two sets of conditions were tested: control condition (arginine 1 g/L, lysine 1 g/L); Test condition 1 (arginine 3 g/L, lysine 5 g/L). Cell growth, viability and titer profiles were comparable between the conditions (FIGS. 63, 64, and 65). A small amount of cell culture harvests were collected every day from day 4 to day 10 from each of the reactors and submitted for Protein A purification and WCX-10 analysis. The percentage of acidic species in the control condition increased from 12.1% (on day 4) to 24.6% (on day 10) (FIG. 66). The percentage of acidic species in the test condition 1 was lower than that observed in the control condition at each corresponding culture day. The percentage of acidic species in the test condition also increased from 8.7% (day 4) to 18.8% (day 10). The rate of increase in acidic species with culture duration also correlated with the drop in viability for both conditions, with a sharp increase on day 8. Thus, along with increasing arginine and lysine concentrations in culture media, choice of harvest day/harvest viability can be used in combination to achieve a desired acidic species reduction.

The increase of the amino acid (arginine, lysine) concentration in basal media may be combined with process pH modulation to achieve further reduction in total acidic species. In this example, a study was carried out in 3 L bioreactors with cell line 1 (producing adalimumab) in media 1. Three sets of conditions were tested in duplicates: Control condition (arginine (1 g/L), lysine (1 g/L), pH 7.1->6.9 in 3 days, pH 6.9 thereafter); Test condition 1 (arginine (3 g/L), lysine (3 g/L), pH 7.1->6.9 in 3 days, pH 6.9 thereafter); Test condition 2 (arginine (3 g/L), lysine (3 g/L), pH 7.1->6.8 in 3 days, pH 6.8 thereafter). In comparison to the control, a slight decrease in VCD profile and harvest titer was observed for condition 2 (FIGS. 67, 68, and 69). The cultures were harvested when the viability was less than 50% and the culture harvests were submitted for Protein A and WCX-10 analysis.

The percentage of acidic species in the control sample was 19.1%. The percentage of acidic species was reduced to 14.3% in test condition 1 and to 12.8% in test condition 2 (FIG. 70). Thus, this demonstrates that the increase of amino acid concentration along with choice of lower final process pH can be used in combination for further reducing the extent of acidic species.

Effect of Supplementation of $CaCl_2$ to Cell Culture Media

The addition of calcium chloride was tested in several experimental systems covering multiple cell lines, media and monoclonal antibodies. Following is a detailed description of two representative experiments where two different cell lines (cell line 2 and cell line 3) were cultured in a chemically defined media (media 1) for the production of adalimumab.

Cell line 2 was cultured in media 1 with different concentrations of calcium (0.14, 0.84 and 1.54 mM). The cultures were performed in shake flasks in batch format with only glucose feed as described in the materials and methods. The cells grew to maximum viable cell densities (VCD) in the range of 22-24.5×10$^6$ cells/ml for the different conditions tested. The viable cell density and viability profiles for all test conditions were comparable (FIGS. 71 and 72). On Day 10 of culture samples were collected for titer analysis (FIG. 73). The titers for all conditions were comparable. On Day 10 duplicate shake flasks were harvested for each condition and then subsequently analyzed using WCX-10 post Protein A purification and the percentages of total peak(s) area corresponding to the acidic species were quantified (FIG. 74). The percentage of acidic species in the 0.14 mM calcium condition was 23.8%. In the sample with the highest tested concentration of calcium in this experiment (1.54 mM), the percentage of acidic species was reduced to 21.6%. A dose dependent decrease in acidic species was observed in test conditions with increased calcium concentration.

Cell line 3 was cultured in media 1 with different total concentrations of calcium (0.14, 0.49, 0.84, 1.19, 1.54, 1.89 g/L). The cultures were performed in shake flasks in batch format with only glucose feed as described in the materials and methods. The cells grew to maximum viable cell densities (VCD) in the range of 9.5-10.5×10$^6$ cells/ml for the different conditions tested. The viable cell density and viability profiles for all test conditions were comparable (FIGS. 75 and 76). On Day 11 of culture, samples were collected for titer analysis. The harvest titers for all conditions were comparable (FIG. 77). On Day 11 of culture, duplicate shake flasks for each of the conditions were harvested and then subsequently analyzed using WCX-10 post Protein A purification and the percentages of total peak(s) area corresponding to the acidic species were quantified (FIG. 78). The percentage of acidic species in the 0.14 mM calcium condition was 23.7%. In the sample with the highest tested concentration of calcium in this experiment (1.89 mM), the percentage of acidic species was reduced to 20.7%. A dose dependent decrease in acidic species was observed in test conditions with increased calcium concentration.

Additional experiments were performed with multiple cell lines in chemically defined or hydrolysate based media to evaluate the wide range of applicability of this method. The experimental setup for each of these experiments was similar to that described in the section above and in the materials and methods section. The summaries of results of the different experiments performed for adalimumab are summarized in FIGS. 79, 80 and 81. A reduction in acidic species with increased calcium concentration was also observed in each case.

In addition to adalimumab, the utility of this method for acidic species reduction was also demonstrated for processes involving two other mAbs. The experimental setup for each of these experiments was similar to that described above. The dose dependent reduction of acidic species with ornithine addition for experiments corresponding to each mAb is summarized in FIGS. 82 and 83. For mAb1, a small yet significant acidic species reduction from 15.4% (0.14 mM calcium sample) to 11.8% (1.54 mM calcium chloride supplemented sample) was observed. For mAb2, a larger dose dependent reduction from 28.9% (0.14 mM calcium sample) to 23.1% (1.40 mM calcium chloride supplemented sample) was observed.

Effect of Increased Concentration of Arginine, Lysine, Calcium Chloride, Niacinamide in Combination In this experiment, the effect of the combined use of the amino acids arginine, lysine, inorganic salt calcium chloride and vitamin niacinamide for acidic species reduction was evaluated. The experiment described here was performed using cell line 2 (producing adalimumab) in chemically defined media (media 1) supplemented with 3% (v/v) PFCHO (proprietary chemically defined medium formulation from SAFC). A central composite DOE experimental design was used in this experiment. The basal media for each condition was supplemented with different concentrations of the four supplements. Cell cultures were carried out in duplicates for each condition. Upon harvest, WCX-10 analysis was performed post Protein A purification. In Table 4, below, the experimental conditions from DOE design, including the concentration of each component supplemented, and the % total acidic species (or AR) obtained for each condition is summarized. Reduction of acidic species through the increased concentration of these components in combination was observed. For instance, condition (#24), where all four components were at their maximum concentration, the % total AR was reported to be reduced to 9.7%. Using the data from the experiment, a model predicting the effects of addition of these components to media for AR reduction ($R^2$: 0.92, P<0.0001) is described in FIG. 84. The model predicted a contribution from each of the four components towards acidic species reduction. It may be also possible to utilize this model to predict the choice of concentrations of these different components to the media, in order to achieve a target reduction in total AR.

TABLE 4

Experimental design and summary for the combined addition of arginine, lysine, calcium chloride and niacinamide

| Conditions | Arginine (g/l) | Lysine (g/l) | Calcium Chloride (mM) | Niacinamide (mM) | % Total AR |
|---|---|---|---|---|---|
| 1 | 0.0 | 4.0 | 0.7 | 0.8 | 13.0 |
| 2 | 0.0 | 6.0 | 1.4 | 0.0 | 12.6 |
| 3 | 4.0 | 2.0 | 0 | 1.6 | 12.3 |
| 4 | 4.0 | 6.0 | 0 | 1.6 | 11.6 |
| 5 | 2.0 | 4.0 | 0.7 | 0.8 | 11.2 |
| 6 | 0.0 | 6.0 | 0 | 0.0 | 15.0 |
| 7 | 0.0 | 6.0 | 1.4 | 1.6 | 10.7 |
| 8 | 0.0 | 2.0 | 0 | 0.0 | 16.7 |
| 9 | 2.0 | 4.0 | 0.7 | 0.8 | 11.0 |
| 10 | 4.0 | 6.0 | 1.4 | 1.6 | 11.0 |
| 11 | 2.0 | 2.0 | 0.7 | 0.8 | 12.9 |
| 12 | 2.0 | 4.0 | 1.4 | 0.8 | 11.1 |
| 13 | 0.0 | 6.0 | 0 | 1.6 | 13.2 |
| 14 | 4.0 | 2.0 | 0 | 0.0 | 12.3 |
| 15 | 2.0 | 4.0 | 0.7 | 0.0 | 13.0 |
| 16 | 2.0 | 4.0 | 0.7 | 1.6 | 11.4 |
| 17 | 0.0 | 2.0 | 1.4 | 1.6 | 12.0 |
| 18 | 2.0 | 4.0 | 0 | 0.8 | 12.0 |
| 19 | 4.0 | 4.0 | 0.7 | 0.8 | 12.0 |

TABLE 4-continued

Experimental design and summary for the combined addition of arginine, lysine, calcium chloride and niacinamide

| Conditions | Arginine (g/l) | Lysine (g/l) | Calcium Chloride (mM) | Niacinamide (mM) | % Total AR |
|---|---|---|---|---|---|
| 20 | 0.0 | 2.0 | 1.4 | 0.0 | 14.0 |
| 21 | 4.0 | 6.0 | 1.4 | 0.0 | 11.0 |
| 22 | 0.0 | 2.0 | 0 | 1.6 | 13.6 |
| 23 | 2.0 | 6.0 | 0.7 | 0.8 | 11.0 |
| 24 | 4.0 | 2.0 | 1.4 | 1.6 | 9.7 |
| 25 | 4.0 | 6.0 | 0 | 0.0 | 11.8 |
| 26 | 4.0 | 2.0 | 1.4 | 0.0 | 10.4 |
| 27 | 2.0 | 4.0 | 0 | 0.0 | 12.7 |

Use of Niacinamide Supplementation to Cell Culture Media for Acidic Species Reduction In addition to the use of niacinamide in combination with other supplements described in the previous section, niacinamide addition may also be used independent of the other supplements as demonstrated in the experiments below for two mAbs: adalimumab and mAb1.

For the experiment corresponding to adalimumab, cell line 1 was cultured in media 1 supplemented with different amounts of niacinamide (0, 0.2, 0.4, 0.8 and 1.6 mM). The cultures were performed in shake flasks in batch format with only glucose feed as described in the materials and methods. The cells grew to maximum VCD in the range of $8.5$-$11 \times 10^6$ cells/ml for the different conditions tested. A slight decrease in the viable cell density profile was observed with the maximum niacinamide supplementation (1.6 mM for this experiment) (FIG. 85). The viability profile for the test conditions were comparable (FIG. 86). On Day 12 of culture, samples were collected for titer analysis. The titers for all conditions were comparable (FIG. 87). On Day 11 and day 12, duplicate shake flasks were harvested for each condition and then subsequently analyzed using WCX-10 post Protein A purification and the percentages of total peak(s) area corresponding to the acidic species were quantified (FIGS. 88 and 89). The percentage of acidic species in the day 10 control sample (without niacinamide supplementation) was 19.6%. In the day 10 sample with the highest tested concentration of niacinamide in this experiment (1.6 mM), the percentage of acidic species was reduced to 15.9%. Similar acidic species reduction with niacinamide supplementation was also observed in the day 12 samples.

For the experiment corresponding to mAb2, a mAb2 producing cell line was cultured in media 1 supplemented with different amounts of niacinamide (0, 0.1, 0.5, 1.0, 3.0 and 6.0 mM). The cultures were performed in shake flasks in batch format with only glucose feed as described in the materials and methods. The cells grew to maximum viable cell densities (VCD) in the range of $14$-$21.5 \times 10^6$ cells/ml for the different conditions tested. A slight decrease in the viable cell density profile was observed for the conditions with 3.0 mM and 6.0 mM niacinamide concentrations (FIG. 90). The viability profiles for all test conditions were comparable (FIG. 91). On Day 12 of culture samples were collected for titer analysis (FIG. 92). The titers for all conditions were comparable. On Day 12 duplicate shake flasks were harvested for each condition and then subsequently analyzed using WCX-10 post Protein A purification and the percentages of total peak(s) area corresponding to the acidic species were quantified (FIG. 93). The percentage of acidic species in the control sample (without niacinamide supplementation) was 27.0%. In the sample with the highest tested concentration of niacinamide in this experiment (6.0 mM), the percentage of acidic species was reduced to 19.8%. A dose dependent decrease in acidic species was observed in test conditions with niacinamide supplementation.

Supplementation of Basic Amino Acids Arginine and Lysine to Cell Culture Media for Reduction of Methylglyoxal (MGO) Modification of Antibody In this experiment, the effect of MGO modification on acidic species reduction was examined. Adalimumab producing cell line 1 was cultured in a chemically defined media (media 1) which was supplemented with amino acids, as described below.

Materials and Methods

Cell Source and Adaptation Cultures

Cells were cultured in their respective growth media (chemically defined media (media 1)) in a combination of vented non-baffled shake flasks (Corning) on a shaker platform at 110 RPM (cell line 1), and 10 L or 20 L wave bags (GE). Cultures were propagated in a 35° C., 5% $CO_2$ incubator in order to obtain the required number of cells to initiate production stage cultures.

Cell Culture Media

For preparation of media 1, the media (IVGN GIA-1, a proprietary basal media formulation from Invitrogen) was supplemented with L-glutamine, sodium bicarbonate, sodium chloride, and methotrexate solution. Production media consisted of all the components in the growth medium, excluding methotrexate. Both growth and production medium were also supplemented with insulin.

Amino acids used for the experiments (arginine (Sigma, A8094) and lysine (Calbiochem, 4400)) were reconstituted in Milli-Q water to make a 100 g/L stock solution, which was subsequently supplemented to both growth and production basal media. After addition of amino acids, media was brought to a pH similar to unsupplemented (control) media using 6N hydrochloric acid/5N NaOH, and it was brought to an osmolality similar to unsupplemented (control) media by adjusting the concentration of sodium chloride.

All media was filtered through Corning 1 L filter systems (0.22 μm PES) and stored at 4° C. until usage.

Production cultures were initiated in 3 L Bioreactors (Applikon). For the bioreactor experiments, 3 L bioreactors (1.5 L working volume) were run at 35° C., 30% DO, 200 rpm, pH set-point of 7.1. The cells were transferred from the seed train to the production stage at a split ratio of 1:5.

Cultures were run in either batch mode and were cultured in the respective production medium (media 1 supplemented with arginine (4 g/L) or lysine (4 g/L)). 1.25% (v/v) of 40% glucose stock solution was fed when the media glucose concentration reduced to less than 3 g/L.

Retention samples for titer analysis, of 2×1.5 mL, were collected daily beginning on Day 8, and frozen at −80° C. The samples taken from each were later submitted for titer analysis.

The harvest procedure of the shake flasks and reactors involved centrifugation of the culture sample at 3,000 RPM for 30 min and storage of supernatant in PETG bottles at −80° C. before submission for Protein A purification and WCX-10 analysis.

WCX-10 Assay

The WCX-10 assay method was employed as described above in the Materials and Methods section.

Lysine-C Peptide Mapping for MGO Quantification

The procedure for lysine-C peptide mapping for MGO quantification was carried out as described above in the Materials and Methods section.

Results and Discussion

The majority of cultures grew to a similar peak VCD in the range of 9-10×10$^6$ cells/mL (FIG. 94A). The viability profiles of the cultures were also comparable with harvest viabilities between 10-25%. The culture duration (10 days) was similar between the conditions (FIG. 94B).

Using WCX-10 analysis on harvest samples post Protein A purification, the percentages of total peak(s) area corresponding to the acidic species were quantified. The percentage of acidic species in the control sample was 36.5%. In the samples from cultures supplemented with arginine and lysine, the percentage of total acidic species was reduced to 20.1% and 28.0%, respectively (FIG. 94C). Significant reduction in % AR1 was also observed in these cultures: from 16.8% in the control samples to 7.3% (arginine supplemented cultures) and 12.8% (lysine supplemented cultures) (FIG. 94C). The extent of MGO modification was also quantified using the Lys-C peptide mapping and reported as the percentage of MGO modified peptides among those that are more susceptible to MGO modification. From these results, it is apparent that % MGO modification was also significantly reduced in the cultures supplemented with the amino acids (FIG. 94D).

Example 2

Method for Reducing the Extent of Acidic Species in Cell Culture by Adjusting Process Parameters The experiments described below in the instant Example demonstrate that altering cell culture process parameters on-line can be used to modulate and/or reduce the acidic species of a protein of interest, e.g., the antibody adalimumab or mAb2. For example, an increased dissolved oxygen concentration and/or a decrease in final pH can lead to reductions in AR.

Materials and Methods

Cell Source and Adaptation Cultures

Two adalimumab producing CHO cell lines (cell line 1 and cell line 3) and a mAb2 producing cell line were employed in the studies covered in this Example. Upon thaw, adalimumab producing cell line 3 was cultured in chemically defined growth media (media 1) in a combination of vented shake flasks on a shaker platform at 140 rpm and 20 L wave bags. Cultures were propagated in a 36° C., 5% CO$_2$ incubator to obtain the required number of cells to be able to initiate production stage cultures.

Upon thaw, adalimumab producing cell line 1 was cultured in a hydrolysate based growth media (media 2) in a combination of vented shake flasks on a shaker platform at 110 rpm and 20 L wavebags in a 35° C., 5% CO$_2$ incubator. In some cases, the culture might be transferred into a seed reactor with pH 7.1, 35° C. and 30% DO. The culture would be adapted to either media 1 or media 2 by propagated in a 10 L or 20 L wavebag for 7-13 days with one or two passages before initiating production stage cultures.

Upon thaw, mAb2 producing cells were cultured in media 1 in a combination of vented non-baffled shake flasks (Corning) on a shaker platform at 140 RPM and 20 L wave bags (GE). Cultures were propagated in a 35° C., 5% CO$_2$ incubator to obtain the required number of cells to be able to initiate production stage cultures.

Cell Culture Media

Media 1, the chemical defined growth or production media, was prepared from basal IVGN CD media (proprietary formulation). For preparation of the IVGN CD media formulation, the proprietary media was supplemented with L-glutamine, sodium bicarbonate, sodium chloride, and methotrexate solution. Production media consisted of all the components in the growth medium, excluding methotrexate. For cell line 1 and mAb2, the medium was also supplemented with insulin. In addition, 10 mM or 5 mM of Galactose (Sigma, G5388) and 0.2 µM or 10 µM of Manganese (Sigma, M1787) were supplemented into production medium for cell line 3 or 1, respectively. Osmolality was adjusted by the concentration of sodium chloride. All media was filtered through filter systems (0.22 µm PES) and stored at 4° C. until usage.

Media 2 is the hydrolysate based media, which contains basal proprietary media, Bacto TC Yeastolate and Phytone Peptone.

Production Cultures

Production cultures were initiated in 3 L Bioreactors (Applikon). The bioreactors (1.5-2.0 L working volume) were run at the following conditions (except for the different experimental conditions): 35° C., 30% DO (dissolved oxygen), 200 rpm, pH profile from 7.1 to 6.9 in three days and pH 6.9 thereafter. In all experiments, the cells were transferred from the wavebag to the production stage at a split ratio of 1:5.6 (except mAb2 with a ratio of 1:5). When the media glucose concentration reduced to less than 3 g/L, approximately 1.25% (v/v) of 40% glucose stock solution was fed.

The harvest procedure of reactors involved centrifugation of the culture sample at 3,000 RPM for 30 min and storage of supernatant in PETG bottles at −80° C. before submission for Protein A purification and WCX-10 analysis.

WCX-10 Assay

The acidic species and other variants present in cell culture harvest samples were quantified. Cation exchange chromatography was performed on a Dionex ProPac WCX-10, Analytical column (Dionex, Calif.). For adalimumab producing cell lines, a Shimadzu LC10A HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb B used different buffers. The mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak corresponding to the drug product are together represented as the acidic peaks.

Results

Effect of Process pH in Media 1 with Cell Line 1

Five different pH conditions were assessed in this study: 7.1, 7.0, 6.9, 6.8 and 6.7. The cultures were started at pH set point of 7.1; then were ramped down to the target pH set points within 4 days. All cultures reached the same maximum viable cell density on day 8, except for the culture at pH 6.7 condition, in which the maximum cell density was much lower than the other cultures (FIG. 95). In addition, the viability of the culture at pH 7.1 and pH 7.0 dropped much earlier than the other cultures. The viability of cultures at pH 7.1 and pH 7.0 were 38% and 54% on day 10, respectively; while the viability of the cultures at lower pH (including pH 6.9, 6.8 and 6.7) was above 70% on the same day (FIG. 96). Samples taken on the last day of the cultures were measured for IgG concentration. The titer of each tested condition increased corresponding to the decrease in pH, from 1.2 g/L in the pH 7.1 condition to 1.8 g/L in the pH 6.8 condition; however, product titer was not continued to increase at pH 6.7 (1.6 g/L) (FIG. 97). The cultures were harvested either on day 10 or on day 12. The harvest was Protein A purified, then analyzed using WCX-10. The resulting peak areas from WCX-10 analysis were quantified (FIG. 98). The percentage of acidic species decreased corresponding to the decrease in pH, from 56.0% in the pH 7.1 condition to 14.0% in the pH 6.7 condition. Since the cultures at pH 6.9, 6.8 and 6.7 were at 70% viability on day 10, additional samples were taken on day 12 for these cultures, when viability reached ~50%. WCX-10 analysis was also performed for these samples. The percentage of acidic species on day 12 was increased for these three conditions (i.e., pH 6.9, 6.8 and 6.7) comparing to day 10; however, the increase in the percentage of acidic species was smaller at lower pH. The percentage of acidic species increased 18.8% (pH 6.9), 8.1% (pH 6.8) and 3.5% (pH 6.7), respectively from day 10 (70% viability) to day 12 (50% viability). Therefore, the percentage of acidic species was lower at lower pH on day 12 too. The percent acidic species decreased with decrease in pH from 39.1% in the pH 6.9 condition to 17.5% in the pH6.7 condition, for a total reduction of 21.6% on day 12.

The effect of process pH to specifically reduce particular acidic variants within the larger fraction of total acidic species was also evaluated. In Table 5, a summary of the extent of some of the sub-species of the acidic species fraction have been presented. Along with the reduction in total acidic species, the methods presented in this section may also be used for reduction of sub-species that include, but not limited to, AR1, AR2 and MGO modified product variants.

significant effect on the cell growth and viability with this cell line and media. Cell density was lower at higher pH and viability also dropped earlier at higher pH (FIGS. 103 and 104). The cells were harvested either on day 10 or when viability dropped to equal or less than 50%. The titer was slightly increased as the pH was reduced, reached the highest titer at pH 6.8 condition (FIG. 105). The resulting peak areas from WCX-10 analysis were quantified (FIG. 106). The percent acidic species decreased with decrease in pH from 29.7% in the pH 7.1 condition to 21.5% in the pH6.7 condition, for a total reduction of 8.2%.

Effect of Dissolved Oxygen (DO) in Media 2 with Cell Line 1 at 35° C.

Three different dissolved oxygen (DO) conditions were assessed in this study: 20%, 30% and 50%. The cultures were set at 35° C. The cell density and viability were very comparable at different DO conditions (FIGS. 107 and 108). The cultures were harvested at the target viability of 50% for each condition. The harvest titer was higher at 50% DO compared to 20% DO (FIG. 109). The harvest was also taken through Protein A purification before WCX-10 analysis. The percentage of acidic species in each of the test conditions was 20.6% (20% DO), 19.0% (30% DO), and 17.7% (50% DO), respectively (FIG. 110). The percentage of acidic species was in general lower at higher dissolved oxygen concentrations. The percentage of acidic species decreased with increase in DO from 20.6% in the 20% DO condition to 17.7% in the 50% DO condition, for a total reduction of 2.9%.

Effect of Dissolved Oxygen (DO) in Media 2 with Cell Line 1 at 33° C.

Three different DO conditions were assessed in this study: 20%, 30% and 60%. The cell density, viability and product

TABLE 5

Effect of process pH on reduction of sub-species of acidic variants

| | | | | Sample | | | | | | |
|---|---|---|---|---|---|---|---|---|---|---|
| | | | | | | | % MGO modified species | | | |
| Final | | | | LIGHT CHAIN | | | HEAVY CHAIN | | | |
| pH | % AR | % AR1 | % AR2 | Arg 30 | Arg 93 | Arg 108 | Arg 16 (19) | Arg 259 | Arg 359 | Arg 420 | TOTAL |
| 7.1 | 56.0 | 32.8 | 23.3 | 26.1 | 10.6 | 0.2 | 6.1 | 2.7 | 3.5 | 0.5 | 49.7 |
| 6.9 | 39.1 | 18.9 | 20.2 | 9.5 | 3.8 | 0.0 | 2.2 | 0.9 | 1.2 | 0.2 | 18.8 |
| 6.7 | 17.5 | 5.2 | 12.2 | 1.2 | 0.5 | 0.0 | 0.2 | 0.1 | 0.1 | 0.0 | 2.0 |

Effect of Process pH in Media 2 with Cell Line 1

Three different pH conditions were assessed in this study: 7.0, 6.9, and 6.8. The cultures were started at pH of 7.1; then were ramped down to the target pH set points within 3 days of culture. The viable cell density and viability were comparable across the different pH set points until day 8. After day 8, the viable cell density and viability were slightly higher with lower pH set points (FIGS. 99 and 100). The cultures were harvested on ~50% viability. The product titer was slightly higher at pH 6.8 comparing to pH 6.9 and 7.0 (FIG. 101). The resulting peak areas from WCX-10 analysis were quantified (FIG. 102). The percentage of acidic species decreased with decrease in pH from 20.7% in the pH 7.0 condition to 18.1% in the pH6.8 condition, for a total reduction of 2.6%.

Effect of Process pH in Media 1 with Cell Line 3

Five different pH conditions were assessed in this study: 7.1 7.0, 6.9, 6.8, and 6.7. The cultures were started at pH set point of 7.1; then were ramped down to the target pH set points within 4 days of culture. The pH set points showed titer were very comparable at different DO condition (FIGS. 111, 112 and 113). The percentage of acidic species in each of the test conditions was 20.1% (20% DO), 17.8% (30% DO), and 17.7% (60% DO), respectively (FIG. 114). The percentage of acidic species was in general lower at higher dissolved oxygen concentrations. The percentage of acidic species decreased with increase in DO from 20.1% in the 20% DO condition to 17.7% in the 60% DO condition, for a total reduction of 2.4%.

Effect of Dissolved Oxygen (DO) in Media 1 with Cell Line 1 at 35° C.

Three different DO conditions were assessed in this study: 20%, 30% and 50%. The cultures were set at 35° C. The cell density and viability were very comparable at different DO conditions (FIGS. 115 and 116). The cultures were harvested at the target viability of 40% for each condition. The harvest titer was higher at 30% and 50% DO comparing to 20% DO (FIG. 117). The harvest was also taken through Protein A purification before WCX-10 analysis. The percentage of acidic species in each of the test conditions was 23.9% (20% DO), 22.4% (30% DO), and 20.3% (50% DO), respectively (FIG. 118). The percentage of acidic species was in general lower at higher dissolved oxygen concentrations. The percentage of acidic species decreased with increase in DO from 23.9% in the 20% DO condition to 20.3% in the 50% DO condition, for a total reduction of 3.6%.

Effect of Dissolved Oxygen (DO) in Media 1 with Cell Line 3

The study was performed at four different temperature levels (33° C., 34° C., 35° C. and 36° C.) with two different DO conditions (20% DO and 50% DO). In general, the cell growth at different dissolved oxygen levels was similar except at 35° C., in which the cell density was lower at 50% DO (FIG. 119). The cultures were harvested either on day 10 or at ~50% viability (FIG. 120). The titer at ~50% viability is comparable at different DO conditions (FIG. 121). The percentage of acidic species was in general lower at higher dissolved oxygen at each tested temperature condition (FIG. 122). On day 10, the percentage of acidic species decreased with increase in DO at 36° C. from 25.2% in the 20% DO condition to 22.7% in the 50% DO condition, which is 2.5% of decrease; the percentage of acidic species decreased with increase in DO at 35° C. from 23.2% in the 20% DO condition to 19.4% in the 50% DO condition, for a total reduction of 3.8%; the percentage of acidic species decreased with increase in DO at 34° C. from 18.2% in the 20% DO condition to 17.1% in the 50% DO condition, for a total reduction of 1.1% and the percentage of acidic species decreased with increase in DO at 33° C. from 14.3% in the 20% DO condition to 12.9% in the 50% DO condition, for a total reduction of 1.4%. On day 12, when the viability was at ~50% for the 34° C. test conditions, the percentage of acidic species decreased with increase in DO from 21.5% in the 20% DO condition to 20.6% in the 50% DO condition, for a total reduction of 0.9%. Lastly, on day 14, when the viability was at ~50% for the 33° C. test conditions, the percentage of acidic species decreased with increase in DO from 19.7% in the 20% DO condition to 17.9% in the 50% DO condition, for a total reduction of 1.8%. In summary, at all tested temperature conditions on different harvest days, the percentage of acidic species was lower at higher dissolved oxygen concentrations.

Effect of Dissolved Oxygen (DO) in Media 1 with mAb2

Six different DO conditions were assessed: 10%, 20%, 30%, 50%, 60% and 80%. The cultures were set at 35° C. In general, the cell density, viability and titer at different dissolved oxygen levels were comparable (FIGS. 123, 124 and 125). The percentage of acidic species in each of the test conditions was estimated to be 26.5% (10% DO), 27.3% (20% DO), 27.3% (30% DO), 25.8% (50% DO), 24.4% (60% DO) and 24.5% (80% DO), respectively (FIG. 126). The percentage of acidic species was in general lower at higher dissolved oxygen. The percentage of acidic species decreased with increase in DO from 27.3% in the 20% DO condition to 24.5% in the 80% DO condition, for a total reduction of 2.8%.

Example 3

Method for Reducing Acidic Species by the Addition of Amino Acids to Clarified Cell Culture Harvest and by Modifying the pH of the Clarified Harvest The present Example describes processes for reducing and controlling levels of acidic species in antibody preparations. Specifically, this Example provides a method for reducing the acidic variant content in clarified harvest, as well as a method for reducing the formation rate of acidic species in clarified harvest. The method involves adding additives like various amino acids to clarified harvest or adjusting the pH of the clarified harvest using acidic substances.

As shown below, antibody acidic species in clarified harvest can be reduced by adding additives such as arginine or histidine to clarified harvest at concentrations of more than 100 mM and 50 mM, respectively. AR reduction can also be achieved by pH adjustment of the clarified harvest to pH 6 or pH 5. In addition, the rate of acidic variant formation can be reduced through the use of arginine or histidine in a concentration dependent manner, or by low pH treatment of the clarified harvest.

Materials and Methods

Clarified Harvest Material

Different batches of adalimumab clarified harvest material were employed in the following experiments described below. Clarified harvest is liquid material containing a composition of interest, e.g., a monoclonal antibody of interest that has been extracted from a fermentation bioreactor after undergoing centrifugation to remove large solid particles and subsequent filtration to remove finer solid particles and impurities from the material. Clarified harvest was used for low pH treatment studies described herein. Clarified harvest was also used for the experiments to study the effect of amino acid concentration on the presence of acidic species in clarified harvest, and for acid type-pH treatment studies described herein. Different batches of mAb-B and mAb-C clarified harvest material were employed for experiments to study the effect of amino acid and low pH treatment studies on the presence of acidic species described herein.

Preparation of Materials

The clarified harvest material was first adjusted to pH 4 using 3M citric acid. The material at pH 4 was then agitated for 60 minutes before adjusting the pH to a target pH of 5, 6 or 7 with 3M sodium hydroxide. The material was then agitated for a further 60 minutes. The samples were then subjected to centrifugation at 7300×g for 15 minutes in a Sorvall Evolution RC with an SLA-3000 centrifuge bowl. The supernatants obtained from the centrifuged material were then depth filtered using B1HC depth filters (Millipore) followed by 0.22 μm sterile filters. The filtrates of different pH were then subjected to holding for different period of time for evaluating the formation rate of acidic variants. After the holding, the material was purified with Protein A affinity column and the eluate was sampled and analyzed using the WCX-10 method. The preparation scheme is shown below in FIG. 127.

The material to study the effect of arginine on acidic species was prepared in two ways. For lower target arginine concentrations of 5 mM, 10 mM, 30 mM and 100 mM, they were made by adding the appropriate amount of 0.5M arginine stock buffer at pH 7 (pH adjusted with acetic acid) to attain the target arginine concentrations needed. For higher target arginine concentrations of 50 mM, 100 mM, 300 mM, 500 mM, 760 mM, 1M and 2M, they were made by adding the appropriate amount of arginine (solid) to the samples to attain the target arginine concentrations, with subsequent titration to a final pH of 7 using glacial acetic acid. Arginine was adjusted to a final concentration of 100 mM using the two methods to determine if the method of preparation would result in different effects. For all the experiments, following the arginine addition, treated clarified harvests were held at room temperature for the indicated duration followed by purification with Protein A column and analysis of acidic variants. This study provided two results; (1) data of samples from Day 0 gave the effects of arginine on reducing acidic species in clarified harvest, (2) data of samples with different holding days gave effect of arginine on reducing the formation rate of acidic species. The preparation scheme is shown in FIG. 128.

The material to study the effect of histidine was prepared with target concentrations of 5 mM, 10 mM, 30 mM 50 mM, 100 mM, 200 mM and 250 mM. The samples were prepared by adding the appropriate amount of histidine (solid) to the samples to attain the target histidine concentrations, with subsequent titration to a final pH of 7 using glacial acetic acid. The sample preparation scheme is shown in FIG. 129.

The material to study the effect of lysine was prepared with target concentrations of 5 mM, 10 mM, 30 mM 50 mM, 100 mM, 200 mM, 300 mM, 500 mM and 1000 mM. The samples were prepared by adding the appropriate amount of lysine hydrochloride (solid) to the samples to attain the target lysine concentrations, with subsequent titration to a final pH of 7 using hydrochloric acid. The sample preparation scheme is shown below in FIG. 130.

The material to study the effect of methionine was prepared with target concentrations of 5 mM, 10 mM, 30 mM 50 mM, 100 mM, 200 mM and 300 mM. The samples were prepared by adding the appropriate amount of methionine (solid) to the samples to attain the target methionine concentrations, with subsequent titration to a final pH of 7 using glacial acetic acid. The sample preparation scheme is shown in FIG. 131.

The material to study the effect of different amino acids was prepared with different target concentrations for each of the 20 amino acids evaluated as well as two controls using sodium acetate in place of an amino acid, and the other simply bringing the pH of the clarified harvest down to pH 7 using glacial acetic acid. The target concentrations for the amino acids are shown below in Table 6.

TABLE 6

Amino Acid Target Concentrations

| Amino Acid | Concentration (mM) |
|---|---|
| Alanine | 100 |
| Arginine | 100 |
| Asparagine | 100 |
| Aspartic Acid | 30 |
| Cysteine | 100 |
| Glutamic Acid | 30 |
| Glutamine | 100 |
| Glycine | 100 |
| Histidine | 100 |
| Isoleucine | 100 |
| Leucine | 100 |
| Lysine | 100 |
| Methionine | 100 |
| Phenylalanine | 100 |
| Proline | 100 |
| Serine | 100 |
| Threonine | 100 |
| Tryptophan | 30 |
| Tyrosine | 2 |
| Valine | 100 |
| NaAc | 100 |

The samples were prepared by adding the appropriate amount of amino acid (solid) to the samples to attain the target amino acid concentrations as shown in Table 6, with subsequent titration to a final pH of 7 using glacial acetic acid. The sample preparation scheme is shown in FIG. 132.

The material to study the effect of additives other than amino acids was prepared with different target concentrations for each of the additives evaluated as well as a control in which sodium hydroxide was used in place of arginine to bring the pH of the material to pH 10 before neutralizing it back to pH 7 with glacial acetic acid. The target concentrations for the additives are shown below in Table 7.

TABLE 7

Alternative Additive Target Concentrations

| Additive | Low Conc | High Conc |
|---|---|---|
| Sucrose | 0.1M | 1M |
| Trehalose | 0.1M | 1M |
| Mannitol | 4% w/v | 10% w/v |
| Glycerol | 1% v/v | 10% v/v |
| PEG | 1% w/v | 2% w/v |
| Tween80 | 0.5% v/v | 2% v/v |

The samples were prepared by adding the appropriate amount of additive to the samples to attain the target amino acid concentrations as shown in Tables 6 or 7, with subsequent titration to a final pH of 7 using glacial acetic acid.

The material to study the effect of the aforementioned methods on CDM clarified harvest was prepared using the following scheme shown in FIG. 133.

The mAb B hydrolysate clarified harvest was used to study the effect of the aforementioned methods.

The mAb C hydrolysate clarified harvest was used to study the effect of the aforementioned methods.

Hold Studies for Treated Clarified Harvest

After the aforementioned sample preparations, the samples were placed in separate sterile stainless steel containers for the purpose of holding at either 4° C. or at room temperature. For each material, different containers were used for each day of holding evaluated. For the acidified samples, the acidic variant compositions of the samples were evaluated on days 0, 3, 7 and 14 of holding at either temperature. For the arginine containing materials, the acidic variant compositions of the samples were evaluated on days 0, 5 and 8 of holding at room temperature. For the histidine containing materials, the acidic variant compositions of the samples were evaluated on days 0, 3 and 7 of holding at room temperature.

Acid Type and pH Effects on Clarified Harvest

The effects of acid type, clarified harvest pH and arginine content on acidic variant reduction were evaluated in this study. The samples were prepared in triplicates on 3 consecutive days to target arginine concentrations of either 0 mM (no arginine added) or 500 mM, then titrated with either glacial acetic acid, phosphoric acid, 3M citric acid or 6M hydrochloric acid to target pH values of either 5, 6 or 7. One other sample was prepared by adding a 2M arginine acetate pH 7 stock buffer to clarified harvest to attain a target arginine concentration of 500 mM. The sample preparation scheme is shown in FIG. 134.

Protein A Purification

Protein A purification of the samples was performed using a 5 mL rProtein A FF Hitrap column (GE Healthcare) at 10 g adalimumab/L resin loading and a operating flow rate of 3.4 mL/min. Five column volumes (CVs) of equilibration (1×PBS pH 7.4) is followed by loading of the sample, then washing of the column with equilibration buffer to remove non-specifically bound impurities, followed by elution of the protein with 0.1M Acetic acid, 0.15M sodium chloride.

The eluate samples were collected and neutralized to pH 6.9-7.2 with 1M Tris pH 9.5 at 45-75 minutes after collection. The samples were then frozen at −80° C. for at least one day before thawing and subjecting to WCX-10 analysis.

Effects of Purification Method, Acid Concentration and Neutralization on Clarified Harvest The effects of purification methods with different types of chromatography resins, acid concentration and pH neutralization on acidic variant reduction were evaluated in this study. The following samples were prepared as shown below in Table 8.

TABLE 8

Acid Concentration Sample Treatments

| Sample | Treatment |
|---|---|
| Control | None |
| 3M Citric Acid pH 6 | Titrate to pH 6 with 3M Citric Acid |
| 1M Citric Acid pH 6 | Titrate to pH 6 with 1M Citric Acid |
| Glacial Acetic Acid pH 6 | Titrate to pH 6 with Glacial Acetic Acid |
| 3M Acetic Acid pH 6 | Titrate to pH 6 with 3M Acetic Acid |
| 3M Citric Acid pH 5 | Titrate to pH 5 with 3M Citric Acid |
| 3M Acetic Acid pH 5 | Titrate to pH 5 with 3M Acetic Acid |
| 3M Citric Acid pH 5 to 7 | Titrate to pH 5 with 3M Citric Acid, then 3M Tris to pH 7 |
| 3M Acetic Acid pH 5 to 7 | Titrate to pH 5 with 3M Acetic Acid, then 3M Tris to pH 7 |

Each of the material made was then subjected to either Mabselect Sure or Fractogel S capture in duplicate. The eluate samples are collected and neutralized to pH 6.9-7.2 with 1M Tris pH 9.5 at 45-75 minutes after collection. The samples are then frozen at −80° C. for at least one day before thawing and subjecting to WCX-10 analysis.

Acidic Variant Analysis (WCX-10 Assay)

Cation exchange chromatography was performed on a 4 mm×250 mm Dionex ProPac WCX-10 Analytical column (Dionex, Calif.). A Shimadzu LC10A HPLC system was used to perform the HPLC assay. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation is based on the relative area percent of detected peaks. The peaks that elute at relative residence time less than that of the dominant Lysine 0 peak are together represented as the acidic variant peaks (AR).

Results

Effect of Low pH Treatment with Subsequent Neutralization

The results of the low pH treatment with subsequent neutralization are shown below in FIGS. 135 and 136. FIG. 136 shows that the low pH treatment with subsequent neutralization to pH 5 or 6 reduces the rate of acidic variant formation over time. However, there is no significant reduction in initial acidic variant content, as shown in FIG. 135.

Effect of Arginine Treatment

The results of the arginine treatment are shown in FIG. 137 and FIG. 138. FIGS. 137 and 138 show that the sample preparation method resulted in different levels of acidic species in clarified harvest. Adding a 0.5M arginine pH 7 stock buffer tends to increase acidic species, while adding pure arginine with subsequent acetic acid titration to pH 7 reduced acidic variants at arginine concentrations of greater than 100 mM. Moreover, the effect due to treatment method is demonstrated when comparing the two 100 mM arginine samples, which show an absolute difference of 1% in acidic variants between the two methods.

FIG. 139 shows that the rate of acidic variant formation decreases with increasing arginine concentration in clarified harvest, plateauing at around concentrations of 500 mM arginine and higher. However, the two methods of sample preparation do not result in significantly different formation rate of acidic variants.

Effect of Histidine Treatment

The results of the histidine treatment are shown in FIG. 140 and FIG. 141. Similar to arginine treatment effect, as shown in FIG. 149, when histidine was added to clarified harvest with subsequent pH neutralization with acetic acid, acidic variants were reduced at histidine concentrations higher than 50 mM. FIG. 141 shows that the rate of acidic variants formation decreases with increasing histidine concentration in clarified harvest, plateauing at around concentrations of 200 mM histidine and higher.

Effect of Lysine Treatment

The results of the lysine treatment are summarized in FIG. 142 and FIG. 143. Similar to arginine treatment effect, as shown in FIG. 149, when lysine was added to clarified harvest with subsequent pH neutralization with acetic acid, acidic variants were significantly reduced by ~1% or more. FIG. 153 shows that the rate of acidic variants formation decreases with increasing lysine concentration in clarified harvest.

Effect of Methionine Treatment

The results of the methionine treatment are summarized below in FIGS. 154 and 165. Similar to arginine treatment effect, as shown in FIG. 149, when methionine was added to clarified harvest with subsequent pH neutralization with acetic acid, acidic variants were significantly reduced by ~1% or more at concentrations of >10 mM. FIG. 145 shows that the rate of acidic variants formation is not affected significantly by methionine presence in clarified harvest.

Effect of Other Amino Acid Treatment

The results of the treatments with the various amino acids are summarized below in FIGS. 146 and 147. As shown in FIG. 146, the addition of 14 amino acids including arginine, histidine, lysine and methionine resulted in lower amounts of acidic variant content in clarified harvest. The addition of sodium acetate or the use of acetic acid also caused a reduction in acidic variant content as well. FIG. 147 shows that the rate of acidic variants formation is reduced by several amino acids including arginine, histidine, lysine, aspartic acid, glutamic acid, and leucine.

Effect of Alternative Additive Treatment

The results of the treatments with the other additives are summarized below in FIGS. 148 and 149. As shown in FIG. 148, the addition of any of the additives did not result in lower acidic variant content in adalimumab hydrolysate clarified harvest. However, FIG. 149 shows that the rate of acidic variants formation is reduced by most of the additives.

Effect of Low pH/Arginine Treatment on Adalimumab CDM Clarified Harvest

The results of CDM clarified harvest study are summarized below in FIGS. 150 and 151. As shown in FIG. 150, low pH/arginine treatment did not result in lower acidic variant content in adalimumab CDM clarified harvest. However, FIG. 151 shows that the rate of acidic variants formation is reduced significantly by all the treatments.

Effect of Low pH/Arginine Treatment on mAb B Hydrolysate Clarified Harvest

The results of mAb B hydrolysate clarified harvest study are summarized below in FIGS. 152 and 153. As shown in FIGS. 152 and 153, low pH/arginine treatment results in both lower acidic variant content and slower rates of acidic variants formation in mAb B hydrolysate clarified harvest.

Effect of Low pH/Arginine Treatment on mAb C Hydrolysate Clarified Harvest

The results of mAb C hydrolysate clarified harvest study are summarized below in FIGS. 154 and 155. As shown in FIGS. 154 and 155, low pH/arginine treatment results in both a lower acidic variant content and slower rates of acidic variants formation in mAb C hydrolysate clarified harvest.

Effect of Acid Type and pH

The results obtained from the acid type-pH study are summarized in FIG. 156. Greater acidic species reduction is obtained at lower pH. Arginine addition also reduces acidic species content further, but not to a significant extent when taking the high concentrations (500 mM) used into consideration. The results also show that acidic species reduction of ~1% can be achieved with the usage of an arginine acetate stock buffer, although using pure arginine powder with subsequent acid titration performs slightly better. With regard to acid type used for pH adjustment, there were no significant differences between different acids observed.

Effect of Purification Method, Acid Concentration and Neutralization

The results obtained from the study are summarized in FIGS. 157, 158, 159, and 160. FIGS. 157 and 158 indicate that when the acid used is of higher concentration, there is an decrease in acidic variant content in hydrolysate clarified harvest as compared to a lower concentration acid being used. FIGS. 159 and 160 show that when the clarified harvest is subjected to base neutralization to pH 7 after being treated with low pH, there is an increase in acidic variant content. The figures also show that the Fractogel resin is better able to clear acidic variants than Mabselect Sure.

Example 4

Method for Reducing AR in Cell Culture Using a Continuous Media Perfusion Technology As demonstrated in Example 3, above, generation or formation of acidic species in a population of proteins may occur during the hold of the antibody in clarified harvest or spent media. Thus, the possibility of enhanced stability of the product antibody or a reduction in acidic species generation was explored using a continuous/perfusion based cell culture technology. Control or reduction in the amount of acidic species present in the population of proteins obtained at the end of cell culture can be accomplished by modifying the exchange rate of fresh medium into the bioreactor (or removal of spent medium with product antibody out of the bioreactor).

Materials and Methods

Cell Source

One adalimumab producing CHO cell line (cell line 1) was employed in the study covered here. Upon thaw, the vial was cultured in a chemically defined growth media (media 1) in a series of vented shake flasks on a shaker platform at 110 rpm in a 35° C., 5% $CO_2$ incubator. Cultures were propagated to obtain a sufficient number of cells for inoculation of the perfusion cultibag.

Cell Culture Media

A chemically defined growth or production media was used in this study. For preparation of the media formulation, the proprietary media (Invitrogen) was supplemented with L-glutamine, sodium bicarbonate, sodium chloride, recombinant human insulin and methotrexate solution. Perfusion stage media consisted of all the components in the growth medium, with the exception of a higher concentration of recombinant human insulin and the exclusion of methotrexate solution.

Perfusion Culture

The perfusion culture was carried out with the Sartorius BIOSTAT RM 20 optical perfusion system (SN#00582112) in a Sartorius Cultibag RM 10 L perfusion pro 1.2my (lot 1205-014) perfusion bag. The perfusion bag was run with a working culture volume of 1.5 L and operation conditions of; pH: 7.00, dissolved oxygen 30%, 25 rpm, 35° C., an air overlay of 0.3 slpm and a $CO_2$ overlay of 15 sccm. pH control was initiated on day three of the culture. pH was controlled with 0.5M sodium hydroxide and $CO_2$ additions.

Perfusion was carried out by 'harvesting' spent culture through an integrated 1.2 µm filter integrated into the perfusion cultibag. Fresh media was added to the culture through a feed line at the same rate as the harvest. Perfusion began on day four of the process at a rate of 1.0 exchanges per day (ex/day). The perfusion rate was adjusted throughout the run to accommodate glucose needs, lactate accumulation and sampling plans. Perfusion cell-free harvest samples were collected at perfusion rates of 1.5, 3.0 and 6.0 exchange volumes/day on day 5-6 of perfusion. A fresh harvest bag was used for each harvest sample. The samples were then purified using Protein A and analyzed using WCX-10 assay.

The perfusion culture was ended on day 8 of the process.

WCX-10 Assay

The acidic species and other charge variants present in cell culture harvest samples were quantified. Cation exchange chromatography was performed on a Dionex ProPac WCX-10, Analytical column (Dionex, Calif.).

The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb2 samples used different buffers. The mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm. Quantitation is based on the relative area percent of detected peaks, as described above.

Results

Effect of Use of Perfusion Technology and Choice of Medium Exchange Rates on Acidic Species Adalimumab producing cell line 1 was cultured in media 1 and the cultures were carried out as described in the materials and methods. As described in Table 8, the exchange rates were modified over a period of 24 hrs between day 5 and day 6 to explore the influence of medium exchange rates on the extent of acidic species. At a continuous medium exchange rate of 1.5 volumes/day, the product antibody in spent medium was collected in a harvest bag over a period of 17 hrs. The harvest bag was then exchanged with a new bag and the old bag was transferred to 4° C. Subsequently and in succession, the medium exchange rates were increased to 3 and 6 volumes/day and the product harvest was collected over a time period of 5 and 2 hrs, respectively. After an overnight hold at 4° C., the three harvest samples were processed through Protein A and analyzed for acidic species using WCX-10. The percentage of acidic species in the sample with a medium exchange rate of 1.5 volumes/day was 8.1%. In the sample with the highest tested exchange rate in this experiment (6 volumes/day), the percentage of acidic species was reduced to 6%. An exchange rate dependent reduction in acidic species was observed in the three samples (Table 9). Reductions in different sub-species within the acidic variants (AR1 and AR2) were also noted. An increase in volumetric productivity, with exchange rate, was also observed.

TABLE 9

Effect of medium exchange rates in a perfusion bioreactor on acidic species

| Start Time (day, hrs:min) | Exchange rate (no. of working volumes/day) | Exchange time (for collection in harvest bag) (hrs) | Harvest bag Volumetric Productivity (mg/l-hr) | % Total AR | % AR1 | % AR2 |
|---|---|---|---|---|---|---|
| Day 5, 16:00 | 1.5 | 17 | 10.94 | 8.1 | 2.0 | 6.1 |
| Day 6, 10:25 | 3 | 5 | 39.80 | 6.9 | 1.7 | 5.2 |
| Day 6, 15:25 | 6 | 2 | 69.50 | 6.0 | 1.3 | 4.7 |

Example 5

Method for Acidic Species Reduction Through the Use of Continuous Perfusion Technology and Addition of Amino Acids to Culture Medium As set forth above in Example 4, reduction in the amount of acidic species present in the population of proteins obtained at the end of cell culture can be accomplished by modifying the exchange rate of fresh medium into the bioreactor (or removal of spent medium with product antibody out of the bioreactor). In this Example, the ability to further reduce acidic species through the use of high medium exchange rates in combination with supplementation of basic amino acids (arginine and lysine) to the culture medium is described.

Materials and Methods

Cell Source

An adalimumab producing CHO cell line (cell line 1) was employed. Upon thaw, the vial was cultured in a chemically defined growth media (media 1) in a series of vented shake flasks on a shaker platform at 110 rpm in a 35° C., 5% $CO_2$ incubator. Cultures were propagated to obtain a sufficient number of cells for inoculation of the perfusion cultibag.

Cell Culture Media

A chemically defined growth or production media was used in this study. For preparation of the media formulation, the proprietary media (Invitrogen) was supplemented with L-glutamine, sodium bicarbonate, sodium chloride, recombinant human insulin and methotrexate solution. Perfusion stage media consisted of all the components in the growth medium, with the exception of a higher concentration of recombinant human insulin and the exclusion of methotrexate solution. Arginine and lysine were added as powders directly to the media solution. After the amino acid addition the pH was adjusted to that of the unsupplemented media using 5N NaOH and 5N HCL as necessary, and the osmolality was adjusted to that of the unsupplemented media by varying the concentration of sodium chloride.

Perfusion Culture

The perfusion culture was carried out with the Sartorius BIOSTAT RM 20 optical perfusion system (SN#00582112) in a Sartorius Cultibag RM 10 L perfusion pro 1.2my (lot 1205-014) perfusion bag. The perfusion bag was run with a working culture volume of 1.5 L and operation conditions of; pH: 7.00, dissolved oxygen 30%, 25 rpm, 35° C., an air overlay of 0.3 slpm and a $CO_2$ overlay of 15 sccm. pH control was initiated on day three of the culture. pH was controlled with 0.5M sodium hydroxide and $CO_2$ additions.

Perfusion was carried out by 'harvesting' spent culture through an integrated 1.2 μm filter integrated into the perfusion cultibag. Fresh media was added to the culture through a feed line at the same rate as the harvest. The perfusion rate was adjusted throughout the run to accommodate glucose needs, lactate accumulation and sampling plans. Perfusion cell-free harvest samples were collected at perfusion rates of 1.5, 3.0, 4.0, 6.0 and 8.0 exchange volumes/day on day 6-8 of perfusion. A fresh harvest bag was used for each harvest sample. The samples were then purified using Protein A and analyzed using WCX-10 assay.

WCX-10 Assay

The acidic species and other charge variants present in cell culture harvest samples were quantified. Cation exchange chromatography was performed on a Dionex ProPac WCX-10, Analytical column (Dionex, Calif.).

The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb2 samples used different buffers. The mobile phases used were 20 mM (4-Morpholino) ethane-sulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm. Quantitation is based on the relative area percent of detected peaks, as described above.

Results: Effect of Use of Perfusion Technology and Choice of Medium Exchange Rates on Acidic Species Adalimumab producing cell line 1 was cultured in media 1 and the cultures were carried out as described in the materials and methods. The exchange rates were modified over a period of 2 days between day 6 and day 8 to explore the influence of medium exchange rates on the extent of acidic species. At a continuous medium exchange rate of 1.5 volumes/day, the product antibody in spent medium was collected in a harvest bag over a period of 22 hrs. The harvest bag was then exchanged with a new bag and the old bag was transferred to 4° C. Subsequently and in succession, the medium exchange rates were increased to 3 and 6 volumes/day on day 7 and to 4 and 8 volumes/day on day 8 and the product harvests were collected and transferred to 4° C. The harvest samples were processed through Protein A and analyzed for acidic species using WCX-10. The percentage of acidic species in the control sample with a medium exchange rate of 1.5 volumes/day was 7.7%. The percentage of acidic species in the arginine and lysine supplemented cell culture with a medium exchange rate of 1.5 volumes/day was 4.3%. In the sample with the highest tested exchange rate in this experiment (8 volumes/day), the percentage of acidic species was reduced to 5.4% in the control sample, and reduced to 3.0% in the arginine and lysine supplemented cell culture sample. An exchange rate dependent reduction in acidic species was observed in both the cultures (FIG. 161). Thus, the combination of arginine/lysine supplementation to culture media along with exchange rate modulation can be used to further reduce AR.

Example 6

Upstream and Downstream Process Combinations to Achieve Target % AR or AR Reductions Upstream and downstream process technologies, e.g., cell culture and chromatographic separations, of the inventions disclosed herein can be combined together or combined with methods in the art to provide a final target AR value or achieve a % AR reduction. Upstream methods for AR reduction include, but are not limited to, those described in the instant application. Downstream methods for AR reduction are also described herein. Exemplary upstream and downstream process technologies include, but are not limited to: cell culture additives and conditions; clarified harvest additives and pH/salt conditions; mixed mode media separations; anion exchange media separations; and cation exchange media separations.

The instant Example demonstrates the combined effect of one or more of these technologies in achieving a target AR value or AR reduction, thereby facilitating the preparation of an antibody material having a specific charge heterogeneity. Additional examples of combinations of downstream technologies and upstream technologies are provided herein.

In this Example, the combination of upstream and downstream methods involves the reduction of acidic species in 3 L bioreactor cell cultures supplemented with arginine (2 g/L) and lysine (4 g/L) as has been previously demonstrated in the instant application. The results of that strategy are summarized in Table 10. The total acidic species was reduced from 20.5% in the control sample to 10.2% in sample from cultures that were supplemented with the additives. In this study, adalimumab producing cell line 1 was cultured in media 1 (chemically defined media) supplemented with amino acid arginine (2 g/L) and lysine (4 g/L) in a 300 L bioreactor. On Day 12 of culture, the culture was harvested and then subsequently analyzed using WCX-10 post Protein A purification and the percentages of total peak(s) area corresponding to the acidic species were quantified. The percentage of acidic species was estimated to be 9.1% in the 300 L harvest sample.

TABLE 10

| AR levels achieved with use of upstream technologies | | | | | | | | |
|---|---|---|---|---|---|---|---|---|
| 3 L Bioreactor | | | | | | 300 L Bioreactor | | |
| Control | | | Arginine (2 g/L) + Lysine (4 g/L) | | | Arginine (2 g/L) + Lysine (4 g/L) | | |
| AR1 (%) | AR2 (%) | Total AR (%) | AR1 (%) | AR2 (%) | Total AR (%) | AR1 (%) | AR2 (%) | Total AR (%) |
| 6.3 | 14.2 | 20.5 | 2.6 | 7.6 | 10.2 | 2.4 | 6.7 | 9.1 |

The material produced by the 300 L Bioreactor employing arginine and lysine additions, that effectively reduced the AR levels to 9.1% was purified using a downstream process employing Mixed Mode chromatography as the primary AR reduction method.

Adalimumab was purified by a Protein A chromatography step followed with a low pH viral inactivation step. The filtered viral inactivated material was buffer exchanged and loaded onto a Capto Adhere column. The Flow Through of Capto Adhere material was then purified with a HIC column with bind/elute mode as well as Flow Through mode. As shown in Table 11, AR reduction was achieved primarily with MM step, with some contribution from other steps. The table also shows that additional product related substances such as aggregates and process related impurities such as HCP can be effectively reduced employing these combined technologies.

TABLE 11

| Complete Downstream Process Train with Protein A Capture - AR, HMW and HCP reduction | | | | |
|---|---|---|---|---|
| Process | Yield (%) | % AR reduction | % HMW reduction | HCP LRF |
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF(FT) Filtrate | 96.1% | No reduction | No reduction | 0.10 |
| BDS (FT) | 103.8% | No reduction | No reduction | No reduction |

As is evident from the above example, the MM method further reduced the AR levels, by 2.26%. Therefore upstream technologies for reduction can be combined with downstream technologies to achieve AR levels/AR reduction.

Example 7

Anion Exchange (AEX) Chromatography Examples

Materials & Methods
Chromatography Method
Except where noted, the Materials and Methods described in connection with the instant example were also employed in Examples 8 and 9, below.

Pre-packed resin columns were used in the following experiments, except where specified. The column was equilibrated in a buffer system with appropriate pH and conductivity. The column load was prepared from Protein A affinity chromatography eluates or concentrated CEX chromatography elutes by buffer exchange (if the eluates were with different buffer components from the mixed mode target buffer system) or addition of the stock solutions and/or water to obtain the target pH and conductivity as specified (if the eluates were with the same buffer components as the mixed mode target buffer system). The prepared load material was filtered and loaded on the column according to the target load amount (g protein/L resin) as specified followed by washing with the equilibration buffer or buffer similar to equilibration buffer with volumes as specified. The column Flow Through/Wash were collected as fractions or as a pool. Mixed mode column was regenerated with 0.1 M acetic acid, 0.15 M NaCl pH3, or 0.1 M Acetic acid solution, pH 3, or as specified. 1M NaOH solution was used for column cleaning.

Buffer Preparation Method

Buffers for AEX were prepared targeting specific ion concentration for the anion by fixing the anion concentration (acid) to the target value, and adjusting the solution with the cationic component (base) to achieve the appropriate pH. For example, to prepare a 10 mM Acetate-Tris buffer solution, pH 8.7, glacial acetic acid was dissolved in water to a target concentration of 10 mM and adjusted with concentrated Tris-base to pH 8.7. Also for example, to prepare a 10 mM Formate-Tris buffer solution, pH 8.7, formic acid was dissolved in water to a target concentration of 10 mM and adjusted with concentrated Tris-base to pH 8.7.

Buffers for CEX were prepared targeting specific ion concentration for the cation by fixing the cation concentration (base) to the target value, and adjusting the solution with the anionic component (base) to achieve the appropriate pH. For example, to prepare a 140 mM Tris-Formate buffer solution, pH 7.5, Tris base was dissolved in water to a target concentration of 140 mM and adjusted with formic acid to pH 7.5.

AR Reduction and Recovery Calculations

In general, the Flow Through/wash fractions were collected and analyzed with WCX-10 method for AR levels. By actual or calculated pooling of the fractions the recovery and the corresponding AR levels were calculated.

WCX-10 for Adalimumab

The acidic species and other charge variants present in the adalimumab process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks. The peaks that elute at relative residence time less than a certain time are together represented as the acidic peaks.

WCX-10 for mAb-B

The acidic species and other charge variants present in the mAb-B process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 20 mM 4-Morpholineethanesulfonic acid (MES), pH 6.5 (Mobile phase A) and 20 mM 4-Morpholineethanesulfonic acid (MES), 500 mM Sodium Chloride pH 6.5 (Mobile phase B). A binary gradient (87% A, 13% B: 0-5 min; 87% A, 13% B: 5-35 min; 75% A, 25% B: 35-40 min; 0% A, 100% B: 40-43 min; 87% A, 13% B: 43-46 min; 87% A, 13% B: 46-55 min) was used with detection at 280 nm, bw 8 nm; ref 360 nm, bw 100 nm.

Quantitation was based on the relative area percent of detected peaks. All peaks eluting prior to the Main Isoform peak were summed as the acidic region, and all peaks eluting after the LYS-2 peaks will be summed as the basic region.

WCX-10 for mAb-C

The mAb-C method was employed towards the quantification of the acidic species and other charge variants present mAb-C process samples. Cation exchange chromatography was performed on a Dionex ProPac WCX-10, Analytical column 4 mm×250 mm (Dionex, Calif.). An Agilent 1200 HPLC system was used as the HPLC. The mobile phases used were 20 mM 4-Morpholineethanesulfonic acid (MES), pH 6.0 (Mobile phase A) and 20 mM 4-Morpholineethanesulfonic acid (MES), 250 mM Sodium Chloride pH 6.0 (Mobile phase B). A binary gradient (97% A, 3% B: 0-1 min; 79% A, 21% B: 1-46 min; 0% A, 100% B: 46-47 min; 0% A, 100% B: 47-52 min; 97% A, 3% B: 52-53 min; 97% A, 3% B: 53-60 min) was used with detection at 280 nm, bw 8 nm; ref 360 nm, bw 100 nm.

Quantitation was based on the relative area percent of detected peaks. All peaks eluting prior to the Main Isoform peak will be summed as the acidic region, and all peaks eluting after the Main Isoform peak will be summed as the basic region.

Size Exclusion Chromatography

The molecular weight distribution of collected samples were quantified according to the following methods. Size exclusion chromatography (SEC) was performed using a TSK-gel G3000SW×L, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification is based on the relative area of detected peaks.

Host Cell Protein (HCP) ELISA

HCP assay is based on process specific antigen based ELISA. Sample dilutions were applied to achieve readings within the calibration range. The limit of quantitation of the assay is 0.625 ng/mL.

UV spectroscopy $A_{280}$

UV A280 was used to determine protein concentrations for the samples post Protein A elution. The assay was performed on an Agilent UV Spectrophotometer. The protein concentration was determined using Beer-Lambert's Law, A=∈lc, where A is Absorbance, E is the extinction coefficient, 1 is the path length, and c is the concentration. The absorbance was taken at 280 nm, the path length was 1 cm, and the extinction coefficients were 1.39 for adalimumab, 1.38 for mAb B, and 1.43 for mAb C.

Example AEX 7.1

Determining Operating Conditions Appropriate for a Mab: Media: Buffer Combination The demonstration of the current invention for a specific antibody & resin is provided in this example, and consists of
1. Choosing an anion concentration that allows product and impurities to bind at a given pH above the pI of the product.
2. Performing a pH gradient elution covering a range above, at, and below the pI of the product.
3. Determining pH range in which the protein elutes from the anion exchange media In this example, adalimumab and Poros 50PI were chosen. The experiment was performed at acetate (anion) concentration of 5 mM. The column was equilibrated with 5 mM acetate/Tris at a pH of 9.0. Adalimumab was prepared at 5 mM acetate/Tris pH 9.0 and loaded to the column at 20 g-protein/L of resin. The column was washed with 10 CVs of the equilibration buffer. A pH gradient from 9.0 to 7.0 at an anion concentration of 5 mM acetate/Tris was then performed. The process chromatograms are shown in FIG. 165.

The demonstration of the current invention for a specific antibody & resin is provided in this example, and consists of
1. For a given pH, choosing a starting anion concentration that allows product and impurities to bind to the AEX adsorbent.
2. Loading a small amount of protein to the column and then performing a linear gradient elution by increasing the anion concentration keeping pH constant.
3. Determining anion concentration range in which the protein elutes from the anion exchange media.

In this example, adalimumab and Poros 50HQ were chosen. The experiment was performed at a pH 8.7. The column was equilibrated with 10 mM acetate/Tris at pH 8.7. Adalimumab was prepared at 10 mM acetate/Tris pH 8.7 and loaded to the column at 20 g-protein/L of resin. The column was washed with 10 CVs of the equilibration buffer. A linear gradient from 10-100 mM Acetate/Tris at pH 8.7 was performed. The process chromatograms are shown in FIG. 166.

This general approach is used to determine the appropriate operating condition, example shown in Table 12, for any resin/mAb combination, to implement the invention.

TABLE 12

Example Experimental Design Scope determined from pH and anion gradient elution
Poros 50HQ - 300 g/L Loading - 30 g/L Fractionation

| | |
|---|---|
| pH Range | 8.2-9.0 |
| Anion Concentration (acetate) | 10-20 mM |

In practicing the current invention, the acidic species reduction desired can be achieved by appropriate pooling of the load and wash fractions. By collecting and subsequently determining the product quality of each fraction throughout the load and wash, the accumulative AR reduction and accumulative yield can be calculated using the weighted averages up to a given fraction. Additionally, the instantaneous yield can be estimated by comparing the protein recovered against the total protein loaded to the column at a given fraction. Sample calculations are shown below:

Sample Calculation A: Accumulative Yield up to a given fraction $$\text{Accumulative Yield} = \frac{\text{Accumulated Protein Mass Recovered up to Fraction}}{\text{Total Mass Protein Load}}$$

Sample Calculation B: Accumulative AR reduction up to a given fraction $$\text{Accumulative } AR \text{ Reduction} = \text{Load } AR \% - \frac{\text{Accumulated Acidic Species Mass Recovered up to Fraction}}{\text{Accumulated Total Protein Mass Recovered up to Fraction}}$$

Sample Calculation C: Instantaneous Yield up to a given fraction $$\text{Instanceous Yield} = \frac{\text{Accumulated Protein Mass Recovered up to Fraction}}{\text{Total Protein Mass Loaded to Column at Fraction}}$$

The demonstration of the current invention for a specific antibody & resin is provided in this example, and consists of
1. For a given pH and anion concentration and anion exchange media.
2. Loading the anion exchange media in excess of the dynamic binding capacity for the product for the given condition.
3. Washing the column with a buffer containing a similar pH and anion concentration used for the equilibration and loading steps.
4. Collecting fractions throughout the loading and wash steps and subsequently determining the product quality profile (e.g. AR, aggregate, etc.).

In this example, adalimumab and Poros 50PI were chosen. The experiment was performed at 5 mM acetate/arginine pH 8.8. The column was equilibrated with 5 mM acetate/arginine at pH 8.8. Adalimumab was prepared at 5 mM acetate/arginine pH 8.8 and loaded to the column at 300 g-protein/L-resin. The column was washed with 20 CVs of the equilibration buffer. Fractions were collected in volumes representing 30 g-protein/L-resin, shown in FIG. 167. Each fraction was then analyzed for product quality and the accumulative yield and AR reduction calculated, shown in Table 13. From this example, it is clear to one skilled in the art to determine a run condition which delivers a targeted product quality and/or step yield.

This general approach is used to evaluate the performance for a given operating condition for any resin/mAb/buffer combination.

TABLE 13

Cumulative Yield and AR Reduction from FIG. 167

| | | Cumulative | |
|---|---|---|---|
| Fraction | Load | Yield | ΔAR |
| A2 | 7 g/L | 0.0% | 10.8% |
| A3* | 37 g/L | 0.5% | 10.8% |
| A4 | 67 g/L | 6.7% | 9.7% |
| A5 | 97 g/L | 16.7% | 8.9% |
| A6 | 127 g/L | 26.9% | 8.4% |
| B1 | 157 g/L | 37.0% | 7.7% |
| B2 | 187 g/L | 47.1% | 7.1% |
| B3 | 217 g/L | 57.4% | 6.4% |
| B4 | 247 g/L | 67.8% | 5.8% |
| B5 | 277 g/L | 78.0% | 5.3% |
| B6 | 300 g/L | 84.4% | 5.0% |
| B7 | Wash | 87.0% | 4.8% |
| C1 | Wash | 88.5% | 4.7% |
| C2 | Wash | 89.6% | 4.6% |

*Dynamic Binding Capacity (DBC) = 39 g/L

Example AEX 7.2

Demonstration of AR Reduction with AEX Adsorbents

This data set demonstrates the AR reduction achieved with three different AEX adsorbents. Each resin was evaluated using adalimumab at an acetate concentration determined from the process outlined in Example 7.1 and at pH values below, near, and above the pI (e.g. pH 8.5 to 9.0). Table 14 outlines the results from these experiments.

TABLE 14

Effect of AEX Resins on AR reduction of Adalimumab

| Resin | Buffer Condition | Load | Yield | ΔAR |
|---|---|---|---|---|
| Poros 50PI | 5 mM Acetate/Tris pH 8.5 | 150 g/L | 90% | 2.4% |
|  | 5 mM Acetate/Tris pH 8.5 | 300 g/L | 94% | 0.9% |
|  | 5 mM Acetate/Tris pH 8.7 | 150 g/L | 87% | 3.6% |
|  | 5 mM Acetate/Tris pH 8.7 | 300 g/L | 94% | 1.2% |
|  | 5 mM Acetate/Tris pH 9.0 | 150 g/L | 83% | 3.9% |
|  | 5 mM Acetate/Tris pH 9.0 | 300 g/L | 92% | 1.5% |
| Poros 50HQ | 18 mM Acetate/Tris pH 8.5 | 250 g/L | 91% | 3.8% |
|  | 18 mM Acetate/Tris pH 8.5 | 350 g/L | 88% | 2.2% |
|  | 18 mM Acetate/Tris pH 8.7 | 250 g/L | 85% | 6.0% |
|  | 18 mM Acetate/Tris pH 8.7 | 350 g/L | 84% | 3.1% |
|  | 18 mM Acetate/Tris pH 8.9 | 250 g/L | 67% | 5.9% |
|  | 18 mM Acetate/Tris pH 8.9 | 350 g/L | 75% | 3.6% |
| CaptoDEAE | 10 mM Acetate/Tris pH 8.5 | 150 g/L | 98% | 0.7% |
|  | 10 mM Acetate/Tris pH 8.5 | 300 g/L | 97% | 0.1% |
|  | 10 mM Acetate/Tris pH 8.7 | 150 g/L | 78% | 7.1% |
|  | 10 mM Acetate/Tris pH 8.7 | 300 g/L | 95% | 2.5% |
|  | 10 mM Acetate/Tris pH 9.0 | 150 g/L | 29% | 9.2% |
|  | 10 mM Acetate/Tris pH 9.0 | 300 g/L | 82% | 5.0% |

This data set is compiled to demonstrate the AR reduction achieved with eight different AEX adsorbents. Each resin was tested using an advanced screening method using the process outlined in Example 7.1, and subjected to four runs using adalimumab at two different pH (e.g., pH 8.7 and 9.0) and two different acetate concentrations (e.g. 10 mM and 20 mM). In these experiments, the instantaneous (e.g. not accumulative) AR reduction was measured by analyzing the load fraction at 150 g/L and subsequently compared across all resins. Table 15 outlines the results from these experiments.

TABLE 15

Advanced Screen of AEX Resins for AR reduction of adalimumab

| Resin | pH | Acetate | Instantaneous AR Reduction @ 150 g/L |
|---|---|---|---|
| Poros 50HQ | 8.7 | 10 mM | 15.0% |
|  |  | 20 mM | 10.7% |
|  | 9.0 | 10 mM | 8.6% |
|  |  | 20 mM | 13.4% |
| Poros 50PI | 8.7 | 10 mM | 6.2% |
|  |  | 20 mM | −0.1% |
|  | 9.0 | 10 mM | 6.5% |
|  |  | 20 mM | 3.0% |
| Capto DEAE | 8.7 | 10 mM | 9.3% |
|  |  | 20 mM | −0.2% |
|  | 9.0 | 10 mM | 8.6% |
|  |  | 20 mM | 7.8% |
| Capto Q Impres | 8.7 | 10 mM | 12.3% |
|  |  | 20 mM | 4.2% |
|  | 9.0 | 10 mM | 12.3% |
|  |  | 20 mM | 6.5% |
| QAE-550C | 8.7 | 10 mM | 10.1% |
|  |  | 20 mM | 3.5% |
|  | 9.0 | 10 mM | 7.8% |
|  |  | 20 mM | 4.5% |
| DEAE 650M | 8.7 | 10 mM | 5.2% |
|  |  | 20 mM | 0.1% |
|  | 9.0 | 10 mM | 6.9% |
|  |  | 20 mM | −2.7% |
| GigaCap Q 650M | 8.7 | 10 mM | 8.1% |
|  |  | 20 mM | 5.8% |
|  | 9.0 | 10 mM | 1.8% |
|  |  | 20 mM | 0.4% |
| TMAE HiCap | 8.7 | 10 mM | 4.1% |
|  |  | 20 mM | 2.8% |
|  | 9.0 | 10 mM | 1.2% |
|  |  | 20 mM | −0.1% |

This data set is compiled to demonstrate the AR reduction achieved with two different AEX chromatographic membranes. Each membrane was tested using conditions outlined in Table 15. The results from these experiments are presented in Table 16.

TABLE 16

Effect of AEX Chromatographic Membrane on AR reduction of Adalimumab

| Chromatographic Membrane | Equil/Wash Buffer | Load | Yield | ΔAR |
|---|---|---|---|---|
| Sartobind STIC | 10 mM Acetate/Tris pH 8.7 | 500 g/L | 94% | 1.7% |
|  | 20 mM Acetate/Tris pH 9.0 | 500 g/L | 100% | 0.7% |
| Sartobind Q | 20 mM Acetate/Tris pH 9.0 | 500 g/L | 100% | 0.3% |

This data set is compiled to demonstrate the AR reduction achieved with two different charged depth filters. The results from these experiments are presented in Table 17.

TABLE 17

Effect of Charged Depth Filters on AR reduction of adalimumab

| Depth Filter Media | Equil/Wash Buffer | Load | Yield | ΔAR |
|---|---|---|---|---|
| CUNO BioCap 25 | 18 mM Acetate/Tris pH 8.7 | 500 g/m² | 92% | 1.9% |
| X0HC | 18 mM Acetate/Tris pH 8.7 | 500 g/m² | 84% | 1.1% |

Example AEX 7.3

Demonstration of AR Reduction with Other Antibodies, Mab B and Mab C

AR reduction technology of the current invention has been demonstrated with multiple antibodies using AEX adsorbents. Antibodies have different amount charged residues and at different positions, leading to a charge interaction behavior on an AEX column that differs from one antibody to another. Therefore the impact of anion type, anion concentration is different for each antibody.

Table 18 and Table 19 below show the data for mAb B and mAb C. The data clearly demonstrates that the AR reduction technology works very effectively for other antibodies.

TABLE 18

AR reduction for mAb B, pI ~9.1

| Resin | Buffer Condition | pH | Load | Yield | ΔAR |
|---|---|---|---|---|---|
| Poros 50PI | 5 mM Acetate/Tris | 9.5 | 300 g/L | 83% | 1.1% |
|  |  | 9.1 | 300 g/L | 94% | 1.6% |
|  |  | 8.5 | 300 g/L | 98% | <0.5% |
| Poros 50HQ | 10 mM Acetate/Tris | 9.5 | 300 g/L | 69% | <0.5% |
|  |  | 9.1 | 300 g/L | 78% | 5.7% |
|  |  | 8.5 | 300 g/L | 81% | 3.4% |
| Capto DEAE | 10 mM Acetate/Tris | 9.5 | 300 g/L | 69% | 4.2% |
|  |  | 9.1 | 300 g/L | 82% | 4.9% |
|  |  | 8.5 | 300 g/L | 96% | <0.5% |

TABLE 19

AR reduction for mAb C, pI ~7.0

| Resin | Buffer Condition | pH | Load | Yield | ΔAR |
|---|---|---|---|---|---|
| Poros 50PI | 12 mM Acetate/Tris | 7.5 | 300 g/L | 90% | 2.6% |
|  |  | 7.0 | 300 g/L | 89% | 2.2% |
|  |  | 6.5 | 300 g/L | 87% | 4.0% |

TABLE 19-continued

AR reduction for mAb C, pI ~7.0

| Resin | Buffer Condition | pH | Load | Yield | ΔAR |
|---|---|---|---|---|---|
| Poros 50HQ | 45 mM Acetate/Tris | 7.5 | 300 g/L | 86% | 1.2% |
| | | 7.0 | 300 g/L | 88% | 1.2% |
| | | 6.5 | 300 g/L | 91% | 0.7% |
| Capto DEAE | 25 mM Acetate/Tris | 7.5 | 300 g/L | 79% | 1.8% |
| | | 7.0 | 300 g/L | 80% | 1.9% |
| | | 6.5 | 300 g/L | 89% | 1.8% |

Example AEX 7.4

Demonstration of AR Reduction with Different pH Conditions—Adalimumab

The AR species in the current invention is bound during the loading step; therefore the binding pH is a key variable. The anion concentration that provides the desired performance will vary with the operational pH.

In this example, data compiled from different experiments is shown to demonstrate the impact of the pH choice, relative to the pI of the protein on AR reduction. This data set provides the basis for one skilled in the art to determine a pH range to perform the experiments to implement the current invention. Furthermore, this reiterates the fact that the pH choice depends on several factors and the relationship between pH and AR reduction is also mAb dependent In this example, adalimumab and Poros 50PI were chosen. The experiments were performed at a concentration of 5 mM acetate/arginine at each pH specified. Adalimumab was prepared at 5 mM acetate/arginine at each pH specified and loaded to the column at 300 g-protein/L of resin. The column was washed with 20 CVs of the equilibration buffer. The results showing the pH effect on AR reduction is shown in FIG. 168.

It is also clear that the AR reduction can be achieved with the present invention with a range of pH choices in the range of ±0.5 pH units from the pI of multiple mAbs, which are listed in Table 20. Each of these experiments was performed with Poros50HQ resin at a 300 g/L load with an acetate/Tris buffer system.

TABLE 20

AR reduction at pH above, at, and below protein pI

| Range | pH-pI | Antibody | Yield | ΔAR |
|---|---|---|---|---|
| pH > pI | 0.2 | adalimumab | 71% | 7.0% |
| | 0.5 | mAb B | 69% | 3.4% |
| | 0.5 | mAb C | 86% | 1.2% |
| pH ~pI | 0 | adalimumab | 86% | 5.9% |
| | 0 | mAb B | 78% | 5.7% |
| | 0 | mAb C | 88% | 1.2% |
| pH < pI | −0.2 | adalimumab | 93% | 4.1% |
| | −0.5 | mAb B | 81% | <0.5% |
| | −0.5 | mAb C | 91% | 0.7% |

Example AEX 7.5

Demonstration of AR Reduction with Different Ion Concentrations—Adalimumab

Anion concentration is a key variable in the performance of anion exchange chromatography. For every combination of antibody/resin/pH there is a range of anion concentrations that provides AR reduction; the strategy outlined in Example 7.1 can be followed to determine the AR reduction and the corresponding recovery for each anion concentration.

Table 21 below shows the effect of anion concentration on AR reduction. The table also includes the effect of anion concentration for different pH values. The data demonstrates that the AR reduction can be effectively achieved over a range of anion concentrations at each pH and that the concentration ranges depend on the pH.

TABLE 21

Effect of Anion Concentration and pH on AR reduction

| Resin | pH | Buffer Condition | Load | Yield | ΔAR |
|---|---|---|---|---|---|
| Poros 50PI | 9 | 5 mM Acetate/Arginine | 300 g/L | 81% | 4.8% |
| | | 10 mM Acetate/Arginine | 227 g/L | 80% | 2.4% |
| | | 18.5 mM Acetate/Arginine | 107 g/L | 88% | 1.0% |
| | 8.8 | 5 mM Acetate/Arginine | 300 g/L | 93% | 4.5% |
| | | 10 mM Acetate/Arginine | 227 g/L | 88% | 2.5% |
| | | 18.5 mM Acetate/Arginine | 108 g/L | 96% | 1.2% |

Example AEX 7.6

Demonstration of AR Reduction with Different Buffer Systems with Adalimumab

The anion type and concentration are key variables in Anion Exchange Chromatography. The invention has been demonstrated using Acetate and Formate as the anion type and Tris and arginine as the counter cation type. The optimal pH and cation concentration is different for each cation type/mixture and was derived by using the strategy outlined above in Example 7.1. Table 22 shows the data of AR reduction and corresponding recovery for the different anion/cation types.

TABLE 22

Effect of Anion/Cation Type AR reduction

| Resin | Buffer Condition | Load | Yield | ΔAR |
|---|---|---|---|---|
| Poros 50PI | 5 mM Acetate/Tris, pH 8.7 | 300 g/L | 94% | 1.2% |
| | 2.5 mM Formate/Tris, pH 8.7 | 300 g/L | 92% | 1.3% |
| | 5 mM Acetate/Arginine, pH 8.8 | 300 g/L | 93% | 4.5% |
| Poros 50HQ | 15 mM Acetate/Arginine, pH 8.7 | 300 g/L | 89% | 3.2% |
| | 10 mM Formate/Tris, pH 8.7 | 300 g/L | 83% | 4.9% |
| | 18 mM Acetate/Tris, pH 8.7 | 300 g/L | 86% | 5.9% |
| Capto DEAE | 10 mM Acetate/Tris, pH 8.7 | 300 g/L | 95% | 2.5% |
| | 10 mM Formate/Tris, pH 8.7 | 300 g/L | 94% | 1.0% |
| | 5 mM Acetate/Arginine, pH 9.0 | 200 g/L | 41% | 7.5% |

Example AEX 7.7

Demonstration of AR Reduction with Different Loading

Furthermore, the strategy outlined in Example 7.1 to reduce acidic species through careful control of buffer anion type, anion concentration, AEX adsorbent, and pH can be applied to any range of protein loading. A range of relevant protein loadings (e.g. 100-350 g/L) for Poros 50HQ at pH 8.7 using Acetate as the anion is shown in Table 23, displaying a robust AR reduction across the loading range investigated.

TABLE 23

Impact of Column loading

| Load | Yield (100-100 mAU) | ΔAR |
|---|---|---|
| 100 g/L | 78% | 9.7% |
| 200 g/L | 78% | 4.7% |
| 250 g/L | 85% | 6.0% |
| 300 g/L | 89% | 3.9% |
| 350 g/L | 84% | 3.1% |

Example AEX 7.8

Demonstration of AR Reduction with Different Load Concentration

Furthermore, the strategy outlined in Example 7.1 to reduce acidic species through careful control of buffer anion type, anion concentration, AEX adsorbent, and pH can be applied to any range of column feed streams of varying protein concentration. A range of varying protein load concentration for a 300 g/L load of adalimumab to Poros 50HQ at 15 mM acetate/Tris pH 8.7 is shown in Table 24.

TABLE 24

Effect of Protein Load concentration

| Load Concentration | Yield (100-100 mAU) | ΔAR |
|---|---|---|
| 5 mg/mL | 90% | 4.7% |
| 10 mg/mL | 86% | 4.5% |
| 15 mg/mL | 85% | 6.3% |
| 20 mg/mL | 84% | 6.2% |

Example AEX 7.9

Alternative Wash Modalities

In this example, adalimumab and Poros50HQ resin were selected. In each experiment, variations were made in the equilibration, loading, and washing pH values at a given acetate concentration (as specified). Table 25 and Table 26 show the effect of the pH variation in the step yield and AR reduction.

TABLE 25

Differences in pH in Equil/Wash/Load
Poros 50HQ - 15 mM Acetate/Tris - pH 8.7-200 g/L

| Equilibration pH | Load pH | Wash pH | Yield (100-100 mAU) | ΔAR |
|---|---|---|---|---|
| 8.7 | 8.7 | 8.5 | 83% | 8.7% |
| 9 | 8.5 | 8.5 | 89% | 5.1% |
| 9 | 100 g/L at pH 9.0<br>100 g/L at pH 8.5 | 8.5 | 94% | 4.5% |

TABLE 26

Differences in pH in Load/Wash
Poros 50HQ - 18 mM Acetate/Tris pH 8.7

| Load pH | Wash pH | Load | Yield | ΔAR |
|---|---|---|---|---|
| 8.6 | 8.4 | 75 g/L | 88.8% | 4.1% |
| 8.6 | 8.5 | 125 g/L | 89.5% | 4.2% |
| 8.6 | 8.6 | 100 g/L | 75.5% | 5.3% |
| 8.7 | 8.4 | 100 g/L | 93.8% | 4.1% |
| 8.7 | 8.5 | 100 g/L | 81.7% | 3.5% |
| 8.7 | 8.5 | 75 g/L | 94.5% | 4.0% |
| 8.7 | 8.6 | 125 g/L | 81.1% | 5.4% |
| 8.7 | 8.6 | 75 g/L | 65.8% | 6.5% |
| 8.8 | 8.4 | 125 g/L | 93.5% | 3.8% |
| 8.8 | 8.5 | 100 g/L | 83.7% | 5.8% |
| 8.8 | 8.6 | 100 g/L | 78.4% | 6.4% |
| 8.8 | 8.6 | 75 g/L | 72.7% | 7.0% |

As discussed in the previous sections, the operational pH and its relation to the product pI is important in the reduction of AR species in AEX. Similarly, the operational pH relative to the pKa of the AEX adsorbent is also important as many mAbs have pI similar to the pKa of the AEX adsorbent. This effect is shown in FIG. 187 for mAb B with several different AEX adsorbents, with different pKa values, run at with an acetate/Tris buffer at pH 9.1.

As described in previous sections, the AR for adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 27. The method of the current invention can effectively reduce AR2 levels, as an overall decrease in AR levels is achieved. The method can be used to achieve a target absolute level, as exemplified by the data presented in Table 27. Multiple species are present under the group of AR2 and that the current method of invention can be used to reduce such subspecies. The method of the current invention can effectively achieve AR reduction as well as achieve a target absolute level of acidic species as exemplified by the data presented in Table 27.

TABLE 27

AR1, AR2, and AR removal

| Resin | Buffer Condition | pH | Load | Yield | ΔAR1 | Final AR1 | ΔAR2 | Final AR2 | ΔAR |
|---|---|---|---|---|---|---|---|---|---|
| Poros 50PI | 5 mM Acetate/Tris | 8.5 | 150 g/L | 90% | 0.7% | 1.5% | 1.7% | 9.4% | 2.4% |
| | | | 300 g/L | 94% | 0.3% | 1.9% | 0.6% | 10.5% | 0.9% |
| | | 8.7 | 150 g/L | 87% | 0.9% | 1.2% | 2.7% | 8.2% | 3.6% |
| | | | 300 g/L | 94% | 0.4% | 1.7% | 0.8% | 10.1% | 1.2% |
| | | 8.9 | 150 g/L | 83% | 1.1% | 1.4% | 2.8% | 8.4% | 3.9% |
| | | | 300 g/L | 92% | 0.7% | 1.8% | 0.7% | 10.5% | 1.5% |

TABLE 27-continued

AR1, AR2, and AR removal

| Resin | Buffer Condition | pH | Load | Yield | ΔAR1 | Final AR1 | ΔAR2 | Final AR2 | ΔAR |
|---|---|---|---|---|---|---|---|---|---|
| Poros 50HQ | 18 mM Acetate/Tris | 8.5 | 250 g/L | 91% | 2.9% | 1.1% | 0.9% | 10.8% | 3.8% |
| | | | 350 g/L | 88% | 2.7% | 1.3% | −0.5% | 12.2% | 2.2% |
| | | 8.7 | 250 g/L | 88% | 3.1% | 0.9% | 2.9% | 9.0% | 6.0% |
| | | | 350 g/L | 84% | 2.8% | 1.2% | 0.3% | 11.6% | 3.1% |
| | | 8.9 | 250 g/L | 67% | 2.6% | 1.4% | 3.2% | 8.6% | 5.9% |
| | | | 350 g/L | 75% | 2.3% | 1.7% | 1.3% | 10.5% | 3.6% |
| CaptoDEAE | 10 mM Acetate/Tris | 8.5 | 150 g/L | 98% | −0.1% | 2.1% | 0.8% | 10.0% | 0.7% |
| | | | 300 g/L | 97% | 0.0% | 2.0% | 0.1% | 10.8% | 0.1% |
| | | 8.7 | 150 g/L | 78% | 2.4% | 0.8% | 4.7% | 6.4% | 7.1% |
| | | | 300 g/L | 95% | 1.5% | 1.7% | 1.0% | 10.1% | 2.5% |
| | | 8.9 | 150 g/L | 29% | 2.1% | 0.8% | 8.0% | 3.0% | 10.2% |
| | | | 300 g/L | 82% | 1.7% | 1.2% | 3.3% | 7.7% | 5.0% |

Example AEX 7.10

Demonstration of HCP and Aggregate Reduction in Addition to AR Reduction

AEX chromatography is effective in reducing aggregate and HCP levels. In the present invention, it has been demonstrated that HCP and aggregate levels can be effectively reduced under operating conditions selected for AR reduction. Table 28 and Table 29 shows the aggregate and HCP removal achieved along with AR reduction. The data clearly shows that other process related and product related substances/impurities can be achieved using the current invention on the AEX adsorbents, and hence functions as an effective polishing step in the large scale purification of monoclonal antibodies.

TABLE 28

Aggregate removal during AEX Chromatography

| Buffer Condition | Load | Yield | ΔAggregate Absolute | ΔAggregate Relative | ΔAR |
|---|---|---|---|---|---|
| 5 mM Acetate/Tris, pH 9.0 | 300 g/L | 81% | 0.92% | 93% | 4.5% |
| 10 mM Acetate/Tris, pH 9.0 | 227 g/L | 80% | 0.81% | 88% | 2.4% |
| 18.5 mM Acetate/Tris, pH 9.0 | 107 g/L | 88% | 0.37% | 41% | 1.0% |
| 5 mM Acetate/Tris, pH 8.8 | 300 g/L | 93% | 0.91% | 91% | 4.5% |
| 10 mM Acetate/Arginine, pH 8.8 | 227 g/L | 88% | 0.67% | 77% | 2.5% |
| 18.5 mM Acetate/Arginine, pH 8.8 | 108 g/L | 96% | 0.34% | 40% | 1.2% |

TABLE 29

HCP Removal during AEX Chromatography
Poros 50PI - adalimumab - 300 g/L

| Buffer Condition | Yield | Load HCP (ng/mL) | Pool HCP (ng/mL) | HCP (LRF) | ΔAR |
|---|---|---|---|---|---|
| 5 mM Acetate/Tris, pH 9.0 | 81% | 11,617 | 69 | 2.2 | 4.8% |
| 10 mM Acetate/Tris, pH 9.0 | 95% | | 83 | 2.1 | 0.8% |
| 5 mM Acetate/Tris, pH 8.8 | 93% | 13,507 | 51 | 2.4 | 4.5% |
| 10 mM Acetate/Arginine, pH 8.8 | 97% | | 84 | 2.2 | 1.5% |

Example AEX 7.11

Demonstration of Means of Controlling AR Reduction

Controlling the final product quality by modifying the process based on the quality of the intermediate material is an approach that has been proposed as an effective way of ensuring product quality, with the view of ensuring safety and efficacy.

Considering that the AR levels generated during cell culture and other upstream steps can be variable, it is desirable to design a downstream process step that implements a means of controlling the product quality; and to further have a specific means of controlling a process parameter to influence the quality of the product.

In the current invention, such a control is possible, as the pH and load (i.e., g/L) are parameters that can be modified to achieve a desired separation of the AR species. For example, to achieve a higher level of AR reduction at a given anion concentration and pH, the load to the column can be reduced. Additionally, for a given anion concentration and loading, the pH can be increased in order to achieve a higher reduction in AR species.

As an example, and not to be restrictive in any manner, it has been demonstrated in this example that the AR levels can be controlled by changing the pH of the load and wash solutions as well as the total load to the column. A pilot scale Poros HQ column (10 cm diameter×22.5 cm height, 1.8 L), was used for this study.

The load material and the stock buffer are both prepared at 18 mM Acetate/Tris the specified pH by titrating the affinity captured material with a stock Tris solution. The AR level of the load material was the same for both runs. This experiment demonstrates how the final AR level can be modulated, while maintaining acceptable yields, by adjusting the pH and protein load to the column, shown in Table 30.

TABLE 30

Modulating AR Reduction using Process Analytical Technology approach

| Buffer Condition | Load | Yield | ΔAR | Final AR |
|---|---|---|---|---|
| 18 mM Acetate/Tris, pH 8.7 | 200 g/L | 77% | 5.6% | 5.5% |
| 18 mM Acetate/Tris, pH 8.5 | 300 g/L | 89% | 3.1% | 8.2% |

Example AEX 7.12

AEX with Tris/Formate Buffer System: Acidic Species Reduction for Adalimumab on Poros 50HQ in a Formic Acid Buffer System This Example provides demonstration of the use of a Tris/Formate buffer system for AR reduction using AEX. In practicing the current Example, the acidic species reduction desired can be achieved by appropriate pooling of the load and wash fractions. By collecting and subsequently determining the product quality of each fraction throughout the load and wash, the accumulative AR reduction and accumulative yield can be calculated using the weighted averages up to a given fraction. Additionally, the instantaneous yield can be estimated by comparing the protein recovered against the total protein loaded to the column at a given fraction.

AEX Adsorbent

Poros 50HQ (Applied Biosciences, part#1-2459-11), a rigid 50 µm polymeric bead with a backbone consisting of cross-linked poly[styrene-divinylbenzene], was used in this experiment.

AEX Chromatography Method

Poros 50HQ was packed in 1.0 cm×10.0 cm (OmniFit) columns. The column was equilibrated in a buffer system with appropriate pH and conductivity. The load was prepared in the equilibration buffer by addition of the stock solutions to obtain the target ion concentrations and loaded on the column, followed by washing with the equilibration buffer for 20 CV. The antibody product was collected in the flow-through and wash fractions during the load and washing steps. The columns/housings were then regenerated with 100 mM formate and 1M of NaOH solution was used for column cleaning.

Sample calculations are shown below:

Sample Calculation A: Accumulative Yield up to a given fraction $$\text{Accumulative Yield} = \frac{\text{Accumulated Protein Mass Recovered up to Fraction}}{\text{Total Mass Protein Load}}$$

Sample Calculation B: Accumulative AR Reduction up to a given fraction $$\text{Accumulative } AR \text{ Reduction} = \text{Load } AR\% = \frac{\text{Accumulated Acidic Species Mass Recovered up to Fraction}}{\text{Accumulated Total Protein Mass Recovered up to Fraction}}$$

Sample Calculation C: Instantaneous Yield up to a given fraction $$\text{Instantaneous Yield} = \frac{\text{Accumulated Protein Mass Recovered up to Fraction}}{\text{Total Protein Mass Loaded to Column at Fraction}}$$

In this Example, adalimumab and Poros 50HQ were chosen. The experiment was performed at 10 mM, 15 mM, 20 mM, 30 mM, and 40 mM formate/Tris pH 8.8. The column was equilibrated with the respective formate/Tris at pH 8.8 for each run. Adalimumab was prepared at 10 mM, 15 mM, 20 mM, 30 mM, and 40 mM formate/Tris pH 8.8 and loaded to the column at 300-500 g-protein/L-resin. Fractions were collected in volumes representing ~25 g-protein/L-resin. These fractions were analyzed for product quality, accumulative yield, and accumulative AR reduction throughout the run (shown in FIG. 189). The instantaneous yield and AR reduction at 100, 200, 300, 400, and 500 g/L load are tabulated in Table 31. This example demonstrates the effectiveness of the Tris/Formate buffer system in general and specifically the effectiveness of the Formate anion on the AEX column for AR reduction. Further it confirms that the AEX AR reduction method applies to a variety of buffer systems.

TABLE 31

Accumulative Yield and AR Reduction for a range of Formic Acid concentrations from FIG. 189

| Load | 10 mM | | 15 mM | | 20 mM | | 30 mM | | 40 mM | |
| --- | --- | --- | --- | --- | --- | --- | --- | --- | --- | --- |
| g/L | Yield | ΔAR | Yield | ΔAR | Yield | ΔAR | Yield | ΔAR | Yield | ΔAR |
| 100 | 32% | 9.2% | 54% | 8.7% | 62% | 8.4% | 69% | 5.5% | 75% | 4.5% |
| 200 | 64% | 7.4% | 74% | 6.8% | 78% | 6.0% | 82% | 3.2% | 85% | 2.6% |
| 300 | 75% | 6.1% | 82% | 5.3% | 85% | 4.4% | 84% | 2.2% | 86% | 1.8% |
| 400 | 81% | 5.1% | 86% | 4.2% | 88% | 3.3% | — | — | — | — |
| 500 | 83% | 4.5% | 87% | 3.6% | 89% | 2.8% | — | — | — | — |

Example 8

Cation Exchange Chromatography Examples

Example CEX 8.1

Determining Operating Conditions Appropriate for a Mab: Resin: Buffer Combination The demonstration of the current invention for a specific antibody & resin is provided in this example, and consists of
1. Choosing a pH that is below the pI of the protein.
2. Choosing a NaCl concentration in the range of 100 to 150 mM and performing the experiments at, for example, 115, 125, 135 concentrations.
3. Determining the acidic species distribution in the Flow Through/wash fraction vs. the elution.
4. Choosing a NaCl concentration that provides the desired acidic species levels and recovery In this example, adalimumab was chosen and Poros XS was chosen. The experiments were performed at pH 6.0. The process chromatograms are shown in FIG. 169. The recovery vs. AR reduction curves for each of the experiments is shown in FIG. 170 and Table 32. From this set of experiments, a sodium concentration of 125 mM can be chosen and such that the recovery of the eluate is 74%, which provides an AR reduction of 5.4%. Alternately, an AR reduction value of 5.4% can be chosen which will provide a recovery of ~75%.

This general approach is used to determine the appropriate operating condition for any resin/mAb combination, to implement the invention.

In practicing certain embodiments of the current invention, the acidic species reduction desired can be achieved by appropriate pooling of the elution fraction with the wash fractions. In the example described in the previous section the elution fractions can be pooled with wash fractions as shown in Table 32 to achieve AR reductions from about 1 percent to about 7 percent depending on the fractions pooled. This approach can be implemented to achieve a target yield and AR reduction as exemplified in FIG. 170.

TABLE 32

Wash fractions and eluate combination versus AR reduction

| Wash Fractions | Recovery (%) | % AR reduction |
|---|---|---|
| Eluate | 74 | 5.4 |
| Eluate + Fraction 1 | 82 | 4.3 |
| Eluate + Fraction 1 + Fraction 2 | 88 | 3.0 |
| Eluate + Fraction 1 + Fraction 2 + Fraction 3 | 95 | 0.9 |
| Eluate + Fraction 1 + Fraction 2 + Fraction 3 + Fraction 4 | 96 | 0.1 |

Example CEX 8.2

Demonstration of AR Reduction with CEX Adsorbents

This data set is compiled to demonstrate the AR reduction achieved with 8 different CEX adsorbents. Conditions were derived for each resin based on the strategy outlined in Example 8.1, above. Table 33 outlines the conditions used and the AR reduction achieved and the corresponding recovery achieved.

The data clearly shows that the technology is robust in delivering AR reduction in all the 10 resins. As described in Example 8.1, above, the AR reduction can be balanced with recovery and an optimal condition can be chosen. Experiments were performed at pH 7.5. 29 mM Tris-acetate was used for pH control.

TABLE 33

Effect of CEX adsorbents on AR reduction

| Resin | Tris concentration (mM) | Yield (%) | % AR Reduction |
|---|---|---|---|
| Poros XS | 135 | 103.3 | 0.7 |
|  | 140 | 78.6 | 6.8 |
|  | 145 | 72.6 | 7.3 |
| Poros HS | 100 | 70.0 | 6.7 |
|  | 105 | 68.7 | 7.1 |
|  | 110 | 60.6 | 7.6 |
| Capto SP ImpRes | 50 | 71.5 | 5.7 |
|  | 55 | 61.0 | 6.3 |
|  | 60 | 46.2 | 6.8 |
| Nuvia S | 75 | 67.6 | 10.0 |
|  | 80 | 54.3 | 10.8 |
|  | 85 | 41.0 | 12.2 |
| Giga Cap CM 650 | 55 | 70.3 | 6.0 |
|  | 57.5 | 62.7 | 7.0 |
|  | 60 | 55.6 | 8.6 |
| Eshmuno S | 65 | 52.7 | 9.0 |
|  | 70 | 35.4 | 11.2 |
|  | 75 | 22.7 | 12.2 |
| Giga Cap S 650 | 65 | 66.3 | 8.4 |
|  | 70 | 43.6 | 11.1 |
|  | 75 | 31.4 | 12.1 |
| CM Hyper D | 45 | 72.2 | 8.9 |
|  | 47.5 | 63.2 | 9.9 |
|  | 50 | 51.5 | 10.3 |

Example CEX 8.3

Demonstration of AR Reduction with Other Antibodies: mAb B and mAb C

AR reduction technology of the current invention has been demonstrated with multiple antibodies using CEX Adsorbents. Antibodies have different amounts of charged residues and at different positions, leading to a charge interaction behavior on a CEX column that differs from one antibody to another. Therefore the impact of cation type, cation concentration is different for each antibody.

For each antibody/resin combination, the experimental strategy outlined in Example 8.1, above, was employed to determine the cation concentration for each cation type that provided AR reduction.

Table 34 and Table 35 below shows the data for mAb B and mAb C. The data clearly demonstrates that the AR reduction technology works very effectively for other antibodies. It is also clear that the concentration ranges are different between different antibodies. The pH range chosen was related to the isoelectric point of the antibody and was chosen to be approximately 1 to 2 units less than the pI of the molecule.

TABLE 34

AR reduction for mAb B

| Resin | Buffer System | Concentration (mM) | pH | Yield (%) | % AR Reduction |
|---|---|---|---|---|---|
| Poros XS | Tris Acetate | 120 | 7.5 | 57.2 | 8.4 |
|  |  | 125 |  | 46.5 | 9.3 |
|  |  | 130 |  | 37.1 | 10.3 |
| Nuvia S |  | 85 |  | 72.5 | 16.6 |
|  |  | 90 |  | 56.1 | 16.9 |
|  |  | 95 |  | 44.2 | 17 |
| CM Hyper D |  | 50 |  | 73 | 8.2 |
|  |  | 55 |  | 62 | 9.2 |
|  |  | 60 |  | 52.6 | 9.2 |

TABLE 35

AR reduction for mAb C

| Resin | Buffer System | Concentration (mM) | pH | Yield (%) | Load % AR | % AR Reduction |
|---|---|---|---|---|---|---|
| Poros XS | Tris Acetate | 40 | 6.0 | 87.4 | 15.6 | 8.5 |
|  |  | 45 |  | 56.8 | 15.7 | 12.8 |
|  |  | 50 |  | 31.3 | 15.7 | 14.3 |
| Nuvia S |  | 35 |  | 45.1 | 11.5 | 11.2 |
|  |  | 37 |  | 28.5 | 15.4 | 15.2 |
|  |  | 40 |  | 15.3 | 15.2 | 15.2 |
| CM Hyper D |  | 18 |  | 83.6 | 16.3 | 6.3 |
|  |  | 20 |  | 64.9 | 16.3 | 11.2 |
|  |  | 22 |  | 50.7 | 16.4 | 12.3 |

Example CEX 8.4

Demonstration of AR Reduction with Different pH Conditions—Adalimumab

The AR species in the current invention is removed in the Flow through/Wash fraction. Therefore the binding pH is a key variable. The cation concentration that provides the desired performance will vary with the binding pH. Therefore for each binding pH, the experimental strategy outlined in Example 8.1, above, is carried out to determine the range of ion concentration that results in AR reduction.

The results of the experiments with different pHs for adalimumab is shown in Table 36. As can be seen, at lower pH, the cation concentration required to achieve AR removal in the wash fraction is higher. It is unexpected that the AR reduction is significantly more robust and optimal at higher pHs (closer to pI) than at lower pHs. It is not obvious to one skilled in the art to operate a cation exchange chromatography at pH closer to pI as shown in Table 37. Literature data suggests an optimal pH of at least 3 units less than the pI of the molecule.

TABLE 36

Effect of pH on AR reduction

| pH | Resin | Buffer System | Buffer Concentration (mM) | Yield (%) | % AR Reduction |
|---|---|---|---|---|---|
| 5.5 | Poros XS | Tris Acetate | 350 | 58.2 | 5.9 |
| 6.5 | | | 225 | 61.4 | 6.4 |
| 7 | | | 170 | 75.3 | 5.6 |
| 7.5 | | | 140 | 78.6 | 6.8 |
| 8 | | | 125 | 75.8 | 5.7 |
| 7.5 | CM Hyper D | Ammonium Sulfate | 4 | 77.9 | 7.4 |
| 6 | | Sodium Chloride | 45 | 86.1 | 4 |
| 6.8 | | | 30 | 71.5 | 7 |
| 7.5 | | | 10 | 71.3 | 6.8 |
| 7.5 | | Tris Acetate | 45 | 72.2 | 8.9 |

TABLE 37

Effect of delta pH and pI on AR reduction

| pI-pH | Antibody | Resin | Buffer system | [Cation] (mM) | Yield (%) | % AR Reduction |
|---|---|---|---|---|---|---|
| 1.1 | adalimumab | Poros XS | Arginine/Tris Acetate | 60/29 | 58.9 | 7.8 |
| 2.2 | | | Sodium Chloride | 125 | 73.5 | 5.4 |
| 1.8 | | | | 75 | 90 | 1.5 |
| 1.1 | | | | 50 | 72.1 | 7.2 |
| 3.1 | | | Tris Acetate | 350 | 58.2 | 5.9 |
| 2.1 | | | | 225 | 61.4 | 6.4 |
| 1.6 | | | | 170 | 75.3 | 5.6 |
| 1.1 | | | | 145 | 72.6 | 7.3 |
| 0.6 | | | | 125 | 75.8 | 5.7 |
| 1.6 | mAb B | Poros XS | Tris Acetate | 120 | 57.2 | 8.4 |
| 1.6 | | CM Hyper D | Tris Acetate | 50 | 73 | 8.2 |
| 1.6 | | Nuvia S | Tris Acetate | 85 | 72.5 | 8.4 |
| 1.0 | mAb C | Poros XS | Tris Acetate | 40 | 87.4 | 8.5 |
| 1.0 | | CM Hyper D | Tris Acetate | 18 | 83.6 | 6.3 |
| 1.0 | | Nuvia S | Tris Acetate | 35 | 45.1 | 11.2 |

Example CEX 8.5

Demonstration of AR Reduction with Different Ion Concentrations—Adalimumab

Cation concentration is a key variable in the performance of cation exchange chromatography. For every combination of antibody/resin/pH there is a range of cation concentrations that provides AR reduction; the strategy outlined in Example 8.1, above, can be followed to determine the AR reduction and the corresponding recovery for each cation concentration.

Table 38 below shows the effect of cation concentration on AR reduction. The table also includes the effect of cation concentration for different pH values. The data demonstrates that the AR reduction can be effectively achieved over a range of cation concentrations at each pH and that the concentration ranges depend on the pH. The table also includes an example of the concentration range for a different cation type.

TABLE 38

Effect of cation concentration and pH on AR reduction

| Cation concentration (mM) | Buffer system | pH | Resin | Yield (%) | % AR Reduction |
|---|---|---|---|---|---|
| 60/29 | Arginine/Tris Acetate | 7.5 | Poros XS | 58.9 | 7.8 |
| 65/29 | | | | 47.4 | 8.7 |
| 23 | | | | 80.5 | 5.8 |
| 25 | | | | 72.9 | 7.3 |
| 27 | | | | 52.2 | 9.5 |
| 115 | Sodium Chloride | 6 | | 85.4 | 4.2 |
| 125 | | | | 73.5 | 5.4 |
| 130 | | | | 48.7 | 7.1 |
| 75 | | 6.8 | | 90 | 1.5 |
| 90 | | | | 53.7 | 2.1 |
| 45 | | 7.5 | | 60.7 | 7.9 |
| 50 | | | | 72.1 | 7.2 |
| 350 | Tris Acetate | 5.5 | | 58.2 | 5.9 |
| 375 | | | | 38.4 | 7.4 |
| 400 | | | | 29.9 | 6.2 |
| 225 | | 6.5 | | 61.4 | 6.4 |
| 250 | | | | 59.5 | 6.6 |
| 275 | | | | 37.6 | 7.8 |
| 300 | | | | 21.6 | 8.8 |
| 165 | | 7 | | 83.8 | 4.3 |
| 170 | | | | 75.3 | 5.6 |
| 175 | | | | 70.3 | 5.7 |
| 140 | | 7.5 | | 78.6 | 6.8 |
| 145 | | | | 72.6 | 7.3 |
| 150 | | | | 69.2 | 7.8 |
| 175 | | | | 29.8 | 10.3 |
| 125 | | 8 | | 75.8 | 5.7 |
| 130 | | | | 67.7 | 6.5 |
| 135 | | | | 57.4 | 7.5 |

Example CEX 8.6

Demonstration of AR Reduction with Different Buffer Systems with Adalimumab The cation type and concentration are key variables in Cation Exchange Chromatography. The invention has been demonstrated with Tris, Sodium/Tris, Ammonium/Tris and Arginine/Tris as cation types/mixtures with effective reduction of AR in each case. As one skilled in the art would appreciate the optimal pH and cation concentration is different for each cation type/mixture and was derived by using the strategy outlined in Example 8.1, above. Experiment were performed at pH 7.5. 29 mM Tris-acetate was used for pH control. Table 39 shows the data of AR reduction and corresponding recovery for the different cation types/mixtures.

TABLE 39

Effect of cation types/mixtures on AR reduction

| Buffer System | Resin | Cation concentration (mM) | pH | Yield (%) | % AR Reduction |
|---|---|---|---|---|---|
| Arginine/Tris acetate | Poros XS | 60 | 7.5 | 58.9 | 7.8 |
| Ammonium Sulfate | | 25 | | 72.9 | 7.3 |
| Sodium Chloride | | 50 | | 72.1 | 7.2 |
| Tris Acetate | | 140 | | 78.6 | 6.8 |
| Ammonium Sulfate | CM Hyper D | 4 | | 77.9 | 7.4 |
| Sodium Chloride | | 10 | | 71.3 | 6.8 |
| Tris Acetate | | 45 | | 72.2 | 8.9 |
| Ammonium Sulfate | Nuvia S | 11 | | 66.6 | 12.6 |
| Sodium Chloride | | 20 | | 75.9 | 10.5 |
| Tris Acetate | | 75 | | 67.6 | 10 |

Example CEX 8.7

Demonstration of AR Reduction with Different Loading

Furthermore, the strategy outlined in Example 8.1, above, to reduce acidic species through careful control of buffer cation type, concentration and pH can be applied to any range of protein loading which represents an operational mode of binding followed by elution, i.e. not overloaded or a column load factor below that of the adsorbents binding capacity. A range of relevant protein loadings for Poros XS at pH 7.5 using Tris as the cation is shown in Table 40 showing robust AR reduction.

TABLE 40

Impact of Column loading

| Column Loading (g product/L resin) | Buffer System | Concentration (mM) | pH | Yield (%) | % AR Reduction |
|---|---|---|---|---|---|
| 25 | Tris | 160 | 7.5 | 83.6 | 6.4 |
| 30 | | 155 | | 79.4 | 6.0 |
| 35 | | 140 | | 87.4 | 4.8 |
| 38 | | 140 | | 83.5 | 5.0 |
| 40 | | 140 | | 76.4 | 6.0 |
| 42 | | 140 | | 74.5 | 5.7 |
| 45 | | 140 | | 67.0 | 6.6 |

Example CEX 8.8

Demonstration of AR Reduction with Different Load Concentration

Furthermore, the strategy outlined in Example 8.1, above, to reduce acidic species through careful control of buffer cation type, concentration and pH can be applied to any range of column feed streams of varying protein concentration. A range of varying protein load concentration for Poros XS at pH 7.5 using Tris as the cation is shown in Table 41 showing robust AR reduction.

TABLE 41

Effect of Protein Load concentration

| Load Concentration (mg/mL) | Resin | Buffer System | Concentration (mM) | pH | Yield (%) | % AR Reduction |
|---|---|---|---|---|---|---|
| 3 | Poros XS | Tris Acetate | 140 | 7.5 | 77.3 | 7 |
| 4 | | | 145 | | 60.7 | 7 |
| 5 | | | 140 | | 78.7 | 6.7 |
| 5 | | | 145 | | 64.1 | 7 |
| 6 | | | 145 | | 59.5 | 6.9 |
| 7 | | | 140 | | 77.6 | 6.5 |

As described above, the AR for adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 42.

The specific species comprising the AR1 species can be identified and quantitated, to demonstrate reduction of such species by methods of the current invention. Two of such species, glycated mAb, and MGO modified mAb have been identified and shown to be reduced by the methods of this invention. While these species are among the acidic species part of the charge variants, the acidic species typically described in the literature is the deamidated mAb, which is distinctly different.

TABLE 42

The final impurity level

| Buffer System | Cation Conc. (mM) | pH | Yield (%) | % Final AR1 | % Final AR |
|---|---|---|---|---|---|
| Arginine/Tris | 60 | 7.5 | 58.9 | 0.3 | 5.8 |
| Acetate | 65 | 7.5 | 47.4 | 0.3 | 4.7 |
| Ammonium | 23 | 7.5 | 80.5 | 0.6 | 8.3 |
| Sulfate | 25 | 7.5 | 72.9 | 0 | 6.4 |
| | 27 | 7.5 | 52.2 | 0.4 | 5.0 |
| Sodium Chloride | 115 | 6 | 85.4 | 1.3 | 10.2 |
| | 125 | 6 | 73.5 | 0 | 8.1 |
| | 135 | 6 | 48.7 | 0 | 6.1 |
| | 75 | 6.8 | 90 | 1.4 | 10.9 |
| | 90 | 6.8 | 53.7 | 0.7 | 11.2 |
| | 45 | 7.5 | 60.7 | 0 | 6.2 |
| | 50 | 7.5 | 72.1 | 0 | 7.8 |
| Tris Acetate | 350 | 5.5 | 58.2 | 0 | 7.7 |
| | 375 | 5.5 | 38.4 | 0.1 | 6.2 |
| | 400 | 5.5 | 29.9 | 1.5 | 7.3 |
| | 225 | 6.5 | 61.4 | 0.8 | 7.2 |
| | 250 | 6.5 | 59.5 | 0 | 6.8 |
| | 275 | 6.5 | 37.6 | 0 | 5.6 |
| | 300 | 6.5 | 21.6 | 0 | 4.7 |

The method of the current invention can effectively reduce AR2 levels, as an overall decrease in AR levels is achieved. The method can be used to achieve a target absolute level, as exemplified by the data presented in Table 42.

The method of the current invention can effectively achieve AR reduction as well as achieve a target absolute level of acidic species as exemplified by the data presented in Table 42.

Example CEX 8.9

Demonstration of Glycated and Methylglyoxylated Species Reduction

The strategy outlined in Example 8.1, above, to reduce acidic species through careful control of buffer cation type, concentration and pH can be further extended to specific post-translational modifications. While acidic species are defined in the application as impurities that are less retained than the main peak on an analytical weak cation exchange (WCX) HPLC column, specific known product related substances derived from cellular metabolism modification such as glycation and methylglyoxal (MGO) can be specifically identified as being part of the acidic species. FIG. 171 and FIG. 172 shows the outcome of in-vitro labeling experiments which demonstrate that glycation and MGO modified antibody are unique species that are resolved by the WCX method in the AR1 region of the chromatogram and can be enriched in vitro. Furthermore, the invention described here shows that glycated and MGO modified antibody can be effectively removed through the careful control of buffer cation type, concentration and pH using the CEX as described in Example 8.1, above. Quantitative reduction of AR1 and hence the glycated and MGO species by CEX and CEX-Mixed Mode resins is show in Table 43 and Table 44.

TABLE 43

Glycated species removal

| Resin | Buffer System | Conc. (mM) | pH | Yield (%) | Load % AR1 | Load % AR | % AR1 Reduction | % AR Reduction |
|---|---|---|---|---|---|---|---|---|
| Poros XS | Tris | 135 | 7.5 | 54.0 | 40.8 | 58.6 | 30.8 | 34.8 |

TABLE 44

MGO peak removal

| Resin | Buffer System | Concentration (mM) | pH | Yield (%) | % AR1 Reduction | % AR Reduction |
|---|---|---|---|---|---|---|
| Toyo Pearl MX TRP 650M | Tris | 80 | 7.5 | 66.7 | 2.8 | 7.2 |
| Poros XS | | 145 | | 64.1 | 2.7 | 7 |
| Nuvia S | | 90 | | 48.5 | 3.1 | 9.6 |

Example CEX 8.10

Demonstration of Lysine Distribution Modification

The strategy outlined in Example 8.1, above, to reduce acidic species also can be used to modulate the distribution of C-terminal Lys variants of monoclonal antibodies, a known post-translational modification leading to charge heterogeneity. Some minor changes in the distribution of Lys isoforms is expected through the reduction of acidic species as the WCX analysis is a compositional analysis. However, through careful control of buffer cation type, concentration and pH care, in addition to reducing acidic species, the elution pool can be enriched for the more basic isoforms (Lys 1 and Lys2). Table 45 and FIG. 173 depicts a non-limited example of the impact of pH and cation (Tris) concentration on basic isoform enrichment.

TABLE 45

Change in Lysine distribution during CEX Chromatography - impact of Tris concentration

| % LYS0 decrease | % LYS1 Increase | % LYS2 Increase | Buffer System | Buffer Concentration (mM) | pH |
|---|---|---|---|---|---|
| 1.6 | 4.4 | 2.7 | Tris | 350 | 5.5 |
| 5 | 6.5 | 5.5 | Acetate | 375 | |
| 9.7 | 7.5 | 11.9 | | 400 | |
| 1.9 | 5 | 2.9 | | 225 | 6.5 |
| 1.9 | 5.3 | 3 | | 250 | |
| 6.1 | 7.4 | 6 | | 275 | |
| 11.8 | 8.6 | 10.8 | | 300 | |
| 0.2 | 5.2 | 1.6 | | 140 | 7.5 |
| 0.6 | 5.7 | 1.8 | | 145 | |
| 1.8 | 6.8 | 2.4 | | 150 | |
| 16.4 | 14.9 | 10.3 | | 175 | |

Example CEX 8.11

Demonstration of HCP and Aggregate Reduction in Addition to AR Reduction

In the present invention, it has been demonstrated that HCP and aggregate levels can be effectively reduced by appropriate adjustment of the elution conditions, after washing off the AR enriched species in the Flow Through/wash fractions.

Table 46 and Table 47 shows the HCP and aggregate removal achieved along with AR reduction. The data clearly shows that other process related impurities and product related substances can be achieved using the current invention on the CEX adsorbents, and hence functions as an effective polishing step in the large scale purification of monoclonal antibodies.

TABLE 46

Aggregate removal during CEX Chromatography

| Resin | Antibody | Buffer system | pH | % Aggregate Reduction | % Fragment Reduction | % Monomer Increase |
|---|---|---|---|---|---|---|
| CM Hyper D | adalimumab | 5 mM Ammonium Sulfate | 7.5 | 0.04 | 0.17 | 0.2 |
| | | 45 mM Tris Acetate | | 0.01 | 0.18 | 0.19 |
| Nuvia S | | 11.5 mM Ammonium Sulfate | | 0.16 | 0.17 | 0.33 |
| | | 75 mM Tris Acetate | | 0.09 | 0.11 | 0.2 |
| | | 22.5 mM Sodium Chloride | | 0.08 | 0.19 | 0.27 |
| Poros XS | | 27 mM Ammonium Sulfate | | 0.75 | 0.27 | 1.02 |
| | | 140 mM Tris Acetate | | 0.51 | 0.41 | 0.92 |
| | | 145 mM Tris Acetate | | 0.58 | 0.41 | 0.98 |
| Nuvia S | mAb B | 85 mM Tris Acetate | | 0.19 | 0.27 | 0.47 |
| Poros XS | | 130 mM Tris Acetate | | 0.36 | 0.04 | 0.39 |
| Nuvia S | mAb C | 35 mM Tris Acetate | 6.0 | 0.07 | 0.01 | 0.07 |
| Poros XS | | 50 mM Tris Acetate | | 0.27 | 0 | 0.28 |

TABLE 47

HCP Removal during CEX Chromatography

| Resin | Antibody | Buffer system | pH | Load HCP (ng/mg) | Eluate Pool HCP (ng/mg) | Reduction fold |
|---|---|---|---|---|---|---|
| CM Hyper D | adalimumab | 5 mM Ammonium Sulfate | 7.5 | 8105 | 3844 | 2.1 |
| | | 45 mM Tris | | 8628 | 5615 | 1.5 |
| Nuvia S | | 11.5 mM Ammonium Sulfate | | 5314 | 2405 | 2.2 |
| | | 75 mM Tris Acetate | | 17317 | 12845 | 1.4 |
| | | 22.5 mM Sodium Chloride | | 9091 | 4115 | 2.2 |
| Poros XS | | 27 mM Ammonium Sulfate | | 21857 | 12574 | 1.0 |
| | | 140 mM Tris Acetate | | 14732 | 9181 | 1.7 |
| | | 145 mM Tris Acetate | | 15359 | 10113 | 1.6 |
| Nuvia S | mAb B | 85 mM Tris Acetate | | 735 | 319 | 2.3 |
| Poros XS | | 130 mM Tris Acetate | | 2183 | 404 | 5.4 |
| Nuvia S | mAb C | 35 mM Tris Acetate | 6.0 | 27 | 31 | 0.9 |
| Poros XS | | 50 mM Tris Acetate | | 25 | 15 | 1.7 |

Example CEX 8.12

Demonstration of Means of Controlling AR Reduction

Controlling the final product quality by modifying the process based on the quality of the intermediate material is an approach that has been proposed as an effective way of ensuring product quality, with the view of ensuring safety and efficacy.

Considering that the AR levels generated during cell culture and other upstream steps can be variable, it is desirable to design a downstream process step that implements a means of controlling the product quality and to further have a specific means of controlling a process parameter to influence the quality of the product.

In the current invention, such a control is possible, as the cation concentration is a single parameter that can be modified to achieve a desired separation of the AR species. For example, to achieve a higher level of AR reduction, the Tris concentration of the loading material and the wash buffer can be decreased, such that the AR enriched species is collected in the Flow Through fraction.

As an example, and not to be restrictive in any manner, it has been demonstrated in this example that the AR levels can be controlled by changing the Tris concentration of the load and wash solutions. A pilot scale Poros XS column (10 cm diameter×22 cm height, 1.7 L), was used for this study.

The load material and the stock buffer are both prepared at 300 mM Tris concentration at the same pH. The AR level of the load material was measured to be X %. The load material and equilibration/wash buffer are in-line diluted to the target Tris concentration based on predetermined correlation between the AR levels and Tris concentration. As demonstrated in the example, when the Tris concentration was adjusted to 156 mM, a final AR reduction of 4.1% was achieved, whereas when the Tris concentration was adjusted to 150 mM, a final AR level of 3.1 was achieved (Table 48). This allows very predictable control of the AR levels ensuring achievement of the desired product quality.

TABLE 48

Controlling AR Reduction using Process Analytical Technology approach

| Tris conc (mM) | Yield (%) | % AR Reduction |
|---|---|---|
| 156 | 51.9 | 4.1 |
| 150 | 70.5 | 3.1 |
| 131 | 95.3 | 1.3 |

In addition to the acidic species reduction demonstrated in Example CEX 8.1 through careful control of the pH cation type and concentration in the load (process stream) and equilibration/wash buffers, the composition of the elution buffer can also be used to further improve the product quality profiles. The impact of various cation types, concentration and pH were tested for eluting the product. There is a wide selection for elution buffer as shown in Table 49. The experiments were performed using Poros XS resin.

TABLE 49

Elution buffer types on aggregates removal

| Buffer System | pH | Yield (%) | % Aggregate Reduction |
|---|---|---|---|
| 200 mM Sodium Sulfate/29 mM Tris Acetate | 5.2 | 76.1 | 0.36 |
| 160 mM Sodium Sulfate/29 mM Tris Acetate | 5.2 | 82.3 | 0.82 |
| 150M Sodium Sulfate/29 mM Tris Acetate | 5.2 | 78.8 | 0.90 |
| 140M Sodium Sulfate/29 mM Tris Acetate | 5.2 | 78.2 | 1.00 |
| 400 mM Sodium Sulfate/29 mM Tris Acetate | 4.0 | 78.5 | 0.98 |
| 100 mM Sodium Sulfate/140 mM Tris Acetate | 5.2 | 70.9 | 1.25 |
| 150 mM Sodium Sulfate/140 mM Tris Acetate | 5.2 | 79.6 | 1.05 |
| 140M Sodium Sulfate/140 mM Tris Acetate | 5.2 | 75.4 | 1.07 |
| 130 mM Sodium Sulfate/140 mM Tris Acetate | 5.2 | 78.2 | 1.07 |
| 300 mM Sodium Sulfate/30 mM Tris Acetate | 4.6 | 80.3 | 0.57 |
| 150 mM Sodium Sulfate/29 mM Tris Acetate | 7.5 | 75.0 | 0.92 |

Example CEX 8.13

Demonstration of AR Reduction with Cation—HIC Mixed Mode Resin

The strategy outlined in Example 8.1, above, to reduce acidic species through careful control of buffer cation type, concentration and pH can be expanded to include other chromatography adsorbents such as mixed mode or multi-modal absorbents which include a cation exchange mechanism. Table 50 outlines the conditions used and the AR reduction achieved for two cation-hydrophobic interaction mixed mode resins. The data clearly shows that the technology outlined in Example 8.1 is robust in delivering AR reduction for these types of resins across in addition to traditional cation exchange adsorbents. As described in Example 8.1, the AR reduction can be balanced with recovery and an optimal condition can be chosen. As a further demonstration, mAb 2 was also evaluated (Table 51) with the same outcome showing the same relationship between cation concentration, recovery and AR reduction. As previously shown in Example 8.1, the optimal condition for different molecules varies. Furthermore, this technology when applied to CEX-HIC mixed mode resins also shows reduction of impurities as previously described.

TABLE 50

Adalimumab AR Reduction by Cation Exchange Mixed Mode Chromatography

| Resin | Buffer System | Tris Concentration (mM) | pH | Yield (%) | % AR Reduction |
|---|---|---|---|---|---|
| Nuvia C Prime | Tris Acetate | 70 | 7.5 | 63.8 | 6.5 |
| | | 72.5 | 7.5 | 61.1 | 6.0 |
| | | 75 | 7.5 | 57.1 | 6.7 |
| Toyo Pearl MX Trp 650M | | 75 | 7.5 | 80 | 5.7 |
| | | 80 | 7.5 | 66.7 | 7.2 |
| | | 85 | 7.5 | 51.8 | 8.6 |

TABLE 51 mAb B AR Reduction by Cation Exchange Mixed Mode Chromatography

| Resin | Buffer System | Concentration (mM) | pH | Yield (%) | % AR Reduction |
|---|---|---|---|---|---|
| Nuvia C Prime | Tris Acetate | 75 | 7.5 | 86.0 | 2.0 |
| | | 85 | 7.5 | 74.6 | 5.9 |
| | | 95 | 7.5 | 61.3 | 6.8 |
| Toyo Pearl MX Trp 650M | | 90 | 7.5 | 81.1 | 6.4 |
| | | 95 | 7.5 | 68.8 | 8.8 |
| | | 100 | 7.5 | 53.5 | 10.7 |

As described in previous sections, the AR for adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 52A with Tables 52B and 52C indicating the levels of additional process-related impurities or acidic species.

The specific species comprising the AR1 species can be identified and quantitated, to demonstrate reduction of such species by methods of the current invention. While these species are among the acidic species part of the charge variants, the acidic species typically described in the literature is the deamidated mAb, which is distinctly different. These results show that the Cation Exchange Resin with additional pendant hydrophobic interaction functionality, is able to provide AR reduction effectively, similar to the CEX Adsorbents.

TABLE 52A

Final acidic species level for adalimumab

| Resin | Buffer System | Tris Concentration (mM) | pH | Yield (%) | Final % AR1 | Final % AR2 | Final % AR |
|---|---|---|---|---|---|---|---|
| Nuvia C Prime | Tris Acetate | 70 | 7.5 | 63.8 | 0.39 | 4.64 | 5.03 |
| | | 72.5 | 7.5 | 61.1 | 0.36 | 4.4 | 4.75 |
| | | 75 | 7.5 | 63.8 | 0.39 | 4.06 | 4.45 |
| Toyo Pearl MX Trp 650M | | 75 | 7.5 | 80 | 0.6 | 4.2 | 4.8 |
| | | 80 | 7.5 | 66.7 | 0.5 | 3.2 | 3.7 |
| | | 85 | 7.5 | 51.8 | 0.2 | 2.2 | 2.4 |

TABLE 52B

Aggregates/Fragments Reduction by Cation Exchange Mixed Mode Chromatography

| Resin | Antibody | Buffer System | pH | % Aggregate Reduction | % Fragment Reduction | % Monomer Increase |
|---|---|---|---|---|---|---|
| Nuvia C prime | adalimumab | 70 mM Tris | 7.5 | 0.3 | 0.34 | 0.63 |
| Toyo Pearl MX Trp 650M | | 75 mM Tris | | 0.08 | 0.56 | 0.65 |
| Nuvia C prime | mAb B | 85 mM Tris | | 0.87 | 1.18 | 2.04 |
| Toyo Pearl MX Trp 650M | | 95 mM Tris | | 0.0 | 1.8 | 1.8 |

TABLE 52C

HCP Reduction by Cation Exchange Mixed Mode Chromatography

| Resin | Antibody | Buffer | pH | Load HCP (ng/mg) | Eluate pool HCP (ng/mg) | Fold Reduction |
|---|---|---|---|---|---|---|
| Toyo Pearl MX Trp 650M | adalimumab | 70 mM Tris | 7.5 | 202.6 | 38.9 | 5.2 |
| Nuvia C prime | | 75 mM Tris | | 205.5 | 72.8 | 2.8 |
| Toyo Pearl MX Trp 650M | mAb B | 95 mM Tris | | 983.3 | 137.1 | 7.2 |
| Nuvia C prime | | 85 mM Tris | | 1011.3 | 88.2 | 11.5 |

Example 8.14

CEX with Tris/Formate Buffer System: AR Reduction with Different Tris/Formate Concentrations—Adalimumab This Example provides a demonstration of AR reduction using a Tris/Formate buffer system and CEX. Cation (e.g. Tris) concentration is a key variable in the performance of cation exchange chromatography.

CEX Adsorbent:

Poros XS (Applied Biosciences, part#4404338), a rigid 50 μm polymeric bead with a backbone consisting of cross-linked poly[styrene-divinylbenzene], was used in this experiment.

CEX Chromatography Method

Poros XS was packed in 1.0 cm×10.0 cm (OmniFit) columns. The column was equilibrated in a buffer system with appropriate pH and conductivity. The column load was prepared in the equilibration buffer by buffer exchange or addition of the stock solutions to obtain the target ion concentrations as specified and loaded on the column at approximately 40 g protein/L resin (or as specified) followed by washing with the equilibration buffer for 20 CV (or as specified). The antibody product was then eluted, and the column regenerated.

In this Example, adalimumab and Poros XS were chosen. The experiment was performed at Tris concentrations of 120-150 mM buffered to pH 7.5 with formic acid. The column was equilibrated with the respective Tris/Formate at pH 7.5 for each run. Adalimumab was prepared at the respective Tris/Formate pH 7.5 and loaded to the column at 35-45 g-protein/L-resin. The column was then washed with 20 CVs with the equilibration buffer, and then eluted with a 140 mM Tris/Formate+140 mM Sodium Sulfate buffer at pH 5.2. The eluate was analyzed for product quality and yield.

Table 53, below, shows the effect of Tris concentration on AR reduction and aggregate reduction for adalimumab on Poros XS in a Tris/Formate buffer system at a pH of 7.5. The data demonstrates that AR and aggregate reduction can be effectively achieved over a range of Tris concentrations and column loadings. This example demonstrates the effectiveness of the Tris/Formate buffer system in general and specifically the effectiveness of the Tris cation in the context of the Formate on the CEX column for AR reduction. Further, it confirms that the CEX AR reduction method applies to a variety of buffer systems.

Wash Volumes for CEX Chromatography

The experiments were performed using Protein A eluate as CEX loading material. Run 1 was performed under the load/wash buffer conditions of 128 mM Tris-formate buffer system, pH 7.5, 40 g/L loading. Wash was performed with 20 CV of the wash buffer. Run 2 was performed under the load/wash buffer conditions of 160 mM Tris-formate buffer system, pH 7.5, 40 g/L loading. Wash was performed with 6 CV of the wash buffer.

As shown in Table 54, Run 1 and Run 2 gave similar yield and AR reduction. Therefore, these results demonstrate that process performance can be achieved by varying the wash volume with corresponding loading conditions.

TABLE 54

Wash volume effect on AR reduction and yield

| Product quality | Run 1 (20 CV Wash) | Run 2 (6 CV Wash) |
|---|---|---|
| % Yield | 92.1 | 89.6 |
| % Load AR1 | 3.44 | 3.43 |
| % Eluate AR1 | 1.43 | 1.21 |
| % AR1 Reduction | 2.01 | 2.22 |
| % Load AR2 | 10.44 | 9.87 |
| % Eluate AR2 | 9.25 | 8.86 |
| % AR2 reduction | 1.19 | 1.01 |
| % Total load AR | 13.88 | 13.3 |
| % Total eluate AR | 10.68 | 10.07 |
| % total AR reduction | 3.20 | 3.23 |

Example 9

Mixed Mode Chromatography Examples

Example MM 9.1

Resin and pH Combination

In this Example one of the approaches outlined in the general description was employed to determine the operating conditions to implement the invention. Specifically, a response surface design DOE was applied to evaluate mAb AR reductions and recovery yields.

The demonstration of the current invention for a specific antibody & resin is provided in this Example, and consists of
1. Choosing a pH in the range of 6.8 to 8.4.
2. Choosing a conductivity in the range of 2.3 to 13.7 mS/cm.

TABLE 53

Effect of Tris concentration at pH 7.5 on AR and aggregate reduction

| Tris Concentration | Loading g/L | Yield | AR Reduction | AR1 Reduction | Final AR1 | AR2 Reduction | Final AR2 | Aggregate Reduction |
|---|---|---|---|---|---|---|---|---|
| 120 mM | 35 | 96% | 0.5% | 0.4% | 0.1% | 0.1% | 4.2% | 0.1% |
|  | 40 | 88% | 1.8% | 0.6% | 0.0% | 1.3% | 2.9% | 0.2% |
| 125 mM | 35 | 90% | 2.4% | 0.5% | 0.1% | 1.8% | 3.0% | 0.2% |
|  | 40 | 78% | 3.0% | 0.6% | 0.0% | 2.4% | 2.4% | 0.2% |
| 130 mM | 35 | 76% | 3.1% | 2.3% | 0.8% | 1.0% | 8.5% | 1.3% |
|  | 40 | 64% | 4.0% | 2.5% | 0.4% | 2.7% | 6.9% | 1.4% |
|  | 45 | 70% | 4.0% | 2.4% | 0.3% | 3.6% | 6.0% | 1.5% |
| 135 mM | 35 | 78% | 5.6% | 0.8% | 0.0% | 4.8% | 2.8% | 0.3% |
|  | 40 | 58% | 5.3% | 0.8% | 0.0% | 4.4% | 3.1% | 0.2% |
| 140 mM | 35 | 63% | 6.1% | 2.5% | 0.3% | 3.5% | 6.4% | 1.3% |
|  | 40 | 55% | 6.0% | 2.4% | 0.3% | 4.3% | 5.3% | 1.3% |
|  | 45 | 55% | 5.8% | 2.4% | 0.3% | 4.8% | 4.9% | 1.0% |
| 145 mM | 35 | 55% | 4.1% | 0.6% | 0.0% | 3.5% | 1.7% | 0.3% |
|  | 40 | 44% | 4.2% | 0.6% | 0.0% | 3.6% | 1.6% | 0.3% |
| 150 mM | 35 | 50% | 7.4% | 2.4% | 0.2% | 5.0% | 4.5% | 1.1% |
|  | 40 | 44% | 7.4% | 2.6% | 0.3% | 5.5% | 4.3% | 0.7% |
|  | 45 | 40% | 6.9% | 2.5% | 0.2% | 5.7% | 4.1% | 0.5% |

3. Determining the acidic species distribution in the Flow Through/wash fractions.
4. Choosing an optimal pH and conductivity that provides the desired acidic species levels and recovery In this example, adalimumab and resin Capto Adhere were chosen. The experiments were performed with Tris/Acetate buffer system at target pH and conductivity listed in Table 55. The load material was from Protein A affinity capture and pH adjusted. This study demonstrated the effect of loading pH and conductivity on acidic species reduction. The acidic species reduction can be significantly affected by operating pH. AR reduction increased with increasing pH and/or decreasing conductivity (Table 55, Table 56 and FIG. 174)

TABLE 55

DOE study condition

| Tris Acetate Buffer | Range | Edge points for Response Surface |
|---|---|---|
| pH | 7.0-8.2 | 6.8, 8.4 |
| Conductivity | 4.0-12.0 | 2.3, 13.7 |

TABLE 56

DOE Study Operating Conditions and Results

| DOE exp | pH | Conductivity (mS/cm) | ΔAR (%) | Yield (%) |
|---|---|---|---|---|
| 1 | 7.0 | 4.0 | 0.4 | 83 |
| 2 | 7.6 | 8.0 | 0.4 | 73 |
| 3 | 7.6 | 2.3 | 1.3 | 82 |
| 4 | 7.6 | 8.0 | 0.6 | 68 |
| 5 | 7.6 | 8.0 | 0.2 | 70 |
| 6 | 7.6 | 8.0 | −0.2 | 69 |
| 7 | 8.2 | 4.0 | 2.1 | 67 |
| 8 | 7.6 | 8.0 | 1.3 | 69 |
| 9 | 7.0 | 12.0 | −0.2 | 70 |
| 10 | 7.6 | 8.0 | 1.2 | 71 |
| 11 | 8.2 | 12.0 | 1.4 | 74 |
| 12 | 6.8 | 8.0 | 1.2 | 76 |
| 13 | 8.4 | 8.0 | 1.8 | 67 |
| 14 | 7.6 | 8.0 | 1.4 | 71 |
| 15 | 7.6 | 13.7 | 1.0 | 74 |
| 16 | 7.6 | 8.0 | 1.6 | 70 |

Note:
AR reductions and protein recovery yields were calculated based on the Flow Through fractions at about loading 200 g protein per L of resin.

Example MM 9.2

Fraction Pooling

In this example, adalimumab and resin Capto Adhere were chosen. The experiments were performed with Tris/Acetate buffer system at pH 7.85 and conductivity of 2.5 mS/cm. The load material was from Protein A affinity capture and pH adjusted. Column Flow Through was fractionated throughout the entire load and wash phases. Each fraction was analyzed for acidic species and protein recovery. FIG. 175, FIG. 176 and Table 57 demonstrate AR reduction achieved with the corresponding recovery. These AR reductions and recoveries correspond to the cumulative pools of the fractions from the start to the various points during the load/wash. This is depicted in Table 57 where the AR reductions corresponding to each of these pools. This data is plotted in FIG. 175.

TABLE 57

Cumulative AR reduction in Flow Through/wash fractions

| Flow Through Fraction (Load & wash) | Yield (%) | Δ AR1 (%) | Δ AR2 (%) | Δ AR (%) | ΔLys (%) |
|---|---|---|---|---|---|
| A2 | 23 | 2.56 | 3.13 | 5.69 | 5.61 |
| A2 + A3 | 45 | 2.31 | 2.19 | 4.49 | 4.37 |
| A2 + A3 + A4 | 58 | 1.83 | 1.89 | 3.72 | 3.63 |
| A2 + A3 + A4 + A5 | 65 | 1.57 | 1.58 | 3.15 | 3.06 |
| A2 + A3 + A4 + A5 + A6 | 73 | 1.38 | 1.32 | 2.70 | 2.61 |
| A2 + A3 + A4 + A5 + A6 + B7 | 86 | 1.26 | 1.12 | 2.38 | 2.30 |
| A2 + A3 + A4 + A5 + A6 + B7 + B6 | 89 | 1.19 | 0.91 | 2.09 | 2.02 |
| A2 + A3 + A4 + A5 + A6 + B7 + B6 + B5 | 90 | 1.14 | 0.82 | 1.96 | 1.89 |

Note:
"A" Fractions are load fractions and "B" Fractions are wash fractions

Example MM 9.3

Demonstration of AR Reduction with Mixed Mode Adsorbents

In this Example, adalimumab was chosen. The experiments were performed with Tris/Acetate buffer system at pH 7.85 and conductivity of 2.5, 3.5, and 4.5 mS/cm. The same load material was applied to different mixed mode resin columns. The load material was from Protein A affinity capture and pH adjusted. Table 58 shows that all three mixed mode resins could reduce mAb acidic species. Due to the differences of resin ligands, the AR reduction level may slightly vary under certain conditions.

TABLE 58

Adalimumab AR Reduction and Protein Recovery Yields Processed with Different Mixed Mode media

| | Tris/Ac Buffer | | | | | | | | |
|---|---|---|---|---|---|---|---|---|---|
| | Capto Adhere pH 7.85 | | | HEA pH 7.85 | | | PPA pH 7.85 | | |
| Operating Conditions | 4.5 mS/cm | 3.5 mS/cm | 2.5 mS/cm | 4.5 mS/cm | 3.5 mS/cm | 2.5 mS/cm | 4.5 mS/cm | 3.5 mS/cm | 2.5 mS/cm |
| Yield (%) | 50 | 52 | 58 | 49 | 52 | 56 | 40 | 43 | 47 |
| AR Reduction (%) | 1.8 | 3.8 | 3.7 | 1.1 | 2.7 | 3.2 | 1.4 | 2.2 | 3.5 |

TABLE 58-continued

Adalimumab AR Reduction and Protein Recovery Yields Processed with Different Mixed Mode media

| | Tris/Ac Buffer | | | | | | | | |
|---|---|---|---|---|---|---|---|---|---|
| Operating | Capto Adhere pH 7.85 | | | HEA pH 7.85 | | | PPA pH 7.85 | | |
| Conditions | 4.5 mS/cm | 3.5 mS/cm | 2.5 mS/cm | 4.5 mS/cm | 3.5 mS/cm | 2.5 mS/cm | 4.5 mS/cm | 3.5 mS/cm | 2.5 mS/cm |
| Yield (%) | 68 | 71 | 73 | 65 | 75 | 69 | 61 | 64 | 63 |
| AR Reduction (%) | 1.1 | 2.7 | 2.7 | 0.5 | 1.8 | 2.1 | 0.4 | 1.9 | 2.6 |

Example MM 9.4

Demonstration of AR Reduction with Other Antibodies: mAb B and mAb C

In this Example, another two different monoclonal antibodies besides adalimumab (mAb B and mAb C) and resin Capto Adhere was chosen. The experiments were performed with Tris/Acetate buffer system at multiple pH and conductivity condition. The load materials of all mAbs were from Protein A affinity capture and pH adjusted. mAb C was also applied to another two MM resins besides Capto Adhere under the same operating conditions. Table 59 outlines the operating conditions and the AR reduction achieved and the corresponding recovery achieved. The results demonstrate that the technology can also reduce acidic species for other monoclonal antibodies with optimal pH and conductivity conditions. Experiments were performed with Tris-acetate buffer system.

TABLE 59

AR Reductions and Protein Recovery for different mAb with Capto Adhere columns

| mAb | pH | conductivity (mS/cm) | ΔAR (%) | Yield (%) |
|---|---|---|---|---|
| adalimumab | 7.85 | 3.5 | 3.8 | 52 |
| | 7.85 | 2.5 | 3.7 | 58 |
| mAb B | 6.8 | 3.0 | 6.3 | 51 |
| | 6.8 | 4.5 | 4.2 | 53 |
| | 7.0 | 3.0 | 5.1 | 77 |
| | 8.0 | 3.0 | 3.4 | 60 |
| mAb C | 9.0 | 3.0 | 5.3 | 73 |
| | 8.5 | 3.0 | 3.5 | 54 |
| | 8.0 | 3.0 | 3.7 | 50 |

FIG. 177 displays the mAb B cumulative pool AR broke through the column of Capto Adhere operated at pH 7.0 and conductivity of 3.0 mS/cm with Tris-Acetate buffer. FIG. 178 shows the mAb C cumulative pool AR broke through the column of Capto Adhere operated at pH 8.5 and conductivity of 3.0 mS/cm with Tris-Acetate buffer. Both of graphs demonstrate similar AR breakthrough curves with different AR values comparing to adalimumab (FIG. 176). FIG. 179 presents the AR breakthrough curves of Mab C with three different mixed mode resins with Tris-acetate buffer operated at pH 8.5 and conductivity of 3.0 mS/cm. The data clearly demonstrates that the AR reduction technology using mixed mode resins works very effectively for other antibodies.

Example MM 9.5

Demonstration of Relative pH on AR Reduction with Different Resins Using Adalimumab Antibody Material In this Example, data compiled from different experiments is shown to demonstrate the impact of the pH choice, relative to the pI of the protein on AR reduction. This data set provides the basis for one skilled in the art to determine a pH range to implement the current invention. Further, this reiterates the fact that the pH choice depends on several factors and the relationship between pH and AR reduction is also mAb dependent. FIG. 180 demonstrates the impact of pH-pI and conductivity on AR reduction which compiled data from the experiments performed with Capto Adhere under conditions listed in Table 60. FIG. 181 shows the impact of pH-pI and conductivity on mAb B AR reduction including the experiments operated with Tris/Acetate buffer system and multiple mixed mode resins under the conditions listed in Table 61. FIG. 182 shows the impact of pH-pI and conductivity on mAb C AR reduction including the experiments operated with Tris/Acetate buffer system and multiple mixed mode resins under the conditions listed in Table 62. All the load materials were from Protein A affinity capture and pH adjusted. It is also clear that the AR reduction can be achieved with the present invention with a range of pH choices, in the range of +0.5 to −2.5 pH units from pI for adalimumab. One skilled in the art can choose an appropriate pH to achieve a target AR reduction.

TABLE 60

Operating conditions and AR reductions for adalimumab

| Buffer system | pH | pH-pI | Conductivity (mS/cm) | AR reduction |
|---|---|---|---|---|
| Tris/Ac | 7 | −2.02 | 4 | 0.4 |
| | 7.6 | −1.42 | 8 | 0.4 |
| | 7.6 | −1.42 | 2.3 | 1.3 |
| | 7.6 | −1.42 | 8 | 0.6 |
| | 7.6 | −1.42 | 8 | 0.2 |
| | 7.6 | −1.42 | 8 | −0.2 |
| | 8.2 | −0.82 | 4 | 2.1 |
| | 7.6 | −1.42 | 8 | 1.3 |
| | 7 | −2.02 | 12 | −0.2 |
| | 7.6 | −1.42 | 8 | 1.2 |
| | 8.2 | −0.82 | 12 | 1.4 |
| | 6.8 | −2.27 | 8 | 1.2 |
| | 8.4 | −0.57 | 8 | 1.8 |
| | 7.6 | −1.42 | 8 | 1.4 |
| | 7.6 | −1.42 | 13.7 | 1.0 |
| | 7.6 | −1.42 | 8 | 1.6 |
| | 7.5 | −1.52 | 3.75 | 1.7 |
| | 7.6 | −1.42 | 2.5 | 2.7 |

TABLE 60-continued

Operating conditions and AR reductions for adalimumab

| Buffer system | pH | pH-pI | Conductivity (mS/cm) | AR reduction |
|---|---|---|---|---|
| | 7.6 | −1.42 | 2.5 | 2.0 |
| | 7.6 | −1.42 | 5 | 1.3 |
| | 7.6 | −1.42 | 5 | 1.1 |
| | 7.85 | −1.17 | 2 | 3.5 |
| | 7.85 | −1.17 | 3.75 | 3.2 |
| | 7.85 | −1.17 | 3.75 | 2.1 |
| | 7.85 | −1.17 | 3.75 | 2.8 |
| | 7.85 | −1.17 | 3.75 | 2.2 |
| | 7.85 | −1.17 | 5.5 | 2.1 |
| | 8.1 | −0.92 | 2.5 | 5.0 |
| | 8.1 | −0.92 | 2.5 | 2.6 |
| | 8.1 | −0.92 | 5 | −0.2 |
| | 8.1 | −0.92 | 5 | −1.1 |
| | 8.2 | −0.82 | 3.75 | 2.9 |
| Arg/Ac | 8.5 | −0.52 | 1 | 6.8 |
| | 9.0 | −0.02 | 1 | 6.5 |
| | 9.5 | 0.48 | 1 | 1.9 |
| Trol/Ac | 7.85 | −1.17 | 1 | 5.7 |
| | 8.0 | −1.02 | 1 | 8.0 |
| | 8.5 | −0.52 | 1 | 6.0 |

TABLE 61

Operating conditions and AR reductions for mAb B

| | pH | pH-pI | Conductivity (mS/cm) | AR reduction |
|---|---|---|---|---|
| Capto Adhere | 6.8 | −0.45 | 3 | 6.3 |
| | 7 | −0.25 | 3 | 6.2 |
| | 7.5 | 0.25 | 3 | 4.0 |
| | 8 | 0.75 | 3 | 3.2 |
| | 6.8 | −0.45 | 4.5 | 4.1 |
| | 7.5 | 0.25 | 4.5 | 3.3 |
| PPA | 6.8 | −0.45 | 3 | 1.1 |
| | 7 | −0.25 | 3 | 0.9 |
| | 7.5 | 0.25 | 3 | 1.3 |
| | 8 | 0.75 | 3 | 0.5 |
| | 6.8 | −0.45 | 4.5 | 1.6 |
| | 7.5 | 0.25 | 4.5 | 3.0 |
| HEA | 6.8 | −0.45 | 3 | 1.8 |
| | 7 | −0.25 | 3 | 1.4 |
| | 7.5 | 0.25 | 3 | 3.6 |
| | 8 | 0.75 | 3 | 0.7 |
| | 6.8 | −0.45 | 4.5 | 2.2 |
| | 7.5 | 0.25 | 4.5 | 0.9 |

TABLE 62

Operating conditions and AR reductions for mAb C

| | pH | pH-pI | Conductivity (mS/cm) | Δ % AR |
|---|---|---|---|---|
| Capto Adhere | 8.0 | −1.11 | 1 | 1.5 |
| | 8.5 | −0.61 | 1 | 3.5 |
| | 9.0 | −0.11 | 1 | 5.4 |
| PPA | 8.0 | −1.11 | 1 | −0.4 |
| | 8.5 | −0.61 | 1 | 1.1 |
| | 9.0 | −0.11 | 1 | 2.1 |
| HEA | 8.0 | −1.11 | 1 | −1.6 |
| | 8.5 | −0.61 | 1 | 1.9 |
| | 9.0 | −0.11 | 1 | 2.8 |

Example MM 9.6

Effect of pH on AR Reduction

Response surface design DOE was applied to evaluate the impact of pH and conductivity on mAb AR reductions. In this example, adalimumab and Capto Adhere were chosen. The experiments were performed with Tris/Acetate buffer system. The load material was from Protein A affinity capture and pH adjusted. Besides the pH and conductivity ranged tested and demonstrated in Table 63 and Table 64, higher pH ranges were also studied (FIG. 183).

The results in FIG. 183 and FIG. 184 demonstrated that mAb acidic species can be reduced at wide pH range from 6.8 to 9.5.

TABLE 63

DOE study condition

| Tris Acetate Buffer | Range | Edge points for Response Surface |
|---|---|---|
| pH | 7.0-8.2 | 6.8, 8.4 |
| Conductivity | 4.0-12.0 | 2.3, 13.7 |

TABLE 64

AR reduction and Yield in DOE study

| Experiment # | pH | Conductivity | ΔAR | Yield |
|---|---|---|---|---|
| 1 | 7.0 | 4.0 | 0.4 | 83 |
| 2 | 7.6 | 8.0 | 0.4 | 73 |
| 3 | 7.6 | 2.3 | 1.3 | 82 |
| 4 | 7.6 | 8.0 | 0.6 | 68 |
| 5 | 7.6 | 8.0 | 0.2 | 70 |
| 6 | 7.6 | 8.0 | −0.2 | 69 |
| 7 | 8.2 | 4.0 | 2.1 | 67 |
| 8 | 7.6 | 8.0 | 1.3 | 69 |
| 9 | 7.0 | 12.0 | −0.2 | 70 |
| 10 | 7.6 | 8.0 | 1.2 | 71 |
| 11 | 8.2 | 12.0 | 1.4 | 74 |
| 12 | 6.8 | 8.0 | 1.2 | 76 |
| 13 | 8.4 | 8.0 | 1.8 | 67 |
| 14 | 7.6 | 8.0 | 1.4 | 71 |
| 15 | 7.6 | 13.7 | 1.0 | 74 |
| 16 | 7.6 | 8.0 | 1.6 | 70 |

Note:
AR reductions and protein recovery yields were calculated based on the Flow Through fractions at about loading 200 g protein per L of resin Example MM 9.7

Demonstration of AR Reduction with Different Ion Concentrations/Ion Strength—Adalimumab In this Example, adalimumab was chosen. Besides the conductivity range tested presented before, lower conductivity and higher conductivity ranges were also studied with the Capto Adhere. Table 65 and Table 66 display the DOE study conditions using Capto Adhere columns with Tris/Acetate buffer system. The load material was from Protein A affinity capture and pH adjusted. Column Flow Through pool was collected in each run from 50 mAU of UV A280 on the ascending and 150 mAU on the descending side of the peak. FIG. 185 demonstrates the effect of pH (6.8 to 8.4), conductivity (2.3 to 13.7 mS/cm), and protein load amount (116 to 354 g/L). FIG. 186 demonstrates the AR reduction at conductivity as low as 1 mS/cm. Table 67 demonstrates the AR reduction at conductivity 86 mS/cm with Ammonia Sulfate-Tris-Acetate buffer system.

The results demonstrated that mAb acidic species can be reduced at wide conductivity ranges from 1 to 86 MS/CM.

TABLE 65

DOE study condition

| Tris Acetate Buffer | Range | Edge points for Response Surface |
|---|---|---|
| pH | 7.6-8.1 | 7.5, 8.2 |
| Conductivity | 2.5-5.0 | 2.0, 5.5 |
| Protein load amount (g/L) | 150-320 | 116, 354 |

TABLE 66

DOE operating condition and results

| pH | Conductivity (mS/cm) | Load amount (g/L) | ΔAR (%) | Yield (%) |
|---|---|---|---|---|
| 7.5 | 3.75 | 235 | 1.7 | 89 |
| 7.6 | 2.5 | 150 | 2.7 | 94 |
| 7.6 | 2.5 | 320 | 2.0 | 95 |
| 7.6 | 5 | 150 | 1.3 | 97 |
| 7.6 | 5 | 320 | 1.1 | 103 |
| 7.85 | 2 | 235 | 3.5 | 94 |
| 7.85 | 3.75 | 116 | 3.2 | 86 |
| 7.85 | 3.75 | 235 | 2.1 | 90 |
| 7.85 | 3.75 | 235 | 2.8 | 90 |
| 7.85 | 3.75 | 354 | 2.2 | 91 |
| 7.85 | 5.5 | 235 | 2.1 | 92 |
| 8.1 | 2.5 | 150 | 5.0 | 80 |
| 8.1 | 2.5 | 320 | 2.6 | 87 |
| 8.1 | 5 | 150 | −0.2 | 95 |
| 8.1 | 5 | 320 | −1.1 | 98 |
| 8.2 | 3.75 | 235 | 2.9 | 90 |

TABLE 67

AR reduction and protein recovery at conductivity of 86 mS/cm and pH 7.9

| Conductivity (mS/cm) | pH | Yield (%) | ΔAR (%) |
|---|---|---|---|
| 86 | 7.9 | 62 | 2.7 |
|  |  | 87 | 2.0 |
|  |  | 91 | 1.8 |
| 86 | 7.9 | 59 | 1.4 |
|  |  | 81 | 1.1 |
|  |  | 94 | 0.7 |

Note: adalimumab in Protein A eluate containing 25 mM acetate and 18 mM Tris or 0.89 mM Tris were pH adjusted to pH 3.5 with 3M Acetic acid solution and neutralized to pH 7.9 with 3M Tris solution. One part of this viral inactivated material was then diluted by adding 0.3 part of a stock buffer containing 2.2 M $(NH_4)_2SO_4$/90 mM Tris/60 mM Acetic pH 7.9 to reach conductivity of 86 mS/cm.

Example MM 9.8

Demonstration of AR Reduction with Different Buffer Systems with Adalimumab

In this Example, adalimumab and resin Capto Adhere were chosen. The experiments were performed with different buffer systems listed in the tables below at multiple pH and conductivity condition. The load material pH was adjusted from Protein A eluate or CEX eluate. The results in Table 68 and Table 69 demonstrates that mAb acidic species can be reduced using various buffer systems.

TABLE 68

Effect of Cation type on mAb acidic species reduction and recovery yield

Tris/Acetae

| Operating Condition | Capto Adhere pH 7.85 | | | HEA pH 7.85 | | | PPA pH 7.85 | | |
|---|---|---|---|---|---|---|---|---|---|
|  | 4.5 mS/cm | 3.5 mS/cm | 2.5 mS/cm | 4.5 mS/cm | 3.5 mS/cm | 2.5 mS/cm | 4.5 mS/cm | 3.5 mS/cm | 2.5 mS/cm |
| % Yield | 50 | 52 | 58 | 49 | 52 | 56 | 40 | 64 | 63 |
| Δ % AR | 1.8 | 3.8 | 3.7 | 1.1 | 2.7 | 3.2 | 1.4 | 1.9 | 2.6 |

Arginine/Acetate

| Operating Condition | ~1 mS/cm | | | ~1 mS/cm | | | ~1 mS/cm | | |
|---|---|---|---|---|---|---|---|---|---|
|  | pH 8.5 | pH 9.0 | pH 9.5 | pH 8.5 | pH 9.0 | pH 9.5 | pH 8.5 | pH 9.0 | pH 9.5 |
| % Yield | 65 | 62 | 49 | 77 | 71 | 66 | 69 | 70 | 71 |
| Δ % AR | 8.6 | 6.5 | 1.9 | 4.9 | 3.5 | N/R | 4.5 | 1.9 | 0.6 |

Trolamine/Acetate

| Operating Condition | ~1 mS/cm | | | ~1 mS/cm | | | ~1 mS/cm | | |
|---|---|---|---|---|---|---|---|---|---|
|  | pH 7.85 | pH 8.0 | pH 8.5 | pH 7.85 | pH 8.0 | pH 8.5 | pH 7.85 | pH 8.0 | pH 8.5 |
| % Yield | 62 | 54 | 49 | 69 | 64 | 58 | 64 | 64 | 590 |
| Δ % AR | 4.1 | 6.0 | 4.6 | 1.7 | 2.9 | 3.0 | 1.4 | 2.1 | 2.1 |

Note:
Load material was adalimumab from Protein A affinity capture and pH adjusted

TABLE 69

Effect of Anion type on mAb acidic species reduction and recovery yield

| Buffer | load amt (g/L) | conductivity (mS/cm) | pH | Yield (%) | Δ % AR |
|---|---|---|---|---|---|
| Tris/Acetate[1] | 200 | 4.00 | 7.80 | 90 | 1.6 |
| NaPhosphaste/Citrate/Trolamine/NaCl[2] | 200 | 3.53 | 7.87 | 87 | 1.5 |
| Tris/Formate[1] | 300 | 0.92 | 8.50 | 69 | 3.7 |

[1]Load material was adalimumab from Protein A affinity capture and pH adjusted
[2]The load material was adalimumab from CEX capture and pH adjusted

Example MM 9.9

Demonstration of AR Reduction with Different Loading

The experiments were performed with Tris/Acetate buffer system under the conditions in Table 66. The load material was adalimumab from Protein A affinity capture and pH adjusted. Column Flow Through pool was collected in each run from 50 mAU of UV A280 on the ascending and 150 mAU on the descending side of the peak. As seen from the profile (FIG. 186), the loading capacity has an impact on AR reduction but the AR reduction can be achieved over a wide range of loading capacities, and is merely a trade-off between AR reduction and recovery.

Example MM 9.10

Demonstration of AR Reduction with Different Load Concentration

In this example, Capto Adhere was chosen. The experiment was performed with Tris/Acetate buffer system at pH 7.8±0.1 and conductivity 3.0±0.05 mS/cm. The load material was adalimumab from concentrated CEX capture and pH adjusted. The prepared load material was then split to be two parts. One was directly loaded on to a Capto adhere column; the other part was diluted 2 folds with equilibration buffer to make different protein concentration. Table 70 demonstrates that the load protein concentration did not have significant impact on mAb acidic species reduction.

TABLE 70

Adalimumab AR Reduction and Yield with Different Load Protein Concentration

| Capture step | Buffer | Load amount (g/L) | Conductivity (mS/cm) | pH | Load protein conc. (g/L) | Yield (%) | Δ % AR |
|---|---|---|---|---|---|---|---|
| CEX | Tris/Acetate | 200 | 2.9 | 7.8 | 22.0 | 87 | 2.4 |
| CEX | Tris/Acetate | 200 | 3.0 | 7.7 | 11.0 | 89 | 2.1 |
| CEX | NaPhiosphaste/Citrate/Trolamine/NaCl | 200 | 3.5 | 7.9 | 4.9 | 87 | 1.5 |
| Protein A | Tris/Acetate | 200 | 3.1 | 7.8 | 9.0 | 89 | 2.5 |
| Protein A | Tris/Acetate | 200 | 4.0 | 7.8 | 11.8 | 90 | 1.6 |
| Protein A | Tris/Acetate | 200 | 3.0 | 7.8 | 9.9 | 93 | 2.4 |
| Protein A | Tris/Acetate | 208 | 3.0 | 7.8 | 8.4 | 95 | 3.2 |
| Protein A | Tris/Acetate | 222 | 3.0 | 7.9 | 12.9 | 89 | 3.4 |

Example MM 9.11

Alternative Wash Modalities

In this example, mAb adalimumab and resin Capto Adhere were chosen. The experiments were performed with Tris/acetate buffer system and the load material pH was adjusted from Protein A eluates. The equilibration buffer for both run was Tris/Acetic acid pH 7.8±0.1 and conductivity of 3.0±0.1 mS/cm. In the gradient conductivity wash study, second buffer was Tris/Acetic acid pH 7.8±0.1 and conductivity 6.0 mS/cm.

The results demonstrated that post load pH and conductivity can be varied with minimal AR reduction impacted (see Table 71).

TABLE 71

Comparison of AR reduction and yield under different wash conditions

| Experiment | Wash | Load conductivity (mS/cm) | load pH | Load conc (mg/mL) | Yield (%) | Wash CV | Δ % AR |
|---|---|---|---|---|---|---|---|
| Equilibration buffer wash | Equilibration buffer (Tris/Ac pH 7.8 and 3.0 mS/cm) wash only | 3.09 | 7.85 | 9.04 | 89 | 16.4 | 2.5 |

TABLE 71-continued

Comparison of AR reduction and yield under different wash conditions

| Experiment | Wash | Load conductivity (mS/cm) | load pH | Load conc (mg/mL) | Yield (%) | Wash CV | Δ % AR |
|---|---|---|---|---|---|---|---|
| Gradient conductivity wash | 1CV Equilibration buffer 10CV gradient conductivity wash from 100% Tris/Ac pH 7.8, 3.0 mS/cm to 100% Tris/Ac pH 7.8, 6 mS/cm, | 3.04 | 7.78 | 7.17 | 91 | 8.0 | 2.2 |

Example MM 9.12

Demonstration of Achievement of Absolute Value of AR Levels in Antibody Preparations Using Mixed Mode Chromatography In this example, mAb adalimumab was chosen. The experiments were performed with multiple buffer systems and multiple MM absorbents under conditions listed in Table 72. The load materials pH was adjusted from Protein A eluates.

As described above, the AR for adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated. Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 72.

Example MM 9.13

Demonstration of HCP and Aggregate Reduction in Addition to AR Reduction

Besides the acidic species reduction, the MM adsorbent is able to reduce other product/process related substances/impurities effectively. In the implementation of the current invention the fact that AR reduction is effected, other impurities/substances are expected to be cleared significantly as they should bind stronger than the acidic species. The data shown in Table 73 and Table 74 demonstrates significant HCP and aggregate reductions with different resins, buffer systems, pH, conductivities and molecules

TABLE 72

Acidic species level in MM resin Flow Through

| Resin | Buffer | pH | Conductivity (mS/cm) | Yield (%) | FT % AR1 | FT % AR2 |
|---|---|---|---|---|---|---|
| Capto Adhere | Tris/Acetate | 7.85 | 4.5 | 50 | 2.8 | 9.7 |
| | | 7.85 | 4.5 | 68 | 3.0 | 10.3 |
| | | 7.85 | 3.5 | 52 | 1.6 | 10.0 |
| | | 7.85 | 3.5 | 71 | 2.2 | 10.5 |
| | | 7.85 | 3.0 | 93 | 3.2 | 9.7 |
| | | 7.85 | 2.5 | 58 | 1.7 | 9.4 |
| | | 7.85 | 2.5 | 72 | 2.2 | 10.0 |
| | Arginine/Acetate | 8.5 | 1 | 65 | 1.2 | 6.1 |
| | | 9.0 | 1 | 62 | 1.6 | 7.2 |
| | | 9.5 | 1 | 49 | 0.8 | 11.8 |
| | Trolamine/Acetate | 7.9 | 1 | 44 | 1.5 | 6.6 |
| | | 7.9 | 1 | 62 | 1.8 | 8.0 |
| | | 8.0 | 1 | 37 | 1.1 | 5.8 |
| | | 8.0 | 1 | 54 | 1.2 | 7.7 |
| | | 8.5 | 1 | 32 | 1.7 | 9.0 |
| | | 8.5 | 1 | 49 | 1.9 | 10.1 |
| | Tris/Formate | 8.5 | 1 | 69 | 0.6 | 6.4 |
| HEA | Arginine/Acetate | 8.5 | 1 | 77 | 1.6 | 8.5 |
| | | 9.0 | 1 | 71 | 0.8 | 12.0 |
| PPA | Arginine/Acetate | 8.5 | 1 | 69 | 2.2 | 8.7 |
| | | 9.0 | 1 | 70 | 1.0 | 13.5 |
| | | 9.5 | 1 | 71 | 0.7 | 13.1 |

TABLE 73

Aggregate reduction

| | Conductivity (mS/cm) | pH | Buffer | medium | Δ % HMW |
|---|---|---|---|---|---|
| adalimumab | 3.75 | 7.5 | Tris/Acetate | Capto Adhere | 0.7 |
| | 2.5 | 7.6 | | | 0.9 |
| | 2 | 7.85 | | | 0.9 |
| | 3.75 | 7.85 | | | 1.0 |
| | 5.5 | 7.85 | | | 0.7 |
| | 2.5 | 8.1 | | | 1.0 |
| | 3.75 | 8.2 | | | 0.8 |
| | 4.0 | 8.2 | | | 1.0 |
| | 8.0 | 6.8 | | | 0.2 |
| | 8.0 | 8.4 | | | 1.0 |
| | 1.0 | 8.5 | Arginine/Acetate | Capto Adhere | 0.5 |
| | 1.0 | 9.0 | | | 0.8 |
| | 1.0 | 9.5 | | | 0.9 |
| | 1.0 | 8.5 | | HEA | 0.4 |
| | 1.0 | 9.0 | | | 2.5 |
| | 1.0 | 9.5 | | | 0.7 |
| | 1.0 | 8.5 | | PPA | 0.5 |
| | 1.0 | 9.0 | | | 2.8 |
| | 1.0 | 9.5 | | | 0.4 |
| mAb C | 3.0 | 8 | Tris/Acetate | Capto Adhere | 1.0 |
| | 3.0 | 8.5 | | Capto Adhere | 1.1 |
| | 3.0 | 9 | | Capto Adhere | 0.6 |
| | 3.0 | 8 | | PPA | 0.7 |
| | 3.0 | 8.5 | | PPA | 0.5 |
| | 3.0 | 8 | | HEA | 0.7 |
| | 3.0 | 8.5 | | HEA | 0.6 |

TABLE 74

HCP Log reduction

| | Conductivity (mS/cm) | pH | Buffer | medium | HCP LRF |
|---|---|---|---|---|---|
| adalimumab | 3.75 | 7.5 | Tris/Acetate | Capto Adhere | 1.5 |
| | 2.5 | 7.6 | | | 1.7 |
| | 2.0 | 7.85 | | | 2.2 |
| | 3.75 | 7.85 | | | 1.9 |
| | 5.5 | 7.85 | | | 1.4 |
| | 2.5 | 8.1 | | | 2.3 |
| | 3.75 | 8.2 | | | 2.1 |
| | 4.0 | 8.2 | | | 1.7 |
| | 8.0 | 6.8 | | | 0.3 |
| | 8.0 | 8.4 | | | 0.7 |
| mAb B | 3 | 6.8 | | Capto Adhere | 2.0 |
| | 4.5 | 6.8 | | | 1.3 |
| | 3 | 6.8 | | PPA | 1.2 |
| | 4.5 | 6.8 | | | 1.2 |
| | 3 | 6.8 | | HEA | 1.3 |
| | 4.5 | 6.8 | | | 1.1 |

Example MM 9.14

Combinations of MM with Alternative Separation Strategies

Acidic species reduction by MM adsorbents is expected to be performed after capture of the antibody by other means, or after one or more intermediate steps following the capture step. In the Examples below the MM adsorbent steps were performed either following a Cation Exchange Capture step or Protein A affinity capture step. As shown in Table 75, AR reduction was achieved at two different conductivities following Protein A Chromatography and CEX Chromatography.

TABLE 75

AR Reduction with different source materials

| Capture | Buffer | conductivity (mS/cm) | pH | Yield (%) | Δ % AR |
|---|---|---|---|---|---|
| Protein A | Tris/Acetate | 3.1 | 7.8 | 89 | 2.5 |
| Protein A | | 4.0 | 7.8 | 90 | 1.6 |
| CEX | | 2.9 | 7.8 | 87 | 2.4 |
| CEX | | 3.0 | 7.7 | 89 | 2.1 |

Adalimumab was purified by a CEX chromatography step followed with a low pH viral inactivation step. The filtered viral inactivated material was buffer exchanged and loaded onto a Capto Adhere column. The Flow Through of Capto Adhere material was then purified with a HIC column with bind/elute mode. As shown in Table 76, AR reduction was achieved primarily with MM step, with some contribution from other steps.

TABLE 76

Complete Process train with CEX Chromatography Capture- AR Reduction

| | Δ % AR | Δ % Lys | Yield (%) |
|---|---|---|---|
| CEX eluate | n/a | n/a | n/a |
| MM Load | 0.29 | 0.34 | 90% |
| MM Flow Through | 2.57 | 2.57 | 93% |
| HIC eluate | 0.95 | 0.94 | 97% |

Adalimumab was purified using a Protein A chromatography step followed with a low pH viral inactivation step. The filtered viral inactivated material was buffer exchanged and loaded onto a Capto Adhere column. The Flow Through of Capto Adhere material was then purified with a HIC column with bind/elute mode as well as Flow Through mode. As shown in Table 77, AR reduction was achieved primarily with MM step, with some contribution from other steps.

TABLE 77

Complete Process Train with Protein A Capture - AR, HMW and HCP reduction

| Process | Yield (%) | % AR reduction | % HMW reduction | HCP LRF |
|---|---|---|---|---|
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF(FT) Filtrate | 96.1% | No reduction | No reduction | 0.10 |
| BDS (FT) | 103.8% | No reduction | No reduction | No reduction |

Example 10

Upstream and Downstream Process Combinations to Achieve Target % AR or AR Reductions The instant example demonstrates the combined effect of one or more upstream and downstream process technology in achieving a target AR value or AR reduction, thereby facilitating the preparation of an antibody composition having a specific charge heterogeneity.

Example 10.1

Combination of Upstream and Downstream Technologies Using MM

In this Example, the combination of upstream and downstream methods involves the reduction of acidic species in 3 L bioreactor cell cultures supplemented with arginine (2 g/L) and lysine (4 g/L). The results of that strategy are summarized in Table 78. The total acidic species was reduced from 20.5% in the control sample to 10.2% in sample from cultures that were supplemented with the additives.

In this study, adalimumab producing cell line 1 was cultured in media 1 (chemically defined media) supplemented with amino acid arginine (2 g/L) and lysine (4 g/L) in a 300 L bioreactor. On Day 12 of culture, the culture was harvested and then subsequently analyzed using WCX-10 post Protein A purification and the percentages of total peak(s) area corresponding to the acidic species were quantified. The percentage of acidic species was estimated to be 9.1% in the 300 L harvest sample.

TABLE 78

AR levels achieved with use of upstream technologies

| | 3 L Bioreactor | | | | | | 300 L Bioreactor | | |
|---|---|---|---|---|---|---|---|---|---|
| | Control | | | Arginine (2 g/L) + Lysine (4 g/L) | | | Arginine (2 g/L) + Lysine (4 g/L) | | |
| AR1 (%) | AR2 (%) | Total AR (%) | AR1 (%) | AR2 (%) | Total AR (%) | AR1 (%) | AR2 (%) | Total AR (%) |
| 6.3 | 14.2 | 20.5 | 2.6 | 7.6 | 10.2 | 2.4 | 6.7 | 9.1 |

The material produced by the 300 L Bioreactor employing arginine and lysine additions, that effectively reduced the AR levels to 9.1% was purified using a downstream process employing Mixed Mode chromatography as the primary AR reduction method.

Adalimumab was purified by a Protein A chromatography step followed with a low pH viral inactivation step. The filtered viral inactivated material was buffer exchanged and loaded onto a Capto Adhere column. The Flow Through of Capto Adhere material was then purified with a HIC column with bind/elute mode as well as Flow Through mode. As shown in Table 79, AR reduction was achieved primarily with MM step, with some contribution from other steps. The table also shows that additional product related substances such as aggregates and process related impurities such as HCP can be effectively reduced employing these combined technologies.

TABLE 79

Complete Downstream Process Train with Protein A Capture - AR, HMW and HCP reduction

| Process | Yield (%) | % AR reduction | % HMW reduction | HCP LRF |
|---|---|---|---|---|
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF(FT) Filtrate | 96.1% | No reduction | No reduction | 0.10 |
| BDS (FT) | 103.8% | No reduction | No reduction | No reduction |

As is evident from the above example, the MM method further reduced the AR levels by 2.26%. Therefore upstream technologies for reduction can be combined with downstream technologies to achieve desired AR levels/AR reduction.

Example 10.2

Demonstration of AR Reduction in Process Combinations

The methods described above for reducing acidic species using cation exchange can be used as an independent operation or in combination with other process steps that provide additional acidic species reduction or those providing additional complementary and supplementary purification (See Tables 80-87). The following process combinations are provided here as non-limiting examples
1. Affinity→MM→CEX
2. Affinity→AEX→CEX
3. Affinity→CEX
4. CEX Capture→CEX

TABLE 80

AR Reduction by Capto Adhere (mixed mode) followed by Poros XS (CEX)

| Step | Yield % | % AR1 | % AR | % AR1 Reduction | % AR Reduction |
|---|---|---|---|---|---|
| MabSure Eluate | | 2.90 | 10.08 | | |
| Viral Inact | 89 | 2.89 | 10.42 | | |
| Mixed Mode FTW | 94 | 2.26 | 8.52 | 0.64 | 1.90 |
| CEX Load | | 2.29 | 8.97 | | |
| CEX Eluate | 91 | 0.25 | 4.88 | 2.04 | 4.10 |
| Overall | 76 | | | 2.65 | 5.20 |

TABLE 81

Aggregate reduction by combination of Capto Adhere (mix mode) Poros XS (CEX)

| Step | Yield % | % Monomer | % Aggregate | % Fragment | % Mono increase | % Agg. decrease | % Frag decrease |
|---|---|---|---|---|---|---|---|
| MabSure Eluate | | 99.08 | 0.85 | 0.08 | | | |
| Viral Inact | 89 | 99.14 | 0.73 | 0.13 | | | |
| Mixed Mode FTW | 96 | 99.64 | 0.26 | 0.10 | 0.50 | 0.47 | 0.03 |
| CEX Load | | 99.64 | 0.26 | 0.10 | | | |
| CEX Eluate | 89 | 99.74 | 0.18 | 0.08 | 0.10 | 0.08 | 0.02 |
| overall | 76 | | | | 0.66 | 0.67 | 0.00 |

TABLE 82

AR Reduction by Poros PI (AEX) followed by Poros XS (CEX)

| AEX CEX Cycle C Step | Yield % | % AR1 | % AR | % AR1 Reduction | % AR Reduction |
|---|---|---|---|---|---|
| MabSure Eluate | | 2.90 | 10.08 | | |
| AEX Load | | 2.73 | 10.16 | | |
| AEX FTW | 90 | 1.64 | 6.7 | 1.09 | 3.46 |
| Viral Inact | 100 | 1.39 | 6.03 | | |
| CEX Load | | 2.76 | 6.18 | | |
| CEX Eluate | 91 | 0.15 | 3.22 | 2.61 | 2.96 |
| Overall | 82 | | | 2.75 | 6.86 |

TABLE 83

Aggregate reduction Poros PI (AEX) Poros XS (CEX)

| AEX CEX Cycle C Step | Yield % | % Monomer | % Aggregate | % Fragment | % Mono increase | % Agg. decrease | % Frag decrease |
|---|---|---|---|---|---|---|---|
| MabSure Eluate | | 99.08 | 0.85 | 0.08 | | | |
| AEX Load | | 98.67 | 1.25 | 0.03 | | | |
| AEX FTW | 90 | 99.88 | 0.05 | 0.07 | 1.21 | 1.2 | −0.04 |
| Viral Inact | 100 | 99.94 | 0.05 | 0.02 | | | |
| CEX Load | | 99.64 | 0.26 | 0.10 | | | |
| CEX Eluate | 91 | 99.79 | 0.13 | 0.08 | 0.14 | 0.13 | 0.02 |
| Overall | 82 | | | | 0.71 | 0.72 | 0.00 |

TABLE 84

AR reduction from an Affinity capture pool followed by Poros XS (CEX)

| Step | Yield % | % AR1 | % AR | % AR1 Reduction | % AR Reduction |
|---|---|---|---|---|---|
| MabSure Eluate | | 3.0 | 10.5 | | |
| CEX Eluate | 82.7 | 0.3 | 4.9 | 2.8 | 5.6 |

TABLE 85

Aggregate reduction: Affinity capture pool followed by Poros XS (CEX)

| Step | Yield % | % Monomer | % Aggregate | % Fragment | % Mono increase | % Agg. decrease | % Frag decrease |
|---|---|---|---|---|---|---|---|
| MabSure Eluate | | 98.5 | 1.4 | 0.1 | | | |
| CEX Eluate | 82.7 | 99.7 | 0.2 | 0.1 | 1.2 | 1.2 | 0.0 |

TABLE 86

AR reduction CEX Capture (Fractogel SO3) followed by Poros XS (CEX) 145 mM TA Poros XS adalimumab

| Step | Yield % | % AR1 | % AR | % AR1 Reduction | % AR Reduction |
|---|---|---|---|---|---|
| Concentrated Fractogel Eluate VI | | 3.3 | 14.0 | | |
| CEX Eluate | 72.6 | 0.44 | 6.7 | 2.8 | 7.3 |

TABLE 87

Aggregate reduction: CEX Capture (Fractogel) followed by Poros XS (CEX) 145 mM TA Poros XS adalimumab

| Step | Yield % | % Monomer | % Aggregate | % Fragment | % Mono increase | % Agg. decrease | % Frag decrease |
|---|---|---|---|---|---|---|---|
| Concentrated Fractogel Eluate VI | | 97.9 | 1.5 | 0.7 | | | |
| CEX Eluate | 72.6 | 98.7 | 1.1 | 0.2 | 0.9 | 0.4 | 0.5 |

Example 10.3

Process Combination: Protein A, AEX, CEX Combination with Tris/Formate Buffer System In Example 10.3, AR reduction through a process combination of Protein A affinity capture followed by fine purification with AEX and CEX chromatography in a Tris/Formate buffer system was examined.

Materials and Methods

Materials

Antibody

Adalimumab monoclonal antibody preparation was obtained after affinity capture of the clarified harvest. The eluate from the capture step was buffer exchanged as required.

AEX Adsorbent:

Poros 50HQ (Applied Biosciences, part#1-2459-11), a rigid 50 μm polymeric bead with a backbone consisting of cross-linked poly[styrene-divinylbenzene] was used in this experiment.

CEX Adsorbent:

Poros XS (Applied Biosciences, part#4404338), a rigid 50 μm polymeric bead with a backbone consisting of cross-linked poly[styrene-divinylbenzene], was used in this experiment.

Methods

AEX Chromatography Method

Poros 50HQ was packed in 1.0 cm×10.0 cm (OmniFit) columns. The column was equilibrated in a buffer system with appropriate pH and conductivity. The load was prepared in the equilibration buffer by addition of the stock solutions to obtain the target ion concentrations, as specified, and loaded on the column, as specified, followed by washing with the equilibration buffer for 20 CV. The antibody product was collected in the flow-through and wash fractions during the load and washing steps. The columns/housings were then regenerated with 100 mM formate and 1M of NaOH solution was used for column cleaning.

CEX Chromatography Method

Poros XS was packed in 1.0 cm×10.0 cm (OmniFit) columns. The column was equilibrated in a buffer system with appropriate pH and conductivity. The column load was prepared in the equilibration buffer by buffer exchange or addition of the stock solutions to obtain the target ion concentrations as specified and loaded on the column at approximately 40 g protein/L resin (or as specified) followed by washing with the equilibration buffer for 20 CV (or as specified). The antibody product was then eluted, and the column regenerated.

Buffer Preparation Method

Buffers for AEX were prepared targeting a specific ion concentration for the anion by fixing the anion concentration (acid) to the target value, and adjusting the solution with the cationic component (base) to achieve the appropriate pH. For example, to prepare a 10 mM Formate-Tris buffer solution, pH 8.7, formic acid was dissolved in water to a target concentration of 10 mM and adjusted with concentrated Tris-base to pH 8.7.

Buffers for CEX were prepared targeting a specific ion concentration for the cation by fixing the cation concentration (base) to the target value, and adjusting the solution with the anionic component (base) to achieve the appropriate pH. For example to prepare a 140 mM Tris-Formate buffer solution, pH 7.5, Tris base was dissolved in water to a target concentration of 140 mM and adjusted with Formic Acid to pH 7.5.

AR Reduction and Recovery Calculations

In general, eluate fractions and Flow Through (FT)/Wash fractions were collected and analyzed with a WCX-10 method for AR levels. By actual or calculated pooling of the fractions the recovery and the corresponding AR levels were calculated.

Analytical Methods

WCX-10 for Adalimumab

The acidic species and other charge variants present in the adalimumab process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks. The peaks that elute at relative residence time less than a certain time are together represented as the acidic peaks.

Size Exclusion Chromatography

The molecular-weight distribution of collected samples was quantified according to the following methods. Size exclusion chromatography (SEC) was performed using a TSK-gel G3000SWxL, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification was based on the relative area of detected peaks.

UV spectroscopy $A_{280}$

UV A280 was used to determine protein concentrations for the samples post protein A elution. The assay was performed on an Agilent UV Spectrophotometer. The protein concentration was determined using Beer-Lambert's Law, $A=\varepsilon c l$, where A is Absorbance, $\varepsilon$ is the extinction coefficient, l is the path length, and c is the concentration. The absorbance was taken at 280 nm, the path length was 1 cm, and the extinction coefficients were 1.39 for Adalimumab, 1.38 for mAb B, and 1.43 for mAb C.

Results

AR reduction through a process combination of Protein A affinity capture followed by fine purification with Poros 50HQ and Poros XS in a Tris/Formate buffer system was carried out as follows, resulting in a final AR of 1.4%. This exemplary low AR process followed the flow path set forth in FIG. 190.

Protein A

For Protein A affinity capture, a 2.2×20 cm MabSelect SuRe (GE Healthcare) column was packed and qualified by HETP/Asymmetry analysis. The chromatography was run in bind-elute mode with a 4-minute residence time. Columns were loaded with 37 g mAb protein per liter of resin.

The column was washed with a high concentration Tris/Formate buffer, rinsed with a low concentration Tris/Formate buffer and subsequently eluted with a low pH Tris/Formate buffer. The column was then regenerated and cleaned with hydroxide solutions appropriate for the resin.

The MabSelect SuRe™ eluate pool was titrated to pH 3.7 with formic acid and held for an hour. The acidified materials were mixed for 1 hour at ambient temperature. The VI pool was neutralized with to a pH of 8.7 (i.e., AEX Load). The AEX load was filtered prior to loading.

AEX Chromatography

All AEX chromatography experiments were carried out on an AKTAavant25 system using a 1.0 cm diameter×9.5 cm length column packed with Poros 50HQ resin, and qualified by HETP/Asymmetry analysis. Each experiment was performed at ambient temperature. The AEX step was performed at 225 g/L of resin loading. Equilibration and loading was performed with a low concentration Formate/Tris buffer, e.g., a 15 mM Formate/Tris buffer at a pH of 8.7. Wash was performed with Acetate and Tris at the same pH. Each run was performed at ambient temperature with a load concentration of ~10 g/L at a residence time of 3 minutes. The column was regenerated and cleaned with solutions appropriate for the resin.

The Flow Through was collected in the following fractions: 100 mAu-175 g/L, 175 g/L-200 g/L, 200 g/L-225 g/L+1 CV of wash. The fractions were then measured by A280 mass spectroscopy and analyzed by WCX-10 and SEC assays.

Poros 50HQ FTW pool was adjusted to 135 mM Tris/Formate pH 7.5 using stock solutions of Tris and Formic acid.

CEX Chromatography

All CEX chromatography experiments were carried out on an AKTAavant150 system using a 1.0 cm diameter×11 cm length column packed with Poros XS resin, and qualified by HETP/Asymmetry analysis. Each experiment was performed at ambient temperature, with a 5.8 mg/mL load, 40 g\L resin loading, and a residence time of 6 minutes. Equilibration, loading, and wash was performed with a high concentration Tris/Formate buffer at a pH of 7.5. Elution was with sodium sulfate and Tris/Formate buffers. The eluate was collected in one fraction from 400 mAU to 100 mAU. Three cycles were performed. The column was regenerated and cleaned with solutions appropriate for the resin.

Viral filtration was performed on the Poros XS Eluate before the UFDF processing, using a Virosart CPV Viral Filter.

Ultracel 3 Biomax 30-kDa filters were used for diafiltration (into water) and concentration of the CEX Eluate.

The cumulative AR of the Poros50HQ fractions was below 6% allowing them to be pooled together, and adjusted to CEX Load conditions. Three cycles of CEX were performed. All three CEX eluate cycles had an AR below 3% and a HMW below 0.2% and were pooled together.

The step yield for each unit operation is listed in Table 88 with a final overall yield of 38% being achieved. The process was able to achieve an adalimumab composition with a final AR of 1.4% (an AR1 of 0.0% and an AR2 of 1.4%) and final HMW of 0.10%.

TABLE 88

Step Yields for Low AR Material Generation

| Step | Yield | AR % | AR1 % | AR2 % | HMW |
|---|---|---|---|---|---|
| MabSuRe | 86% | 10.0% | 1.6% | 8.4% | NA |
| Poros 50HQ-FTW | 80% | 5.4% | 0.8% | 4.6% | NA |
| Poros 50XS | 55% | 1.4% | 0.0% | 1.4% | 0.13% |
| Overall | 38% | 1.4% | 0.0% | 1.4% | 0.10% |

Example 11

AR Reduction Using "Recycled" AEX and CEX Technologies

This Example describes the "recycle" mode of chromatography for AR reduction using AEX, CEX, and MM technologies.

Materials and Methods

Materials

Antibody

Adalimumab monoclonal antibody preparation was material obtained after affinity capture of a clarified harvest. The eluate from the capture step was buffer exchanged as required.

AEX Adsorbent:

Poros 50HQ (Applied Biosciences, part#1-2459-11), a rigid 50 μm polymeric bead with a backbone consisting of cross-linked poly[styrene-divinylbenzene], was used in this experiment.

CEX Adsorbent:

Poros XS (Applied Biosciences, part#4404338), a rigid 50 μm polymeric bead with a backbone consisting of cross-linked poly[styrene-divinylbenzene], was used in this experiment.

Methods

AEX Chromatography Method

Poros 50HQ was packed in 1.0 cm×10.0 cm (OmniFit) columns. The column was equilibrated in a buffer system with appropriate pH and conductivity. The load was prepared in the equilibration buffer by addition of the stock solutions to obtain the target ion concentrations and loaded on the column, followed by washing with the equilibration buffer for 20 CV. The antibody product was collected in the flow-through and wash fractions during the load and washing steps. The columns/housings were then regenerated with 100 mM formate and 1M of NaOH solution was used for column cleaning.

CEX Chromatography Method

Poros XS was packed in 1.0 cm×10.0 cm (OmniFit) columns. The column was equilibrated in a buffer system with appropriate pH and conductivity. The column load was prepared in the equilibration buffer by buffer exchange or addition of the stock solutions to obtain the target ion concentrations as specified and loaded on the column at approximately 40 g protein/L resin (or as specified) followed by washing with the equilibration buffer for 20 CV (or as specified). The antibody product was then eluted, and the column regenerated.

Buffer Preparation Method

Buffers for AEX were prepared targeting specific ion concentration for the anion by fixing the anion concentration (acid) to the target value, and adjusting the solution with the cationic component (base) to achieve the appropriate pH. For example, to prepare a 10 mM Formate-Tris buffer solution, pH 8.7, formic acid was dissolved in water to a target concentration of 10 mM and adjusted with concentrated Tris-base to pH 8.7.

Buffers for CEX were prepared targeting specific ion concentration for the cation by fixing the cation concentration (base) to the target value, and adjusting the solution with the anionic component (base) to achieve the appropriate pH. For example to prepare a 140 mM Tris-Formate buffer solution, pH 7.5, Tris base was dissolved in water to a target concentration of 140 mM and adjusted with Formic Acid to pH 7.5.

AR Reduction and Recovery Calculations

In general, eluate fractions and Flow Through/wash fractions were collected and analyzed with WCX-10 method for AR levels. By actual or calculated pooling of the fractions the recovery and the corresponding AR levels were calculated.

Analytical Methods

WCX-10 for Adalimumab

The acidic species and other charge variants present in the adalimumab process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks. The peaks that elute at relative residence time less than a certain time are represented together as the acidic peaks.

Size Exclusion Chromatography

The molecular-weight distribution of collected samples was quantified according to the following methods. Size exclusion chromatography (SEC) was performed using a TSK-gel G3000SWxL, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification is based on the relative area of detected peaks.

UV spectroscopy $A_{280}$

UV A280 spectroscopy was used to determine protein concentrations for the samples post Protein A elution. The assay was performed on an Agilent UV Spectrophotometer. The protein concentration was determined using Beer-Lambert's Law, A=ɛc, where A is Absorbance, ɛ is the extinction coefficient, 1 is the path length, and c is the concentration. The absorbance was taken at 280 nm, the path length was 1 cm, and the extinction coefficients were 1.39 for adalimumab, 1.38 for mAb B, and 1.43 for mAb C.

Example 11.1

Recycled AEX Chromatography

In this Example, a cycling strategy was employed to increase the recovery yield for a given target product quality attribute. The AR reduction for a given Formate concentration and pH can be modulated by adjusting the load. Also, the recovery yield is fixed for a given loading. In this strategy, the load is chosen to achieve a target AR level in the Flow Through fraction. The column is then eluted with a Formate concentration that is slightly higher than the load. The elutate is collected, and then diluted with water to match the load Formate concentration, and added back into the load tank. This column cycle is repeated several times (and is referred to as "recycled" chromatography).

For this experiment, the target AR level in the Flow Through (FT) pool was set at 5%. The Poros50HQ column was first loaded to 200 g/L of resin and the Flow Through was collected at 20 g/L of protein loaded on the resin with the equilibration/wash buffer and load condition 15 mM Acetate/Tris pH8.7. The Flow Through fractions were run on WCX-10 assay and the cumulative AR breakthrough was calculated. The cumulative AR breakthrough of 5% was observed to occur at 150 g/L of protein loaded onto the resin and all the subsequent experiments were run at 150 g/L loading.

The cycling phase involved the scheme detailed in Table 89. The AEX load was prepared by adjusting the MabSelect SuRe eluate with 3M Tris to the appropriate pH and diluted to 15 mM Acetate and then filtered. The Flow Through of the load and wash were collected in two separate vessels. The wash was spiked with enough MabSelect SuRe Eluate to perform another cycle at 150 g/L and the condition was adjusted to 15 mM Acetate/Tris pH8.7. A total of 4 cycles were performed using the sequence of steps described above. Each run was performed at ambient temperature with a residence time of 3 minutes following the chromatographic conditions listed in Table 89. The flow-through was collected in one fraction from 100 mAu until the end of step, and the wash was collected from the beginning of the step to 50 mAU. The FT Wash was then measured by A280 and analyzed by the WCX-10, and SEC assays.

TABLE 89

AEX Chromatography Conditions

| Step | Solution | Column Volumes |
|---|---|---|
| Equilibration* | 15 mM Acetate/Tris pH 8.7 | 30 |
| Load* | adalimumab ~15 mM Acetate/Tris pH 8.7 | 150 g/L of resin |
| Wash* | 30 mM Acetate/Tris pH 8.5 | Wash down to 50 mAu |
| Regeneration | 100 mM Acetate/Tris + 500 mM NaCl pH 3.5 | 5 |

Cycling the wash fraction on the AEX column as a means of controlling the level of process impurities was implemented in this study. The wash fraction was collected at each cycle($C_n$) and adjusted to proper loading conditions and loaded at the subsequent cycle ($C_{n+1}$). The loading amount was dialed in to provide an AR breakthrough of 5%. A total of four cycles were performed.

TABLE 90

AEX Cycling Product Quality

| Cycle | Yield (%) | Load AR (%) | FT AR (%) | Wash AR (%) | Regen AR (%) | Load Lys (%) | FT Lys (%) | Wash Lys (%) | Regen Lys (%) |
|---|---|---|---|---|---|---|---|---|---|
| 1 | 64.8 | 13.2 | 5.1 | 24.8 | 89.1 | 85.8 | 93.7 | 74.3 | 10.3 |
| 2 | 65.3 | 16.5 | 6.1 | 33.9 | 90.1 | 82.6 | 92.9 | 65.2 | 9.0 |
| 3 | 58.5 | 18.6 | 5.9 | 36.1 | 90.1 | 80.6 | 93.0 | 63.0 | 9.1 |
| 4 | 58.2 | 18.4 | 5.9 | 38.4 | 85.1 | 80.8 | 93.1 | 60.8 | 8.8 |

The step yield and product quality is listed in Table 90. The % lysine (sum lysine variants, i.e., Lys 0, Lys 1 and Lys 2 which are mAbs containing 0, 1 or 2 terminal lysines) is the quantitation of the desired (non-AR containing) fraction of the product and is provided here to show that the recycle method is able to recover over 93% of the desired product. Product containing higher levels of AR is recovered in the Wash fraction of each cycle, which is then recycled back onto the subsequent AEX cycle. The recycling of the wash fraction improves the cumulative yield and while maintaining the product quality as shown in Table 91. The Cumulative Yield increased from 65% to 81% in the four cycles, while maintaining the AR level at ~6% and the monomer level at ~99.4%.

TABLE 91

Cumulative Product Quality for AEX Cycling

| Cycle | Cumulative Yield (%) | Cumulative AR (%) | Cumulative AR1 (%) | Cumulative AR2 (%) | Cumulative Lys (%) | Cumulative Monomer (%) |
|---|---|---|---|---|---|---|
| 1 | 65 | 5.1 | 0.6 | 4.5 | 93.7 | 99.4 |
| 2 | 77 | 5.6 | 0.6 | 5.6 | 93.3 | 99.5 |
| 3 | 79 | 5.7 | 0.7 | 5.1 | 93.2 | 99.4 |
| 4 | 81 | 5.8 | 0.7 | 5.1 | 93.2 | 99.3 |

Example 11.2

Recycled CEX Chromatography

These experiments were performed using Protein A eluate as CEX loading material. Cycle 1 (control) was performed under load/wash buffer conditions of 160 mM tris-acetatet, pH 7.5, 40 g protein/L resin. Cycle 2 was performed by combining part of the wash from Cycle 1 and fresh Protein A eluate as loading material. The earlier wash (prior to reaching the peak) which contained higher AR was discarded and the rest of the wash was included in the load. The loading and wash conditions were the same as Cycle 1. Cycle 3 and Cycle 4 were performed the same way as Cycle 2.

The results shown in Table 92 indicate that the recycle chromatography with four runs increase the yield from 53.4% to 65.1%. AR reduction for Cycle 1 is 8.84% and whereas with the 4 cycle Recycle Chromatography is 7.79%. While achieving similar product quality, the recycle chromatography approach can significantly improve the yield.

TABLE 92

Recycle Chromatography impact on AR reduction and yield

| Product Quality | Cycle 1 | Cycle 2 | Cycle 3 | Cycle 4 | Recycle Chrom. |
|---|---|---|---|---|---|
| Yield (%) | 53.4 | 52.2 | 52.1 | 51.6 | 65.1 |
| % AR1 in load | 3.75 | 3.71 | 3.31 | 3.40 | n/a |
| % AR1 in eluate | 0.02 | 0.08 | 0.05 | 0.02 | 0.03 |
| % AR 1 reduction | 3.72 | 3.64 | 3.26 | 3.38 | 3.72 |
| % AR2 in load | 9.6 | 11.5 | 12.0 | 12.0 | n/a |
| % AR2 in eluate | 4.48 | 5.61 | 6.00 | 6.06 | 5.52 |
| % AR 2 reduction | 5.11 | 5.88 | 5.96 | 5.98 | 4.07 |
| Total AR (%) in load | 13.3 | 15.2 | 15.3 | 15.4 | n/a |
| Total AR (%) in eluate | 4.51 | 5.69 | 6.05 | 6.08 | 5.55 |
| % Total AR reduction | 8.84 | 9.51 | 9.22 | 9.36 | 7.79 |

Example 11.3

AR Reduction Using MM Recycled Chromatography

The following Materials and Methods were used for Example 11.3.

Materials and Methods

Material captured by Protein A affinity chromatography

Adalimumab clarified harvest material obtained from 300 L bioreactor (SUL101912) was loaded on a Protein A affinity column chromatography (such as MabSelect SuRe) and eluted with designed buffer system containing only buffer components used in downstream processes product trains. In the case of this study, adalimumab bound on MabSelect SuRe resin was eluted with 20 mM acetic acid.

Resin

Multimodal media have ligands and/or base matrix with multiple functional groups giving a different selectivity compared to traditional ion exchange media. In these examples, the multimodal media having anion exchange and hydrophobic interaction functional groups are shown to remove acidic species as well as other impurities from antibody preparations.

Capto adhere (GE Healthcare, HiScreen™ prepacked column, Cat#28-9269-81), a strong anion exchanger with multimodal functionality, was evaluated in this study. Its base matrix is a highly cross-linked agarose with a ligand (N-Benzyl-N-methyl ethanol amine) that exhibits many functionalities for interaction, such as ionic interaction, hydrogen bonding and hydrophobic interaction. Those ligands offer different selectivity and hydrophobicity options for protein separations.

Capto Adhere Ligand Structure

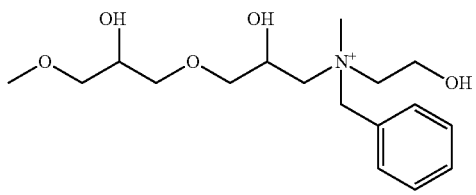 [SMILES: COCC(O)COCC(O)C[N+](C)(CCO)Cc1ccccc1]

Methods

Chromatography Method

Pre-packed resin column was used in the following experiments. The column was equilibrated in a buffer system with appropriate pH and conductivity. The process is illustrated as FIG. 191. The column load was prepared from Protein A affinity chromatography. The prepared load material was filtered and loaded on the column according to the target load amount (g protein/L resin) as specified followed by washing with the equilibration buffer and wash buffer similar to equilibration buffer with volumes as specified. The column Flow Through during load was collected as a pool and the column Flow Through during wash was collected separately. The column was then regenerated with 0.1M Acetic acid (pH 3) solution for next cycle use. The cycle A wash pool was mixed with Protein A eluate to make e antibody material to load at the target capacity for the following cycle. pH and conductivity of the combined pool (Wash pool+Protein A Eluate) was adjusted with 2M Tris and Milli Q water to achieve designed pH and conductivity. This material was then filtered through a 0.45 μm filter (Corning polystyrene).

Buffer Preparation Method

Buffers were prepared targeting specific pH and conductivity by starting with an anionic component solution (acid) to a target value, and adjusting the solution with the cationic component (base) to achieve the appropriate pH and subsequently adding water to achieve the target conductivity. For example to prepare a Tris-Acetate buffer solution with pH 7.85 and conductivity of 2.5 mS/cm, a 250 mM acetic acid solution was adjusted pH to 7.85±0.05 with 3 M Tris solution, the solution conductivity was then adjusted to 2.5±0.5 mS/cm with addition of water, final solution pH was then confirmed or adjusted to 7.85±0.05 by addition of 3 M acetic acid solution or 3 M or 2M Tris solution as needed.

In this study, Tris/Acetate buffer with pH 7.9 and conductivity 2.5 mS/cm was used for column equilibration; Tris/Acetate buffer with pH 7.9 and conductivity 5.0 mS/cm was used for post load wash buffer.

Capto Adhere load material preparation

Cycle A:

The Protein A eluate was titrated to pH 7.9 with 2M Tris and diluted to conductivity of 2.5 mS/cm with Milli Q water. The prepared material was then filtered with 0.22 μm filter before load to column.

Cycle B:

The entire cycle A wash pool was mixed with Protein A eluate to make enough load for the following cycle. pH and conductivity was adjusted after mixing with 2M Tris and Milli Q water to achieve pH 7.9 and conductivity of 2.5 mS/cm. This material was then filtered through a 0.45 μm filter (Corning polystyrene filter) before load to column.

Cycle C:

The entire cycle B wash pool was mixed with Protein A eluate to make enough load for the following cycle. pH and conductivity was adjusted after mixing with 2M Tris and Milli Q water to achieve pH 7.9 and conductivity of 2.5 mS/cm. This material was then filtered through a 0.45 μm filter (Corning polystyrene filter) before load to column.

Cycle D:

The entire cycle C wash pool was mixed with Protein A eluate to make enough load for the following cycle. pH and conductivity was adjusted after mixing with 2M Tris and Milli Q water to achieve pH 7.9 and conductivity of 2.5 mS/cm. This material was then filtered through a 0.45 μm filter (Corning polystyrene filter) before load to column.

AR Reduction and Recovery Calculations

In general, the Flow Through/wash fractions were collected and analyzed with WCX-10 method for AR levels. By actual or calculated pooling of the fractions the recovery and the corresponding AR levels were calculated.

Analytical Methods

WCX-10 for Adalimumab

The acidic species and other charge variants present in the adalimumab process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks. The peaks that elute at relative residence time less than a certain time are together represented as the acidic peaks.

UV spectroscopy $A_{280}$

UV $A_{280}$ was used to determine protein concentrations for the samples post Protein A elution. The assay was performed on an Agilent UV Spectrophotometer. The protein concentration was determined using Beer-Lambert's Law, $A=\epsilon lc$, where A is Absorbance, $\epsilon$ is the extinction coefficient, l is the path length, and c is the concentration. The absorbance was taken at 280 nm, the path length was 1 cm, and the extinction coefficients were 1.39 for adalimumab.

Demonstration of Recycle and Continuous Chromatography

In this Example, adalimumab and resin Capto Adhere were chosen. 75 grams of adalimumab per liter of resin was loaded on a Capto Adhere column in each cycle and a total four cycles were performed. A single run with 100 g/L of load material loaded on the Capto Adhere column was run as a reference to compare the AR reduction and mAb recovery. FIG. 192 illustrates percent AR in load, flow-through pool (FT), wash pool (wash) of each cycle of the MM process, and the cumulative % AR in overall FT. As shown in FIG. 192, the load % AR in each cycle increased due to higher % AR in wash pool obtained from previous cycle was re-processed, which led to slight increase of % AR in flow-through pool.

It is clear from FIG. 192 that the AR levels are maintained in the collected pools in all four cycles, achieving an overall reduction of approximately 5%. Thus, it is evident that the recycle mode can maintain the product AR levels. Table 93 shows the recovery obtained for each step and the overall recovery. It is evident that the recycle mode results in significant improvement in recovery (a 10% increase) when the four cycles are run, as compared to a single run achieving similar product quality. As seen in Table 93, cumulative recovery increases with each additional cycle. Therefore, additional improvement can be achieved by increasing the number of cycles. Moreover, when comparing the performance in cycle 1 vs. the performance in cycles 1 to 4 (cumulative), it is clear that a 20% increase in recovery can be achieved by using mode of chromatography.

TABLE 93

Acidic Species Reduction and mAb recovery in a Proof-of-Concept continuous MM chromatography

| Cycle | Load amount per cycle (g/L) | Cumulative yield (%) | Cumulative % AR | step Δ % AR | Cumultive Δ % AR |
|---|---|---|---|---|---|
| single run | 100 | 62 | 7.7 | 4.1 | 4.1 |
| 1 | 75 | 52 | 6.3 | 5.5 | 5.5 |
| 2 | 75 | 62 | 6.5 | 6.6 | 5.3 |
| 3 | 75 | 67 | 6.7 | 7.1 | 5.1 |
| 4 | 75 | 72 | 6.8 | 7.1 | 5.0 |

Example 12

Storage of AR Reduction

The current invention provides a method for reducing acidic species for a given protein of interest. In this Example, adalimumab was prepared using a combination of supplementation of arginine and lysine to cell culture as shown in this invention along with AEX and CEX purification technologies, as described herein, to produce a Low-AR and High-AR sample with a final AR of 2.5% and 6.9%, respectively. Both samples were incubated in a controlled environment at 25° C. and 65% relative humidity for 10 weeks, and the AR measured every two weeks. FIG. 164 shows the growth of AR for each sample over the 10 week incubation. It is evident from FIG. 164 the growth rate of AR is linear and similar between both the Low-AR and High-AR samples. Based on these results the reduced AR material can be stored 3 fold longer before reaching the same AR level as the High-AR sample. This is a significant utility as this can be very beneficial in storage handling and use of the antibody or other proteins for therapeutic use. Moreover, as indicated above, the formation of storage-derived AR can be inhibited when the preparation is stored under particular conditions. For example, an aqueous formulation can be stored at a particular temperature to partially or completely inhibit AR formation. In addition, formation or storage-derived AR can be partially inhibited in an aqueous formulation stored at between about 2° C. and 8° C., and completely inhibited when stored at −80° C. Moreover, a low AR composition can be lyophilized to partially or completely inhibit the formation of storage-derived AR.

Example 13

Increased Biological Activity of Low AR Compositions

This Example describes the increased efficacy of an exemplary low AR composition comprising adalimumab in vivo. The low AR composition used in this Example was produced as described in Example 8.14, above, using a CEX reduction method. In particular, the low AR composition used in this example was produced using a Poros XS column in a Tris/Formate buffer system at a pH of 7.5. The low AR composition has an AR of 3.1%, wherein the composition comprises 0.1% AR1 and 3.0% AR2. In this example, this composition is referred to as the "low AR composition."

Animal Model for Arthritis

In order to study the efficacy of this low AR adalimumab composition, experiments were carried out in vivo using human TNF-Tg197 mice. The TNF-Tg197 mouse model is a well recognized mouse model of arthritis used to test antihuman TNFα treatment modalities. The TNF-Tg197 mouse model is described in Keffer, J. et al., (1991) EMBO J 10:4025-4031, the contents of which are incorporated herein by reference. The transgenic mice carrying human TNF gene were developed to study the effects of excess TNF production in vivo.

Tg197 mice develop swelling in the ankle joints of both hind paws and impaired movement, which is very similar to human rheumatoid arthritis. Clinical signs of disease in Tg197 mice start at 4 weeks of age and include slower weight gain, joint distortion and swelling, joint deformation and ankylosis and impaired movement. Histopathological analysis reveals hyperplasia of synovial membrane, leukocyte infiltration at around 3 weeks of age, and then pannus formation, articular cartilage destruction and massive production of fibrous tissue at advanced stage of disease at 9-11 weeks of age. This model has been used in the development of anti-TNFα biologics, including adalimumab.

Methods

Groups of mice (6 males and 6 females), were administered one of the following adalimumab formulations: low AR composition (group 5), low host cell protein (HCP) composition (group 7), AR1 composition (containing only AR1 acidic variants) (group 8), and Lys-1/2 composition (containing only Lys 1 and Lys 2 variants) (group 9). These compositions (fractions) are shown in the chromatograph in FIG. 193. Another group of mice was administered a control composition, also referred to as the "control AR composition," or "normal" composition, which contains adalimumab with unmodified AR levels and unmodified Lys variants. A placebo group, comprising 6 mice, was also included.

Each composition, including the control AR composition, was administered to the mice in each group beginning with a tolerizing dose of adalimumab at age 1 week, and followed by additional weekly dosages of 1 mg/kg for 10 weeks. From weeks 2.5 through weeks 13.5, weekly measurements of weight and arthritic scores were taken and weekly serum collection was made. In addition, at the end of the study, tissue samples from perfused mice were obtained and analyzed. The following tissues were harvested for testing drug levels, anti-drug antibodies (ADA), and complexed and free TNF levels: front paws, inguinal, popliteal and mesenteric lymph nodes, spleen, tail (for skin sample), knees. The femur and spine tissues were harvested for micro-CT scanning.

Results

As shown in FIG. 194A, the mice receiving the low AR composition had the lowest arthritic scores of all of the compositions tested, including the control AR composition, indicating increased efficacy in the treatment of arthritis. Furthermore, as shown in FIG. 194B, the mice administered the low AR composition exhibited an average weight gain that was comparable to the control composition, indicating safety of the low AR composition and a lack of adverse effects of the low AR composition that impact weight gain and growth of the mice.

As shown in FIG. 195, during the 12-13 week treatment period of the mice, the low AR composition provided the best protection against development of arthritis in the mice, as measured by arthritic scores, as compared to the other compositions tested. The Lys-1/2 composition was the next most effective. The AR1 composition offered the least protection against development of arthritic scores, and it was less protective than the control AR composition.

Serum levels of ADA and drug levels were measured from 3 to 14 weeks of age. As shown in FIG. 196B, animals administered the low AR composition exhibited low average levels of ADA across the time frame measured. In addition, animals administered the low AR composition exhibited drug serum levels comparable to the control (FIG. 196A), indicating that a lack of presence of the drug in the serum was not responsible for the low levels of serum ADA.

As set forth in FIG. 197, cumulative serum concentration values (PK) during the ten week treatment period was highest for the animals administered the low AR composition and lowest for the animals administered the AR1 composition. The Lys-1/2 composition was the next best following the low AR composition, and was higher than the AR control composition. As also shown in FIG. 197, the highest ADA titers were observed for animals administered the AR1 composition and the lowest for animals administered the low AR composition.

Furthermore, complexed TNF levels show that cumulative serum concentration values during the ten week treatment period were highest for animals administered the control AR composition and lowest for the animals administered the AR1 composition (FIG. 198). Cumulative serum concentration values for the low AR composition were slightly less than the levels of the control AR composition.

A histopathology evaluation of the joints of the mice indicated that the best protection was afforded by the low AR composition and the Lys-1/2 composition, indicating that the low AR composition and the Lys-1/2 composition protect against the formation of arthritis in the joints in vivo. As shown in FIG. 199, the low AR composition protected against cell infiltration, synovial proliferation, proteoglycan loss, cartilage destruction, and bone erosion more effectively than the other compositions, including the control AR composition. Protection by the AR1 composition was lower than the control AR composition, indicating a detrimental effect by AR1 with respect to joint damage.

FIGS. 200A-D illustrate the average drug (PK) levels for various tissues (paw, lymph node, spleen, skin, knee and serum) for the low AR composition, the control AR composition, the AR1 composition, and the Lys-1/2 composition. As shown therein, animals administered the low AR composition had drug levels as high or higher than animals administered the other compositions tested.

FIG. 201A-D illustrates average ADA levels in the same tissues for the same compositions (the low AR composition, the control AR composition, the AR1 composition, and the Lys-1/2 composition). As shown in FIG. 201A-D, for the low AR composition, the highest ADA concentrations are present in the paws (which corresponds to the location of the highest levels of inflammation in the animals), and the serum.

FIGS. 202A-D and 203A-D show the results of a micro CT analysis of spines and femurs obtained from the transgenic mice at the end of the study that were administered low AR composition, control AR composition, AR1 composition, Lys-1/2 composition, as well as naïve, (control) and placebo. Samples were analyzed for L5 vertebra bone volume, L5 vertebra trabecular number, L5 vertebra trabecular thickness, and L5 vertebra trabecular space. As shown in FIGS. 202A-D and 203A-D, the low AR composition and the Lys-1/2 composition resulted in greater bone volume, trabecular number, trabecular thickness and trabecular space, as compared to the control (normal) AR composition.

FIGS. 204A-D show additional results of a micro CT analysis of spines and femurs obtained from the transgenic mice at the end of the study that were administered low AR composition, control AR composition, AR1 composition, Lys-1/2 composition, as well as naïve (control), and placebo. Samples were analyzed for trabecula bone volume at the femoral metaphysis, trabecular number at the femoral metaphysis, trabecular thickness at the femoral metaphysis, and trabecular separation at the femoral metaphysis. As shown in FIGS. 204A-D, the low AR composition resulted in greater trabecula bone volume at the femoral metaphysis, trabecular number at the femoral metaphysis, and trabecular thickness at the femoral metaphysis, as compared to the control (normal) AR composition.

Furthermore, FIGS. 205 and 206 show actual micro CT images of the spine and femur, respectively, from each of six groups of mice administered the following compositions: naïve, vehicle (control), low AR composition (group 5), low host cell protein (HCP) composition (group 7), AR1 composition (containing only AR1 acidic variants) (group 8), and Lys-1/2 composition (containing only Lys 1 and Lys 2 variants) (group 9). As seen in both the spine and the femur, the low AR composition (group 5), provided protection from bone erosion, as compared to the vehicle, as there is less bone erosion visible in the group 5 image as compared to the vehicle.

The results of these experiments demonstrate that a weekly dose of 1 mg/kg adalimumab in TNF-Tg197 mice provides protection from arthritis development as measured by arthritic scores and histopathology scores (radiologic damage involving cartilage and bone as well as local inflammation) in the TNF-Tg197 mouse model. Thus, the control AR composition, with normal level of AR variants, was efficacious at a certain level.

Formulations containing either the low AR formulation or the Lys-1/2 composition provided greatest protection, as compared to the control AR group, from development of arthritis as measured by arthritic scores and histopathology scores, and showed increased efficacy, as compared to the control AR group, in all parameters tested including cell infiltration, synovial proliferation, proteoglycan loss, cartilage destruction, and bone erosion. Accordingly, the low AR composition and the Lys-1/2 composition have increased efficacy in the treatment and prevention of arthritis as compared to the control AR composition.

The adalimumab AR1 composition was less efficacious than the normal AR containing adalimumab control group in all aspects interrogated in the current study: less weight gain, higher arthritic scores, and higher histopathology scores in the joints, indicating a detrimental effect exerted by AR1.

Noteworthy differences were observed in serum levels of the various formulations include the following: the animals treated with the AR1 composition had the lowest concentration of adalimumab as compared to the other groups, and the animals treated with the low AR composition had the highest concentration of adalimumab as compared to the other groups. The AR1 composition also had the highest titers of ADA in serum.

\* \* \*

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The contents of all cited references, including literature references, issued patents, and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference: U.S. Provisional Patent Application 61/893,123, entitled "STABLE SOLID PROTEIN COMPOSITIONS AND METHODS OF MAKING SAME", filed on Oct. 18, 2013; U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013; U.S. Provisional Patent Application 61/892,710, entitled "MUTATED ANTI-TNFα ANTIBODIES AND METHODS OF THEIR USE", filed on Oct. 18, 2013; U.S. Provisional Patent Application 61/893,088, entitled "MODULATED LYSINE VARIANT SPECIES AND METHODS FOR PRODUCING AND USING THE SAME", filed on Oct. 18, 2013; and U.S. Provisional Patent Application 61/893,131, entitled "PURIFICATION OF PROTEINS USING HYDROPHOBIC INTERACTION CHROMATOGRAPHY", filed on Oct. 18, 2013.

The invention claimed is:

1. A method for producing a composition comprising an immunoglobulin comprising the 6 CDR domains of adalimumab, the method comprising:

contacting a first sample comprising the immunoglobulin, wherein the sample comprises more than 10% total acidic species of the immunoglobulin, to a first chromatography media in the presence of a loading buffer to produce a first chromatography sample, wherein the first chromatography media is selected from the group consisting of an ion exchange chromatography media, an affinity chromatography media and a hydrophobic interaction chromatography (HIC) media, wherein the first chromatography sample comprises a composition of the immunoglobulin comprising less than 10% total acidic species of the immunoglobulin, wherein the acidic species of the immunoglobulin correspond to the peaks that elute earlier than the main peak in a WCX-10 HPLC chromatogram of the immunoglobulin, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

2. The method of claim 1, wherein producing the first chromatography sample comprises washing the first chromatography media with a wash buffer.

3. The method of claim 2, wherein the wash buffer is the same as the loading buffer.

4. The method of claim 1, wherein the first chromatography sample is a flow through chromatography sample which comprises less than 10% total acidic species of the immunoglobulin.

5. The method of claim 1, wherein producing the first chromatography sample comprises eluting the first chromatography sample, thereby producing a first eluted sample which comprises less than 10% total acidic species of the immunoglobulin.

6. The method of claim 5, further comprising contacting the first eluted sample to a second chromatography media and eluting the sample, thereby producing a second eluted sample, wherein the second chromatography media is selected from the group consisting of an ion exchange chromatography media, an affinity chromatography media and a hydrophobic interaction chromatography (HIC) media.

7. The method of claim 6, further comprising contacting the second eluted sample to a third chromatography media and eluting the sample, thereby producing a third eluted sample, wherein the third chromatography media is selected from the group consisting of an ion exchange chromatography media, an affinity chromatography media and a hydrophobic interaction chromatography (HIC) media.

8. The method of claim 7, wherein the first chromatography media is an affinity chromatography media, the second chromatography media is an ion exchange chromatography media and the third chromatography media is a hydrophobic interaction chromatography (HIC) media.

9. The method of claim 7, wherein the first chromatography media is an affinity chromatography media, the second chromatography media is an ion exchange chromatography media and the third chromatography media is an ion exchange chromatography media.

10. The method of claim 9, wherein the affinity chromatography media is a protein A chromatography media, the ion exchange chromatography media used as the second chromatography media is an anion exchange (AEX) chromatography media and the ion exchange chromatography media used as the third chromatography media is a cation exchange (CEX) chromatography media.

11. The method of claim 1, wherein the first chromatography media is an ion exchange chromatography media selected from the group consisting of an anion exchange (AEX) chromatography adsorbent material, a cation exchange (CEX) chromatography adsorbent material, a cation exchange mixed mode media, and an anion exchange mixed mode media.

12. The method of claim 11, wherein the cation exchange (CEX) adsorbent material is selected from the group consisting of a CEX resin and a CEX membrane adsorber.

13. The method of claim 11, wherein the anion exchange (AEX) adsorbent material is selected from the group consisting of an AEX resin and an AEX membrane adsorber.

14. The method of claim 1, wherein the first chromatography media is an affinity chromatography media.

15. The method of claim 14, wherein the affinity chromatography media is a Protein A chromatography media.

16. The method of claim 1, wherein the first chromatography media is a hydrophobic interaction chromatography (HIC) media.

17. The method of claim 1, wherein the first chromatography media is a mixed mode media comprising ion exchange and hydrophobic interaction functional groups.

18. The method of claim 1, wherein the first chromatography media is a CEX adsorbent material or a mixed mode media, and the pH of the loading buffer is lower than the isoelectric point of adalimumab.

19. The method of claim 1, wherein the immunoglobulin is adalimumab and wherein the total acidic species of adalimumab comprise a first acidic region (AR1) and a second acidic region (AR2).

20. The composition of claim 19, wherein the first acidic region (AR1) and the second acidic region (AR2) comprise charge variants, structure variants and fragmentation variants.

21. The composition of claim 20, wherein the charge variants comprise one or more of deamidation variants, glycation variants, afucosylation variants, MGO variants or citric acid variants, the structure variants comprise one or more of glycosylation variants or acetonation variants, and the fragmentation variants comprise one or more of Fab fragment variants, C-terminal truncation variants or variants missing a heavy chain variable domain.

22. The method of claim 1, wherein the composition comprises 9% or less, 8% or less, 7% or less, 6% or less, 5% or less, 4.5% or less, 4% or less, 3.5% or less, 3% or less, 2.5% or less, or 2% or less total acidic species of the immunoglobulin comprising the 6 CDR domains of adalimumab.

23. The method of claim 1, wherein the immunoglobulin is adalimumab.

24. The method of claim 1, wherein the composition comprises 1.4% to 10% total acidic species of the immunoglobulin comprising the 6 CDR domains of adalimumab.

25. The method of claim 1, wherein the composition comprises 1.4% or less total acidic species of the immunoglobulin comprising the 6 CDR domains of adalimumab.

26. A method for producing a composition comprising an immunoglobulin comprising the 6 CDR domains of adalimumab, the method comprising:
- (a) contacting a first sample comprising the immunoglobulin, wherein the sample comprises more than 10% total acidic species of the immunoglobulin, to an affinity chromatography media in a first loading buffer, and eluting a first eluted sample from the affinity chromatography media;
- (b) contacting the first eluted sample to a second chromatography media in a second loading buffer and eluting a second eluted sample from the second chromatography media; and
- (c) contacting the second eluted sample to a third chromatography media in a third loading buffer and eluting a third eluted sample from the third chromatography media;

wherein the third eluted sample comprises a composition of the immunoglobulin comprising less than 10% total acidic species of the immunoglobulin, wherein the acidic species of the immunoglobulin correspond to the peaks that elute earlier than the main peak in a WCX-10 HPLC chromatogram of the immunoglobulin, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

27. The method of claim 26, wherein the second chromatography media is selected from the group consisting of an anion exchange (AEX) chromatography adsorbent material, a cation exchange (CEX) chromatography adsorbent material, a mixed mode media, a cation exchange mixed mode media, and an anion exchange mixed mode media.

28. The method of claim 26, wherein the third chromatography media is selected from the group consisting of an anion exchange (AEX) chromatography adsorbent material a cation exchange (CEX) chromatography adsorbent material, a mixed mode media, a cation exchange mixed mode media, and an anion exchange mixed mode media.

29. The method of claim 26, wherein the second loading buffer, the third loading buffer, or both the second and third loading buffers are a Tris/Formate buffer.

30. The method of claim 26, wherein the composition comprises 1.4% to 10% total acidic species of the immunoglobulin comprising the 6 CDR domains of adalimumab.

31. The method of claim 26, wherein the composition comprises 1.4% or less total acidic species of the immunoglobulin comprising the 6 CDR domains of adalimumab.

32. The method of claim 26, wherein the composition comprises 9% or less, 8% or less, 7% or less, 6% or less, 5% or less, 4.5% or less, 4% or less, 3.5% or less, 3% or less, 2.5% or less, or 2% or less total acidic species of the immunoglobulin comprising the 6 CDR domains of adalimumab.

33. The method of claim 26, wherein the immunoglobulin is adalimumab.

34. A method for producing a composition comprising an immunoglobulin comprising the 6 CDR domains of adalimumab, the method comprising:
(a) contacting a first sample comprising the immunoglobulin, wherein the sample comprises more than 10% total acidic species of the immunoglobulin, to a protein A chromatography media in a first loading buffer, and eluting a first eluted sample from the protein A chromatography media;
(b) contacting the first eluted sample to an anion exchange (AEX) chromatography media in a second loading buffer and eluting a second eluted sample from the AEX chromatography media; and
(c) contacting the second eluted sample to a cation exchange (CEX) chromatography media in a third loading buffer and eluting a third eluted sample from the CEX chromatography media;
wherein the third eluted sample comprises a composition of the immunoglobulin comprising less than 10% total acidic species of the immunoglobulin, wherein the acidic species of the immunoglobulin correspond to the peaks that elute earlier than the main peak in a WCX-10 HPLC chromatogram of the immunoglobulin, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

35. The method of claim 34, wherein the immunoglobulin is adalimumab.

36. The method of claim 34, wherein the composition comprises 1.4% to 10% total acidic species of the immunoglobulin comprising the 6 CDR domains of adalimumab.

37. The method of claim 34, wherein the composition comprises 1.4% or less total acidic species of the immunoglobulin comprising the 6 CDR domains of adalimumab.

38. The method of claim 34, wherein the composition comprises 9% or less, 8% or less, 7% or less, 6% or less, 5% or less, 4.5% or less, 4% or less, 3.5% or less, 3% or less, 2.5% or less, or 2% or less total acidic species of the immunoglobulin comprising the 6 CDR domains of adalimumab.

39. A method for producing a composition comprising adalimumab, the method comprising:
(a) contacting a first sample comprising adalimumab, wherein the sample comprises more than 10% total acidic species of adalimumab, to a protein A chromatography media in a first loading buffer, and eluting a first eluted sample from the protein A chromatography media;
(b) contacting the first eluted sample to an anion exchange (AEX) chromatography media in a second loading buffer and eluting a second eluted sample from the AEX chromatography media; and
(c) contacting the second eluted sample to a cation exchange (CEX) chromatography media in a third loading buffer and eluting a third eluted sample from the CEX chromatography media;
wherein the third eluted sample comprises a composition of adalimumab comprising less than 10% total acidic species of adalimumab, wherein the acidic species of adalimumab correspond to the peaks that elute earlier than the main peak in a WCX-10 HPLC chromatogram of adalimumab, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

40. The method of claim 39, wherein the composition comprises 1.4% to 10% total acidic species of adalimumab.

41. The method of claim 39, wherein the composition comprises 1.4% or less total acidic species of adalimumab.

42. The method of claim 39, wherein the composition comprises 9% or less, 8% or less, 7% or less, 6% or less, 5% or less, 4.5% or less, 4% or less, 3.5% or less, 3% or less, 2.5% or less, or 2% or less total acidic species of adalimumab.

* * * * *

UNITED STATES PATENT AND TRADEMARK OFFICE
CERTIFICATE OF CORRECTION

PATENT NO. : 9,315,574 B2
APPLICATION NO. : 14/584619
DATED : April 19, 2016
INVENTOR(S) : Natarajan Ramasubramanyan et al.

It is certified that error appears in the above-identified patent and that said Letters Patent is hereby corrected as shown below:

In the Claims:

In claim 20 (column 190, line 12), delete "composition" and replace with --method--;

In claim 21 (column 190, line 16), delete "composition" and replace with --method--.

Signed and Sealed this
Fourteenth Day of June, 2016

Michelle K. Lee
*Director of the United States Patent and Trademark Office*